US012534728B2

(12) United States Patent
Li et al.

(10) Patent No.: US 12,534,728 B2
(45) Date of Patent: Jan. 27, 2026

(54) RNAI AGENTS FOR INHIBITING EXPRESSION OF 17BETA-HSD TYPE 13 (HSD17B13), COMPOSITIONS THEREOF, AND METHODS OF USE

(71) Applicant: Arrowhead Pharmaceuticals, Inc., Pasadena, CA (US)

(72) Inventors: Zhen Li, Westfield, NJ (US); Rui Zhu, San Diego, CA (US); Shawn A Morales, San Diego, CA (US)

(73) Assignee: Arrowhead Pharmaceuticals, Inc., Pasadena, CA (US)

( * ) Notice: Subject to any disclaimer, the term of this patent is extended or adjusted under 35 U.S.C. 154(b) by 1225 days.

(21) Appl. No.: 17/275,959

(22) PCT Filed: Sep. 18, 2019

(86) PCT No.: PCT/US2019/051707

§ 371 (c)(1),
(2) Date: Mar. 12, 2021

(87) PCT Pub. No.: WO2020/061177

PCT Pub. Date: Mar. 26, 2020

(65) Prior Publication Data

US 2022/0056454 A1 Feb. 24, 2022

Related U.S. Application Data

(60) Provisional application No. 62/890,220, filed on Aug. 22, 2019, provisional application No. 62/773,707, filed on Nov. 30, 2018, provisional application No. 62/733,320, filed on Sep. 19, 2018.

(51) Int. Cl.
*C12N 15/113* (2010.01)
*A61K 31/713* (2006.01)

(52) U.S. Cl.
CPC ........ *C12N 15/1137* (2013.01); *A61K 31/713* (2013.01); *C12N 2310/14* (2013.01); *C12N 2310/315* (2013.01); *C12N 2310/317* (2013.01); *C12N 2310/321* (2013.01); *C12N 2310/322* (2013.01); *C12N 2310/351* (2013.01); *C12N 2320/31* (2013.01)

(58) Field of Classification Search
CPC ............ C12N 15/1137; C12N 2310/14; C12N 2310/315; C12N 2310/317; C12N 2310/321; C12N 2310/322; C12N 2310/351; C12N 2320/31; C12N 2310/323; C12N 2310/331; C12N 2310/343; C12N 2310/346; C12N 2310/3521; C12N 2310/3533; C12N 2310/32; A61K 31/713; A61K 45/06; A61K 47/549; A61K 2300/00; C12Y 101/00; A61P 1/16
See application file for complete search history.

(56) References Cited

U.S. PATENT DOCUMENTS

| | | | |
|---|---|---|---|
| 4,522,811 A | 6/1985 | Eppstein et al. | |
| 5,885,968 A | 3/1999 | Biessen et al. | |
| 5,998,203 A | 12/1999 | Matulic-Adamic et al. | |
| 9,260,471 B2 | 2/2016 | Cancilla et al. | |
| 9,290,760 B2 | 3/2016 | Rajeev et al. | |
| 10,787,647 B2 | 9/2020 | Abul-Husn et al. | |
| 11,180,757 B1 | 11/2021 | Hinkle et al. | |
| 11,702,700 B2 | 7/2023 | Xin et al. | |
| 2003/0004102 A1 | 1/2003 | Ashkenazi et al. | |
| 2007/0219169 A1 | 9/2007 | Becourt et al. | |
| 2008/0113351 A1 | 5/2008 | Naito et al. | |
| 2010/0028879 A1 | 2/2010 | Labrie et al. | |
| 2010/0056384 A1 | 3/2010 | Hobbs et al. | |
| 2011/0054005 A1 | 3/2011 | Naito et al. | |
| 2012/0052487 A9 | 3/2012 | Khvorova et al. | |
| 2017/0096665 A1 | 4/2017 | Melquist et al. | |
| 2017/0253875 A1* | 9/2017 | Rozema | C07H 15/04 |

(Continued)

FOREIGN PATENT DOCUMENTS

| | | |
|---|---|---|
| CN | 104698108 B | 6/2015 |
| CN | 103520724 B | 5/2016 |

(Continued)

OTHER PUBLICATIONS

Haringsma (et al. 2012. mRNA knockdown by single strand RNA is improved by chemical modifications. Nuc. Ac. Res. 40[9]:4125-4136) (Year: 2012).*
U.S. Appl. No. 18/854,700, filed Oct. 2024.*
Szabo et al.; "Alcohol-Related Liver Disease: Areas of Consensus, Unmet Needs and Opportunities for Further Study"; Hepatology; vol. 69; Issue 5; pp. 2271-2283; 2019.
Tang, et al.; "A mouse knockout library for secreted and transmembrane proteins"; Nature Biotechnology; 28 (7):749-755 plus Online Methods and Supplementary Information; 2010.

(Continued)

*Primary Examiner* — Nancy J Leith
*Assistant Examiner* — Ruth Sophia Arieti
(74) *Attorney, Agent, or Firm* — Carly Shanahan

(57) ABSTRACT

The present disclosure relates to RNAi agents, e.g., double stranded RNAi agents, able to inhibit 17β-hydroxysteroid dehydrogenase type 13 (HSD17B13 or 17β-HSD13) gene expression. Also disclosed are pharmaceutical compositions that include HSD17B13 RNAi agents and methods of use thereof. The HSD17B13 RNAi agents disclosed herein may be conjugated to targeting ligands to facilitate the delivery to cells, including to hepatocytes. Delivery of the HSD17B13 RNAi agents in vivo provides for inhibition of HSD17B13 gene expression. The RNAi agents can be used in methods of treatment of HSD17B13-related diseases and disorders, including non-alcoholic fatty liver disease (NAFLD), non-alcoholic steatohepatitis (NASH), hepatic fibrosis, and alcoholic or non-alcoholic liver diseases, including cirrhosis.

45 Claims, 42 Drawing Sheets

Specification includes a Sequence Listing.

(56) References Cited

U.S. PATENT DOCUMENTS

| | | | | |
|---|---|---|---|---|
| 2018/0179553 | A1 | 6/2018 | Watson et al. | |
| 2018/0216084 | A1 | 8/2018 | Abul-Husn et al. | |
| 2018/0216104 | A1* | 8/2018 | Abul-Husn .......... | A61K 38/465 |
| 2019/0106794 | A1 | 4/2019 | Rankin et al. | |
| 2019/0211333 | A1* | 7/2019 | Rozema ............... | C12N 15/113 |
| 2020/0354693 | A1 | 11/2020 | Abul-Husn et al. | |
| 2024/0002857 | A1* | 1/2024 | Zhang ................ | C12N 15/1137 |

FOREIGN PATENT DOCUMENTS

| | | | | |
|---|---|---|---|---|
| WO | 1995029255 | A1 | 11/1995 | |
| WO | 1997020942 | A1 | 6/1997 | |
| WO | 2000/053722 | A2 | 9/2000 | |
| WO | 2004110459 | A1 | 12/2004 | |
| WO | 2005108415 | A2 | 11/2005 | |
| WO | 2006006948 | A2 | 1/2006 | |
| WO | 2008/022309 | A2 | 2/2008 | |
| WO | 2010028110 | A2 | 3/2010 | |
| WO | 2011/104169 | A1 | 9/2011 | |
| WO | 2012/083185 | A2 | 6/2012 | |
| WO | 2013/032829 | A1 | 3/2013 | |
| WO | 2013/158141 | A1 | 10/2013 | |
| WO | 2013177060 | A2 | 11/2013 | |
| WO | 2013190075 | A2 | 12/2013 | |
| WO | 2016011080 | A2 | 1/2016 | |
| WO | 2016081444 | A1 | 5/2016 | |
| WO | 2017048620 | A1 | 3/2017 | |
| WO | 2017/156012 | A1 | 9/2017 | |
| WO | 2018/044350 | A1 | 3/2018 | |
| WO | 2018/132432 | A1 | 7/2018 | |
| WO | 2018136702 | A1 | 7/2018 | |
| WO | WO-2018136758 | A1 * | 7/2018 | ........... A61K 31/713 |
| WO | 2019183329 | A1 | 9/2019 | |
| WO | WO-2019183164 | A1 * | 9/2019 | ......... A61K 31/7088 |
| WO | 2020061177 | A1 | 3/2020 | |

OTHER PUBLICATIONS

Thursz, Mark et al.; "Alcohol-related liver disease: Areas of consensus, unmet needs and opportunities for further study"; Journal of Hepatology; vol. 70; pp. 521-530; 2019.

Trepo, et al.; "PNPLA3 gene in liver diseases"; J. Hepatol.; 65(2):399-412; 2016.

Van Der Meer, et al.; "Association Between Sustained Virological Response and All-Cause Mortality Among Patients With Chronic Hepatitis C and Advanced Hepatic Fibrosis"; JAMA; 308(24):2584-2593; 2012.

Vernon, et al.; "Systematic review: the epidemiology and natural history of non-alcoholic fatty liver disease and non-alcoholic steatohepatitis in adults"; Alimentary Pharmacology and Therapeutics; 34:274-285; 2011.

Victor, et al.; "The Dallas Heart Study: A Population-Based Probability Sample for the Multidisciplinary Study of Ethnic Differences in Cardiovascular Health"; Am. J. Cardiol.; 93(12):1473-1480; 2004.

Willer, et al.; "METAL: fast and efficient meta-analysis of genomewide association scans"; Bioinformatics; 26(17):2190-2191; 2010.

Williams, et al.; "Prevalence of nonalcoholic fatty liver disease and nonalcoholic steatohepatitis among a largely middle-aged population utilizing ultrasound and liver biopsy: a prospective study"; Gastroenterology; 140(1):124-131; 2011.

Wong, et al.; "Nonalcoholic Steatohepatitis is the Second Lading Etiology of Liver Disease Among Adults Awaiting Liver Transplantation in the United States"; Gastroenterology; 148(3):547-555; 2015.

Yang, et al.; "GCTA: A Tool for Genome-wide Complex Trait Analysis"; Am. J. Hum. Genet.; 88(1):76-82; 2011.

Yang et al.; "A 17-Beta-Hydroxysteroid Dehydrogenase 13 Variant Protects From Hepatocellular Carcinoma Development in Alcoholic Liver Disease"; Heptatology; vol. 70, No. 1; 2019.

Younossi, et al.; "Changes in the Prevalence of the Most Common Causes of Chronic Liver Diseases in the United States From 1988-2008"; Clin. Gastroenterol. Hepatol.; 9:524-530; 2011.

Yuan, et al.; "Population-Based Genome-wide Association Studies Reveal Six Loci Influencing Plasma Levels of Liver Enzymes"; Am. J. Hum. Genet.; 83(4):520-528; 2008.

Zhang, et al.; "PowerBLAST: A New Network BLAST Application for Interactive or Automated Sequence Analysis and Annotation"; Genome Res.; 7(6):649-656; 1997.

Zhang et al.; "High-fat diet enhanced retinal dehydrogenase activity, but suppressed retinol dehydrogenase activity in liver of rats"; Journal of Pharmacological Sciences; vol. 127; Issue 4; pp. 430-438; 2015.

Zhang et al.; "Omic studies reveal the pathogenic lipid droplet proteins in non-alcoholic fatty liver disease"; Protein Cell; 2017; 8(1):4-13.

Written Opinion and International Search Report for corresponding International Application No. PCT/US2018/014357 dated Jun. 4, 2018.

Written Opinion and International Search Report for corresponding International Application No. PCT/US2018/014454 dated May 28, 2018.

Written Opinion and International Search Report for corresponding International Application No. PCT/US2019/023079 dated Jun. 14, 2019.

Written Opinion and International Search Report for corresponding International Application No. PCT/US2019/023333 dated May 13, 2019.

Written Opinion and International Search Report for corresponding International Application No. PCT/US2019/051707 dated Jan. 14, 2020.

Bhinder Bhavneet et al: "An Arrayed Genome-Scale Lentiviral-Enabled Short Hairpin RNA Screen Identifies Lethal and Rescuer Gene Candidates", ASSAY and Drug Development Technologies, vol. 11, No. 3, Apr. 1, 2013 (Apr. 1, 2013), pp. 173-190, XP093063197.

Bhinder Bhavneet et al: "Supplementary Tabel 1—An Arrayed Genome-Scale Lentiviral-Enabled Short Hairpin RNA Screen Identifies Lethal and Rescuer Gene Candidates", ASSAY and Drug Development Technologies, Apr. 1, 2013 (Apr. 1, 2013), pp. 1-380, XP093063199.

Database EMBL [Online] Apr. 18, 2011 (Apr. 18, 2011), "WO 2005116204-A/227426: Double strand polynucleotides generating RNA interference.", XP093063384, retrieved from EBI accession No. EM_PAT:FW820900 Database accession No. FW820900.

Database EMBL [Online] Apr. 18, 2011 (Apr. 18, 2011), "WO 2005116204-A/227425: Double strand polynucleotides generating RNA interference.", XP093063381, retrieved from EBI accession No. EM_PAT:FW820899 Database accession No. FW820899.

Database EMBL [Online] Apr. 18, 2011 (Apr. 18, 2011), "WO 2005116204-A/227418: Double strand polynucleotides generating RNA interference.", XP093063389, retrieved from EBI accession No. EM_PAT:FW820892 Database accession No. FW820892.

Database EMBL [Online] Apr. 18, 2011 (Apr. 18, 2011), "WO 2005116204-A/227417: Double strand polynucleotides generating RNA interference.", XP093063391, retrieved from EBI accession No. EM_PAT:FW820891 Database accession No. FW820891.

Wen Su et al., Comparative proteomic study reveals 17ß-HSD13 as a pathogenic protein in nonalcoholic fatty live disease, 111 PNAS 11437-11442 (2014)).

S.T. Iobst and K. Drickamer, J.B.C., 1996, 271, 6686.

Connolly et al., 1982, J. Biol. Chem, 257, 939-945.

Biessen et al. J. Med. Chem. 1995 vol. 39 p. 1538-1546.

Zhang G et al., "High levels of foreign gene expression in hepatocytes after tail vein injection of naked plasmid DNA." Human Gene Therapy 1999 vol. 10, p. 1735-1737.

F. Czaudema, Nucleic Acids Res., 2003, 31(11), 2705-16.

Kumiko UI-Tei et al., Q & A about RNAi Experiments, Yodosha Co., Ltd., 2006, pp. 52-53 and 88-96.

Kochanek, et al.; "Deaths: Final Data for 2014"; Natl. Viral Stat. Rep.; 65(4):1-122; 2016.

Kozlitina, et al.; "Exome-wide association study identifies a TM6SF2 variant that confers susceptibility to nonalcoholic fatty liver disease"; Nat. Genet.; 46(4): 352-356; 2014.

(56) References Cited

OTHER PUBLICATIONS

Kozlitina, et al.; "HSD17B13 and Chronic Liver Disease in Blacks and Hispanics"; NEJM; vol. 379; Issue 19; pp. 1876-1877; 2018.
Krazeisen, et al.; "Phytoestrogens inhibit human 17ß-hydroxysteroid dehydrogenase type 5"; Molecular and Cellular Endocrinology; vol. 171, Issues 1-2; pp. 151-162; 2001.
Lazo, et al.; "Prevalence of nonalcoholic fatty liver disease in the United States: the Third National Health and Nutrition Examination Survey, 1988-1994"; Am J. Epidemiol; 178(1):38-45; 2013.
Leippe, et al.; "Bioluminescent Nicotinamide Adenine Dinucleotide Detection Assays Part 1: Technology and Features"; 2014; https://;www.promega.com/resources/pubhub/bioluminescent-nicotinamide-adenine-dinucleotide-detection-assays/.
Li, et al.; "Fast and accurate short read alignment with Burrows-Wheeler transform"; Bioinformatics; 25(14):1754-1760; 2009.
Li, et al.; "LTB4 causes macrophage-mediated inflammation and directly induces insulin resistance in obesity"; Nat. Med.; 21(3):239-247; 2015.
Liu, et al.; "Molecular cloning and expression analysis of a new gene for short-chain dehydrogenase/reductase 9"; Acta Biochim. Pol.; 54(1):213-218; 2007.
Liu, et al.; "TM6SF2 rs58542926 influences hepatic fibrosis progression in patients with non-alcoholic fatty liver disease"; Nat. Commun.; 5:4309; pp. 1-6; 2014.
Luukkonen et al.; "Hydroxysteroid 17-ß dehydrogenase 13 variant increases phospholipids and protects against fibrosis in nonalcoholic fatty liver disease"; insight.jci.org; https://doi.org/10.1172/jci.insight.132158; 2020.
Ma et al.; "17-Beta Hydroxysteroid Dehydrogenase 13 is a Hepatic Retinol Dehydrogenase Associated With Histological Features of Nonalcoholic Fatty Liver Disease"; Hepatology; vol. 69, No. 4; pp. 1504-1519; 2019.
Ma et al.; "Characterization of essential domains in HSD17B13 for cellular localization and enzymatic activity"; J. Lipid Res.; 61(11); 1400-1409; 2020.
Mahdessian, et al.; "TM6SF2 is a regulator of liver fat metabolism influencing triglyceride secretion and hepatic lip droplet content"; Proc. Natl Acad Sci U.S.A.; 111(24)8913-8918; 2014.
Maja et al.; "Selection of GalNAc-conjugated siRNAs with limited off-target-driven rt hepatotoxicity"; Nature Communications; 9:723; 2018.
Marchais-Oberwinkler et al.; "17ß-Hydroxysteroid dehydrogenases (17B-HSDs) as therapeutic targets: Protein structures, functions, and recent progress in inhibitor development"; Journal of Steroid Biochemistry & Molecular Biology; 125 (2011) 66-82.
McKenna, et al.; "The Genome Analysis Toolkit: A MapReduce framework for analyzing next-generation DNA sequencing data"; Genome Res.; 20(9):1297-1303; 2010.
Moeller, et al.; "Multifunctionality of human 17ß-hydroxysteroid dehydrogenases"; Mol. Cell. Endocrinol; 248(1-2):47-55; 2006.
Moeller, et al.; "Integrated view on 17beta-hydroxysteroid dehydrogenases"; Molecular and Cellular Endocrinology; vol. 301, Issues 1-2; pp. 7-19; 2009.
Morgan, et al.; "Eradication of Hepatitis C Virus Infection and the Development of Hepatocellular Carcinoma"; Ann. Intern. Med.; 158(5 Pt. 1):329-337 and W-158-W-160; 2013.
NP Cluster Report rs72613567; Retrieved from the internet on Dec. 6, 2021; URL: ncbi.nlm.nig.gov.
Oniki, et al.; "Influence of the PNPLA3 rs738409 Polymorphism on Non-Alcoholic Fatty Liver Disease and Renal Function among Normal Weight Subjects"; PLOS One; DOI: 10.1371/journal.pone.0132640; 2015.
Pirazzi, et al.; "Patatin-like Phospholipase domain-containing 3 (PNPLA3) 1148M (rs738409) affects hepatic VLDL secretion in humans and in vitro"; Journal of Hepatology; vol. 57, Issue 6; pp. 1276-1282; 2012.
Pirola, Carlos et al.; "Splice variant rs72613567 prevents worst histologic outcomes in patients with nonalcoholic fatty liver disease"; Journal of Lipid Research; vol. 60; pp. 176-185; 2019.
Pruim, et al.; "LocusZoom: regional visualization of genome-wide association scan results"; Bioinformatics; 26(18):2336-2337; 2010.
Puri, et al.; "Nonalcoholic Fatty Liver Disease: Definitions, Risk Factors, and Workup"; Clinical Liver Disease; vol. 1, No. 4; 99-103; 2012.
Quadri, et al.; "Mutations in SLC30A10 Cause Parkinsonism and Dystonia with Hypermanganesemia, Polycythemia, and Chronic Liver Disease"; Am J. Hum. Genet .; 90(3): 467-477; 2012.
Ratziu, et al.; "Current efforts and trends in the treatment of NASH"; Journal of Hepatology; vol. 62:S65-75; 2015.
Reid, et al.; "Launching genomics into the cloud: deployment of Mercury, a next generation sequence analysis pipeline"; BMC Bioinformatics; 15:30; 2014.
Rockey et al.; "Liver Biopsy"; Hepatology; 49:1017-1044; 2009.
Romeo, et al.; "Genetic variation in PNPLA3 confers susceptibility to nonalcoholic fatty liver disease"; Nat. Genet.; 40(12):1461-1465; 2008.
Rotman, et al.; "The Association of Genetic Variability in PNPLA3 with Histological Severity of Non-Alcoholic Fatty Liver Disease"; Hepatology; 52(3):894-903; 2010.
Sato, et al.; "Highly specific delivery of siRNA to hepatocytes circumvents endothelial cell-mediated lipid nanoparticle-associated toxicity leading to the safe and efficacious decrease in the hepatitis B virus"; Journal of Controlled Release; vol. 266; pp. 216-225; 2017.
Schiavinato, et al.; "EMILIN-3, peculiar member of elastin microfibril interface-located protein (EMILIN) family, has distinct expression pattern, forms oligomeric assemblies, and serves as transforming growth factor ß (TGF-ß) antagonist"; The Journal of Biological Chemistry, vol. 287, No. 14; pp. 11498-11515; 2012.
Seko et al.; "Attenuated effect of PNPLA3 on hepatic fibrosis by HSD17B13 in Japanese patients with non-alcoholic fatty liver disease"; Liver International; 40:1686-1692; 2020.
Sharp, Phillip A.; "RNA interference—2001"; Genes & Development; 15:485-490; 2001.
Shen, et al.; "The rs738409 (I148M) variant of the PNPLA3 gene and cirrhosis: a meta-analysis"; J. Lipid Res.; 56(1):167-175; 2015.
Sivan et al.; "Identification of Restriction Factors by Human Genome-Wide RNA Interference Screening of Viral Host Range Mutants Exemplified by Discovery of SAMD9 and WDR6 as Inhibitors of the Vaccinia Virus K1L-C7L-Mutant"; mbio.asm.org; Jul./Aug. 2015; vol. 6, Issue 4; e01122-15; pp. 1-9.
Sivan et al.; Supplemental Material: Tables S1.1, Table S1.2, Table S1.3, Table S2 to "Identification of Restriction Factors by Human Genome-Wide RNA Interference Screening of Viral Host Range Mutants Exemplified by Discovery of SAMD9 and WDR6 as Inhibitors of the Vaccinia Virus K1L-C7L-Mutant"; mbio.asm.org; Jul./Aug. 2015; vol. 6, Issue 4; e01122-15; pp. 1-9.
Smagris, et al.; "Inactivation of Tm6sf2, a Gene Defective in Fatty Liver Disease, Impairs Lipidation but Not Secretion of Very Low Density Lipoproteins"; J. Biol. Chem.; vol. 291, No. 20; pp. 10659-10676; 2016.
Smith, et al.; "Comparison of Biosequences"; Advances in Applied Mathematics; 2:482-489; 1981.
Sookoian, et al.; "A nonsynonymous gene variant in the adiponutrin gene is associated with nonalcoholic fatty liver disease severity"; Journal of Lipid Research; 50(10):2111-2116; 2009.
Sookoian, et al.; "Genetic Variation in Transmembrane 6 Superfamily Member 2 and the Risk of Nonalcoholic Fatty Liver Disease and Histological Disease Severity"; Hepatology; 61(2):515-525; 2015.
Sookoian et al.; "Genetics meets Therapy? Exome-wide Association Study Reveals a Loss-of-Function Variant in 17-Beta-Hydroxysteroid Dehydrogenase 13 That Protects Patients From Liver Damage and Nonalcoholic Fatty Liver Disease Progression"; Hepatology; vol. 69, No. 2; pp. 907-910; 2019.
Speliotes, et al.; "Genome-Wide Association Analysis Identifies Variants Associated with Nonalcoholic Fatty Liver Disease That Have Distinct Effects on Metabolic Traits"; PLoS Genet.; 7(3):e1001324; 2011.
Staines, Richard; "Forendo works with Novartis in liver disease, possibly targeting NASH"; Web page https://pharmaphorum.com/news/forendo-works-with-novartis-in-liver-disease-tie-up/; retrieved on Nov. 4, 2021.

(56) References Cited

OTHER PUBLICATIONS

Su, Wen et al.; "Comparative proteomic study reveals 17ß-HSD13 as a pathogenic protein in nonalcoholic fatty liver disease"; Proceedings of the National Academy of Sciences; vol. 111, No. 31; 4:11437-11442; Aug. 5, 2014.

Su, Wen et al.; Liver-Specific Overexpression of 17ß-HSD13 Causes Hepatic Steatosis In Mice; Diabetes 67 (Supplement 1); 2018.

Su, Wen et al. "Role of HSD17B13 in liver physiology and pathophysiology"; Molecular and Cellular Endocrinology; 489 (2019) 119-125.

Sun et al.; "The HSD17B13 rs72613567 variant is associated with lower levels of albuminuria in patients with biopsy-proven nonalcoholic fatty liver disease"; Nutrition, Metabolism and Cardiovascular Diseases; Elsevier, vol. 31; Issue 6; pp. 1822-1831; DOI: 10.1016/j.numecd.2021.02.018; PMID: 33853719; Jun. 7, 2021.

About, Fredegonde et al.; "HCV-Associated Liver Fibrosis and HSD17B13"; The New England Journal of Medicine; 379:19; pp. 1875-1876; 2018.

Abul-Husn et al.; "A Protein-Truncating HSD17B13 Variant and Protection from Chronic Liver Diseases"; NEJM; 1096-1106; 2018.

Abul-Husn et al.; Supplementary Appendix to: "A Protein-Truncating HSD17B13 Variant and Protection from Chronic Liver Diseases"; NEJM; 1096-1106; 2018. (pp. 1-73).

Adam, Marion et al.; "Hydroxysteroid (17ß) dehydrogenase 13 deficiency triggers hepatic steatosis and inflammation in mice" The FASEB Journal; 32, 3434-3447 (2018).

Adam et al.; "Severity of Nonalcoholic Fatty Liver Disease in Type 2 Diabetes Mellitus: Relationship between Nongenetic Factors and PNPLA3/HSD17B13 Polymorphisms"; Diabetes Metab Journal; 43:700-710; 2019.

Alnylam Pharmaceuticals Press Release; "Regeneron and Alnylam Pharmaceuticals Announce Collaboration to Discover New Treatments for Nonalcoholic Steatohepatitis (NASH)"; Website https://investors.alnylam.com/press-release?id=22511 downloaded on Nov. 4, 2021.

Altschul, et al., "Basic Local Alignment Search Tool," J. Mol. Biol., 215(3):403-410, (1990).

Altschul, et al.; "Gapped BLAST and PSI-BLAST: a new generation of protein database search programs,"; Nucleic Acids Res.; 25(17):3389-3402, (1997).

Anstee et al.; "Genome-wide association study of non-alcoholic fatty liver and steatohepatitis in a histologically characterized cohort"; Journal of Hepatology; 73:505-515; 2020.

Baranova et al.; "Systematic review: the epidemiology and natural history of non-alcoholic fatty liver disease and non-alcoholic steatohepatitis in adults"; Alimentary Pharmacology & Therapeutics, 2011;34:274-285.

Baselli et al.; "Beyond fat accumulation, NAFLD genetics converges on lipid droplet biology"; Journal of Lipid Research; vol. 60; Issue 1; pp. 7-8; 2019.

Bellan, Mattia et al.; "Severity of Nonalcoholic Fatty Liver Disease in Type 2 Diabetes Mellitus: Relationship between Nongenetic Factors and PNPLA3/HSD17B13 Polymorphisms"; Diabetes & Metabolism Journal; 43:700-710; 2019.

Benedittis et al.; "Interplay of PNPLA3 and HSD17B13 Variants in Modulating the Risk of Hepatocellular Carcinoma among Hepatitis C Patients"; Gastroenterology Research and Practice; vol. 2020, Article ID 4216451; 8 pages; https://doi.org/10.1155/2020/4216451; 2020.

Brantly, et al.; "Molecular basis of alpha-1-antitrypsin deficiency"; Am. J. Med.; 84(6A):13-31, (1988).

Brasaemle, et al., "Isolation of Lipid Droplets from Cells by Density Gradient Centrifugation," Curr. Protoc. Cell Biol., 3.15.1-3.15.12, (2005).

Browning, et al., "Prevalence of Hepatic Steatosis in an Urban Population in the United States: Impact of Ethnicity," Hepatology, 40(6):1387-1395, (2004).

Business Wire, "Arrowhead Pharmaceuticals Initiates Phase 1/2 Study of ARO-HSD in Normal Healthy Volunteers and Patients with NASH of Suspected NASH", Mar. 3, 2020, pp. 1-2. businesswire.com/news/home/2020030300 5396/en/Arrowhead-Pharmaceuticals-Initiates-Phase-12-Study-ARO-HSD.

Chambers, et al.; "Genome-wide association study identifies loci influencing concentrations of liver enzymes in plasma"; Nature Genetics, 43(11), 1131-1138 plus Online Methods and Supplementary Materials (Nov. 2011).

Cohen, et al.; "Human Fatty Liver Disease: Old Questions and New Insights"; Science, 332(6037):1519-1523, (2011).

Denny, et al., "PheWAS: demonstrating the feasibility of a phenome-wide scan to discover gene-disease associations"; Bioinformatics; 26(9):1205-1210, (2010).

Denny, et al.; "Systematic comparison of phenome-wide association study of electronic medical record data and genome-wide association study data"; Nat. Biotechnol.; 31(12):1102-1110, (2013).

Dewey, et al.; "Distribution and clinical impact of functional variants in 50,726 whole-exome sequences from the DiscovEHR Study"; Science; 354(6319): aaf6814, (2016).

Ding, et al.; "Isolating lipid droplets from multiple species"; Nat. Protoc.; 8(1):43-51, (2013).

Dong, X. Charlie; "A closer look at the mysterious HSD17B131"; J. Lipid Res.; 61(11); 1361-1362; 2020.

Edelman, et al.; "Genetic analysis of nonalcoholic fatty liver disease within a Caribbean-Hispanic population"; Molecular Genetics & Genomic Medicine; 3(6): 558-569; 2015.

Ekstedt et al.; "Natural History of NAFLD/NASH"; Curr Hepatology Rep; 16:391-397; 2017.

Feitosa, et al.; "The ERLIN1-CHUK-SWF19L1 gene cluster influences liver fat deposition and hepatic inflammation in the NHLBI Family Heart Study"; Atherosclerosis; 228(1): 175-180; 2013.

Fire et al.; "Potent and specific genetic interference by double-stranded RNA in Caenorhabditis elegans"; Nature; vol. 391:806-811; 1998.

Ford, et al.; "A new assay for picomole levels of androsterone and testosterone using co-immobilized luciferase, oxidoreductase, and steroid dehydrogenase" Analytical Biochemistry; vol. 110, Issue 1; pp. 43-48; 1981.

Friedman, et al.; "Mechanisms of NAFLD development and therapeutic strategies"; Nature Medicine; vol. 24; pp. 908-922; 2018.

Gellert-Kristensen et al.; "High Risk of Fatty Liver Disease Amplifies the Alanine Transaminase-Lowering Effect of a HSD17B13 Variant"; Hepatology; vol. 71; Issue 1; pp. 56-66; DOI: 10.1002/hep.30799; 2020.

Gellert-Kristensen et al.; "Combined Effect of PNPLA3, TM6SF2, and HSD17B13 Variants on Risk of Cirrhosis and Hepatocellular Carcinoma in the General Population"; vol. 72; Issue 3; pp. 845-856; DOI: 10.1002/hep.31238; PMID: 32190914; 2020.

GenBank Accession No. DR004209; "TC104687 Human liver, large insert, pCMV expression library Homo sapiens CDNA clone TC104687 5' similar to Homo sapiens similar to hydroxysteroid (17-beta) dehydrogenase 11; hydroxysteroid 17-beta dehydrogenase 11 (LOC205983), mRNA sequence"; 2011.

GenBank Accession No. NM001136230; "Homo sapiens hydroxysteroid 17-beta dehydrogenase 13 (HSD17B13), transcript variant B, mRNA"; 2021.

GenBank Accession No. NM178135; Homo sapiens hydroxysteroid 17-beta dehydrogenase 13 (HSD17B13), transcript variant A, mRNA; 2021.

GenBank Accession No. NP001129702; 17-beta hydroxysteroid dehydrogenase 13 isoform B [Homo sapiens]; 2021.

GenBank Accession No. NP835236; 17-beta-hydroxysteroid dehydrogenase 13 isoform A precursor [Homo sapiens]; 2021.

Ghanbari et al.; "Genetic Variations in MicroRNA-Binding Sites Affect MicroRNA-Mediated Regulation of Several Genes Associated with Cardio-metabolic Phenotypes"; Genomic and Precision Medicine; vol. 8; Issue 3; pp. 473-486; DOI: 10.1161/CIRCGENETICS.114.000968; PMID: 25814643; 2015.

Gieger, et al.; "New gene functions in megakaryopoiesis and platelet formation"; Nature; 480(7376): 201-208; plus Supplementary Information; Apr. 24, 2012.

Horiguchi et al; 17ß-Hydroxysteroid dehydrogenase type 13 is a liver-specific lipid droplet-associated protein; Biochemical and Biophysical Research Communications; 370 (2008) 235-238.

(56) References Cited

OTHER PUBLICATIONS

Hotta, et al.; "Association of the rs738409 polymorphism in PNPLA3 with liver damage and the development of nonalcoholic fatty liver disease" BMC Medical Genetics; 11:172; 2010.

Huang, et al.; "Expression and Characterization of a PNPLA3 Protein Isoform (1148M) Associated with Nonalcoholic Fatty Liver Disease"; The Journal of Biological Chemistry; vol. 286, No. 43; pp. 37085-37093; 2011.

Hudert et al.; "Variants in MARC1 and HSD17B13 reduce severity of NAFLD in children, perturb phospholipid metabolism, and suppress fibrotic pathways" https://doi.org/10.1101/2020.06.05.20120956; this version posted Jun. 7, 2020.

Hugh, Thomas; "An HSD17B13 variant reduces cirrhosis risk"; Nature Reviews Gastroenterology and Hepatology; vol. 15; Issue 6; pp. 328-328; 2018.

Janas et al.; "Selection of GalNAc-conjugated siRNAs with limited off-target-driven rat hepatotoxicity"; Nature Comm. 2018; 9:723.

Kahali, et al.; "Insights from Genome-Wide Association Analyses of Nonalcoholic Fatty Liver Disease"; Semin Liver Disease; 35(4); 375-391; 2015.

Kallwitz et al.; "Association of HSD17B13 rs72613567:TA with non-alcoholic fatty liver disease in Hispanics/Latinos"; Liver International; 40:889-893; 2020.

Kampf et al.; "The human liver-specific proteome defined by transcriptomics and antibody-based profiling"; The FASEB Journal; 28, 2901-2914 (2014).

Kitamoto, et al.; "Genome-wide scan revealed that polymorphisms in the PNPLA3, SAMM50, and PARVB genes are associated with development and progression of nonalcoholic fatty liver disease in Japan"; Human Genetics; 132, 783-792; (2013).

Kleiner, et al.; "Design and Validation of a Histological Scoring System for Nonalcoholic Fatty Liver Disease"; Hepatology; 41(6): 1313-1321; 2005.

"Regeneron and Alnylam Pharmaceuticals Announce Collaboration to Discover New Treatments for Nonalcoholic Steatophepatitis (NASH)" Mar. 21, 2018, PRNewswire; https://investor.regeneron.com/NODE/12946/PDF.

* cited by examiner

SEQUENCE LISTING

```
<160> NUMBER OF SEQ ID NOS: 309

<210> SEQ ID NO 1
<211> LENGTH: 2397
<212> TYPE: DNA
<213> ORGANISM: Homo Sapiens
<220> FEATURE:
<223> OTHER INFORMATION: Artificial Sequence hydroxysteroid 17-beta
      dehydrogenase 13 (HSD17B13), transcript variant A, NM_178135.4

<400> SEQUENCE: 1

agacagtacc tcctccctag gactacacaa ggactgaacc agaaggaaga ggacagagca     60

aagccatgaa catcatccta gaaatccttc tgcttctgat caccatcatc tactcctact    120

tggagtcgtt ggtgaagttt ttcattcctc agaggagaaa atctgtggct ggggagattg    180

ttctcattac tggagctggg catggaatag gcaggcagac tacttatgaa tttgcaaaac    240

gacagagcat attggttctg tgggatatta ataagcgcgg tgtggaggaa actgcagctg    300

agtgccgaaa actaggcgtc actgcgcatg cgtatgtggt agactgcagc aacagagaag    360

agatctatcg ctctctaaat caggtgaaga aagaagtggg tgatgtaaca atcgtggtga    420

ataatgctgg gacagtatat ccagccgatc ttctcagcac caaggatgaa gagattacca    480

agacatttga ggtcaacatc ctaggacatt tttggatcac aaaagcactt cttccatcga    540

tgatggagag aaatcatggc cacatcgtca cagtggcttc agtgtgcggc cacgaaggga    600

ttccttacct catcccatat tgttccagca aatttgccgc tgttggcttt cacagaggtc    660

tgacatcaga acttcaggcc ttgggaaaaa ctggtatcaa aacctcatgt ctctgcccag    720

tttttgtgaa tactgggttc accaaaaatc caagcacaag attatggcct gtattggaga    780

cagatgaagt cgtaagaagt ctgatagatg gaatacttac caataagaaa atgatttttg    840

ttccatcgta tatcaatatc tttctgagac tacagaagtt tcttcctgaa cgcgcctcag    900

cgattttaaa tcgtatgcag aatattcaat ttgaagcagt ggttggccac aaaatcaaaa    960

tgaaatgaat aaataagctc cagccagaga tgtatgcatg ataatgatat gaatagtttc   1020
```

```
gaatcaatgc tgcaaagctt tatttcacat tttttcagtc ctgataatat taaaaacatt   1080

ggtttggcac tagcagcagt caaacgaaca agattaatta cctgtcttcc tgtttctcaa   1140

gaatatttac gtagtttttc ataggtctgt ttttcctttc atgcctctta aaaacttctg   1200

tgcttacata aacatactta aaaggttttc tttaagatat tttatttttc catttaaagg   1260

tggacaaaag ctacctccct aaaagtaaat acaaagagaa cttatttaca cagggaaggt   1320

ttaagactgt tcaagtagca ttccaatctg tagccatgcc acagaatatc aacaagaaca   1380

cagaatgagt gcacagctaa gagatcaagt ttcagcaggc agctttatct caacctggac   1440

atattttaag attcagcatt tgaaagattt ccctagcctc ttccttttc attagcccaa    1500

aacggtgcaa ctctattctg gactttatta cttgattctg tcttctgtat aactctgaag   1560

tccaccaaaa gtggaccctc tatatttcct cccttttat agtcttataa gatacattat    1620

gaaaggtgac cgactctatt ttaaatctca gaattttaag ttctagcccc atgataacct   1680

ttttctttgt aatttatgct ttcatatatc cttggtccca gagatgttta gacaatttta   1740

ggctcaaaaa ttaaagctaa cacaggaaaa ggaactgtac tggctattac ataagaaaca   1800

atggacccaa gagaagaaaa ggaagaaaga aaggtttttt ggtttttgtt ttgttttgtt   1860

ttgtttttg tttttttgag atggagtctc actctttcgc ccaggctgga gtgcagtggt    1920

atgatctcag ctcactgcaa gctccacctc ccgggttcac gccattctcc tgcctcagcc   1980

tcctgagtag ctgggactac aggcgcccgc caccacaccc ggctaatttt ttgtattttt   2040

tgtagagacg gggtttcacc atgttagcca agatggtctc gatctcctga cctcgtgatc   2100

cacctgcctc ggcctcccaa agtgctggga ttacgggtgt gagccaccgt gcccagcctt   2160

ttttttttta atagaaaaaa taatccgact cccactacat caagactaat cttgttttgt   2220

gtgtttttca catgtattat agaatgcttt tgcatggact atcctcttgt ttttattaaa   2280

aacaaatgat ttttttaaaa gtcacaaaaa caattcacta aaaataaata tgtcattgtg   2340

ctttaaaaaa ataacctctt gtagttataa aataaaacgt ttgacttcta aactctg      2397
```

<210> SEQ ID NO 2
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 2
ucaucuauca gacuucuuac g 21

<210> SEQ ID NO 3
<211> LENGTH: 21
<212> TYPE: RNA
<213> ORGANISM: Artificial Sequence
<220> FEATURE:
<223> OTHER INFORMATION: RNAi agent antisense strand underlying base sequence

<400> SEQUENCE: 3
ucaucuauca gacuucuuac g 21

<210> SEQ ID NO 4
<211> LENGTH: 21
<212> TYPE: RNA
<213> ORGANISM: Artificial Sequence
<220> FEATURE:
<223> OTHER INFORMATION: RNAi agent antisense strand modified sequence

```
<400> SEQUENCE: 4

ucaucuauca gacuucuuac g                                              21


<210> SEQ ID NO 5
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 5

ugauccaaaa auguccuagg c                                              21


<210> SEQ ID NO 6
<211> LENGTH: 21
<212> TYPE: RNA
<213> ORGANISM: Artificial Sequence
<220> FEATURE:
<223> OTHER INFORMATION: RNAi agent antisense strand underlying base
      sequence

<400> SEQUENCE: 6

ugauccaaaa auguccuagg c                                              21


<210> SEQ ID NO 7
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 7

ugauccaaaa auguccuagg c                                              21


<210> SEQ ID NO 8
<211> LENGTH: 21
<212> TYPE: RNA
<213> ORGANISM: Artificial Sequence
<220> FEATURE:
<223> OTHER INFORMATION: RNAi agent sense strand underlying base
      sequence

<400> SEQUENCE: 8

cguaagaagu cugauagaug a                                              21


<210> SEQ ID NO 9
<211> LENGTH: 21
<212> TYPE: RNA
<213> ORGANISM: Artificial Sequence
<220> FEATURE:
<223> OTHER INFORMATION: RNAi agent sense strand modified sequence

<400> SEQUENCE: 9

cguaagaagu cugauagaug a                                              21


<210> SEQ ID NO 10
<211> LENGTH: 21
<212> TYPE: RNA
<213> ORGANISM: Artificial Sequence
<220> FEATURE:
<223> OTHER INFORMATION: RNAi agent sense strand modified sequence

<400> SEQUENCE: 10

cguaagaagu cugauagaug a                                              21
```

<210> SEQ ID NO 11
<211> LENGTH: 21
<212> TYPE: RNA
<213> ORGANISM: Artificial Sequence
<220> FEATURE:
<223> OTHER INFORMATION: RNAi agent sense strand underlying base sequence
<220> FEATURE:
<221> NAME/KEY: modified_base
<222> LOCATION: 17
<223> OTHER INFORMATION: n = insosine (hypoxanthine)

<400> SEQUENCE: 11
gccuaggaca uuuuugnauc a 21

<210> SEQ ID NO 12
<211> LENGTH: 21
<212> TYPE: RNA
<213> ORGANISM: Artificial Sequence
<220> FEATURE:
<223> OTHER INFORMATION: RNAi agent sense strand modified sequence
<220> FEATURE:
<221> NAME/KEY: modified_base
<222> LOCATION: 17
<223> OTHER INFORMATION: n = 2'-O-methylinosine-3'-phosphate

<400> SEQUENCE: 12
gccuaggaca uuuuugnauc a 21

<210> SEQ ID NO 13
<211> LENGTH: 21
<212> TYPE: RNA
<213> ORGANISM: Artificial Sequence
<220> FEATURE:
<223> OTHER INFORMATION: RNAi agent sense strand modified sequence
<220> FEATURE:
<221> NAME/KEY: modified_base
<222> LOCATION: 17
<223> OTHER INFORMATION: n = 2'-O-methylinosine-3'-phosphate

<400> SEQUENCE: 13
gccuaggaca uuuuugnauc a 21

<210> SEQ ID NO 14
<211> LENGTH: 21
<212> TYPE: RNA
<213> ORGANISM: Artificial Sequence
<220> FEATURE:
<223> OTHER INFORMATION: RNAi agent sense strand underlying base sequence

<400> SEQUENCE: 14
cguaagaagu cugauagaug a 21

<210> SEQ ID NO 15
<211> LENGTH: 21
<212> TYPE: RNA
<213> ORGANISM: Artificial Sequence
<220> FEATURE:
<223> OTHER INFORMATION: RNAi agent sense strand modified sequence

<400> SEQUENCE: 15
cguaagaagu cugauagaug a 21

<210> SEQ ID NO 16
<211> LENGTH: 21
<212> TYPE: RNA
<213> ORGANISM: Artificial Sequence
<220> FEATURE:

<223> OTHER INFORMATION: RNAi agent sense strand modified sequence
<220> FEATURE:
<221> NAME/KEY: modified_base
<222> LOCATION: 17
<223> OTHER INFORMATION: n = 2'-O-methylinosine-3'-phosphate

<400> SEQUENCE: 16
gccuaggaca uuuuugnauc a 21

<210> SEQ ID NO 17
<211> LENGTH: 21
<212> TYPE: RNA
<213> ORGANISM: Artificial Sequence
<220> FEATURE:
<223> OTHER INFORMATION: RNAi agent sense strand modified sequence
<220> FEATURE:
<221> NAME/KEY: modified_base
<222> LOCATION: 17
<223> OTHER INFORMATION: n = 2'-O-methylinosine-3'-phosphate

<400> SEQUENCE: 17
gccuaggaca uuuuugnauc a 21

<210> SEQ ID NO 18
<211> LENGTH: 19
<212> TYPE: RNA
<213> ORGANISM: Artificial Sequence
<220> FEATURE:
<223> OTHER INFORMATION: HSD17B13 mRNA (gene transcript) target sequence

<400> SEQUENCE: 18
uaagaagucu gauagaugg 19

<210> SEQ ID NO 19
<211> LENGTH: 19
<212> TYPE: RNA
<213> ORGANISM: Artificial Sequence
<220> FEATURE:
<223> OTHER INFORMATION: HSD17B13 mRNA (gene transcript) target sequence

<400> SEQUENCE: 19
gaucacaaaa gcacuucuu 19

<210> SEQ ID NO 20
<211> LENGTH: 19
<212> TYPE: RNA
<213> ORGANISM: Artificial Sequence
<220> FEATURE:
<223> OTHER INFORMATION: HSD17B13 mRNA (gene transcript) target sequence

<400> SEQUENCE: 20
cuaggacauu uuuggauca 19

<210> SEQ ID NO 21
<211> LENGTH: 19
<212> TYPE: RNA
<213> ORGANISM: Artificial Sequence
<220> FEATURE:
<223> OTHER INFORMATION: HSD17B13 mRNA (gene transcript) target sequence

<400> SEQUENCE: 21
aggucaacau ccuaggaca 19

<210> SEQ ID NO 22
<211> LENGTH: 19
<212> TYPE: RNA
<213> ORGANISM: Artificial Sequence

```
<220> FEATURE:
<223> OTHER INFORMATION: HSD17B13 mRNA (gene transcript) target sequence

<400> SEQUENCE: 22

cggugcaacu cuauucugg                                                19


<210> SEQ ID NO 23
<211> LENGTH: 19
<212> TYPE: RNA
<213> ORGANISM: Artificial Sequence
<220> FEATURE:
<223> OTHER INFORMATION: HSD17B13 mRNA (gene transcript) target sequence

<400> SEQUENCE: 23

caacauccua ggacauuuu                                                19


<210> SEQ ID NO 24
<211> LENGTH: 19
<212> TYPE: RNA
<213> ORGANISM: Artificial Sequence
<220> FEATURE:
<223> OTHER INFORMATION: HSD17B13 mRNA (gene transcript) target sequence

<400> SEQUENCE: 24

auuauggccu guauuggag                                                19


<210> SEQ ID NO 25
<211> LENGTH: 19
<212> TYPE: RNA
<213> ORGANISM: Artificial Sequence
<220> FEATURE:
<223> OTHER INFORMATION: RNAi agent antisense strand core 19-mer base
      sequence

<400> SEQUENCE: 25

ccaucuauca gacuucuua                                                19


<210> SEQ ID NO 26
<211> LENGTH: 19
<212> TYPE: RNA
<213> ORGANISM: Artificial Sequence
<220> FEATURE:
<223> OTHER INFORMATION: RNAi agent antisense strand core 19-mer base
      sequence

<400> SEQUENCE: 26

ucaucuauca gacuucuua                                                19


<210> SEQ ID NO 27
<211> LENGTH: 19
<212> TYPE: RNA
<213> ORGANISM: Artificial Sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 27

ncaucuauca gacuucuua                                                19


<210> SEQ ID NO 28
<211> LENGTH: 19
<212> TYPE: RNA
<213> ORGANISM: Artificial Sequence
```

<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 28
ncaucuauca gacuucuun 19

<210> SEQ ID NO 29
<211> LENGTH: 19
<212> TYPE: RNA
<213> ORGANISM: Artificial Sequence
<220> FEATURE:
<223> OTHER INFORMATION: RNAi agent antisense strand core 19-mer base
      sequence

<400> SEQUENCE: 29
ccaucuauca gacuucuua 19

<210> SEQ ID NO 30
<211> LENGTH: 19
<212> TYPE: RNA
<213> ORGANISM: Artificial Sequence
<220> FEATURE:
<223> OTHER INFORMATION: RNAi agent antisense strand core 19-mer base
      sequence

<400> SEQUENCE: 30
ucaucuauca gacuucuua 19

<210> SEQ ID NO 31
<211> LENGTH: 19
<212> TYPE: RNA
<213> ORGANISM: Artificial Sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 31
ncaucuauca gacuucuua 19

<210> SEQ ID NO 32
<211> LENGTH: 19
<212> TYPE: RNA
<213> ORGANISM: Artificial Sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 32
ncaucuauca gacuucuun 19

<210> SEQ ID NO 33
<211> LENGTH: 19
<212> TYPE: RNA
<213> ORGANISM: Artificial Sequence
<220> FEATURE:
<223> OTHER INFORMATION: RNAi agent antisense strand core 19-mer base sequence

<400> SEQUENCE: 33
ccaucuauca gacuucuua 19

<210> SEQ ID NO 34
<211> LENGTH: 19
<212> TYPE: RNA
<213> ORGANISM: Artificial Sequence
<220> FEATURE:
<223> OTHER INFORMATION: RNAi agent antisense strand core 19-mer base
sequence

<400> SEQUENCE: 34
ucaucuauca gacuucuua 19

<210> SEQ ID NO 35
<211> LENGTH: 19
<212> TYPE: RNA
<213> ORGANISM: Artificial Sequence
<220> FEATURE:
<223> OTHER INFORMATION: RNAi agent antisense strand core 19-mer base
sequence
<220> FEATURE:
<221> NAME/KEY: modified_base
<222> LOCATION: 1
<223> OTHER INFORMATION: n = any nucleobase

<400> SEQUENCE: 35
ncaucuauca gacuucuua 19

<210> SEQ ID NO 36
<211> LENGTH: 19
<212> TYPE: RNA
<213> ORGANISM: Artificial Sequence
<220> FEATURE:
<223> OTHER INFORMATION: RNAi agent antisense strand core 19-mer base
sequence
<220> FEATURE:
<221> NAME/KEY: modified_base
<222> LOCATION: 1, 19
<223> OTHER INFORMATION: n = any nucleobase

<400> SEQUENCE: 36
ncaucuauca gacuucuun 19

<210> SEQ ID NO 37
<211> LENGTH: 19
<212> TYPE: RNA
<213> ORGANISM: Artificial Sequence
<220> FEATURE:
<223> OTHER INFORMATION: RNAi agent antisense strand core 19-mer base
sequence

<400> SEQUENCE: 37
aagaagugcu uuugugauc 19

<210> SEQ ID NO 38
<211> LENGTH: 19
<212> TYPE: RNA
<213> ORGANISM: Artificial Sequence
<220> FEATURE:
<223> OTHER INFORMATION: RNAi agent antisense strand core 19-mer base
sequence

<400> SEQUENCE: 38
uagaagugcu uuugugauc 19

-continued

<210> SEQ ID NO 39
<211> LENGTH: 19
<212> TYPE: RNA
<213> ORGANISM: Artificial Sequence
<220> FEATURE:
<223> OTHER INFORMATION: RNAi agent antisense strand core 19-mer base
sequence
<220> FEATURE:
<221> NAME/KEY: modified_base
<222> LOCATION: 1
<223> OTHER INFORMATION: n = any nucleobase

<400> SEQUENCE: 39
nagaagugcu uuugugauc 19

<210> SEQ ID NO 40
<211> LENGTH: 19
<212> TYPE: RNA
<213> ORGANISM: Artificial Sequence
<220> FEATURE:
<223> OTHER INFORMATION: RNAi agent antisense strand core 19-mer base
sequence
<220> FEATURE:
<221> NAME/KEY: modified_base
<222> LOCATION: 1, 19
<223> OTHER INFORMATION: n = any nucleobase

<400> SEQUENCE: 40
nagaagugcu uuugugaun 19

<210> SEQ ID NO 41
<211> LENGTH: 19
<212> TYPE: RNA
<213> ORGANISM: Artificial Sequence
<220> FEATURE:
<223> OTHER INFORMATION: RNAi agent antisense strand core 19-mer base
sequence

<400> SEQUENCE: 41
ugauccaaaa auguccuag 19

<210> SEQ ID NO 42
<211> LENGTH: 19
<212> TYPE: RNA
<213> ORGANISM: Artificial Sequence
<220> FEATURE:
<223> OTHER INFORMATION: RNAi agent antisense strand core 19-mer base
sequence

<400> SEQUENCE: 42
agauccaaaa auguccuag 19

<210> SEQ ID NO 43
<211> LENGTH: 19
<212> TYPE: RNA
<213> ORGANISM: Artificial Sequence
<220> FEATURE:
<223> OTHER INFORMATION: RNAi agent antisense strand core 19-mer base
sequence
<220> FEATURE:
<221> NAME/KEY: modified_base
<222> LOCATION: 1
<223> OTHER INFORMATION: n = any nucleobase

<400> SEQUENCE: 43
ngauccaaaa auguccuag 19

<210> SEQ ID NO 44

<211> LENGTH: 19
<212> TYPE: RNA
<213> ORGANISM: Artificial Sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 44
ngauccaaaa auguccuan 19

<210> SEQ ID NO 45
<211> LENGTH: 19
<212> TYPE: RNA
<213> ORGANISM: Artificial Sequence
<220> FEATURE:
<223> OTHER INFORMATION: RNAi agent antisense strand core 19-mer base
      sequence

<400> SEQUENCE: 45
ugauccaaaa auguccuag 19

<210> SEQ ID NO 46
<211> LENGTH: 19
<212> TYPE: RNA
<213> ORGANISM: Artificial Sequence
<220> FEATURE:
<223> OTHER INFORMATION: RNAi agent antisense strand core 19-mer base
      sequence

<400> SEQUENCE: 46
agauccaaaa auguccuag 19

<210> SEQ ID NO 47
<211> LENGTH: 19
<212> TYPE: RNA
<213> ORGANISM: Artificial Sequence
<220> FEATURE:
<223> OTHER INFORMATION: RNAi agent antisense strand core 19-mer base
      sequence
<220> FEATURE:
<221> NAME/KEY: modified_base
<222> LOCATION: 1
<223> OTHER INFORMATION: n = any nucleobase

<400> SEQUENCE: 47
ngauccaaaa auguccuag 19

<210> SEQ ID NO 48
<211> LENGTH: 19
<212> TYPE: RNA
<213> ORGANISM: Artificial Sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 48
ngauccaaaa auguccuan 19

<210> SEQ ID NO 49
<211> LENGTH: 19
<212> TYPE: RNA

<213> ORGANISM: Artificial Sequence
<220> FEATURE:
<223> OTHER INFORMATION: RNAi agent antisense strand core 19-mer base
sequence

<400> SEQUENCE: 49
uguccuagga uguugaccu 19

<210> SEQ ID NO 50
<211> LENGTH: 19
<212> TYPE: RNA
<213> ORGANISM: Artificial Sequence
<220> FEATURE:
<223> OTHER INFORMATION: RNAi agent antisense strand core 19-mer base
sequence

<400> SEQUENCE: 50
aguccuagga uguugaccu 19

<210> SEQ ID NO 51
<211> LENGTH: 19
<212> TYPE: RNA
<213> ORGANISM: Artificial Sequence
<220> FEATURE:
<223> OTHER INFORMATION: RNAi agent antisense strand core 19-mer base
sequence
<220> FEATURE:
<221> NAME/KEY: modified_base
<222> LOCATION: 1
<223> OTHER INFORMATION: n = any nucleobase

<400> SEQUENCE: 51
nguccuagga uguugaccu 19

<210> SEQ ID NO 52
<211> LENGTH: 19
<212> TYPE: RNA
<213> ORGANISM: Artificial Sequence
<220> FEATURE:
<223> OTHER INFORMATION: RNAi agent antisense strand core 19-mer base
sequence
<220> FEATURE:
<221> NAME/KEY: modified_base
<222> LOCATION: 1, 19
<223> OTHER INFORMATION: n = any nucleobase

<400> SEQUENCE: 52
nguccuagga uguugaccn 19

<210> SEQ ID NO 53
<211> LENGTH: 19
<212> TYPE: RNA
<213> ORGANISM: Artificial Sequence
<220> FEATURE:
<223> OTHER INFORMATION: RNAi agent antisense strand core 19-mer base
sequence

<400> SEQUENCE: 53
ccagaauaga guugcaccg 19

<210> SEQ ID NO 54
<211> LENGTH: 19
<212> TYPE: RNA
<213> ORGANISM: Artificial Sequence
<220> FEATURE:
<223> OTHER INFORMATION: RNAi agent antisense strand core 19-mer base
sequence

<400> SEQUENCE: 54
ucagaauaga guugcaccg 19

<210> SEQ ID NO 55
<211> LENGTH: 19
<212> TYPE: RNA
<213> ORGANISM: Artificial Sequence
<220> FEATURE:
<223> OTHER INFORMATION: RNAi agent antisense strand core 19-mer base sequence

<400> SEQUENCE: 55
acagaauaga guugcaccg 19

<210> SEQ ID NO 56
<211> LENGTH: 19
<212> TYPE: RNA
<213> ORGANISM: Artificial Sequence
<220> FEATURE:
<223> OTHER INFORMATION: RNAi agent antisense strand core 19-mer base sequence
<220> FEATURE:
<221> NAME/KEY: modified_base
<222> LOCATION: 1
<223> OTHER INFORMATION: n = any nucleobase

<400> SEQUENCE: 56
ncagaauaga guugcaccg 19

<210> SEQ ID NO 57
<211> LENGTH: 19
<212> TYPE: RNA
<213> ORGANISM: Artificial Sequence
<220> FEATURE:
<223> OTHER INFORMATION: RNAi agent antisense strand core 19-mer base sequence
<220> FEATURE:
<221> NAME/KEY: modified_base
<222> LOCATION: 1, 19
<223> OTHER INFORMATION: n = any nucleobase

<400> SEQUENCE: 57
ncagaauaga guugcaccn 19

<210> SEQ ID NO 58
<211> LENGTH: 19
<212> TYPE: RNA
<213> ORGANISM: Artificial Sequence
<220> FEATURE:
<223> OTHER INFORMATION: RNAi agent antisense strand core 19-mer base sequence

<400> SEQUENCE: 58
aaaauguccu aggauguug 19

<210> SEQ ID NO 59
<211> LENGTH: 19
<212> TYPE: RNA
<213> ORGANISM: Artificial Sequence
<220> FEATURE:
<223> OTHER INFORMATION: RNAi agent antisense strand core 19-mer base sequence

<400> SEQUENCE: 59
uaaauguccu aggauguug 19

<210> SEQ ID NO 60
<211> LENGTH: 19

<212> TYPE: RNA
<213> ORGANISM: Artificial Sequence
<220> FEATURE:
<223> OTHER INFORMATION: RNAi agent antisense strand core 19-mer base sequence
<220> FEATURE:
<221> NAME/KEY: modified_base
<222> LOCATION: 1
<223> OTHER INFORMATION: n = any nucleobase

<400> SEQUENCE: 60
naaauguccu aggauguug 19

<210> SEQ ID NO 61
<211> LENGTH: 19
<212> TYPE: RNA
<213> ORGANISM: Artificial Sequence
<220> FEATURE:
<223> OTHER INFORMATION: RNAi agent antisense strand core 19-mer base sequence
<220> FEATURE:
<221> NAME/KEY: modified_base
<222> LOCATION: 1, 19
<223> OTHER INFORMATION: n = any nucleobase

<400> SEQUENCE: 61
naaauguccu aggauguun 19

<210> SEQ ID NO 62
<211> LENGTH: 19
<212> TYPE: RNA
<213> ORGANISM: Artificial Sequence
<220> FEATURE:
<223> OTHER INFORMATION: RNAi agent antisense strand core 19-mer base sequence

<400> SEQUENCE: 62
cuccaauaca ggccauaau 19

<210> SEQ ID NO 63
<211> LENGTH: 19
<212> TYPE: RNA
<213> ORGANISM: Artificial Sequence
<220> FEATURE:
<223> OTHER INFORMATION: RNAi agent antisense strand core 19-mer base sequence

<400> SEQUENCE: 63
uuccaauaca ggccauaau 19

<210> SEQ ID NO 64
<211> LENGTH: 19
<212> TYPE: RNA
<213> ORGANISM: Artificial Sequence
<220> FEATURE:
<223> OTHER INFORMATION: RNAi agent antisense strand core 19-mer base sequence
<220> FEATURE:
<221> NAME/KEY: modified_base
<222> LOCATION: 1
<223> OTHER INFORMATION: n = any nucleobase

<400> SEQUENCE: 64
nuccaauaca ggccauaau 19

<210> SEQ ID NO 65
<211> LENGTH: 19
<212> TYPE: RNA
<213> ORGANISM: Artificial Sequence
<220> FEATURE:
<223> OTHER INFORMATION: RNAi agent antisense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 65
nuccaauaca ggccauaan 19

<210> SEQ ID NO 66
<211> LENGTH: 19
<212> TYPE: RNA
<213> ORGANISM: Artificial Sequence
<220> FEATURE:
<223> OTHER INFORMATION: RNAi agent sense strand core 19-mer base
      sequence

<400> SEQUENCE: 66
uaagaagucu gauagaugg 19

<210> SEQ ID NO 67
<211> LENGTH: 19
<212> TYPE: RNA
<213> ORGANISM: Artificial Sequence
<220> FEATURE:
<223> OTHER INFORMATION: RNAi agent sense strand core 19-mer base
      sequence

<400> SEQUENCE: 67
uaagaagucu gauagauga 19

<210> SEQ ID NO 68
<211> LENGTH: 19
<212> TYPE: RNA
<213> ORGANISM: Artificial Sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 68
uaagaagucu gauagaugn 19

<210> SEQ ID NO 69
<211> LENGTH: 19
<212> TYPE: RNA
<213> ORGANISM: Artificial Sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 69
naagaagucu gauagaugn 19

<210> SEQ ID NO 70
<211> LENGTH: 19
<212> TYPE: RNA
<213> ORGANISM: Artificial Sequence
<220> FEATURE:
<223> OTHER INFORMATION: RNAi agent sense strand core 19-mer base

```
      sequence
<220> FEATURE:
<221> NAME/KEY: modified_base
<222> LOCATION: 18
<223> OTHER INFORMATION: n = inosine (hypoxanthine)

<400> SEQUENCE: 70

uaagaagucu gauagaung                                                  19


<210> SEQ ID NO 71
<211> LENGTH: 19
<212> TYPE: RNA
<213> ORGANISM: Artificial Sequence
<220> FEATURE:
<223> OTHER INFORMATION: RNAi agent sense strand core 19-mer base
      sequence
<220> FEATURE:
<221> NAME/KEY: modified_base
<222> LOCATION: 18
<223> OTHER INFORMATION: n = inosine (hypoxanthine)

<400> SEQUENCE: 71

uaagaagucu gauagauna                                                  19


<210> SEQ ID NO 72
<211> LENGTH: 19
<212> TYPE: RNA
<213> ORGANISM: Artificial Sequence
<220> FEATURE:
<223> OTHER INFORMATION: RNAi agent sense strand core 19-mer base
      sequence
<220> FEATURE:
<221> NAME/KEY: modified_base
<222> LOCATION: 18
<223> OTHER INFORMATION: n = inosine (hypoxanthine)
<220> FEATURE:
<221> NAME/KEY: modified_base
<222> LOCATION: 19
<223> OTHER INFORMATION: n = any nucleobase

<400> SEQUENCE: 72

uaagaagucu gauagaunn                                                  19


<210> SEQ ID NO 73
<211> LENGTH: 19
<212> TYPE: RNA
<213> ORGANISM: Artificial Sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 18
<223> OTHER INFORMATION: n = inosine (hypoxanthine)

<400> SEQUENCE: 73

naagaagucu gauagaunn                                                  19


<210> SEQ ID NO 74
<211> LENGTH: 19
<212> TYPE: RNA
<213> ORGANISM: Artificial Sequence
<220> FEATURE:
<223> OTHER INFORMATION: RNAi agent sense strand core 19-mer base
      sequence
<220> FEATURE:
<221> NAME/KEY: modified_base
```

<222> LOCATION: 15
<223> OTHER INFORMATION: n = inosine (hypoxanthine)

<400> SEQUENCE: 74
uaagaagucu gauanaugg 19

<210> SEQ ID NO 75
<211> LENGTH: 19
<212> TYPE: RNA
<213> ORGANISM: Artificial Sequence
<220> FEATURE:
<223> OTHER INFORMATION: RNAi agent sense strand core 19-mer base sequence
<220> FEATURE:
<221> NAME/KEY: modified_base
<222> LOCATION: 15
<223> OTHER INFORMATION: n = inosine (hypoxanthine)

<400> SEQUENCE: 75
uaagaagucu gauanauga 19

<210> SEQ ID NO 76
<211> LENGTH: 19
<212> TYPE: RNA
<213> ORGANISM: Artificial Sequence
<220> FEATURE:
<223> OTHER INFORMATION: RNAi agent sense strand core 19-mer base sequence
<220> FEATURE:
<221> NAME/KEY: modified_base
<222> LOCATION: 15
<223> OTHER INFORMATION: n = inosine (hypoxanthine)
<220> FEATURE:
<221> NAME/KEY: modified_base
<222> LOCATION: 19
<223> OTHER INFORMATION: n = any nucleobase

<400> SEQUENCE: 76
uaagaagucu gauanaugn 19

<210> SEQ ID NO 77
<211> LENGTH: 19
<212> TYPE: RNA
<213> ORGANISM: Artificial Sequence
<220> FEATURE:
<223> OTHER INFORMATION: RNAi agent sense strand core 19-mer base sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 15
<223> OTHER INFORMATION: n = inosine (hypoxanthine)

<400> SEQUENCE: 77
naagaagucu gauanaugn 19

<210> SEQ ID NO 78
<211> LENGTH: 19
<212> TYPE: RNA
<213> ORGANISM: Artificial Sequence
<220> FEATURE:
<223> OTHER INFORMATION: RNAi agent sense strand core 19-mer base sequence

<400> SEQUENCE: 78
gaucacaaaa gcacuucuu 19

<210> SEQ ID NO 79
<211> LENGTH: 19
<212> TYPE: RNA
<213> ORGANISM: Artificial Sequence
<220> FEATURE:
<223> OTHER INFORMATION: RNAi agent sense strand core 19-mer base sequence

<400> SEQUENCE: 79
gaucacaaaa gcacuucua 19

<210> SEQ ID NO 80
<211> LENGTH: 19
<212> TYPE: RNA
<213> ORGANISM: Artificial Sequence
<220> FEATURE:
<223> OTHER INFORMATION: RNAi agent sense strand core 19-mer base sequence
<220> FEATURE:
<221> NAME/KEY: modified_base
<222> LOCATION: 19
<223> OTHER INFORMATION: n = any nucleobase

<400> SEQUENCE: 80
gaucacaaaa gcacuucun 19

<210> SEQ ID NO 81
<211> LENGTH: 19
<212> TYPE: RNA
<213> ORGANISM: Artificial Sequence
<220> FEATURE:
<223> OTHER INFORMATION: RNAi agent sense strand core 19-mer base sequence
<220> FEATURE:
<221> NAME/KEY: modified_base
<222> LOCATION: 1, 19
<223> OTHER INFORMATION: n = any nucleobase

<400> SEQUENCE: 81
naucacaaaa gcacuucun 19

<210> SEQ ID NO 82
<211> LENGTH: 19
<212> TYPE: RNA
<213> ORGANISM: Artificial Sequence
<220> FEATURE:
<223> OTHER INFORMATION: RNAi agent sense strand core 19-mer base sequence

<400> SEQUENCE: 82
cuaggacauu uuuggauca 19

<210> SEQ ID NO 83
<211> LENGTH: 19
<212> TYPE: RNA
<213> ORGANISM: Artificial Sequence
<220> FEATURE:
<223> OTHER INFORMATION: RNAi agent sense strand core 19-mer base sequence

<400> SEQUENCE: 83
cuaggacauu uuuggaucu 19

<210> SEQ ID NO 84
<211> LENGTH: 19
<212> TYPE: RNA
<213> ORGANISM: Artificial Sequence
<220> FEATURE:

<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 84
cuaggacauu uuuggaucn 19

<210> SEQ ID NO 85
<211> LENGTH: 19
<212> TYPE: RNA
<213> ORGANISM: Artificial Sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 85
nuaggacauu uuuggaucn 19

<210> SEQ ID NO 86
<211> LENGTH: 19
<212> TYPE: RNA
<213> ORGANISM: Artificial Sequence
<220> FEATURE:
<223> OTHER INFORMATION: RNAi agent sense strand core 19-mer base
      sequence
<220> FEATURE:
<221> NAME/KEY: modified_base
<222> LOCATION: 15
<223> OTHER INFORMATION: n = inosine (hypoxanthine)

<400> SEQUENCE: 86
cuaggacauu uuugnauca 19

<210> SEQ ID NO 87
<211> LENGTH: 19
<212> TYPE: RNA
<213> ORGANISM: Artificial Sequence
<220> FEATURE:
<223> OTHER INFORMATION: RNAi agent sense strand core 19-mer base
      sequence
<220> FEATURE:
<221> NAME/KEY: modified_base
<222> LOCATION: 15
<223> OTHER INFORMATION: n = inosine (hypoxanthine)

<400> SEQUENCE: 87
cuaggacauu uuugnaucu 19

<210> SEQ ID NO 88
<211> LENGTH: 19
<212> TYPE: RNA
<213> ORGANISM: Artificial Sequence
<220> FEATURE:
<223> OTHER INFORMATION: RNAi agent sense strand core 19-mer base
      sequence
<220> FEATURE:
<221> NAME/KEY: modified_base
<222> LOCATION: 15
<223> OTHER INFORMATION: n = inosine (hypoxanthine)
<220> FEATURE:
<221> NAME/KEY: modified_base
<222> LOCATION: 19
<223> OTHER INFORMATION: n = any nucleobase

<400> SEQUENCE: 88
cuaggacauu uuugnaucn 19

<210> SEQ ID NO 89
<211> LENGTH: 19
<212> TYPE: RNA
<213> ORGANISM: Artificial Sequence
<220> FEATURE:
<223> OTHER INFORMATION: RNAi agent sense strand core 19-mer base sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 15
<223> OTHER INFORMATION: n = inosine (hypoxanthine)

<400> SEQUENCE: 89
nuaggacauu uuugnaucn 19

<210> SEQ ID NO 90
<211> LENGTH: 19
<212> TYPE: RNA
<213> ORGANISM: Artificial Sequence
<220> FEATURE:
<223> OTHER INFORMATION: RNAi agent sense strand core 19-mer base sequence

<400> SEQUENCE: 90
aggucaacau ccuaggaca 19

<210> SEQ ID NO 91
<211> LENGTH: 19
<212> TYPE: RNA
<213> ORGANISM: Artificial Sequence
<220> FEATURE:
<223> OTHER INFORMATION: RNAi agent sense strand core 19-mer base sequence

<400> SEQUENCE: 91
aggucaacau ccuaggacu 19

<210> SEQ ID NO 92
<211> LENGTH: 19
<212> TYPE: RNA
<213> ORGANISM: Artificial Sequence
<220> FEATURE:
<223> OTHER INFORMATION: RNAi agent sense strand core 19-mer base sequence
<220> FEATURE:
<221> NAME/KEY: modified_base
<222> LOCATION: 19
<223> OTHER INFORMATION: n = any nucleobase

<400> SEQUENCE: 92
aggucaacau ccuaggacn 19

<210> SEQ ID NO 93
<211> LENGTH: 19
<212> TYPE: RNA
<213> ORGANISM: Artificial Sequence
<220> FEATURE:
<223> OTHER INFORMATION: RNAi agent sense strand core 19-mer base sequence
<220> FEATURE:
<221> NAME/KEY: modified_base
<222> LOCATION: 1, 19

<223> OTHER INFORMATION: n = any nucleobase

<400> SEQUENCE: 93
nggucaacau ccuaggacn 19

<210> SEQ ID NO 94
<211> LENGTH: 19
<212> TYPE: RNA
<213> ORGANISM: Artificial Sequence
<220> FEATURE:
<223> OTHER INFORMATION: RNAi agent sense strand core 19-mer base sequence

<400> SEQUENCE: 94
cggugcaacu cuauucugg 19

<210> SEQ ID NO 95
<211> LENGTH: 19
<212> TYPE: RNA
<213> ORGANISM: Artificial Sequence
<220> FEATURE:
<223> OTHER INFORMATION: RNAi agent sense strand core 19-mer base sequence

<400> SEQUENCE: 95
cggugcaacu cuauucuga 19

<210> SEQ ID NO 96
<211> LENGTH: 19
<212> TYPE: RNA
<213> ORGANISM: Artificial Sequence
<220> FEATURE:
<223> OTHER INFORMATION: RNAi agent sense strand core 19-mer base sequence

<400> SEQUENCE: 96
cggugcaacu cuauucugu 19

<210> SEQ ID NO 97
<211> LENGTH: 19
<212> TYPE: RNA
<213> ORGANISM: Artificial Sequence
<220> FEATURE:
<223> OTHER INFORMATION: RNAi agent sense strand core 19-mer base sequence
<220> FEATURE:
<221> NAME/KEY: modified_base
<222> LOCATION: 19
<223> OTHER INFORMATION: n = any nucleobase

<400> SEQUENCE: 97
cggugcaacu cuauucugn 19

<210> SEQ ID NO 98
<211> LENGTH: 19
<212> TYPE: RNA
<213> ORGANISM: Artificial Sequence
<220> FEATURE:
<223> OTHER INFORMATION: RNAi agent sense strand core 19-mer base sequence
<220> FEATURE:
<221> NAME/KEY: modified_base
<222> LOCATION: 1, 19
<223> OTHER INFORMATION: n = any nucleobase

<400> SEQUENCE: 98
nggugcaacu cuauucugn 19

-continued

```
<210> SEQ ID NO 99
<211> LENGTH: 19
<212> TYPE: RNA
<213> ORGANISM: Artificial Sequence
<220> FEATURE:
<223> OTHER INFORMATION: RNAi agent sense strand core 19-mer base
      sequence

<400> SEQUENCE: 99

caacauccua ggacauuuu                                                19


<210> SEQ ID NO 100
<211> LENGTH: 19
<212> TYPE: RNA
<213> ORGANISM: Artificial Sequence
<220> FEATURE:
<223> OTHER INFORMATION: RNAi agent sense strand core 19-mer base
      sequence

<400> SEQUENCE: 100

caacauccua ggacauuua                                                19


<210> SEQ ID NO 101
<211> LENGTH: 19
<212> TYPE: RNA
<213> ORGANISM: Artificial Sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 101

caacauccua ggacauuun                                                19


<210> SEQ ID NO 102
<211> LENGTH: 19
<212> TYPE: RNA
<213> ORGANISM: Artificial Sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 102

naacauccua ggacauuun                                                19


<210> SEQ ID NO 103
<211> LENGTH: 19
<212> TYPE: RNA
<213> ORGANISM: Artificial Sequence
<220> FEATURE:
<223> OTHER INFORMATION: RNAi agent sense strand core 19-mer base
      sequence

<400> SEQUENCE: 103

auuauggccu guauuggag                                                19


<210> SEQ ID NO 104
<211> LENGTH: 19
<212> TYPE: RNA
<213> ORGANISM: Artificial Sequence
<220> FEATURE:
```

-continued

<223> OTHER INFORMATION: RNAi agent sense strand core 19-mer base
      sequence

<400> SEQUENCE: 104
auuauggccu guauuggaa 19

<210> SEQ ID NO 105
<211> LENGTH: 19
<212> TYPE: RNA
<213> ORGANISM: Artificial Sequence
<220> FEATURE:
<223> OTHER INFORMATION: RNAi agent sense strand core 19-mer base
      sequence
<220> FEATURE:
<221> NAME/KEY: modified_base
<222> LOCATION: 19
<223> OTHER INFORMATION: n = any nucleobase

<400> SEQUENCE: 105
auuauggccu guauuggan 19

<210> SEQ ID NO 106
<211> LENGTH: 19
<212> TYPE: RNA
<213> ORGANISM: Artificial Sequence
<220> FEATURE:
<223> OTHER INFORMATION: RNAi agent sense strand core 19-mer base
      sequence
<220> FEATURE:
<221> NAME/KEY: modified_base
<222> LOCATION: 1, 19
<223> OTHER INFORMATION: n = any nucleobase

<400> SEQUENCE: 106
nuuauggccu guauuggan 19

<210> SEQ ID NO 107
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 107
ucagaauaga guugcaccgu c 21

<210> SEQ ID NO 108
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 108
uguccuagga uguugaccuc a 21

<210> SEQ ID NO 109
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 109
uguccuagga uguugaccuc a 21

<210> SEQ ID NO 110

<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 110
aaaauguccu aggauguuga c 21

<210> SEQ ID NO 111
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 111
ugauccaaaa auguccuagg a 21

<210> SEQ ID NO 112
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 112
uguccuagga uguugaccuc c 21

<210> SEQ ID NO 113
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 113
uguccuagga uguugaccuc u 21

<210> SEQ ID NO 114
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 114
uguccuagga uguugaccuc c 21

<210> SEQ ID NO 115
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 115
uguccuagga uguugaccuc c 21

<210> SEQ ID NO 116
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 116
uguccuagga uguugaccuc c 21

<210> SEQ ID NO 117
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 117
uguccuagga uguugaccuc c 21

<210> SEQ ID NO 118
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 118
uguccuagga uguugaccuc c 21

<210> SEQ ID NO 119
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 119
ugauccaaaa auguccuagg u 21

<210> SEQ ID NO 120
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 120
ugauccaaaa auguccuagg c 21

<210> SEQ ID NO 121
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 121
ugauccaaaa auguccuagg c 21

<210> SEQ ID NO 122
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 122
ugauccaaaa auguccuagg c 21

<210> SEQ ID NO 123
<211> LENGTH: 21
<212> TYPE: RNA

<213> ORGANISM: Artificial Sequence
<220> FEATURE:
<223> OTHER INFORMATION: RNAi agent antisense strand modified sequence

<400> SEQUENCE: 123
ugauccaaaa auguccuagg c 21

<210> SEQ ID NO 124
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 124
ugauccaaaa auguccuagg c 21

<210> SEQ ID NO 125
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 125
aaaauguccu aggauguuga c 21

<210> SEQ ID NO 126
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 126
uagaugaugg ugaucagaag c 21

<210> SEQ ID NO 127
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 127
uacuguccca gcauuauuca c 21

<210> SEQ ID NO 128
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 128
aagaagugcu uuugugaucc a 21

<210> SEQ ID NO 129
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 129
ugucagaccu cugugaaagc c 21

<210> SEQ ID NO 130
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 130
uugaugucag accucuguga c 21

<210> SEQ ID NO 131
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 131
uuccaauaca ggccauaauc c 21

<210> SEQ ID NO 132
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 132
ucaucuauca gacuucuuac g 21

<210> SEQ ID NO 133
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 133
ucagguugag auaaagcugc c 21

<210> SEQ ID NO 134
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 134
uccagaauag aguugcaccg u 21

<210> SEQ ID NO 135
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 135
aaguccagaa uagaguugca c 21

<210> SEQ ID NO 136
<211> LENGTH: 21
<212> TYPE: RNA
<213> ORGANISM: Artificial Sequence
<220> FEATURE:

<223> OTHER INFORMATION: RNAi agent antisense strand modified sequence

<400> SEQUENCE: 136
ucuugaugua gugggagucg g 21

<210> SEQ ID NO 137
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 137
acaagauuag ucuugaugua g 21

<210> SEQ ID NO 138
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 138
ucagaauaga guugcaccgu u 21

<210> SEQ ID NO 139
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 139
ucagaauaga guugcaccgc u 21

<210> SEQ ID NO 140
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 140
ucagaauaga guugcaccgu g 21

<210> SEQ ID NO 141
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 141
ucagaauaga guugcaccgg u 21

<210> SEQ ID NO 142
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 142
ucagaauaga guugcaccgu c 21

<210> SEQ ID NO 143
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 143
ucagaauaga guugcaccgc c 21

<210> SEQ ID NO 144
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 144
ucagaauaga guugcaccgg c 21

<210> SEQ ID NO 145
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 145
ucagaauaga guugcaccgu c 21

<210> SEQ ID NO 146
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 146
agugacucca gguaggagua g 21

<210> SEQ ID NO 147
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 147
aagaacuuua ccagugacuc c 21

<210> SEQ ID NO 148
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 148
aagaacuuua ccagugacuc g 21

<210> SEQ ID NO 149
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 149
uugcagucca ccacaaacac g 21

<210> SEQ ID NO 150
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 150
ucagcaucga uggaaggagu g 21

<210> SEQ ID NO 151
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 151
agaguuucuu cucagcaucg a 21

<210> SEQ ID NO 152
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 152
ucaguauuca cgaacacagg g 21

<210> SEQ ID NO 153
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 153
ucaguauuca cgaacacagg c 21

<210> SEQ ID NO 154
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 154
ugaagaucau uuucuuguug g 21

<210> SEQ ID NO 155
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 155
aagaagugcu uuugugaucc g 21

<210> SEQ ID NO 156
<211> LENGTH: 21

<212> TYPE: RNA
<213> ORGANISM: Artificial Sequence
<220> FEATURE:
<223> OTHER INFORMATION: RNAi agent antisense strand modified sequence

<400> SEQUENCE: 156
aagaagugcu uuugugaucc c 21

<210> SEQ ID NO 157
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 157
uagaagugcu uuugugaucc c 21

<210> SEQ ID NO 158
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 158
aagaagugcu uuugugaucc c 21

<210> SEQ ID NO 159
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 159
aagaagugcu uuugugaucc c 21

<210> SEQ ID NO 160
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 160
uagaagugcu uuugugaucc c 21

<210> SEQ ID NO 161
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 161
ucaucuauca gacuucuuac g 21

<210> SEQ ID NO 162
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 162
ucaucuauca gacuucuuac c 21

<210> SEQ ID NO 163
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 163
ucaucuauca gacuucuuac c 21

<210> SEQ ID NO 164
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 164
aagaagugcu uuugugaucc g 21

<210> SEQ ID NO 165
<211> LENGTH: 21
<212> TYPE: RNA
<213> ORGANISM: Artificial Sequence
<220> FEATURE:
<223> OTHER INFORMATION: RNAi agent antisense strand modified sequence

<400> SEQUENCE: 165
aagaagugcu uuugugaucc c 21

<210> SEQ ID NO 166
<211> LENGTH: 21
<212> TYPE: RNA
<213> ORGANISM: Artificial Sequence
<220> FEATURE:
<223> OTHER INFORMATION: RNAi agent sense strand modified sequence

<400> SEQUENCE: 166
gacggugcaa cucuauucug a 21

<210> SEQ ID NO 167
<211> LENGTH: 21
<212> TYPE: RNA
<213> ORGANISM: Artificial Sequence
<220> FEATURE:
<223> OTHER INFORMATION: RNAi agent sense strand modified sequence

<400> SEQUENCE: 167
ugaggucaac auccuaggac a 21

<210> SEQ ID NO 168
<211> LENGTH: 21
<212> TYPE: RNA
<213> ORGANISM: Artificial Sequence
<220> FEATURE:
<223> OTHER INFORMATION: RNAi agent sense strand modified sequence
<220> FEATURE:
<221> NAME/KEY: modified_base
<222> LOCATION: 18
<223> OTHER INFORMATION: n = 2'-O-methylinosine-3'-phosphate

<400> SEQUENCE: 168
ugaggucaac auccuagnac a 21

-continued

<210> SEQ ID NO 169
<211> LENGTH: 21
<212> TYPE: RNA
<213> ORGANISM: Artificial Sequence
<220> FEATURE:
<223> OTHER INFORMATION: RNAi agent sense strand modified sequence

<400> SEQUENCE: 169
gucaacaucc uaggacauuu u 21

<210> SEQ ID NO 170
<211> LENGTH: 21
<212> TYPE: RNA
<213> ORGANISM: Artificial Sequence
<220> FEATURE:
<223> OTHER INFORMATION: RNAi agent sense strand modified sequence
<220> FEATURE:
<221> NAME/KEY: modified_base
<222> LOCATION: 17
<223> OTHER INFORMATION: n = 2'-O-methyl-2-aminoadenosine-3'-phosphate

<400> SEQUENCE: 170
gucaacaucc uaggacnuuu u 21

<210> SEQ ID NO 171
<211> LENGTH: 21
<212> TYPE: RNA
<213> ORGANISM: Artificial Sequence
<220> FEATURE:
<223> OTHER INFORMATION: RNAi agent sense strand modified sequence

<400> SEQUENCE: 171
uccuaggaca uuuuuggauc a 21

<210> SEQ ID NO 172
<211> LENGTH: 21
<212> TYPE: RNA
<213> ORGANISM: Artificial Sequence
<220> FEATURE:
<223> OTHER INFORMATION: RNAi agent sense strand modified sequence
<220> FEATURE:
<221> NAME/KEY: modified_base
<222> LOCATION: 17
<223> OTHER INFORMATION: n = 2'-O-methylinosine-3'-phosphate

<400> SEQUENCE: 172
uccuaggaca uuuuugnauc a 21

<210> SEQ ID NO 173
<211> LENGTH: 21
<212> TYPE: RNA
<213> ORGANISM: Artificial Sequence
<220> FEATURE:
<223> OTHER INFORMATION: RNAi agent sense strand modified sequence

<400> SEQUENCE: 173
ggaggucaac auccuaggac a 21

<210> SEQ ID NO 174
<211> LENGTH: 21
<212> TYPE: RNA
<213> ORGANISM: Artificial Sequence
<220> FEATURE:
<223> OTHER INFORMATION: RNAi agent sense strand modified sequence

<400> SEQUENCE: 174
agaggucaac auccuaggac a 21

<210> SEQ ID NO 175
<211> LENGTH: 21
<212> TYPE: RNA
<213> ORGANISM: Artificial Sequence
<220> FEATURE:
<223> OTHER INFORMATION: RNAi agent sense strand modified sequence
<220> FEATURE:
<221> NAME/KEY: modified_base
<222> LOCATION: 18
<223> OTHER INFORMATION: n = 2'-O-methylinosine-3'-phosphate

<400> SEQUENCE: 175
ggaggucaac auccuagnac a 21

<210> SEQ ID NO 176
<211> LENGTH: 21
<212> TYPE: RNA
<213> ORGANISM: Artificial Sequence
<220> FEATURE:
<223> OTHER INFORMATION: RNAi agent sense strand modified sequence
<220> FEATURE:
<221> NAME/KEY: modified_base
<222> LOCATION: 17
<223> OTHER INFORMATION: n = 2'-O-methylinosine-3'-phosphate

<400> SEQUENCE: 176
accuaggaca uuuuugnauc a 21

<210> SEQ ID NO 177
<211> LENGTH: 21
<212> TYPE: RNA
<213> ORGANISM: Artificial Sequence
<220> FEATURE:
<223> OTHER INFORMATION: RNAi agent sense strand modified sequence

<400> SEQUENCE: 177
gccuaggaca uuuuuggauc a 21

<210> SEQ ID NO 178
<211> LENGTH: 21
<212> TYPE: RNA
<213> ORGANISM: Artificial Sequence
<220> FEATURE:
<223> OTHER INFORMATION: RNAi agent sense strand modified sequence
<220> FEATURE:
<221> NAME/KEY: modified_base
<222> LOCATION: 17
<223> OTHER INFORMATION: n = 2'-O-methylinosine-3'-phosphate

<400> SEQUENCE: 178
gccuaggaca uuuuugnauc a 21

<210> SEQ ID NO 179
<211> LENGTH: 21
<212> TYPE: RNA
<213> ORGANISM: Artificial Sequence
<220> FEATURE:
<223> OTHER INFORMATION: RNAi agent sense strand modified sequence

<400> SEQUENCE: 179
gcuucugauc accaucaucu a 21

<210> SEQ ID NO 180
<211> LENGTH: 21
<212> TYPE: RNA
<213> ORGANISM: Artificial Sequence
<220> FEATURE:
<223> OTHER INFORMATION: RNAi agent sense strand modified sequence

<400> SEQUENCE: 180
gugaauaaug cugggacagu a 21

<210> SEQ ID NO 181
<211> LENGTH: 21
<212> TYPE: RNA
<213> ORGANISM: Artificial Sequence
<220> FEATURE:
<223> OTHER INFORMATION: RNAi agent sense strand modified sequence

<400> SEQUENCE: 181
uggaucacaa aagcacuucu u 21

<210> SEQ ID NO 182
<211> LENGTH: 21
<212> TYPE: RNA
<213> ORGANISM: Artificial Sequence
<220> FEATURE:
<223> OTHER INFORMATION: RNAi agent sense strand modified sequence

<400> SEQUENCE: 182
ggcuuucaca gaggucugac a 21

<210> SEQ ID NO 183
<211> LENGTH: 21
<212> TYPE: RNA
<213> ORGANISM: Artificial Sequence
<220> FEATURE:
<223> OTHER INFORMATION: RNAi agent sense strand modified sequence

<400> SEQUENCE: 183
gucacagagg ucugacauca a 21

<210> SEQ ID NO 184
<211> LENGTH: 21
<212> TYPE: RNA
<213> ORGANISM: Artificial Sequence
<220> FEATURE:
<223> OTHER INFORMATION: RNAi agent sense strand modified sequence

<400> SEQUENCE: 184
ggauuauggc cuguauugga a 21

<210> SEQ ID NO 185
<211> LENGTH: 21
<212> TYPE: RNA
<213> ORGANISM: Artificial Sequence
<220> FEATURE:
<223> OTHER INFORMATION: RNAi agent sense strand modified sequence

<400> SEQUENCE: 185
cguaagaagu cugauagaug a 21

<210> SEQ ID NO 186
<211> LENGTH: 21
<212> TYPE: RNA
<213> ORGANISM: Artificial Sequence
<220> FEATURE:
<223> OTHER INFORMATION: RNAi agent sense strand modified sequence

<400> SEQUENCE: 186
ggcagcuuua ucucaaccug a 21

<210> SEQ ID NO 187

-continued

<211> LENGTH: 21
<212> TYPE: RNA
<213> ORGANISM: Artificial Sequence
<220> FEATURE:
<223> OTHER INFORMATION: RNAi agent sense strand modified sequence

<400> SEQUENCE: 187
acggugcaac ucuauucugg a 21

<210> SEQ ID NO 188
<211> LENGTH: 21
<212> TYPE: RNA
<213> ORGANISM: Artificial Sequence
<220> FEATURE:
<223> OTHER INFORMATION: RNAi agent sense strand modified sequence

<400> SEQUENCE: 188
gugcaacucu auucuggacu u 21

<210> SEQ ID NO 189
<211> LENGTH: 21
<212> TYPE: RNA
<213> ORGANISM: Artificial Sequence
<220> FEATURE:
<223> OTHER INFORMATION: RNAi agent sense strand modified sequence

<400> SEQUENCE: 189
ccgacuccca cuacaucaag a 21

<210> SEQ ID NO 190
<211> LENGTH: 21
<212> TYPE: RNA
<213> ORGANISM: Artificial Sequence
<220> FEATURE:
<223> OTHER INFORMATION: RNAi agent sense strand modified sequence

<400> SEQUENCE: 190
cuacaucaag acuaaucuug u 21

<210> SEQ ID NO 191
<211> LENGTH: 21
<212> TYPE: RNA
<213> ORGANISM: Artificial Sequence
<220> FEATURE:
<223> OTHER INFORMATION: RNAi agent sense strand modified sequence

<400> SEQUENCE: 191
cggugcaacu cuauucugau u 21

<210> SEQ ID NO 192
<211> LENGTH: 21
<212> TYPE: RNA
<213> ORGANISM: Artificial Sequence
<220> FEATURE:
<223> OTHER INFORMATION: RNAi agent sense strand modified sequence

<400> SEQUENCE: 192
agcggugcaa cucuauucug a 21

<210> SEQ ID NO 193
<211> LENGTH: 21
<212> TYPE: RNA
<213> ORGANISM: Artificial Sequence
<220> FEATURE:
<223> OTHER INFORMATION: RNAi agent sense strand modified sequence

<400> SEQUENCE: 193
cacggugcaa cucuauucug a 21

<210> SEQ ID NO 194
<211> LENGTH: 21
<212> TYPE: RNA
<213> ORGANISM: Artificial Sequence
<220> FEATURE:
<223> OTHER INFORMATION: RNAi agent sense strand modified sequence

<400> SEQUENCE: 194
accggugcaa cucuauucug a 21

<210> SEQ ID NO 195
<211> LENGTH: 21
<212> TYPE: RNA
<213> ORGANISM: Artificial Sequence
<220> FEATURE:
<223> OTHER INFORMATION: RNAi agent sense strand modified sequence
<220> FEATURE:
<221> NAME/KEY: modified_base
<222> LOCATION: 7
<223> OTHER INFORMATION: n = 2'-O-methylinosine-3'-phosphate

<400> SEQUENCE: 195 gacggunc aa cucuauucug a 21

<210> SEQ ID NO 196
<211> LENGTH: 21
<212> TYPE: RNA
<213> ORGANISM: Artificial Sequence
<220> FEATURE:
<223> OTHER INFORMATION: RNAi agent sense strand modified sequence
<220> FEATURE:
<221> NAME/KEY: modified_base
<222> LOCATION: 5
<223> OTHER INFORMATION: n = 2'-O-methylinosine-3'-phosphate

<400> SEQUENCE: 196
gacgnugcaa cucuauucug a 21

<210> SEQ ID NO 197
<211> LENGTH: 21
<212> TYPE: RNA
<213> ORGANISM: Artificial Sequence
<220> FEATURE:
<223> OTHER INFORMATION: RNAi agent sense strand modified sequence
<220> FEATURE:
<221> NAME/KEY: modified_base
<222> LOCATION: 20
<223> OTHER INFORMATION: n = 2'-O-methylinosine-3'-phosphate

<400> SEQUENCE: 197
gacggugcaa cucuauucun a 21

<210> SEQ ID NO 198
<211> LENGTH: 21
<212> TYPE: RNA
<213> ORGANISM: Artificial Sequence
<220> FEATURE:
<223> OTHER INFORMATION: RNAi agent sense strand modified sequence

<400> SEQUENCE: 198
ggcggugcaa cucuauucug a 21

<210> SEQ ID NO 199
<211> LENGTH: 21
<212> TYPE: RNA

<213> ORGANISM: Artificial Sequence
<220> FEATURE:
<223> OTHER INFORMATION: RNAi agent sense strand modified sequence

<400> SEQUENCE: 199
gccggugcaa cucuauucug a 21

<210> SEQ ID NO 200
<211> LENGTH: 21
<212> TYPE: RNA
<213> ORGANISM: Artificial Sequence
<220> FEATURE:
<223> OTHER INFORMATION: RNAi agent sense strand modified sequence

<400> SEQUENCE: 200
cuacuccuac cuggagucac u 21

<210> SEQ ID NO 201
<211> LENGTH: 21
<212> TYPE: RNA
<213> ORGANISM: Artificial Sequence
<220> FEATURE:
<223> OTHER INFORMATION: RNAi agent sense strand modified sequence

<400> SEQUENCE: 201
ggagucacug guaaaguucu u 21

<210> SEQ ID NO 202
<211> LENGTH: 21
<212> TYPE: RNA
<213> ORGANISM: Artificial Sequence
<220> FEATURE:
<223> OTHER INFORMATION: RNAi agent sense strand modified sequence

<400> SEQUENCE: 202
cgagucacug guaaaguucu u 21

<210> SEQ ID NO 203
<211> LENGTH: 21
<212> TYPE: RNA
<213> ORGANISM: Artificial Sequence
<220> FEATURE:
<223> OTHER INFORMATION: RNAi agent sense strand modified sequence

<400> SEQUENCE: 203
cguguuugug guggacugca a 21

<210> SEQ ID NO 204
<211> LENGTH: 21
<212> TYPE: RNA
<213> ORGANISM: Artificial Sequence
<220> FEATURE:
<223> OTHER INFORMATION: RNAi agent sense strand modified sequence

<400> SEQUENCE: 204
cacuccuucc aucgaugcug a 21

<210> SEQ ID NO 205
<211> LENGTH: 21
<212> TYPE: RNA
<213> ORGANISM: Artificial Sequence
<220> FEATURE:
<223> OTHER INFORMATION: RNAi agent sense strand modified sequence

<400> SEQUENCE: 205
ucgaugcuga gaagaaacuc u 21

<210> SEQ ID NO 206
<211> LENGTH: 21
<212> TYPE: RNA
<213> ORGANISM: Artificial Sequence
<220> FEATURE:
<223> OTHER INFORMATION: RNAi agent sense strand modified sequence

<400> SEQUENCE: 206
cccuguguuc gugaauacug a 21

<210> SEQ ID NO 207
<211> LENGTH: 21
<212> TYPE: RNA
<213> ORGANISM: Artificial Sequence
<220> FEATURE:
<223> OTHER INFORMATION: RNAi agent sense strand modified sequence

<400> SEQUENCE: 207
gccuguguuc gugaauacug a 21

<210> SEQ ID NO 208
<211> LENGTH: 21
<212> TYPE: RNA
<213> ORGANISM: Artificial Sequence
<220> FEATURE:
<223> OTHER INFORMATION: RNAi agent sense strand modified sequence

<400> SEQUENCE: 208
ccaacaagaa aaugaucuuc a 21

<210> SEQ ID NO 209
<211> LENGTH: 21
<212> TYPE: RNA
<213> ORGANISM: Artificial Sequence
<220> FEATURE:
<223> OTHER INFORMATION: RNAi agent sense strand modified sequence

<400> SEQUENCE: 209
cggaucacaa aagcacuucu u 21

<210> SEQ ID NO 210
<211> LENGTH: 21
<212> TYPE: RNA
<213> ORGANISM: Artificial Sequence
<220> FEATURE:
<223> OTHER INFORMATION: RNAi agent sense strand modified sequence

<400> SEQUENCE: 210
gggaucacaa aagcacuucu u 21

<210> SEQ ID NO 211
<211> LENGTH: 21
<212> TYPE: RNA
<213> ORGANISM: Artificial Sequence
<220> FEATURE:
<223> OTHER INFORMATION: RNAi agent sense strand modified sequence

<400> SEQUENCE: 211
gggaucacaa aagcacuucu a 21

<210> SEQ ID NO 212
<211> LENGTH: 21
<212> TYPE: RNA
<213> ORGANISM: Artificial Sequence
<220> FEATURE:

<223> OTHER INFORMATION: RNAi agent sense strand modified sequence

<400> SEQUENCE: 212
gggaucacaa aagcacuucu u 21

<210> SEQ ID NO 213
<211> LENGTH: 21
<212> TYPE: RNA
<213> ORGANISM: Artificial Sequence
<220> FEATURE:
<223> OTHER INFORMATION: RNAi agent sense strand modified sequence

<400> SEQUENCE: 213
gggaucacaa aagcacuucu a 21

<210> SEQ ID NO 214
<211> LENGTH: 21
<212> TYPE: RNA
<213> ORGANISM: Artificial Sequence
<220> FEATURE:
<223> OTHER INFORMATION: RNAi agent sense strand modified sequence
<220> FEATURE:
<221> NAME/KEY: modified_base
<222> LOCATION: 20
<223> OTHER INFORMATION: n = 2'-O-methylinosine-3'-phosphate

<400> SEQUENCE: 214
cguaagaagu cugauagaun a 21

<210> SEQ ID NO 215
<211> LENGTH: 21
<212> TYPE: RNA
<213> ORGANISM: Artificial Sequence
<220> FEATURE:
<223> OTHER INFORMATION: RNAi agent sense strand modified sequence

<400> SEQUENCE: 215
gguaagaagu cugauagaug a 21

<210> SEQ ID NO 216
<211> LENGTH: 21
<212> TYPE: RNA
<213> ORGANISM: Artificial Sequence
<220> FEATURE:
<223> OTHER INFORMATION: RNAi agent sense strand modified sequence
<220> FEATURE:
<221> NAME/KEY: modified_base
<222> LOCATION: 20
<223> OTHER INFORMATION: n = 2'-O-methylinosine-3'-phosphate

<400> SEQUENCE: 216
gguaagaagu cugauagaun a 21

<210> SEQ ID NO 217
<211> LENGTH: 21
<212> TYPE: RNA
<213> ORGANISM: Artificial Sequence
<220> FEATURE:
<223> OTHER INFORMATION: RNAi agent sense strand modified sequence
<220> FEATURE:
<221> NAME/KEY: modified_base
<222> LOCATION: 17
<223> OTHER INFORMATION: n = 2'-O-methylinosine-3'-phosphate

<400> SEQUENCE: 217
gguaagaagu cugauanaug a 21

<210> SEQ ID NO 218
<211> LENGTH: 21
<212> TYPE: RNA
<213> ORGANISM: Artificial Sequence
<220> FEATURE:
<223> OTHER INFORMATION: RNAi agent sense strand modified sequence
<220> FEATURE:
<221> NAME/KEY: modified_base
<222> LOCATION: 17
<223> OTHER INFORMATION: n = 2'-O-methylinosine-3'-phosphate

<400> SEQUENCE: 218
gccuaggaca uuuuugnauc a 21

<210> SEQ ID NO 219
<211> LENGTH: 21
<212> TYPE: RNA
<213> ORGANISM: Artificial Sequence
<220> FEATURE:
<223> OTHER INFORMATION: RNAi agent sense strand modified sequence

<400> SEQUENCE: 219
cggaucacaa aagcacuucu u 21

<210> SEQ ID NO 220
<211> LENGTH: 21
<212> TYPE: RNA
<213> ORGANISM: Artificial Sequence
<220> FEATURE:
<223> OTHER INFORMATION: RNAi agent sense strand modified sequence

<400> SEQUENCE: 220
cguaagaagu cugauagaug a 21

<210> SEQ ID NO 221
<211> LENGTH: 21
<212> TYPE: RNA
<213> ORGANISM: Artificial Sequence
<220> FEATURE:
<223> OTHER INFORMATION: RNAi agent antisense strand underlying base sequence

<400> SEQUENCE: 221
ucagaauaga guugcaccgu c 21

<210> SEQ ID NO 222
<211> LENGTH: 21
<212> TYPE: RNA
<213> ORGANISM: Artificial Sequence
<220> FEATURE:
<223> OTHER INFORMATION: RNAi agent antisense strand underlying base sequence

<400> SEQUENCE: 222
uguccuagga uguugaccuc a 21

<210> SEQ ID NO 223
<211> LENGTH: 21
<212> TYPE: RNA
<213> ORGANISM: Artificial Sequence
<220> FEATURE:
<223> OTHER INFORMATION: RNAi agent antisense strand underlying base sequence

<400> SEQUENCE: 223
aaaauguccu aggauguuga c 21

<210> SEQ ID NO 224
<211> LENGTH: 21
<212> TYPE: RNA
<213> ORGANISM: Artificial Sequence
<220> FEATURE:
<223> OTHER INFORMATION: RNAi agent antisense strand underlying base sequence

<400> SEQUENCE: 224
ugauccaaaa auguccuagg a 21

<210> SEQ ID NO 225
<211> LENGTH: 21
<212> TYPE: RNA
<213> ORGANISM: Artificial Sequence
<220> FEATURE:
<223> OTHER INFORMATION: RNAi agent antisense strand underlying base sequence

<400> SEQUENCE: 225
uguccuagga uguugaccuc c 21

<210> SEQ ID NO 226
<211> LENGTH: 21
<212> TYPE: RNA
<213> ORGANISM: Artificial Sequence
<220> FEATURE:
<223> OTHER INFORMATION: RNAi agent antisense strand underlying base sequence

<400> SEQUENCE: 226
uguccuagga uguugaccuc u 21

<210> SEQ ID NO 227
<211> LENGTH: 21
<212> TYPE: RNA
<213> ORGANISM: Artificial Sequence
<220> FEATURE:
<223> OTHER INFORMATION: RNAi agent antisense strand underlying base sequence

<400> SEQUENCE: 227
ugauccaaaa auguccuagg u 21

<210> SEQ ID NO 228
<211> LENGTH: 21
<212> TYPE: RNA
<213> ORGANISM: Artificial Sequence
<220> FEATURE:
<223> OTHER INFORMATION: RNAi agent antisense strand underlying base sequence

<400> SEQUENCE: 228
ugauccaaaa auguccuagg c 21

<210> SEQ ID NO 229
<211> LENGTH: 21
<212> TYPE: RNA
<213> ORGANISM: Artificial Sequence
<220> FEATURE:
<223> OTHER INFORMATION: RNAi agent antisense strand underlying base sequence

<400> SEQUENCE: 229
uagaugaugg ugaucagaag c 21

<210> SEQ ID NO 230

<211> LENGTH: 21
<212> TYPE: RNA
<213> ORGANISM: Artificial Sequence
<220> FEATURE:
<223> OTHER INFORMATION: RNAi agent antisense strand underlying base sequence

<400> SEQUENCE: 230
uacugcccca gcauuauuca c 21

<210> SEQ ID NO 231
<211> LENGTH: 21
<212> TYPE: RNA
<213> ORGANISM: Artificial Sequence
<220> FEATURE:
<223> OTHER INFORMATION: RNAi agent antisense strand underlying base sequence

<400> SEQUENCE: 231
aagaagugcu uuugugaucc a 21

<210> SEQ ID NO 232
<211> LENGTH: 21
<212> TYPE: RNA
<213> ORGANISM: Artificial Sequence
<220> FEATURE:
<223> OTHER INFORMATION: RNAi agent antisense strand underlying base sequence

<400> SEQUENCE: 232
ugucagaccu cugugaaagc c 21

<210> SEQ ID NO 233
<211> LENGTH: 21
<212> TYPE: RNA
<213> ORGANISM: Artificial Sequence
<220> FEATURE:
<223> OTHER INFORMATION: RNAi agent antisense strand underlying base sequence

<400> SEQUENCE: 233
uugaugucag accucuguga c 21

<210> SEQ ID NO 234
<211> LENGTH: 21
<212> TYPE: RNA
<213> ORGANISM: Artificial Sequence
<220> FEATURE:
<223> OTHER INFORMATION: RNAi agent antisense strand underlying base sequence

<400> SEQUENCE: 234
uuccaauaca ggccauaauc c 21

<210> SEQ ID NO 235
<211> LENGTH: 21
<212> TYPE: RNA
<213> ORGANISM: Artificial Sequence
<220> FEATURE:
<223> OTHER INFORMATION: RNAi agent antisense strand underlying base sequence

<400> SEQUENCE: 235
ucaucuauca gacuucuuac g 21

<210> SEQ ID NO 236
<211> LENGTH: 21

<212> TYPE: RNA
<213> ORGANISM: Artificial Sequence
<220> FEATURE:
<223> OTHER INFORMATION: RNAi agent antisense strand underlying base sequence

<400> SEQUENCE: 236
ucagguugag auaaagcugc c 21

<210> SEQ ID NO 237
<211> LENGTH: 21
<212> TYPE: RNA
<213> ORGANISM: Artificial Sequence
<220> FEATURE:
<223> OTHER INFORMATION: RNAi agent antisense strand underlying base sequence

<400> SEQUENCE: 237
uccagaauag aguugcaccg u 21

<210> SEQ ID NO 238
<211> LENGTH: 21
<212> TYPE: RNA
<213> ORGANISM: Artificial Sequence
<220> FEATURE:
<223> OTHER INFORMATION: RNAi agent antisense strand underlying base sequence

<400> SEQUENCE: 238
aaguccagaa uagaguugca c 21

<210> SEQ ID NO 239
<211> LENGTH: 21
<212> TYPE: RNA
<213> ORGANISM: Artificial Sequence
<220> FEATURE:
<223> OTHER INFORMATION: RNAi agent antisense strand underlying base sequence

<400> SEQUENCE: 239
ucuugaugua gugggagucg g 21

<210> SEQ ID NO 240
<211> LENGTH: 21
<212> TYPE: RNA
<213> ORGANISM: Artificial Sequence
<220> FEATURE:
<223> OTHER INFORMATION: RNAi agent antisense strand underlying base sequence

<400> SEQUENCE: 240
acaagauuag ucuugaugua g 21

<210> SEQ ID NO 241
<211> LENGTH: 21
<212> TYPE: RNA
<213> ORGANISM: Artificial Sequence
<220> FEATURE:
<223> OTHER INFORMATION: RNAi agent antisense strand underlying base sequence

<400> SEQUENCE: 241
ucagaauaga guugcaccgu u 21

<210> SEQ ID NO 242
<211> LENGTH: 21
<212> TYPE: RNA

<213> ORGANISM: Artificial Sequence
<220> FEATURE:
<223> OTHER INFORMATION: RNAi agent antisense strand underlying base sequence

<400> SEQUENCE: 242
ucagaauaga guugcaccgc u 21

<210> SEQ ID NO 243
<211> LENGTH: 21
<212> TYPE: RNA
<213> ORGANISM: Artificial Sequence
<220> FEATURE:
<223> OTHER INFORMATION: RNAi agent antisense strand underlying base sequence

<400> SEQUENCE: 243
ucagaauaga guugcaccgu g 21

<210> SEQ ID NO 244
<211> LENGTH: 21
<212> TYPE: RNA
<213> ORGANISM: Artificial Sequence
<220> FEATURE:
<223> OTHER INFORMATION: RNAi agent antisense strand underlying base sequence

<400> SEQUENCE: 244
ucagaauaga guugcaccgg u 21

<210> SEQ ID NO 245
<211> LENGTH: 21
<212> TYPE: RNA
<213> ORGANISM: Artificial Sequence
<220> FEATURE:
<223> OTHER INFORMATION: RNAi agent antisense strand underlying base sequence

<400> SEQUENCE: 245
ucagaauaga guugcaccgc c 21

<210> SEQ ID NO 246
<211> LENGTH: 21
<212> TYPE: RNA
<213> ORGANISM: Artificial Sequence
<220> FEATURE:
<223> OTHER INFORMATION: RNAi agent antisense strand underlying base sequence

<400> SEQUENCE: 246
ucagaauaga guugcaccgg c 21

<210> SEQ ID NO 247
<211> LENGTH: 21
<212> TYPE: RNA
<213> ORGANISM: Artificial Sequence
<220> FEATURE:
<223> OTHER INFORMATION: RNAi agent antisense strand underlying base sequence

<400> SEQUENCE: 247
agugacucca gguaggagua g 21

<210> SEQ ID NO 248
<211> LENGTH: 21
<212> TYPE: RNA
<213> ORGANISM: Artificial Sequence
<220> FEATURE:
<223> OTHER INFORMATION: RNAi agent antisense strand underlying base sequence

<400> SEQUENCE: 248
aagaacuuua ccagugacuc c 21

<210> SEQ ID NO 249
<211> LENGTH: 21
<212> TYPE: RNA
<213> ORGANISM: Artificial Sequence
<220> FEATURE:
<223> OTHER INFORMATION: RNAi agent antisense strand underlying base sequence

<400> SEQUENCE: 249
aagaacuuua ccagugacuc g 21

<210> SEQ ID NO 250
<211> LENGTH: 21
<212> TYPE: RNA
<213> ORGANISM: Artificial Sequence
<220> FEATURE:
<223> OTHER INFORMATION: RNAi agent antisense strand underlying base sequence

<400> SEQUENCE: 250
uugcagucca ccacaaacac g 21

<210> SEQ ID NO 251
<211> LENGTH: 21
<212> TYPE: RNA
<213> ORGANISM: Artificial Sequence
<220> FEATURE:
<223> OTHER INFORMATION: RNAi agent antisense strand underlying base sequence

<400> SEQUENCE: 251
ucagcaucga uggaaggagu g 21

<210> SEQ ID NO 252
<211> LENGTH: 21
<212> TYPE: RNA
<213> ORGANISM: Artificial Sequence
<220> FEATURE:
<223> OTHER INFORMATION: RNAi agent antisense strand underlying base sequence

<400> SEQUENCE: 252
agaguuucuu cucagcaucg a 21

<210> SEQ ID NO 253
<211> LENGTH: 21
<212> TYPE: RNA
<213> ORGANISM: Artificial Sequence
<220> FEATURE:
<223> OTHER INFORMATION: RNAi agent antisense strand underlying base sequence

<400> SEQUENCE: 253
ucaguauuca cgaacacagg g 21

<210> SEQ ID NO 254
<211> LENGTH: 21
<212> TYPE: RNA
<213> ORGANISM: Artificial Sequence
<220> FEATURE:

<223> OTHER INFORMATION: RNAi agent antisense strand underlying base
      sequence

<400> SEQUENCE: 254
ucaguauuca cgaacacagg c                                                21

<210> SEQ ID NO 255
<211> LENGTH: 21
<212> TYPE: RNA
<213> ORGANISM: Artificial Sequence
<220> FEATURE:
<223> OTHER INFORMATION: RNAi agent antisense strand underlying base
      sequence

<400> SEQUENCE: 255
ugaagaucau uuucuuguug g                                                21

<210> SEQ ID NO 256
<211> LENGTH: 21
<212> TYPE: RNA
<213> ORGANISM: Artificial Sequence
<220> FEATURE:
<223> OTHER INFORMATION: RNAi agent antisense strand underlying base
      sequence

<400> SEQUENCE: 256
aagaagugcu uuugugaucc g                                                21

<210> SEQ ID NO 257
<211> LENGTH: 21
<212> TYPE: RNA
<213> ORGANISM: Artificial Sequence
<220> FEATURE:
<223> OTHER INFORMATION: RNAi agent antisense strand underlying base
      sequence

<400> SEQUENCE: 257
aagaagugcu uuugugaucc c                                                21

<210> SEQ ID NO 258
<211> LENGTH: 21
<212> TYPE: RNA
<213> ORGANISM: Artificial Sequence
<220> FEATURE:
<223> OTHER INFORMATION: RNAi agent antisense strand underlying base
      sequence

<400> SEQUENCE: 258
uagaagugcu uuugugaucc c                                                21

<210> SEQ ID NO 259
<211> LENGTH: 21
<212> TYPE: RNA
<213> ORGANISM: Artificial Sequence
<220> FEATURE:
<223> OTHER INFORMATION: RNAi agent antisense strand underlying base
      sequence

<400> SEQUENCE: 259
ucaucuauca gacuucuuac c                                                21

<210> SEQ ID NO 260
<211> LENGTH: 21
<212> TYPE: RNA
<213> ORGANISM: Artificial Sequence
<220> FEATURE:
<223> OTHER INFORMATION: RNAi agent sense strand underlying base sequence

<400> SEQUENCE: 260
gacggugcaa cucuauucug a 21

<210> SEQ ID NO 261
<211> LENGTH: 21
<212> TYPE: RNA
<213> ORGANISM: Artificial Sequence
<220> FEATURE:
<223> OTHER INFORMATION: RNAi agent sense strand underlying base sequence

<400> SEQUENCE: 261
ugaggucaac auccuaggac a 21

<210> SEQ ID NO 262
<211> LENGTH: 21
<212> TYPE: RNA
<213> ORGANISM: Artificial Sequence
<220> FEATURE:
<223> OTHER INFORMATION: RNAi agent sense strand underlying base sequence
<220> FEATURE:
<221> NAME/KEY: modified_base
<222> LOCATION: 18
<223> OTHER INFORMATION: n = insosine (hypoxanthine)

<400> SEQUENCE: 262
ugaggucaac auccuagnac a 21

<210> SEQ ID NO 263
<211> LENGTH: 21
<212> TYPE: RNA
<213> ORGANISM: Artificial Sequence
<220> FEATURE:
<223> OTHER INFORMATION: RNAi agent sense strand underlying base sequence

<400> SEQUENCE: 263
gucaacaucc uaggacauuu u 21

<210> SEQ ID NO 264
<211> LENGTH: 21
<212> TYPE: RNA
<213> ORGANISM: Artificial Sequence
<220> FEATURE:
<223> OTHER INFORMATION: RNAi agent sense strand underlying base sequence
<220> FEATURE:
<221> NAME/KEY: modified_base
<222> LOCATION: 17
<223> OTHER INFORMATION: n = 2-aminoadenine

<400> SEQUENCE: 264
gucaacaucc uaggacnuuu u 21

<210> SEQ ID NO 265
<211> LENGTH: 21
<212> TYPE: RNA
<213> ORGANISM: Artificial Sequence
<220> FEATURE:
<223> OTHER INFORMATION: RNAi agent sense strand underlying base sequence

<400> SEQUENCE: 265
uccuaggaca uuuuuggauc a 21

<210> SEQ ID NO 266
<211> LENGTH: 21
<212> TYPE: RNA
<213> ORGANISM: Artificial Sequence
<220> FEATURE:
<223> OTHER INFORMATION: RNAi agent sense strand underlying base
sequence
<220> FEATURE:
<221> NAME/KEY: modified_base
<222> LOCATION: 17
<223> OTHER INFORMATION: n = insosine (hypoxanthine)

<400> SEQUENCE: 266
uccuaggaca uuuuugnauc a 21

<210> SEQ ID NO 267
<211> LENGTH: 21
<212> TYPE: RNA
<213> ORGANISM: Artificial Sequence
<220> FEATURE:
<223> OTHER INFORMATION: RNAi agent sense strand underlying base
sequence

<400> SEQUENCE: 267
ggaggucaac auccuaggac a 21

<210> SEQ ID NO 268
<211> LENGTH: 21
<212> TYPE: RNA
<213> ORGANISM: Artificial Sequence
<220> FEATURE:
<223> OTHER INFORMATION: RNAi agent sense strand underlying base
sequence

<400> SEQUENCE: 268
agaggucaac auccuaggac a 21

<210> SEQ ID NO 269
<211> LENGTH: 21
<212> TYPE: RNA
<213> ORGANISM: Artificial Sequence
<220> FEATURE:
<223> OTHER INFORMATION: RNAi agent sense strand underlying base
sequence
<220> FEATURE:
<221> NAME/KEY: modified_base
<222> LOCATION: 18
<223> OTHER INFORMATION: n = insosine (hypoxanthine)

<400> SEQUENCE: 269
ggaggucaac auccuagnac a 21

<210> SEQ ID NO 270
<211> LENGTH: 21
<212> TYPE: RNA
<213> ORGANISM: Artificial Sequence
<220> FEATURE:
<223> OTHER INFORMATION: RNAi agent sense strand underlying base
sequence
<220> FEATURE:
<221> NAME/KEY: modified_base
<222> LOCATION: 17
<223> OTHER INFORMATION: n = insosine (hypoxanthine)

<400> SEQUENCE: 270
accuaggaca uuuuugnauc a 21

<210> SEQ ID NO 271

<211> LENGTH: 21
<212> TYPE: RNA
<213> ORGANISM: Artificial Sequence
<220> FEATURE:
<223> OTHER INFORMATION: RNAi agent sense strand underlying base
      sequence

<400> SEQUENCE: 271
gccuaggaca uuuuuggauc a 21

<210> SEQ ID NO 272
<211> LENGTH: 21
<212> TYPE: RNA
<213> ORGANISM: Artificial Sequence
<220> FEATURE:
<223> OTHER INFORMATION: RNAi agent sense strand underlying base
      sequence
<220> FEATURE:
<221> NAME/KEY: modified_base
<222> LOCATION: 17
<223> OTHER INFORMATION: n = insosine (hypoxanthine)

<400> SEQUENCE: 272
gccuaggaca uuuuugnauc a 21

<210> SEQ ID NO 273
<211> LENGTH: 21
<212> TYPE: RNA
<213> ORGANISM: Artificial Sequence
<220> FEATURE:
<223> OTHER INFORMATION: RNAi agent sense strand underlying base
      sequence

<400> SEQUENCE: 273
gcuucugauc accaucaucu a 21

<210> SEQ ID NO 274
<211> LENGTH: 21
<212> TYPE: RNA
<213> ORGANISM: Artificial Sequence
<220> FEATURE:
<223> OTHER INFORMATION: RNAi agent sense strand underlying base
      sequence

<400> SEQUENCE: 274
gugaauaaug cugggacagu a 21

<210> SEQ ID NO 275
<211> LENGTH: 21
<212> TYPE: RNA
<213> ORGANISM: Artificial Sequence
<220> FEATURE:
<223> OTHER INFORMATION: RNAi agent sense strand underlying base
      sequence

<400> SEQUENCE: 275
uggaucacaa aagcacuucu u 21

<210> SEQ ID NO 276
<211> LENGTH: 21
<212> TYPE: RNA
<213> ORGANISM: Artificial Sequence
<220> FEATURE:
<223> OTHER INFORMATION: RNAi agent sense strand underlying base
      sequence

<400> SEQUENCE: 276
ggcuuucaca gaggucugac a 21

<210> SEQ ID NO 277
<211> LENGTH: 21
<212> TYPE: RNA
<213> ORGANISM: Artificial Sequence
<220> FEATURE:
<223> OTHER INFORMATION: RNAi agent sense strand underlying base
      sequence

<400> SEQUENCE: 277
gucacagagg ucugacauca a 21

<210> SEQ ID NO 278
<211> LENGTH: 21
<212> TYPE: RNA
<213> ORGANISM: Artificial Sequence
<220> FEATURE:
<223> OTHER INFORMATION: RNAi agent sense strand underlying base
      sequence

<400> SEQUENCE: 278
ggauuauggc cuguauugga a 21

<210> SEQ ID NO 279
<211> LENGTH: 21
<212> TYPE: RNA
<213> ORGANISM: Artificial Sequence
<220> FEATURE:
<223> OTHER INFORMATION: RNAi agent sense strand underlying base
      sequence

<400> SEQUENCE: 279
cguaagaagu cugauagaug a 21

<210> SEQ ID NO 280
<211> LENGTH: 21
<212> TYPE: RNA
<213> ORGANISM: Artificial Sequence
<220> FEATURE:
<223> OTHER INFORMATION: RNAi agent sense strand underlying base
      sequence

<400> SEQUENCE: 280
ggcagcuuua ucucaaccug a 21

<210> SEQ ID NO 281
<211> LENGTH: 21
<212> TYPE: RNA
<213> ORGANISM: Artificial Sequence
<220> FEATURE:
<223> OTHER INFORMATION: RNAi agent sense strand underlying base
      sequence

<400> SEQUENCE: 281
acggugcaac ucuauucugg a 21

<210> SEQ ID NO 282
<211> LENGTH: 21
<212> TYPE: RNA
<213> ORGANISM: Artificial Sequence
<220> FEATURE:
<223> OTHER INFORMATION: RNAi agent sense strand underlying base
      sequence

<400> SEQUENCE: 282
gugcaacucu auucuggacu u 21

<210> SEQ ID NO 283
<211> LENGTH: 21
<212> TYPE: RNA
<213> ORGANISM: Artificial Sequence
<220> FEATURE:
<223> OTHER INFORMATION: RNAi agent sense strand underlying base sequence

<400> SEQUENCE: 283
ccgacuccca cuacaucaag a 21

<210> SEQ ID NO 284
<211> LENGTH: 21
<212> TYPE: RNA
<213> ORGANISM: Artificial Sequence
<220> FEATURE:
<223> OTHER INFORMATION: RNAi agent sense strand underlying base sequence

<400> SEQUENCE: 284
cuacaucaag acuaaucuug u 21

<210> SEQ ID NO 285
<211> LENGTH: 21
<212> TYPE: RNA
<213> ORGANISM: Artificial Sequence
<220> FEATURE:
<223> OTHER INFORMATION: RNAi agent sense strand underlying base sequence

<400> SEQUENCE: 285
cggugcaacu cuauucugau u 21

<210> SEQ ID NO 286
<211> LENGTH: 21
<212> TYPE: RNA
<213> ORGANISM: Artificial Sequence
<220> FEATURE:
<223> OTHER INFORMATION: RNAi agent sense strand underlying base sequence

<400> SEQUENCE: 286
agcggugcaa cucuauucug a 21

<210> SEQ ID NO 287
<211> LENGTH: 21
<212> TYPE: RNA
<213> ORGANISM: Artificial Sequence
<220> FEATURE:
<223> OTHER INFORMATION: RNAi agent sense strand underlying base sequence

<400> SEQUENCE: 287
cacggugcaa cucuauucug a 21

<210> SEQ ID NO 288
<211> LENGTH: 21
<212> TYPE: RNA
<213> ORGANISM: Artificial Sequence
<220> FEATURE:
<223> OTHER INFORMATION: RNAi agent sense strand underlying base sequence

<400> SEQUENCE: 288
accggugcaa cucuauucug a 21

<210> SEQ ID NO 289
<211> LENGTH: 21
<212> TYPE: RNA
<213> ORGANISM: Artificial Sequence
<220> FEATURE:
<223> OTHER INFORMATION: RNAi agent sense strand underlying base
sequence
<220> FEATURE:
<221> NAME/KEY: modified_base
<222> LOCATION: 7
<223> OTHER INFORMATION: n = insosine (hypoxanthine)

<400> SEQUENCE: 289
gacgguncaa cucuauucug a 21

<210> SEQ ID NO 290
<211> LENGTH: 21
<212> TYPE: RNA
<213> ORGANISM: Artificial Sequence
<220> FEATURE:
<223> OTHER INFORMATION: RNAi agent sense strand underlying base
sequence
<220> FEATURE:
<221> NAME/KEY: modified_base
<222> LOCATION: 5
<223> OTHER INFORMATION: n = insosine (hypoxanthine)

<400> SEQUENCE: 290
gacgnugcaa cucuauucug a 21

<210> SEQ ID NO 291
<211> LENGTH: 21
<212> TYPE: RNA
<213> ORGANISM: Artificial Sequence
<220> FEATURE:
<223> OTHER INFORMATION: RNAi agent sense strand underlying base
sequence
<220> FEATURE:
<221> NAME/KEY: modified_base
<222> LOCATION: 20
<223> OTHER INFORMATION: n = insosine (hypoxanthine)

<400> SEQUENCE: 291
gacggugcaa cucuauucun a 21

<210> SEQ ID NO 292
<211> LENGTH: 21
<212> TYPE: RNA
<213> ORGANISM: Artificial Sequence
<220> FEATURE:
<223> OTHER INFORMATION: RNAi agent sense strand underlying base
sequence

<400> SEQUENCE: 292
ggcggugcaa cucuauucug a 21

<210> SEQ ID NO 293
<211> LENGTH: 21
<212> TYPE: RNA
<213> ORGANISM: Artificial Sequence
<220> FEATURE:
<223> OTHER INFORMATION: RNAi agent sense strand underlying base
sequence

<400> SEQUENCE: 293
gccggugcaa cucuauucug a 21

<210> SEQ ID NO 294
<211> LENGTH: 21

```
<212> TYPE: RNA
<213> ORGANISM: Artificial Sequence
<220> FEATURE:
<223> OTHER INFORMATION: RNAi agent sense strand underlying base
      sequence

<400> SEQUENCE: 294

cuacuccuac cuggagucac u                                              21


<210> SEQ ID NO 295
<211> LENGTH: 21
<212> TYPE: RNA
<213> ORGANISM: Artificial Sequence
<220> FEATURE:
<223> OTHER INFORMATION: RNAi agent sense strand underlying base
      sequence

<400> SEQUENCE: 295

ggagucacug guaaaguucu u                                              21


<210> SEQ ID NO 296
<211> LENGTH: 21
<212> TYPE: RNA
<213> ORGANISM: Artificial Sequence
<220> FEATURE:
<223> OTHER INFORMATION: RNAi agent sense strand underlying base
      sequence

<400> SEQUENCE: 296

cgagucacug guaaaguucu u                                              21


<210> SEQ ID NO 297
<211> LENGTH: 21
<212> TYPE: RNA
<213> ORGANISM: Artificial Sequence
<220> FEATURE:
<223> OTHER INFORMATION: RNAi agent sense strand underlying base
      sequence

<400> SEQUENCE: 297

cguguuugug guggacugca a                                              21


<210> SEQ ID NO 298
<211> LENGTH: 21
<212> TYPE: RNA
<213> ORGANISM: Artificial Sequence
<220> FEATURE:
<223> OTHER INFORMATION: RNAi agent sense strand underlying base
      sequence

<400> SEQUENCE: 298

cacuccuucc aucgaugcug a                                              21


<210> SEQ ID NO 299
<211> LENGTH: 21
<212> TYPE: RNA
<213> ORGANISM: Artificial Sequence
<220> FEATURE:
<223> OTHER INFORMATION: RNAi agent sense strand underlying base
      sequence

<400> SEQUENCE: 299

ucgaugcuga gaagaaacuc u                                              21


<210> SEQ ID NO 300
<211> LENGTH: 21
<212> TYPE: RNA
```

<213> ORGANISM: Artificial Sequence
<220> FEATURE:
<223> OTHER INFORMATION: RNAi agent sense strand underlying base sequence

<400> SEQUENCE: 300
cccuguguuc gugaauacug a 21

<210> SEQ ID NO 301
<211> LENGTH: 21
<212> TYPE: RNA
<213> ORGANISM: Artificial Sequence
<220> FEATURE:
<223> OTHER INFORMATION: RNAi agent sense strand underlying base sequence

<400> SEQUENCE: 301
gccuguguuc gugaauacug a 21

<210> SEQ ID NO 302
<211> LENGTH: 21
<212> TYPE: RNA
<213> ORGANISM: Artificial Sequence
<220> FEATURE:
<223> OTHER INFORMATION: RNAi agent sense strand underlying base sequence

<400> SEQUENCE: 302
ccaacaagaa aaugaucuuc a 21

<210> SEQ ID NO 303
<211> LENGTH: 21
<212> TYPE: RNA
<213> ORGANISM: Artificial Sequence
<220> FEATURE:
<223> OTHER INFORMATION: RNAi agent sense strand underlying base sequence

<400> SEQUENCE: 303
cggaucacaa aagcacuucu u 21

<210> SEQ ID NO 304
<211> LENGTH: 21
<212> TYPE: RNA
<213> ORGANISM: Artificial Sequence
<220> FEATURE:
<223> OTHER INFORMATION: RNAi agent sense strand underlying base sequence

<400> SEQUENCE: 304
gggaucacaa aagcacuucu u 21

<210> SEQ ID NO 305
<211> LENGTH: 21
<212> TYPE: RNA
<213> ORGANISM: Artificial Sequence
<220> FEATURE:
<223> OTHER INFORMATION: RNAi agent sense strand underlying base sequence

<400> SEQUENCE: 305
gggaucacaa aagcacuucu a 21

<210> SEQ ID NO 306
<211> LENGTH: 21
<212> TYPE: RNA
<213> ORGANISM: Artificial Sequence -continued

```
<220> FEATURE:
<223> OTHER INFORMATION: RNAi agent sense strand underlying base
      sequence
<220> FEATURE:
<221> NAME/KEY: modified_base
<222> LOCATION: 20
<223> OTHER INFORMATION: n = insosine (hypoxanthine)

<400> SEQUENCE: 306

cguaagaagu cugauagaun a                                                21


<210> SEQ ID NO 307
<211> LENGTH: 21
<212> TYPE: RNA
<213> ORGANISM: Artificial Sequence
<220> FEATURE:
<223> OTHER INFORMATION: RNAi agent sense strand underlying base
      sequence

<400> SEQUENCE: 307

gguaagaagu cugauagaug a                                                21


<210> SEQ ID NO 308
<211> LENGTH: 21
<212> TYPE: RNA
<213> ORGANISM: Artificial Sequence
<220> FEATURE:
<223> OTHER INFORMATION: RNAi agent sense strand underlying base
      sequence
<220> FEATURE:
<221> NAME/KEY: modified_base
<222> LOCATION: 20
<223> OTHER INFORMATION: n = insosine (hypoxanthine)

<400> SEQUENCE: 308

gguaagaagu cugauagaun a                                                21


<210> SEQ ID NO 309
<211> LENGTH: 21
<212> TYPE: RNA
<213> ORGANISM: Artificial Sequence
<220> FEATURE:
<223> OTHER INFORMATION: RNAi agent sense strand underlying base
      sequence
<220> FEATURE:
<221> NAME/KEY: modified_base
<222> LOCATION: 17
<223> OTHER INFORMATION: n = insosine (hypoxanthine)

<400> SEQUENCE: 309

gguaagaagu cugauanaug a                                                21
```

RNAI AGENTS FOR INHIBITING EXPRESSION OF 17BETA-HSD TYPE 13 (HSD17B13), COMPOSITIONS THEREOF, AND METHODS OF USE

CROSS REFERENCE TO RELATED APPLICATIONS

This application is a U.S. National Phase Application under 35 U.S.C. § 371 of International Patent Application No. PCT/US19/51707, filed on Sep. 18, 2019, which claims priority from U.S. Provisional Patent Application Ser. No. 62/890,220, filed on Aug. 22, 2019, U.S. Provisional Patent Application Ser. No. 62/773,707, filed on Nov. 30, 2018, and U.S. Provisional Patent Application Ser. No. 62/733,320, filed on Sep. 19, 2018, the contents of each of which are incorporated herein by reference in their entirety.

SEQUENCE LISTING

This application contains a Sequence Listing which has been submitted in ASCII format and is hereby incorporated by reference in its entirety. The ASCII copy is named 30667-WO_SEQLIST.txt and is 75 kb in size.

FIELD OF THE INVENTION

The present disclosure relates to RNA interference (RNAi) agents, e.g., double stranded RNAi agents, for inhibition of 17β-hydroxysteroid dehydrogenase type 13 gene expression, compositions that include 17β-hydroxysteroid dehydrogenase type 13 RNAi agents, and methods of use thereof.

BACKGROUND

Hepatic lipid droplet protein 17β-hydroxysteroid dehydrogenase type 13 (commonly referred to as HSD17B13, 17β-HSD13, HSD17β13, 17beta-HSD13, 17beta-HSD type 13, or 17B-HSD13) is a member of the 17beta-hydroxysteroid dehydrogenases (17β-HSD) family. The 17β-HSD family is comprised of 14 enzymes that participate in the reduction or oxidation of sex hormones, fatty acids, and bile acids. Tissue distribution, subcellular localization, and catalytic preference differ between the various family members. The 17β-HSD family exhibits diverse substrate specificities, including steroids, lipids, and retinoids.

17β-HSD13 protein is distributed across a wide range of tissues in the body and is encoded by the HSD17B13 gene (alternatively referred to as the 17β-HSD13 gene). The highest expression level is known to be found in hepatocytes in the liver, whereas low levels can be detected in the ovary, bone marrow, kidney, brain, lung, skeletal muscle, bladder, and testis. The function of 17β-HSD13 is not completely understood, however, some of the 17β-HSD family members, including 17β-HSD-4, -7, -10, and -12, have been shown to participate in carbohydrate and fatty acid metabolism. This suggests that 17β-HSD13 may also play a role in lipid metabolic pathways. It has been reported that hepatic up-regulation of 17β-HSD13 has been observed in patients with fatty liver, which supports a role of this enzyme in the pathogenesis of non-alcoholic fatty liver disease (NAFLD).

Wen Su et al. previously identified 17β-HSD13 as a lipid droplet (LD)-associated protein in NAFLD patients, and reported that 17β-HSD13 was among one of the most abundantly expressed LD proteins specifically localized on the surface of LDs. (Wen Su et al., *Comparative proteomic study reveals* 17β-*HSD*13 *as a pathogenic protein in non-alcoholic fatty live disease,* 111 *PNAS* 11437-11442 (2014)). Further, the level of 17β-HSD13 was found to be up-regulated in the livers of patients and mice with NAFLD. Overexpression resulted in an increase in the number and size of LDs, whereas gene silencing of HSD17B13 attenuated oleic acid-induced LD formation in cultured hepatocytes. Hepatic overexpression of 17β-HSD13 protein in C57BL/6 mice has been shown to significantly increase lipogenesis and triglyceride (TG) contents in the livers, leading to a fatty liver phenotype.

Additional evidence implicating HSD17B13 gene expression in the pathogenesis of NAFLD and non-alcoholic steatohepatitis (NASH) was provided by N. S. Abul-Husn et. al., *A Protein-Truncating HSD*17*B*13 *Variant and Protection from Chronic Liver Disease,* 378 N. Eng. J. Med. 1096-1106 (2018). This group conducted a genome-wide association study, which revealed a splice variant (rs72613567: TA) in HSD17B13 that was associated with reduced levels of alanine amino transferase (ALT) and aspartate amino transferase (AST), indicating less liver injury and inflammation in patients with fatty liver. The splice variant produces a truncated loss of function protein, suggesting that HSD17B13 normally generates a product that can facilitate hepatocellular damage.

NAFLD is a major health concern worldwide. NAFLD is an umbrella term that comprises a continuum of liver conditions varying in severity of injury and resulting fibrosis. Among these, hepatic steatosis (fatty liver) alone is generally referred to as NAFL, and NASH is typically defined as a more severe process with inflammation and hepatocyte damage (steatohepatitis). Generally, NASH is accompanied by fibrosis, which often progresses to cirrhosis. Patients with only NAFL carry a lower risk of adverse outcomes, whereas the presence of NASH increases the risks of liver and non-liver-related outcomes. Adverse hepatic outcomes related to NASH include liver failure, cirrhosis, and hepatocellular carcinoma. Non-liver-associated adverse outcomes are usually related to increased cardiovascular disease and malignancy.

Globally, the prevalence of NAFLD is estimated at ~25%. In the United States, the number of NAFLD cases is projected to grow from 83.1 million in 2015 (~25% of the population) to 100.9 million in 2030. NASH is expected to make up an increased proportion of these cases, rising from 20% to 27% of adults with NAFLD. This rising disease prevalence will undoubtedly lead to an increased economic burden, and will be accompanied by both an increasing number of patients with end-stage liver disease requiring liver transplantation and a dramatic increase in hepatocellular carcinoma. Compared to incidence in other liver diseases, a larger percentage (~35-50%) of hepatocellular carcinoma cases that arise in NASH occur before patients are cirrhotic and routine screening for cancer is conducted. This frequently results in tumors that are larger and less amenable to curative therapies than those with other etiologies.

Alcohol-related liver disease (ARLD) is also prevalent worldwide and refers to a progressive liver disease brought on by excessive, prolonged alcohol use. Various diseases states of ARLD exist and include alcoholic fatty liver (alcoholic steatosis), alcoholic hepatitis, and cirrhosis.

Presently, there are no approved pharmacological agents for the treatment of NASH or other diseases and conditions that fall under NAFLD or ARLD.

SUMMARY

There is a need for novel HSD17B13 gene-specific RNA interference (RNAi) agents (also herein termed RNAi agent, RNAi trigger, or trigger), e.g., double stranded RNAi agents, that are able to selectively and efficiently inhibit the expression of an HSD17B13 gene. Further, there exists a need for compositions that include novel HSD17B13-specific RNAi agents for the treatment of diseases such as, among others, NAFLD, NASH, hepatic fibrosis, and alcoholic or non-alcoholic liver diseases, including cirrhosis.

In general, the present disclosure features novel HSD17B13 gene-specific RNAi agents, compositions that include HSD17B13 RNAi agents, and methods for inhibiting expression of an HSD17B13 gene in vitro and/or in vivo using the HSD17B13 RNAi agents and compositions that include HSD17B13 RNAi agents described herein. The HSD17B13 RNAi agents described herein can selectively and efficiently decrease, inhibit, or silence expression of an HSD17B13 gene in a subject, e.g., a human or animal subject.

The described HSD17B13 RNAi agents can be used in methods for therapeutic treatment (including the prophylactic and preventative treatment) of symptoms and diseases associated with NAFLD, NASH, hepatic fibrosis, and alcoholic or non-alcoholic liver diseases, including cirrhosis. The methods disclosed herein include the administration of one or more HSD17B13 RNAi agents to a subject, e.g., a human or animal subject, using any suitable methods known in the art, such as subcutaneous injection or intravenous administration.

In one aspect, the disclosure features RNAi agents for inhibiting expression of an HSD17B13 gene, wherein the RNAi agent includes a sense strand (also referred to as a passenger strand) and an antisense strand (also referred to as a guide strand). The sense strand and the antisense strand can be partially, substantially, or fully complementary to each other. The length of the RNAi agent sense and antisense strands described herein each can be 16 to 49 nucleotides in length. In some embodiments, the sense and antisense strands are independently 17 to 26 nucleotides in length. The sense and antisense strands can be either the same length or different lengths. In some embodiments, the sense and antisense strands are independently 21 to 26 nucleotides in length. In some embodiments, the sense and antisense strands are independently 21 to 24 nucleotides in length. In some embodiments, both the sense strand and the antisense strand are 21 nucleotides in length. In some embodiments, the antisense strands are independently 18, 19, 20, 21, 22, 23, 24, 25, 26, 27, 28, 29, or 30 nucleotides in length. In some embodiments, the sense strands are independently 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 nucleotides in length. The RNAi agents described herein, upon delivery to a cell expressing HSD17B13, inhibit the expression of one or more HSD17B13 genes in vivo or in vitro.

The HSD17B13 RNAi agents disclosed herein target a human HSD17B13 gene (see, e.g., SEQ ID NO:1). In some embodiments, the HSD17B13 RNAi agents disclosed herein target a portion of an HSD17B13 gene having the sequence of any of the sequences disclosed in Table 1.

Examples of HSD17B13 RNAi agent sense strands and antisense strands that can be included in the HSD17B13 RNAi agents disclosed herein are provided in Table 3 and Table 4. Examples of HSD17B13 RNAi agent duplexes are provided in Table 5, and the chemical structures and schematic diagrams of certain HSD17B13 RNAi agents which are shown linked to targeting ligands that include N-acetyl-galactosamine, are depicted in FIGS. 1A through 10D and FIGS. 11A through 11E. Examples of 19-nucleotide core stretch sequences that consist of or are included in the sense strands and antisense strands of HSD17B13 RNAi agents disclosed herein, are provided in Table 2.

In another aspect, the disclosure features methods for delivering HSD17B13 RNAi agents to liver cells in a subject, such as a mammal, in vivo. Also described herein are compositions for use in such methods.

The one or more HSD17B13 RNAi agents can be delivered to target cells or tissues using any oligonucleotide delivery technology known in the art. In some embodiments, an HSD17B13 RNAi agent is delivered to target cells or tissues by covalently linking or conjugating the RNAi agent to a targeting group, such as an asialoglycoprotein receptor ligand (i.e., a ligand that includes a compound having affinity for the asialoglycoprotein receptor, which is abundantly expressed on hepatocytes in the liver). In some embodiments, an asialoglycoprotein receptor ligand includes, consists of, or consists essentially of, a galactose or galactose-derivative cluster. In some embodiments, an HSD17B13 RNAi agent is linked to a targeting group or targeting ligand that comprises the galactose derivative N-acetyl-galactosamine. In some embodiments, a galactose derivative cluster includes or consists of an N-acetyl-galactosamine trimer or an N-acetyl-galactosamine tetramer.

In some embodiments, the HSD17B13 RNAi agents disclosed herein that are conjugated to targeting groups or targeting ligands that include N-acetyl-galactosamine are selectively internalized by liver cells, and hepatocytes in particular, either through receptor-mediated endocytosis or by other means.

In some embodiments, a targeting group is linked to the 3' or 5' end of the sense strand of an HSD17B13 RNAi agent disclosed herein. In some embodiments, a targeting group is linked to the 5' end of the sense strand.

Examples of targeting ligands and targeting groups useful for delivering the HSD17B13 RNAi agents disclosed herein to hepatocytes are disclosed, for example, in International Patent Application Publication Nos. WO 2018/044350 and WO 2017/156012, which are incorporated by reference herein in their entirety. In some embodiments, the HSD17B13 RNAi agents described herein can be linked to one or more targeting ligands having the structure of (NAG25), (NAG25)s, (NAG26), (NAG26)s, (NAG27), (NAG27)s, (NAG28), (NAG28)s, (NAG29), (NAG29)s, (NAG30), (NAG30)s, (NAG31), (NAG31)s, (NAG32), (NAG32)s, (NAG33), (NAG33)s, (NAG34), (NAG34)s, (NAG35), (NAG35)s, (NAG36), (NAG36)s, (NAG37), (NAG37)s, (NAG38), (NAG38)s, (NAG39), (NAG39)s, each as defined herein in Table 6.

In some embodiments, the HSD17B13 RNAi agents described herein are linked to a targeting ligand that comprises three N-acetyl-galactosamine moieties at the 5' end of the sense strand, where the targeting ligand has the structure of (NAG25), (NAG25)s, (NAG26), (NAG26)s, (NAG27), (NAG27)s, (NAG28), (NAG28)s, (NAG29), (NAG29)s, (NAG30), (NAG30)s, (NAG31), (NAG31)s, (NAG32), (NAG32)s, (NAG33), (NAG33)s, (NAG34), (NAG34)s, (NAG35), (NAG35)s, (NAG36), (NAG36)s, (NAG37), (NAG37)s, (NAG38), (NAG38)s, (NAG39), (NAG39)s, each as defined herein in Table 6.

In some embodiments, described herein are compositions that include one or more HSD17B13 RNAi agents that have the duplex structures disclosed in Table 5.

In another aspect, the disclosure features methods for inhibiting expression of an HSD17B13 gene, wherein the methods include administering to a subject or to a cell of a subject an amount of an HSD17B13 RNAi agent capable of inhibiting the expression of an HSD17B13 gene, wherein the HSD17B13 RNAi agent comprises a sense strand and an antisense strand, and wherein the antisense strand includes the sequence of any one of the antisense strand nucleotide sequences in Table 2 or Table 3. In some embodiments, disclosed herein are methods of inhibiting expression of an HSD17B13 gene, wherein the methods include administering to a subject or to a cell an amount of an HSD17B13 RNAi agent capable of inhibiting the expression of an HSD17B13 gene, wherein the HSD17B13 RNAi agent comprises a sense strand and an antisense strand, and wherein the sense strand includes the sequence of any one of the sense strand nucleotide sequences in Tables 2 or 4. In some embodiments, disclosed herein are methods for inhibiting expression of an HSD17B13 gene in a cell or a subject, wherein the methods include administering to the cell or subject an HSD17B13 RNAi agent having a sense strand comprising the sequence of any of the sequences in Table 4, and an antisense strand comprising the sequence of any of the sequences in Table 3. Compositions for use in such methods are also disclosed herein.

In a further aspect, the disclosure features methods of treatment (including preventative or prophylactic treatment) of diseases or symptoms caused by NAFLD, NASH, hepatic fibrosis, and/or alcoholic or non-alcoholic liver diseases, including cirrhosis, wherein the methods include administering to a subject in need thereof an HSD17B13 RNAi agent having an antisense strand that includes the sequence of any of the sequences in Tables 2 or 3. In some embodiments, described herein are methods of treatment (including preventative treatment) of diseases or symptoms caused by NAFLD, NASH, hepatic fibrosis, and/or alcoholic or non-alcoholic liver diseases, including cirrhosis, wherein the methods include administering to a subject in need thereof an HSD17B13 RNAi agent having a sense strand comprising the sequence of any of the sequences in Tables 2 or 4. Also described herein are compositions for use in such methods.

In some embodiments, compositions for delivering an HSD17B13 RNAi agent to a liver cell, particularly hepatocytes, in vivo, are described, the compositions comprising: an HSD17B13 RNAi agent linked or conjugated to a targeting group. In some embodiments, the targeting group is N-acetyl-galactosamine.

In some embodiments, an HSD17B13 RNAi agent disclosed herein includes an antisense strand that consists of, consists essentially of, or comprises a nucleobase sequence differing by 0 or 1 nucleobases from the nucleotide sequence (5'→3') UCAUCUAUCAGACUUCUUACG (SEQ ID NO:3). In some embodiments, an HSD17B13 RNAi agent disclosed herein includes an antisense strand that consists of, consists essentially of, or comprises a nucleotide sequence differing by no more than 1 nucleotide from the nucleotide sequence (5'→3') UCAUCUAUCAGACUUCUUACG (SEQ ID NO:3), wherein all or substantially all of the nucleotides are modified nucleotides. In some embodiments, an HSD17B13 RNAi agent disclosed herein includes an antisense strand that consists of, consists essentially of, or comprises a nucleobase sequence differing by 0 or 1 nucleobases from the nucleotide sequence (5'→3') UCAUCUAUCAGACUUCUUACG (SEQ ID NO:3), wherein SEQ ID NO:3 is located at positions 1-21 (5'→3') of the antisense strand.

In some embodiments, an HSD17B13 RNAi agent disclosed herein includes an antisense strand that consists of, consists essentially of, or comprises a modified nucleotide sequence differing by no more than 1 nucleotide from the nucleotide sequence (5'→3') usCfsasUfcUfaUfcAfgAfcUfuCfuUfaCfsg (SEQ ID NO:2), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand. As the person of ordinary skill in the art would clearly understand, the inclusion of a phosphorothioate linkage as shown in the modified nucleotide sequences disclosed herein replaces the phosphodiester linkage typically present in oligonucleotides (see, e.g., FIGS. 11A through 11E showing all internucleoside linkages). In some embodiments, an HSD17B13 RNAi agent disclosed herein includes an antisense strand that consists of, consists essentially of, or comprises the nucleotide sequence (5'→3') usCfsasUfcUfaUfcAfgAfcUfuCfuUfaCfsg (SEQ ID NO:2), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand.

In some embodiments, an HSD17B13 RNAi agent disclosed herein includes an antisense strand that consists of, consists essentially of, or comprises a modified nucleotide sequence differing by no more than 1 nucleotide from the nucleotide sequence (5'→3') usCfsasUfcUfaucagAfcUfuCfuUfaCfsg (SEQ ID NO:4), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand. As the person of ordinary skill in the art would clearly understand, the inclusion of a phosphorothioate linkage as shown in the modified nucleotide sequences disclosed herein replaces the phosphodiester linkage typically present in oligonucleotides (see, e.g., FIGS. 11A through 11E showing all internucleoside linkages). In some embodiments, an HSD17B13 RNAi agent disclosed herein includes an antisense strand that consists of, consists essentially of, or comprises the nucleotide sequence (5'→3') usCfsasUfcUfaucagAfcUfuCfuUfaCfsg (SEQ ID NO:4), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand.

In some embodiments, an HSD17B13 RNAi agent disclosed herein includes an antisense strand that consists of, consists essentially of, or comprises a nucleobase sequence differing by 0 or 1 nucleobases from the nucleotide sequence (5'→3') UGAUCCAAAAAUGUCCUAGGC (SEQ ID NO:6). In some embodiments, an HSD17B13 RNAi agent disclosed herein includes an antisense strand that consists of, consists essentially of, or comprises a nucleotide sequence differing by no more than 1 nucleotide from the nucleotide sequence (5'→3') UGAUCCAAAAAUGUCCUAGGC (SEQ ID NO:6), wherein all or substantially all of the nucleotides are modified nucleotides. In some embodiments, an HSD17B13 RNAi agent disclosed herein includes an antisense strand that consists of, consists essentially of, or comprises a nucleobase sequence differing by 0 or 1 nucleobases from the nucleotide sequence (5'→3') UGAUC- CAAAAAUGUCCUAGGC (SEQ ID NO:6), wherein SEQ ID NO:6 is located at positions 1-21 (5'→3') of the antisense strand.

In some embodiments, an HSD17B13 RNAi agent disclosed herein includes an antisense strand that consists of, consists essentially of, or comprises a modified nucleotide sequence differing by no more than 1 nucleotide from the nucleotide sequence (5'→3') usGfsasUfcCfaAfaAfaUfgUfcCfuAfgGfsc (SEQ ID NO:5), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand. As the person of ordinary skill in the art would clearly understand, the inclusion of a phosphorothioate linkage as shown in the modified nucleotide sequences disclosed herein replaces the phosphodiester linkage typically present in oligonucleotides (see, e.g., FIGS. 11A through 11E showing all internucleoside linkages). In some embodiments, an HSD17B13 RNAi agent disclosed herein includes an antisense strand that consists of, consists essentially of, or comprises the nucleotide sequence (5'→3') usGfsasUfcCfaAfaAfaUfgUfcCfuAfgGfsc (SEQ ID NO:5), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand.

In some embodiments, an HSD17B13 RNAi agent disclosed herein includes an antisense strand that consists of, consists essentially of, or comprises a modified nucleotide sequence differing by no more than 1 nucleotide from the nucleotide sequence (5'→3') usGfsasUfcCfaaaaaUfgUfcCfuAfgGfsc (SEQ ID NO:7), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand. As the person of ordinary skill in the art would clearly understand, the inclusion of a phosphorothioate linkage as shown in the modified nucleotide sequences disclosed herein replaces the phosphodiester linkage typically present in oligonucleotides (see, e.g., FIGS. 11A through 11E showing all internucleoside linkages). In some embodiments, an HSD17B13 RNAi agent disclosed herein includes an antisense strand that consists of, consists essentially of, the or comprises nucleotide sequence (5'→3') usGfsasUfcCfaaaaaUfgUfcCfuAfgGfsc (SEQ ID NO:7), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage, and wherein the sense strand is at least substantially complementary to the antisense strand.

In some embodiments, an HSD17B13 RNAi agent disclosed herein includes an antisense strand that consists of, consists essentially of, or comprises a nucleobase sequence differing by 0 or 1 nucleobases from the nucleotide sequence (5'→3') UCAUCUAUCAGACUUCUUACG (SEQ ID NO:3) and a sense strand that consists of, consists essentially of, or comprises a nucleobase sequence differing by 0 or 1 nucleobases from the nucleotide sequence (5'→3') CGUAAGAAGUCUGAUAGAUGA (SEQ ID NO:8). In some embodiments, an HSD17B13 RNAi agent disclosed herein includes an antisense strand that consists of, consists essentially of, or comprises a nucleotide sequence differing by no more than 1 nucleotide from the nucleotide sequence (5'→3') UCAUCUAUCAGACUUCUUACG (SEQ ID NO:3), wherein all or substantially all of the nucleotides are modified nucleotides, and a sense strand that consists of, consists essentially of, or comprises a nucleotide sequence differing by no more than 1 nucleotide from the nucleotide sequence (5'→3') CGUAAGAAGUCUGAUAGAUGA (SEQ ID NO:8), wherein all or substantially all of the nucleotides are modified nucleotides.

In some embodiments, an HSD17B13 RNAi agent disclosed herein includes an antisense strand that consists of, consists essentially of, or comprises a nucleobase sequence differing by 0 or 1 nucleobases from the nucleotide sequence (5'→3') UGAUCCAAAAAUGUCCUAGGC (SEQ ID NO:6) and a sense strand that consists of, consists essentially of, or comprises a nucleobase sequence differing by 0 or 1 nucleobases from the nucleotide sequence (5'→3') GCCUAGGACAUUUUUGIAUCA (SEQ ID NO:11), wherein I represents an inosine (hypoxanthine) nucleotide. In some embodiments, an HSD17B13 RNAi agent disclosed herein includes an antisense strand that consists of, consists essentially of, or comprises a nucleotide sequence differing by no more than 1 nucleotide from the nucleotide sequence (5'→3') UGAUCCAAAAAUGUCCUAGGC (SEQ ID NO:6), wherein all or substantially all of the nucleotides are modified nucleotides, and a sense strand that consists of, consists essentially of, or comprises a nucleotide sequence differing by no more than 1 nucleotide from the nucleotide sequence (5'→3') GCCUAGGACAUUUUUGIAUCA (SEQ ID NO:11), wherein I represents an inosine (hypoxanthine) nucleotide, and wherein all or substantially all of the nucleotides are modified nucleotides.

In some embodiments, an HSD17B13 RNAi agent disclosed herein includes an antisense strand that consists of, consists essentially of, or comprises the modified nucleotide sequence (5'→3') usCfsasUfcUfaUfcAfgAfcUfuCfuUfaCfsg (SEQ ID NO:2), and a sense strand that consists of, consists essentially of, or comprises the modified nucleotide sequence (5'→3') cguaagaaGfUfCfugauagauga (SEQ ID NO:9), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage. In some embodiments, an HSD17B13 RNAi agent disclosed herein includes an antisense strand that consists of, consists essentially of, or comprises the modified nucleotide sequence (5'→3') usCfsasUfcUfaUfcAfgAfcUfuCfuUfaCfsg (SEQ ID NO:2), and a sense strand that consists of, consists essentially of, or comprises the modified nucleotide sequence (5'→3') cguaagaaGfUfCfugauagauga (SEQ ID NO:9), and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes N-acetyl-galactosamine.

In some embodiments, an HSD17B13 RNAi agent disclosed herein includes an antisense strand that consists of, consists essentially of, or comprises the modified nucleotide sequence (5'→3') usCfsasUfcUfaucagAfcUfuCfuUfaCfsg (SEQ ID NO:4), and a sense strand that consists of, consists essentially of, or comprises the modified nucleotide sequence (5'→3') cguaagaaGfuCfuGfauagauga (SEQ ID NO:10), wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; and s represents a phosphorothioate linkage. In some embodiments, an HSD17B13 RNAi agent disclosed herein includes an antisense strand that consists of, consists essentially of, or comprises the modified nucleotide sequence (5'→3') usCfsasUfcUfau-cagAfcUfuCfuUfaCfsg (SEQ ID NO:4), and a sense strand that consists of, consists essentially of, or comprises the modified nucleotide sequence (5'→3') cguaagaaGfuCfuGfauagauga (SEQ ID NO:10), and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes N-acetyl-galactosamine.

In some embodiments, an HSD17B13 RNAi agent disclosed herein includes an antisense strand that consists of, consists essentially of, or comprises the modified nucleotide sequence (5'→3') usGfsasUfcCfaAfaAf-aUfgUfcCfuAfgGfsc (SEQ ID NO:5), and a sense strand that consists of, consists essentially of, or comprises the modified nucleotide sequence (5'→3') gccuaggaCfAfU-fuuuugiauca (SEQ ID NO:12), wherein a, c, g, i, and u represent 2'-O-methyl adenosine, cytidine, guanosine, inosine, or uridine, respectively; Af, Cf, Gf, and Uf represent 2'-fluoro adenosine, cytidine, guanosine, or uridine, respectively; and s represents a phosphorothioate linkage. In some embodiments, an HSD17B13 RNAi agent disclosed herein includes an antisense strand that consists of, consists essentially of, or comprises the modified nucleotide sequence (5'→3') usGfsasUfcCfaAfaAfaUfgUfcCfuAfgGfsc (SEQ ID NO:5), and a sense strand that consists of, consists essentially of, or comprises the modified nucleotide sequence (5'→3') gccuaggaCfAfUfuuuugiauca (SEQ ID NO:12), and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes N-acetyl-galactosamine.

In some embodiments, an HSD17B13 RNAi agent disclosed herein includes an antisense strand that consists of, consists essentially of, or comprises the modified nucleotide sequence (5'→3') usGfsasUfcCfaAfaAf-aUfgUfcCfuAfgGfsc (SEQ ID NO:5), and a sense strand that consists of, consists essentially of, or comprises the modified nucleotide sequence (5'→3') gccuaggaCfaUfuU-fuugiauca (SEQ ID NO:13), wherein a, c, g, i, and u represent 2'-O-methyl adenosine, cytidine, guanosine, inosine, or uridine, respectively; Af, Cf, Gf, and Uf represent 2'-fluoro adenosine, cytidine, guanosine, or uridine, respectively; and s represents a phosphorothioate linkage. In some embodiments, an HSD17B13 RNAi agent disclosed herein includes an antisense strand that consists of, consists essentially of, or comprises the modified nucleotide sequence (5'→3') usGfsasUfcCfaAfaAfaUfgUfcCfuAfgGfsc (SEQ ID NO:5), and a sense strand that consists of, consists essentially of, or comprises the modified nucleotide sequence (5'→3') gccuaggaCfaUfuUfuugiauca (SEQ ID NO:13), and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes N-acetyl-galactosamine.

In some embodiments, an HSD17B13 RNAi agent disclosed herein includes an antisense strand that consists of, consists essentially of, or comprises the modified nucleotide sequence (5'→3') usGfsasUfcCfaaaaaUfgUfcCfuAfgGfsc (SEQ ID NO:7), and a sense strand that consists of, consists essentially of, or comprises the modified nucleotide sequence (5'→3') gccuaggaCfaUfuUfuugiauca (SEQ ID NO:13), wherein a, c, g, i, and u represent 2'-O-methyl adenosine, cytidine, guanosine, inosine, or uridine, respectively; Af, Cf, Gf, and Uf represent 2'-fluoro adenosine, cytidine, guanosine, or uridine, respectively; and s represents a phosphorothioate linkage. In some embodiments, an HSD17B13 RNAi agent disclosed herein includes an antisense strand that consists of, consists essentially of, or comprises the modified nucleotide sequence (5'→3') usGfsa-sUfcCfaaaaaUfgUfcCfuAfgGfsc (SEQ ID NO:7), and a sense strand that consists of, consists essentially of, or comprises the modified nucleotide sequence (5'→3') gcc-uaggaCfaUfuUfuugiauca (SEQ ID NO:13), and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes N-acetyl-galactosamine.

In some embodiments, an HSD17B13 RNAi agent disclosed herein includes an antisense strand that consists of, consists essentially of, or comprises a nucleotide sequence that differs by 0 or 1 nucleotides from one of the following nucleotide sequences (5'→3'):

UCAUCUAUCAGACUUCUUACG (SEQ ID NO:3); or
UGAUCCAAAAAUGUCCUAGGC (SEQ ID NO:6);

wherein the HSD17B13 RNAi agent further includes a sense strand that is at least partially complementary to the antisense strand; and wherein all or substantially all of the nucleotides on both the antisense strand and the sense strand are modified nucleotides.

In some embodiments, an HSD17B13 RNAi agent disclosed herein includes an antisense strand that consists of, consists essentially of, or comprises a nucleotide sequence that differs by 0 or 1 nucleotides from one of the following nucleotide sequences (5'→3'):

UCAUCUAUCAGACUUCUUACG (SEQ ID NO:3); or
UGAUCCAAAAAUGUCCUAGGC (SEQ ID NO:6);

wherein the HSD17B13 RNAi agent further includes a sense strand that is at least partially complementary to the antisense strand; wherein all or substantially all of the nucleotides on both the antisense strand and the sense strand are modified nucleotides; and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes N-acetyl-galactosamine.

In some embodiments, an HSD17B13 RNAi agent disclosed herein includes an antisense strand that consists of, consists essentially of, or comprises a nucleotide sequence that differs by 0 or 1 nucleotides from one of the following nucleotide sequences (5'→3'):

UCAUCUAUCAGACUUCUUACG (SEQ ID NO:3); or
UGAUCCAAAAAUGUCCUAGGC (SEQ ID NO:6);

wherein the HSD17B13 RNAi agent further includes a sense strand that is at least partially complementary to the antisense strand; wherein all or substantially all of the nucleotides on both the antisense strand and the sense strand are modified nucleotides; and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes N-acetyl-galactosamine; and wherein the respective antisense strand sequence is located at positions 1-21 of the antisense strand.

In some embodiments, an HSD17B13 RNAi agent disclosed herein includes an antisense strand and a sense strand, wherein the antisense strand and the sense strand consist of, consist essentially of, or comprise nucleotide sequences that differ by 0 or 1 nucleotides from one of the following nucleotide sequence (5'→3') pairs:

UCAUCUAUCAGACUUCUUACG (SEQ ID NO:3) and CGUAAGAAGUCUGAUAGAUGA (SEQ ID NO:8); or

UGAUCCAAAAAUGUCCUAGGC (SEQ ID NO:6) and GCCUAGGACAUUUUUGIAUCA (SEQ ID NO:11), wherein I represents an inosine (hypoxanthine) nucleotide;

wherein all or substantially all of the nucleotides on both the antisense strand and the sense strand are modified nucleotides.

In some embodiments, an HSD17B13 RNAi agent disclosed herein includes an antisense strand and a sense strand, wherein the antisense strand and the sense strand consist of, consist essentially of, or comprise nucleotide sequences that differ by 0 or 1 nucleotides from one of the following nucleotide sequences (5'→3') pairs:

UCAUCUAUCAGACUUCUUACG (SEQ ID NO:3) and CGUAAGAAGUCUGAUAGAUGA (SEQ ID NO:8); or

UGAUCCAAAAAUGUCCUAGGC (SEQ ID NO:6) and GCCUAGGACAUUUUUGIAUCA (SEQ ID NO:11), wherein I represents an inosine (hypoxanthine) nucleotide;

wherein all or substantially all of the nucleotides on both the antisense strand and the sense strand are modified nucleotides; and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes N-acetyl-galactosamine.

In some embodiments, an HSD17B13 RNAi agent disclosed herein includes an antisense strand that consists of, consists essentially of, or comprises a modified nucleotide sequence that differs by 0 or 1 nucleotides from one of the following nucleotide sequences (5'→3'):

usCfsasUfcUfaUfcAfgAfcUfuCfuUfaCfsg (SEQ ID NO:2);

usCfsasUfcUfaucagAfcUfuCfuUfaCfsg (SEQ ID NO:4);

usGfsasUfcCfaAfaAfaUfgUfcCfuAfgGfsc (SEQ ID NO:5);

usGfsasUfcCfaaaaaUfgUfcCfuAfgGfsc (SEQ ID NO:7);

wherein a, c, g, and u represent 2'-O-methyl adenosine, cytidine, guanosine, or uridine, respectively; Af, Cf, Gf, and Uf represent 2'-fluoro adenosine, cytidine, guanosine, or uridine, respectively; s represents a phosphorothioate linkage; and wherein the HSD17B13 RNAi agent further includes the sense strand that is at least partially complementary to the antisense strand; and wherein all or substantially all of the nucleotides on the sense strand are modified nucleotides.

In some embodiments, an HSD17B13 RNAi agent disclosed herein includes an antisense strand that consists of, consists essentially of, or comprises a modified nucleotide sequence that differs by 0 or 1 nucleotides from one of the following nucleotide sequences (5'→3'):

usCfsasUfcUfaUfcAfgAfcUfuCfuUfaCfsg (SEQ ID NO:2);

usCfsasUfcUfaucagAfcUfuCfuUfaCfsg (SEQ ID NO:4);

usGfsasUfcCfaAfaAfaUfgUfcCfuAfgGfsc (SEQ ID NO:5);

usGfsasUfcCfaaaaaUfgUfcCfuAfgGfsc (SEQ ID NO:7);

wherein the HSD17B13 RNAi agent further includes the sense strand that is at least partially complementary to the antisense strand; wherein all or substantially all of the nucleotides on the sense strand are modified nucleotides; wherein all or substantially all of the nucleotides on both the antisense strand and the sense strand are modified nucleotides; and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes N-acetyl-galactosamine.

In some embodiments, an HSD17B13 RNAi agent disclosed herein includes an antisense strand and a sense strand that consists of, consists essentially of, or comprises modified nucleotide sequences that differs by 0 or 1 nucleotides from one of the following nucleotide sequence pairs (5'→3'):

usCfsasUfcUfaUfcAfgAfcUfuCfuUfaCfsg (SEQ ID NO:2) and cguaagaaGfUfCfugauagauga (SEQ ID NO:9);

usCfsasUfcUfaucagAfcUfuCfuUfaCfsg (SEQ ID NO:4) and cguaagaaGfuCfuGfauagauga (SEQ ID NO:10);

usGfsasUfcCfaAfaAfaUfgUfcCfuAfgGfsc (SEQ ID NO:5) and gccuaggaCfAfUfuuuugiauca (SEQ ID NO:12);

usGfsasUfcCfaAfaAfaUfgUfcCfuAfgGfsc (SEQ ID NO:5) and gccuaggaCfaUfuUfuugiauca (SEQ ID NO:13); or usGfsasUfcCfaaaaaUfgUfcCfuAfgGfsc (SEQ ID NO:7) and gccuaggaCfaUfuUfuugiauca (SEQ ID NO:13);

wherein a, c, g, i, and u represent 2'-O-methyl adenosine, cytidine, guanosine, inosine, or uridine, respectively; Af, Cf, Gf, and Uf represent 2'-fluoro adenosine, cytidine, guanosine, or uridine, respectively; and s represents a phosphorothioate linkage.

In some embodiments, an HSD17B13 RNAi agent disclosed herein includes an antisense strand and a sense strand that consists of, consists essentially of, or comprises one of the following nucleotide sequence pairs (5'→3'):

usCfsasUfcUfaUfcAfgAfcUfuCfuUfaCfsg (SEQ ID NO:2) and cguaagaaGfUfCfugauagauga (SEQ ID NO:9);

usCfsasUfcUfaucagAfcUfuCfuUfaCfsg (SEQ ID NO:4) and cguaagaaGfuCfuGfauagauga (SEQ ID NO:10);

usGfsasUfcCfaAfaAfaUfgUfcCfuAfgGfsc (SEQ ID NO:5) and gccuaggaCfAfUfuuuugiauca (SEQ ID NO:12);

usGfsasUfcCfaAfaAfaUfgUfcCfuAfgGfsc (SEQ ID NO:5) and gccuaggaCfaUfuUfuugiauca (SEQ ID NO:13); or usGfsasUfcCfaaaaaUfgUfcCfuAfgGfsc (SEQ ID NO: 7) and gccuaggaCfaUfuUfuugiauca (SEQ ID NO:13);

wherein a, c, g, i, and u represent 2'-O-methyl adenosine, cytidine, guanosine, inosine, or uridine, respectively; Af, Cf, Gf, and Uf represent 2'-fluoro adenosine, cytidine, guanosine, or uridine, respectively; s represents a phosphorothioate linkage; and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes N-acetyl-galactosamine.

In some embodiments, an HSD17B13 RNAi agent disclosed herein includes an antisense strand that includes a nucleobase sequence that differs by 0 or 1 nucleobases from the nucleotide sequences selected from the group consisting of (5'→3'):

UCAUCUAUCAGACUUCUUA (SEQ ID NO:26); or

UGAUCCAAAAAUGUCCUAG (SEQ ID NO:41).

In some embodiments, an HSD17B13 RNAi agent disclosed herein includes an antisense strand that includes a nucleobase sequence that differs by 0 or 1 nucleobases from the nucleotide sequences selected from the group consisting of (5'→3'):

UCAUCUAUCAGACUUCUUA (SEQ ID NO:26); and

UGAUCCAAAAAUGUCCUAG (SEQ ID NO:41);

wherein all or substantially all of the nucleotides are modified nucleotides.

In some embodiments, an HSD17B13 RNAi agent disclosed herein includes an antisense strand that includes a nucleobase sequence that differs by 0 or 1 nucleobases from the nucleotide sequences selected from the group consisting of (5'→3'):

UCAUCUAUCAGACUUCUUA (SEQ ID NO:26); or

UGAUCCAAAAAUGUCCUAG (SEQ ID NO:41);

wherein all or substantially all of the nucleotides are modified nucleotides, and wherein SEQ ID NO: 26 or SEQ ID NO:41, respectively, is located at nucleotide positions 1-19 (5'→3') of the antisense strand.

In some embodiments, an HSD17B13 RNAi agent disclosed herein includes an antisense strand and a sense strand that each include a nucleobase sequences that differs by 0 or 1 nucleobases from the nucleotide sequence pairs selected from the group consisting of (5'→3'):

UCAUCUAUCAGACUUCUUA (SEQ ID NO:26) and UAAGAAGUCUGAUAGAUGA (SEQ ID NO:67);

UGAUCCAAAAAUGUCCUAG (SEQ ID NO:41) and CUAGGACAUUUUUGIAUCA (SEQ ID NO:86), wherein (I) represents an inosine nucleotide.

In some embodiments, an HSD17B13 RNAi agent disclosed herein includes an antisense strand and a sense strand that each include a nucleobase sequences that differs by 0 or 1 nucleobases from the nucleotide sequence pairs selected from the group consisting of (5'→3'):

UCAUCUAUCAGACUUCUUA (SEQ ID NO:26) and UAAGAAGUCUGAUAGAUGA (SEQ ID NO:67);

UGAUCCAAAAAUGUCCUAG (SEQ ID NO:41) and CUAGGACAUUUUUGIAUCA (SEQ ID NO:86), wherein (I) represents an inosine nucleotide; and wherein all or substantially all of the nucleotides are modified nucleotides.

In some embodiments, the compositions described herein comprising one or more HSD17B13 RNAi agents are packaged in a kit, container, pack, dispenser, pre-filled syringes, or vials. In some embodiments, the compositions described herein are administered parenterally, e.g., by subcutaneous injection.

As used herein, the terms "oligonucleotide" and "polynucleotide" mean a polymer of linked nucleosides each of which can be independently modified or unmodified.

As used herein, an "RNAi agent" (also referred to as an "RNAi trigger") means a composition that contains an RNA or RNA-like (e.g., chemically modified RNA) oligonucleotide molecule that is capable of degrading or inhibiting (e.g., degrades or inhibits under appropriate conditions) translation of messenger RNA (mRNA) transcripts of a target mRNA in a sequence specific manner. As used herein, RNAi agents may operate through the RNA interference mechanism (i.e., inducing RNA interference through interaction with the RNA interference pathway machinery (RNA-induced silencing complex or RISC) of mammalian cells), or by any alternative mechanism(s) or pathway(s). While it is believed that RNAi agents, as that term is used herein, operate primarily through the RNA interference mechanism, the disclosed RNAi agents are not bound by or limited to any particular pathway or mechanism of action. RNAi agents disclosed herein are comprised of a sense strand and an antisense strand, and include, but are not limited to: short (or small) interfering RNAs (siRNAs), double stranded RNAs (dsRNA), micro RNAs (miRNAs), short hairpin RNAs (shRNA), and dicer substrates. The antisense strand of the RNAi agents described herein is at least partially complementary to the mRNA being targeted (i.e. HSD17B13 mRNA). RNAi agents can include one or more modified nucleotides and/or one or more non-phosphodiester linkages.

As used herein, the terms "silence," "reduce," "inhibit," "down-regulate," or "knockdown" when referring to expression of a given gene, mean that the expression of the gene, as measured by the level of RNA transcribed from the gene or the level of polypeptide, protein, or protein subunit translated from the mRNA in a cell, group of cells, tissue, organ, or subject in which the gene is transcribed, is reduced when the cell, group of cells, tissue, organ, or subject is treated with the RNAi agents described herein as compared to a second cell, group of cells, tissue, organ, or subject that has not or have not been so treated.

As used herein, the terms "sequence" and "nucleotide sequence" mean a succession or order of nucleobases or nucleotides, described with a succession of letters using standard nomenclature.

As used herein, a "base," "nucleotide base," or "nucleobase," is a heterocyclic pyrimidine or purine compound that is a component of a nucleotide, and includes the primary purine bases adenine and guanine, and the primary pyrimidine bases cytosine, thymine, and uracil. A nucleobase may further be modified to include, without limitation, universal bases, hydrophobic bases, promiscuous bases, size-expanded bases, and fluorinated bases. (See, e.g., Modified Nucleosides in Biochemistry, Biotechnology and Medicine, Herdewijn, P. ed. Wiley-VCH, 2008). The synthesis of such modified nucleobases (including phosphoramidite compounds that include modified nucleobases) is known in the art.

As used herein, and unless otherwise indicated, the term "complementary," when used to describe a first nucleobase or nucleotide sequence (e.g., RNAi agent sense strand or targeted mRNA) in relation to a second nucleobase or nucleotide sequence (e.g., RNAi agent antisense strand or a single-stranded antisense oligonucleotide), means the ability of an oligonucleotide or polynucleotide including the first nucleotide sequence to hybridize (form base pair hydrogen bonds under mammalian physiological conditions (or otherwise suitable in vivo or in vitro conditions)) and form a duplex or double helical structure under certain standard conditions with an oligonucleotide that includes the second nucleotide sequence. The person of ordinary skill in the art would be able to select the set of conditions most appropriate for a hybridization test. Complementary sequences include Watson-Crick base pairs or non-Watson-Crick base pairs and include natural or modified nucleotides or nucleotide mimics, at least to the extent that the above hybridization requirements are fulfilled. Sequence identity or complementarity is independent of modification. For example, a and Af, as defined herein, are complementary to U (or T) and identical to A for the purposes of determining identity or complementarity.

As used herein, "perfectly complementary" or "fully complementary" means that in a hybridized pair of nucleobase or nucleotide sequence molecules, all (100%) of the bases in a contiguous sequence of a first oligonucleotide will hybridize with the same number of bases in a contiguous sequence of a second oligonucleotide. The contiguous sequence may comprise all or a part of a first or second nucleotide sequence.

As used herein, "partially complementary" means that in a hybridized pair of nucleobase or nucleotide sequence molecules, at least 70%, but not all, of the bases in a contiguous sequence of a first oligonucleotide will hybridize with the same number of bases in a contiguous sequence of a second oligonucleotide. The contiguous sequence may comprise all or a part of a first or second nucleotide sequence.

As used herein, "substantially complementary" means that in a hybridized pair of nucleobase or nucleotide sequence molecules, at least 85%, but not all, of the bases in a contiguous sequence of a first oligonucleotide will hybridize with the same number of bases in a contiguous sequence of a second oligonucleotide. The contiguous sequence may comprise all or a part of a first or second nucleotide sequence.

As used herein, the terms "complementary," "fully complementary," "partially complementary," and "substantially complementary" are used with respect to the nucleobase or nucleotide matching between the sense strand and the antisense strand of an RNAi agent, or between the antisense strand of an RNAi agent and a sequence of an HSD17B13 mRNA.

As used herein, the term "substantially identical" or "substantial identity," as applied to a nucleic acid sequence means the nucleotide sequence (or a portion of a nucleotide sequence) has at least about 85% sequence identity or more, e.g., at least 90%, at least 95%, or at least 99% identity, compared to a reference sequence. Percentage of sequence identity is determined by comparing two optimally aligned sequences over a comparison window. The percentage is calculated by determining the number of positions at which the same type of nucleic acid base occurs in both sequences to yield the number of matched positions, dividing the number of matched positions by the total number of positions in the window of comparison and multiplying the result by 100 to yield the percentage of sequence identity. The inventions disclosed herein encompass nucleotide sequences substantially identical to those disclosed herein.

As used herein, the terms "treat," "treatment," and the like, mean the methods or steps taken to provide relief from or alleviation of the number, severity, and/or frequency of one or more symptoms of a disease in a subject. As used herein, "treat" and "treatment" may include the prevention, management, prophylactic treatment, and/or inhibition or reduction of the number, severity, and/or frequency of one or more symptoms of a disease in a subject.

As used herein, the phrase "introducing into a cell," when referring to an RNAi agent, means functionally delivering the RNAi agent into a cell. The phrase "functional delivery," means delivering the RNAi agent to the cell in a manner that enables the RNAi agent to have the expected biological activity, e.g., sequence-specific inhibition of gene expression.

Unless stated otherwise, use of the symbol 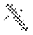 as used herein means that any group or groups may be linked thereto that is in accordance with the scope of the inventions described herein.

As used herein, the term "isomers" refers to compounds that have identical molecular formulae, but that differ in the nature or the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images are termed "enantiomers," or sometimes optical isomers. A carbon atom bonded to four non-identical substituents is termed a "chiral center."

As used herein, unless specifically identified in a structure as having a particular conformation, for each structure in which asymmetric centers are present and thus give rise to enantiomers, diastereomers, or other stereoisomeric configurations, each structure disclosed herein is intended to represent all such possible isomers, including their optically pure and racemic forms. For example, the structures disclosed herein are intended to cover mixtures of diastereomers as well as single stereoisomers.

As used in a claim herein, the phrase "consisting of" excludes any element, step, or ingredient not specified in the claim. When used in a claim herein, the phrase "consisting essentially of" limits the scope of a claim to the specified materials or steps and those that do not materially affect the basic and novel characteristic(s) of the claimed invention.

The person of ordinary skill in the art would readily understand and appreciate that the compounds and compositions disclosed herein may have certain atoms (e.g., N, O, or S atoms) in a protonated or deprotonated state, depending upon the environment in which the compound or composition is placed. Accordingly, as used herein, the structures disclosed herein envisage that certain functional groups, such as, for example, OH, SH, or NH, may be protonated or deprotonated. The disclosure herein is intended to cover the disclosed compounds and compositions regardless of their state of protonation based on the environment (such as pH), as would be readily understood by the person of ordinary skill in the art. Correspondingly, compounds described herein with labile protons or basic atoms should also be understood to represent salt forms of the corresponding compound. Compounds described herein may be in a free acid, free base, or salt form. Pharmaceutically acceptable salts of the compounds described herein should be understood to be within the scope of the invention.

As used herein, the term "linked" or "conjugated" when referring to the connection between two compounds or molecules means that two compounds or molecules are joined by a covalent bond. Unless stated, the terms "linked" and "conjugated" as used herein may refer to the connection between a first compound and a second compound either with or without any intervening atoms or groups of atoms.

As used herein, the term "including" is used to herein mean, and is used interchangeably with, the phrase "including but not limited to." The term "or" is used herein to mean, and is used interchangeably with, the term "and/or," unless the context clearly indicates otherwise.

Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other objects, features, aspects, and advantages of the invention will be apparent from the following detailed description, accompanying figures, and from the claims.

BRIEF DESCRIPTION OF THE DRAWINGS

FIG. 1A to 1D disclose the antisense strand of the nucleotide sequence (5'→3') SEQ ID NO:2 and the sense strand of the nucleotide sequence (5'→3') SEQ ID NO:14.

FIG. 2A to 2D disclose the antisense strand of the nucleotide sequence (5'→3') SEQ ID NO:4 and the sense strand of the nucleotide sequence (5'→3') SEQ ID NO:15.

FIG. 3A to 3D disclose the antisense strand of the nucleotide sequence (5'→3') SEQ ID NO:5 and the sense strand of the nucleotide sequence (5'→3') SEQ ID NO:16.

FIG. 4A to 4D disclose the antisense strand of the nucleotide sequence (5'→3') SEQ ID NO:5 and the sense strand of the nucleotide sequence (5'→3') SEQ ID NO:17.

FIG. 5A to 5D disclose the antisense strand of the nucleotide sequence (5'→3') SEQ ID NO:7 and the sense strand of the nucleotide sequence (5'→3') SEQ ID NO:17.

FIG. 6A to 6D disclose the antisense strand of the nucleotide sequence (5'→3') SEQ ID NO:2 and the sense strand of the nucleotide sequence (5'→3') SEQ ID NO:14.

FIG. 7A to 7D disclose the antisense strand of the nucleotide sequence (5'→3') SEQ ID NO:4, the sense strand of the nucleotide sequence (5'→3') SEQ ID NO:15.

FIG. 8A to 8D disclose the antisense strand of the nucleotide sequence (5'→3') SEQ ID NO:5 and the sense strand of the nucleotide sequence (5'→3') SEQ ID NO:16.

FIG. 9A to 9D disclose the antisense strand of the nucleotide sequence (5'→3') SEQ ID NO:5 and the sense strand of the nucleotide sequence (5'→3') SEQ ID NO:17.

FIG. 10A to 10D disclose the antisense strand of the nucleotide sequence (5'→3') SEQ ID NO:7 and the sense strand of the nucleotide sequence (5'→3') SEQ ID NO: 17.

FIGS. 1 & 6). The following abbreviations are used in FIGS. 11A to 11E: a, c, g, i, and u are 2'-O-methyl modified nucleotides; Af, Cf, Gf, and Uf are 2'-fluoro modified nucleotides; o is a phosphodiester linkage; s is a phosphorothioate linkage; invAb is an inverted abasic residue; and (NAG37)s is a tridentate N-acetyl-galactosamine targeting ligand having the structure depicted in Table 6. FIG. 11A discloses the nucleotide sequences of SEQ ID NOs: 2 and 14 (5'→3') for the antisense strand and the sense strand respectively.

FIG. 11B discloses the nucleotide sequences of SEQ ID NOs: 4 and 15 (5'→3') for the antisense strand and the sense strand respectively.

FIG. 11C discloses the nucleotide sequences of SEQ ID NOs: 5 and 16 (5'→3') for the antisense strand and the sense strand respectively.

FIG. 11D discloses the nucleotide sequences of SEQ ID NOs: 5 and 17 (5'→3') for the antisense strand and the sense strand respectively.

FIG. 11D discloses the nucleotide sequences of SEQ ID NOs: 7 and 17 (5'→3') for the antisense strand and the sense strand respectively.

DETAILED DESCRIPTION

RNAi Agents

Described herein are RNAi agents for inhibiting expression of an HSD17B13 gene (referred to herein as HSD17B13 or 17β-HSD13 RNAi agents, or HSD17B13 or 17β-HSD13 RNAi triggers). Each HSD17B13 RNAi agent comprises a sense strand and an antisense strand. The sense strand and the antisense strand each can be 16 to 49 nucleotides in length. The sense and antisense strands can be either the same length or they can be different lengths. In some embodiments, the sense and antisense strands are each independently 17 to 27 nucleotides in length. In some embodiments, the sense and antisense strands are each independently 19-21 nucleotides in length. In some embodiments, both the sense and antisense strands are each 21-26 nucleotides in length. In some embodiments, the sense and antisense strands are each 21-24 nucleotides in length. In some embodiments, the sense strand is about 19 nucleotides in length while the antisense strand is about 21 nucleotides in length. In some embodiments, the sense strand is about 21 nucleotides in length while the antisense strand is about 23 nucleotides in length. In some embodiments, a sense strand is 23 nucleotides in length and an antisense strand is 21 nucleotides in length. In some embodiments, both the sense and antisense strands are each 21 nucleotides in length. In some embodiments, the RNAi agent sense and antisense strands are each independently 16, 17, 18, 19, 20, 21, 22, 23, 24, 25, 26, or 27 nucleotides in length. In some embodiments, a double-stranded RNAi agent has a duplex length of about 16, 17, 18, 19, 20, 21, 22, 23 or 24 nucleotides.

Figure 1A:
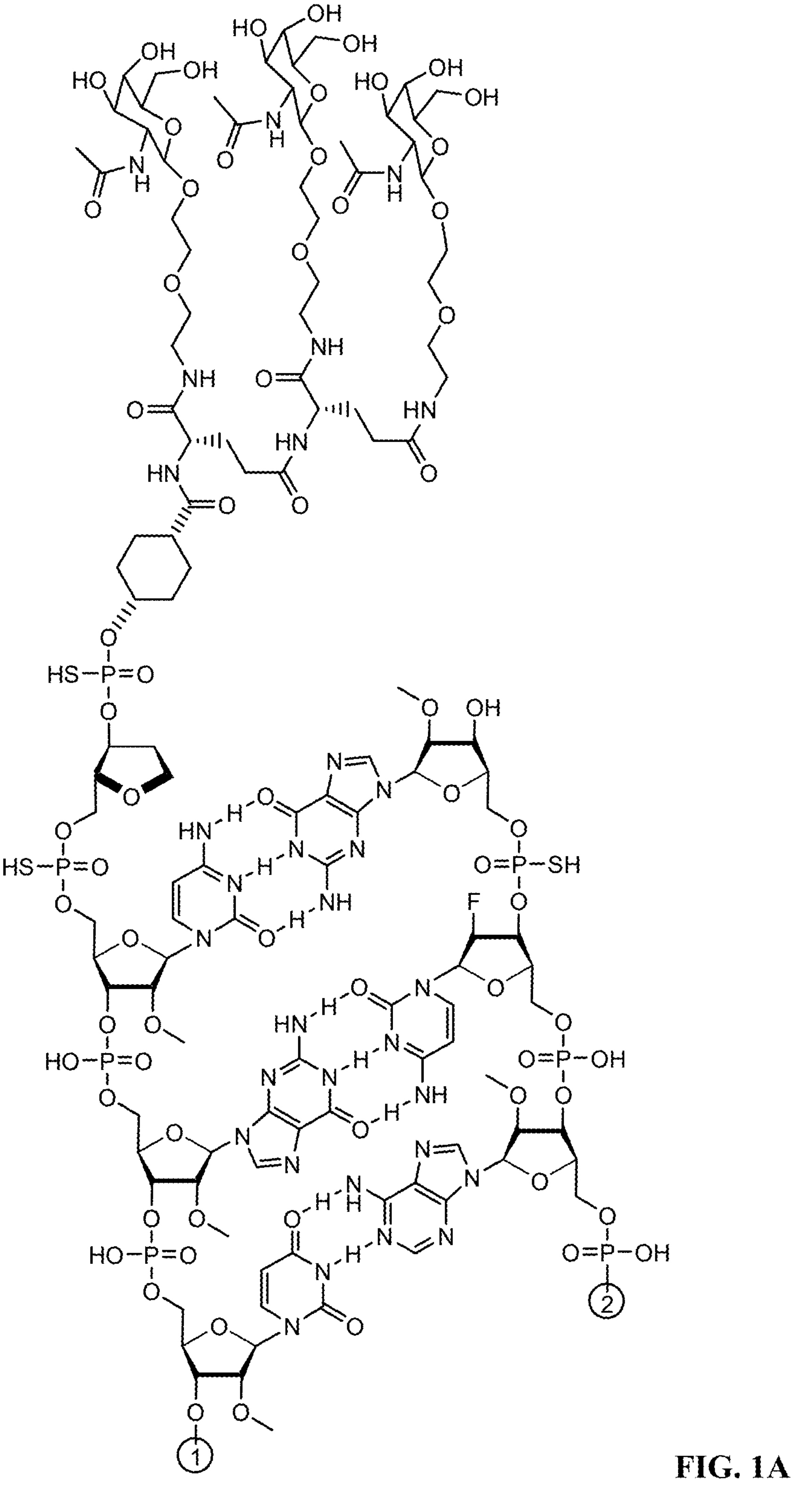
FIG. 1A to 1D. Chemical structure representation of HSD17B13 RNAi agent AD06214 conjugated to the tridentate N-acetyl-galactosamine targeting ligand of (NAG37)s at the 5' terminal end of the sense strand, shown in a free acid form.
Figure 1B:
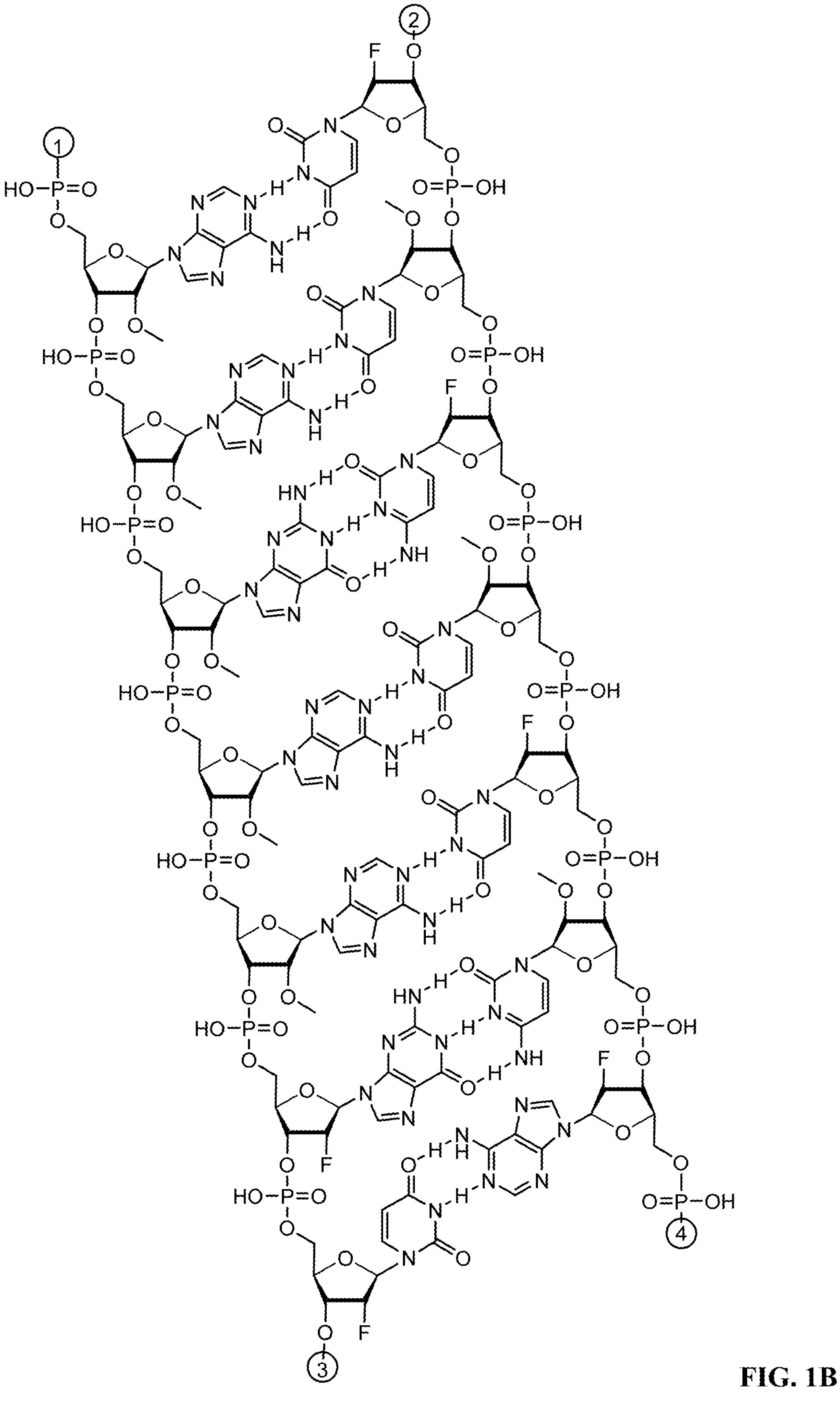
Figure 1C:
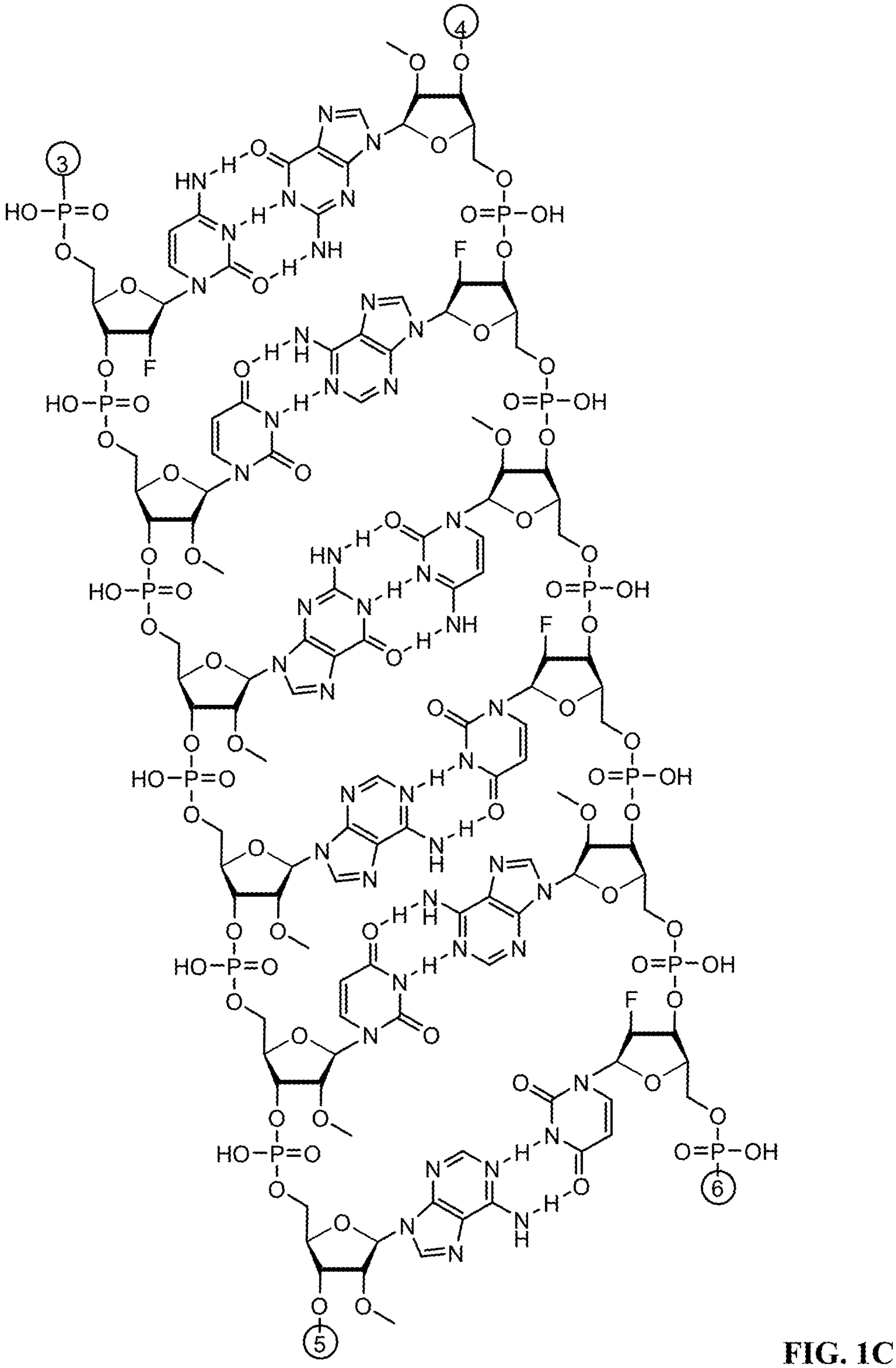
Figure 1D:
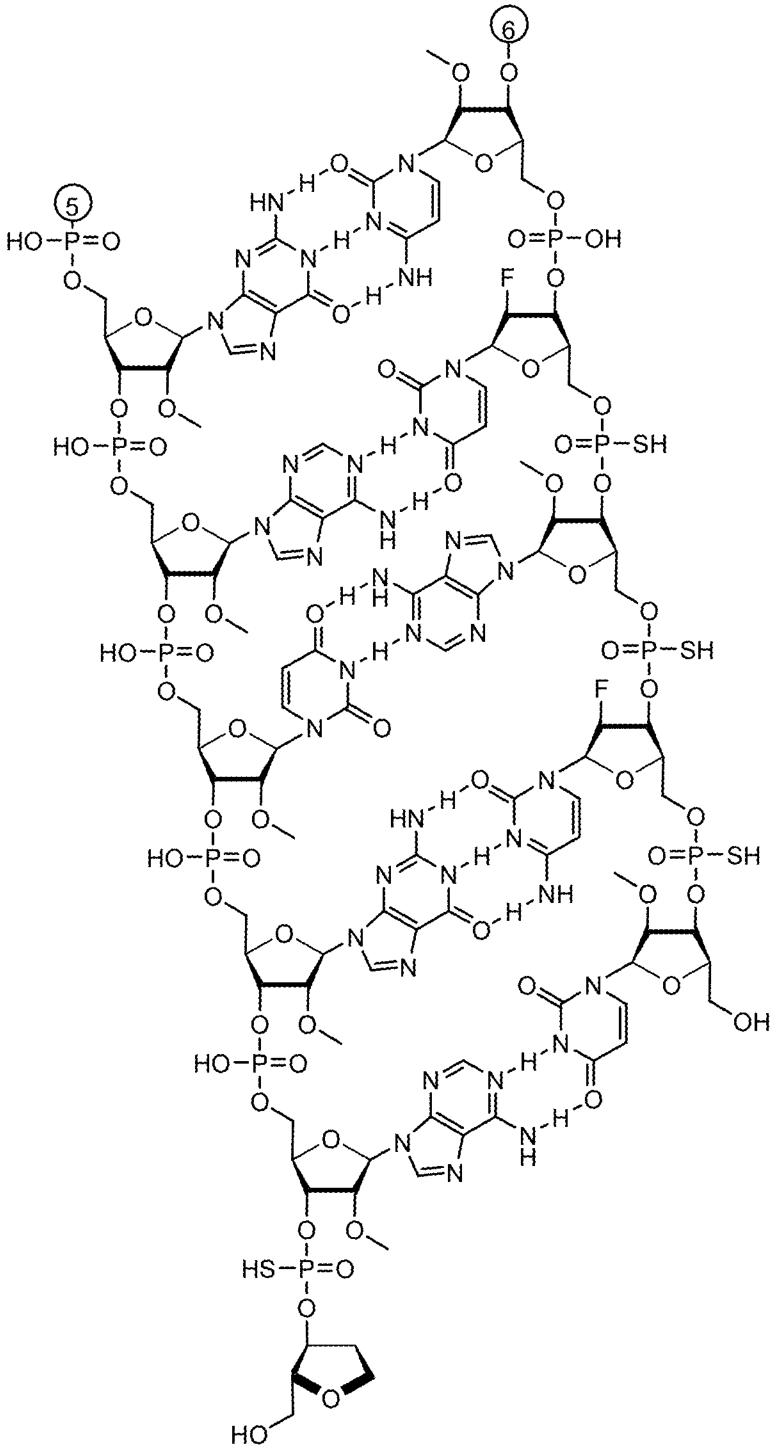
Figure 2A:
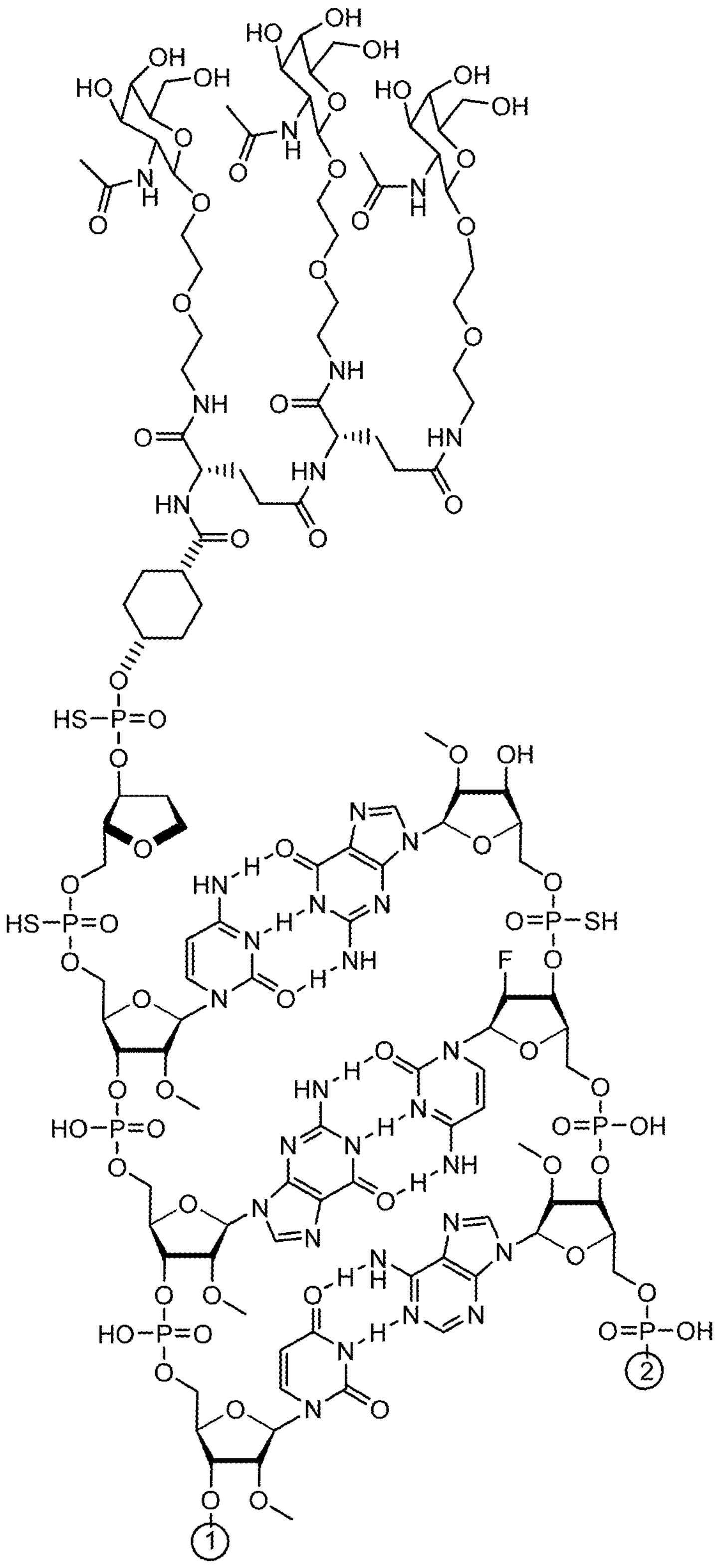
FIG. 2A to 2D. Chemical structure representation of HSD17B13 RNAi agent AD06280 conjugated to the tridentate N-acetyl-galactosamine targeting ligand of (NAG37)s at the 5' terminal end of the sense strand, shown in a free acid form.
Figure 2B:
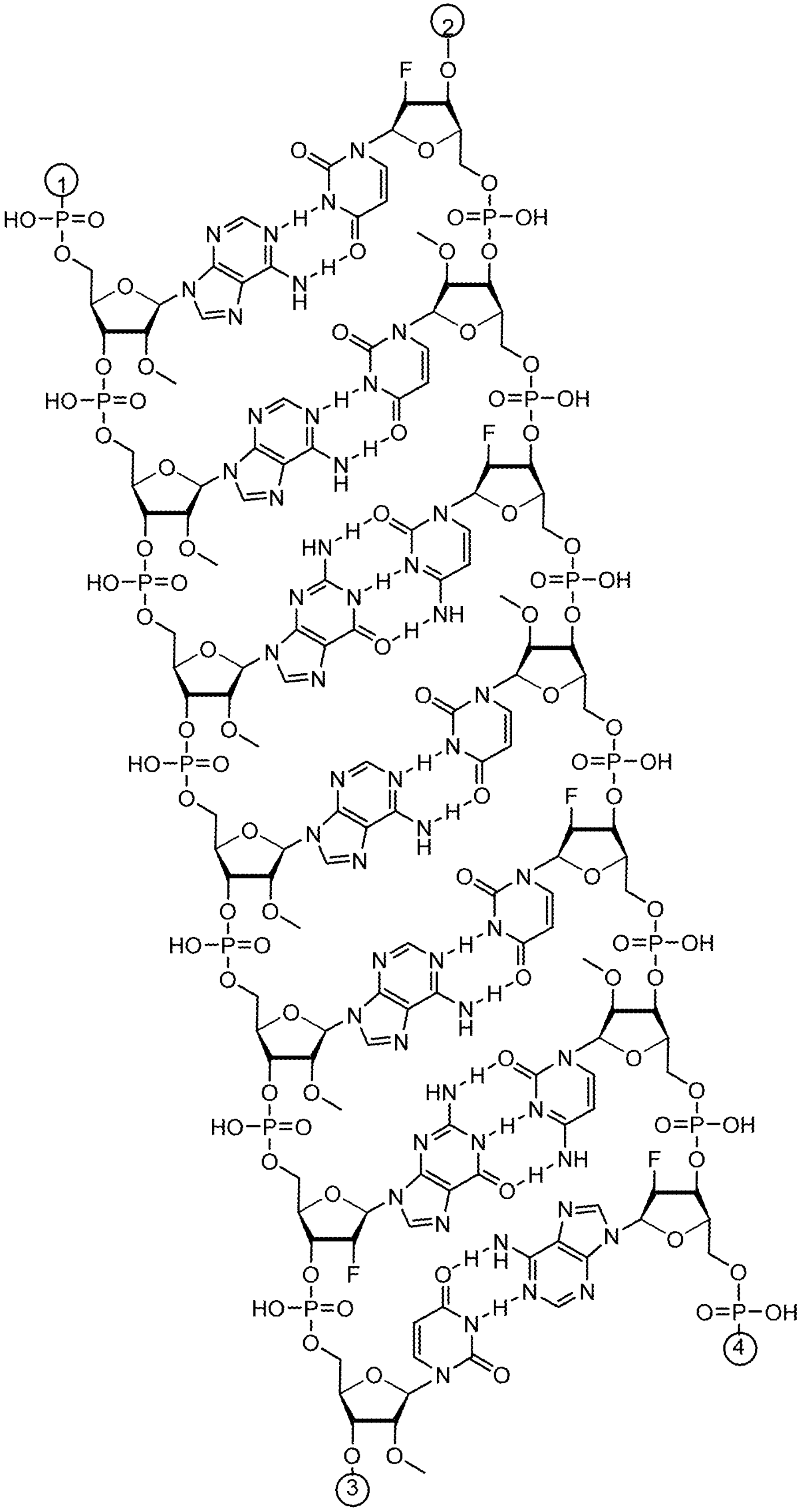
Figure 2C:
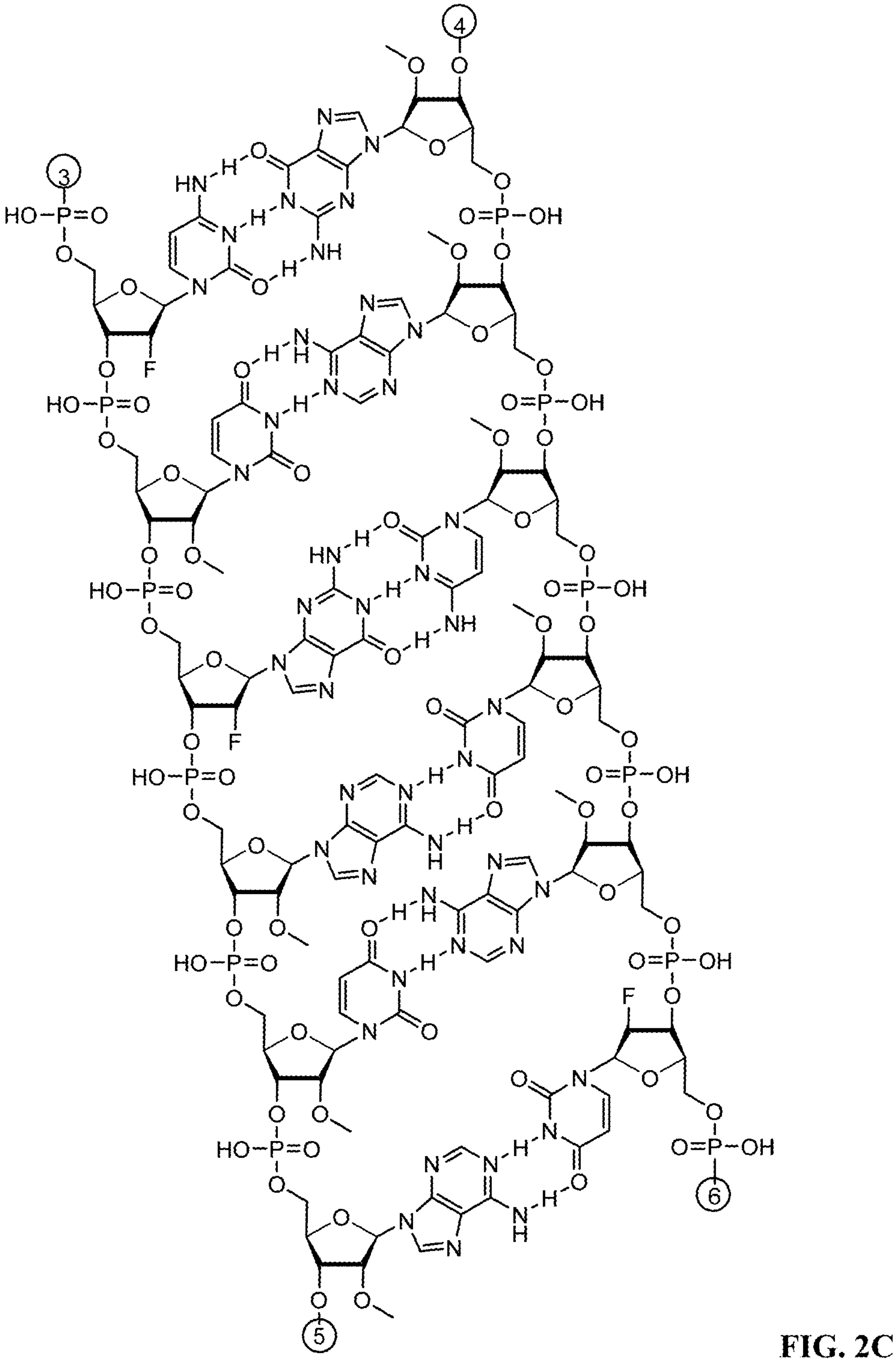
Figure 2D:
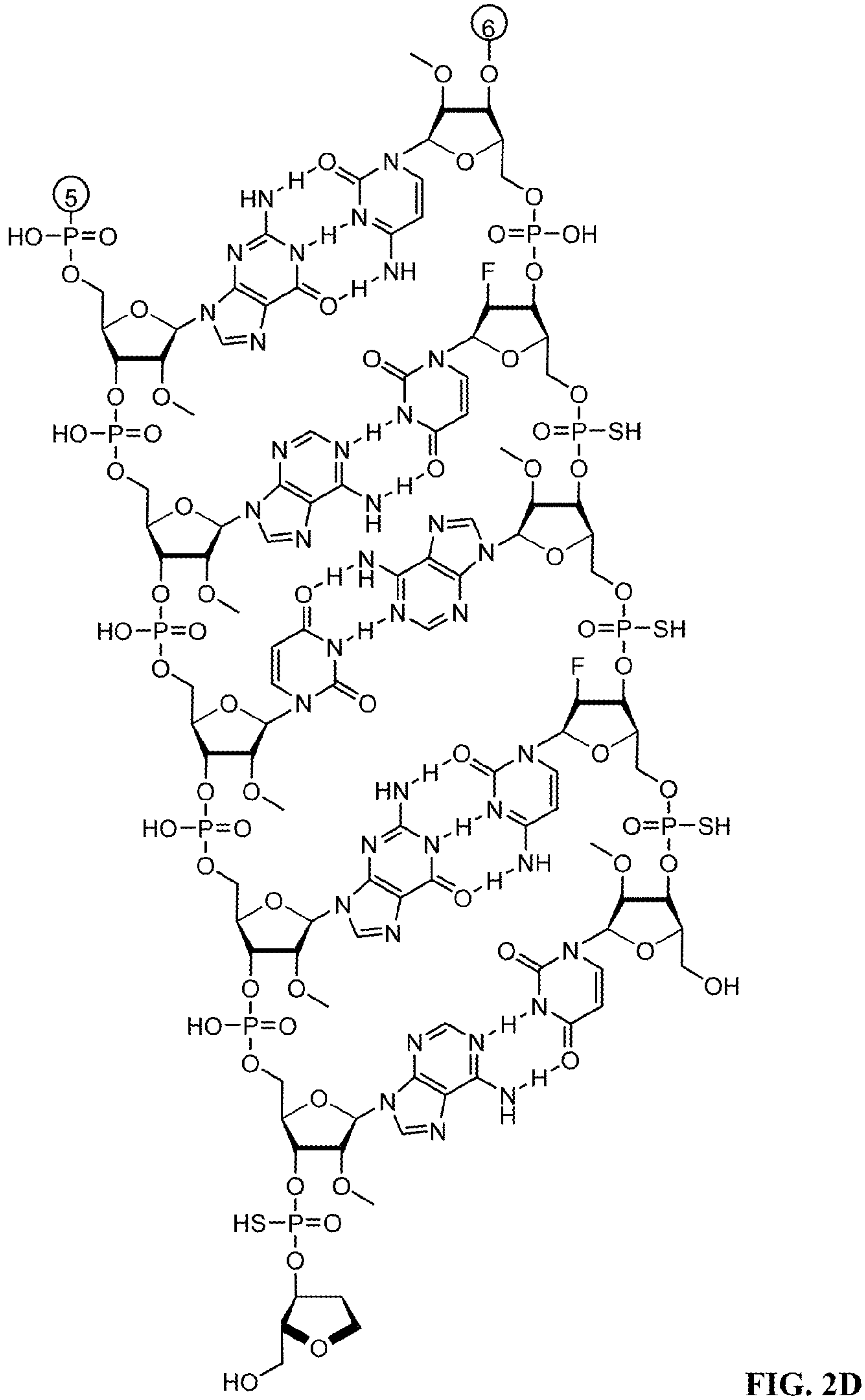
Figure 3A:
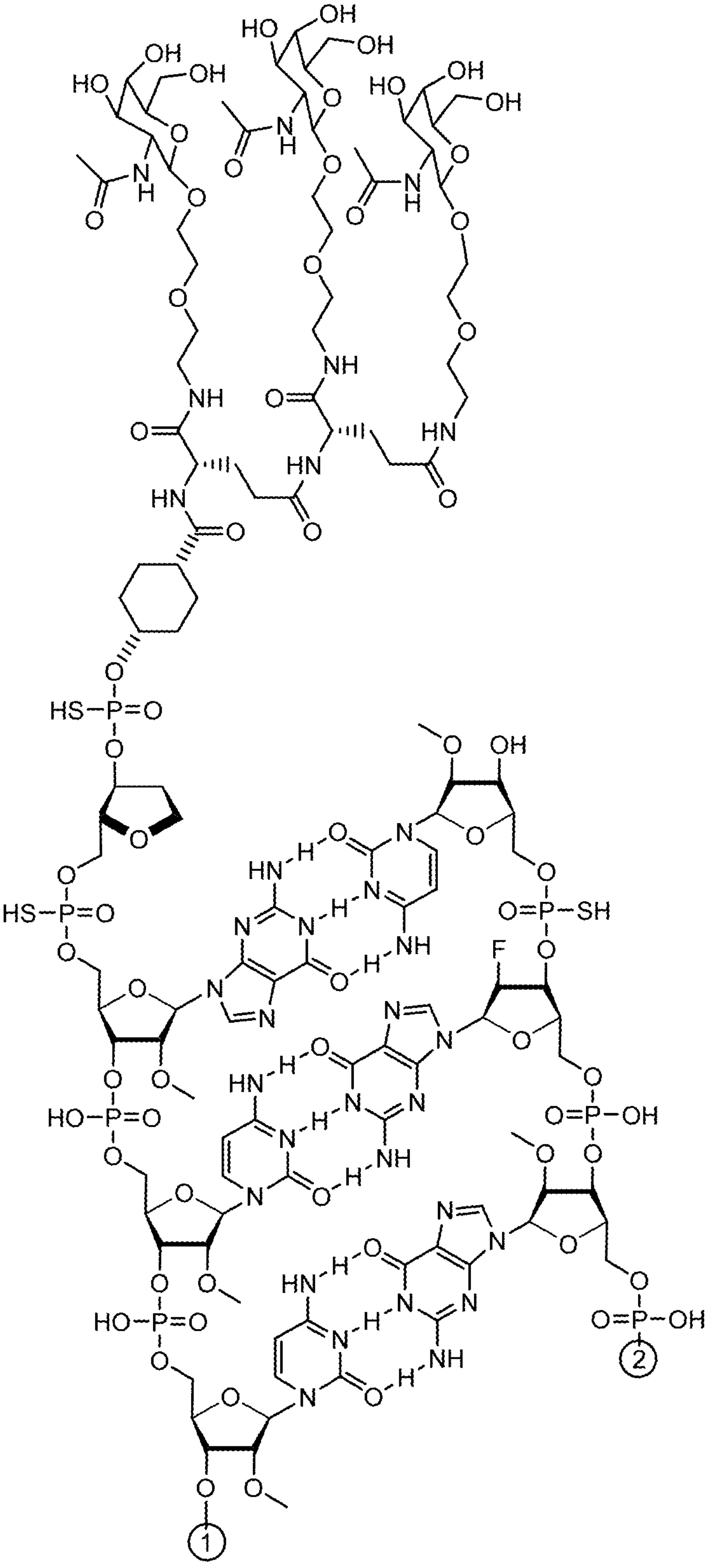
FIG. 3A to 3D. Chemical structure representation of HSD17B13 RNAi agent AD06187 conjugated to the tridentate N-acetyl-galactosamine targeting ligand of (NAG37)s at the 5' terminal end of the sense strand, shown in a free acid form.
Figure 3B:
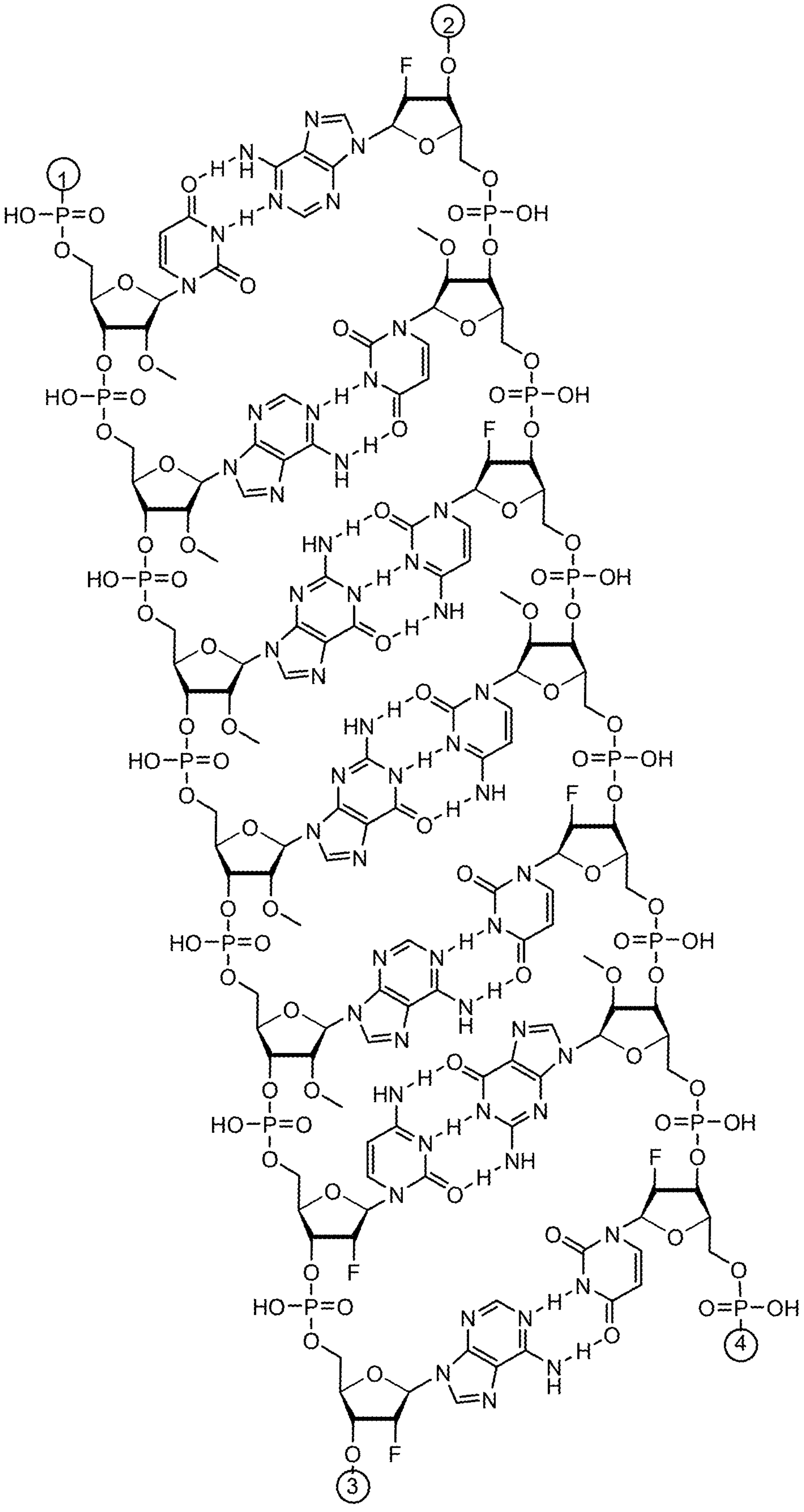
Figure 3C:
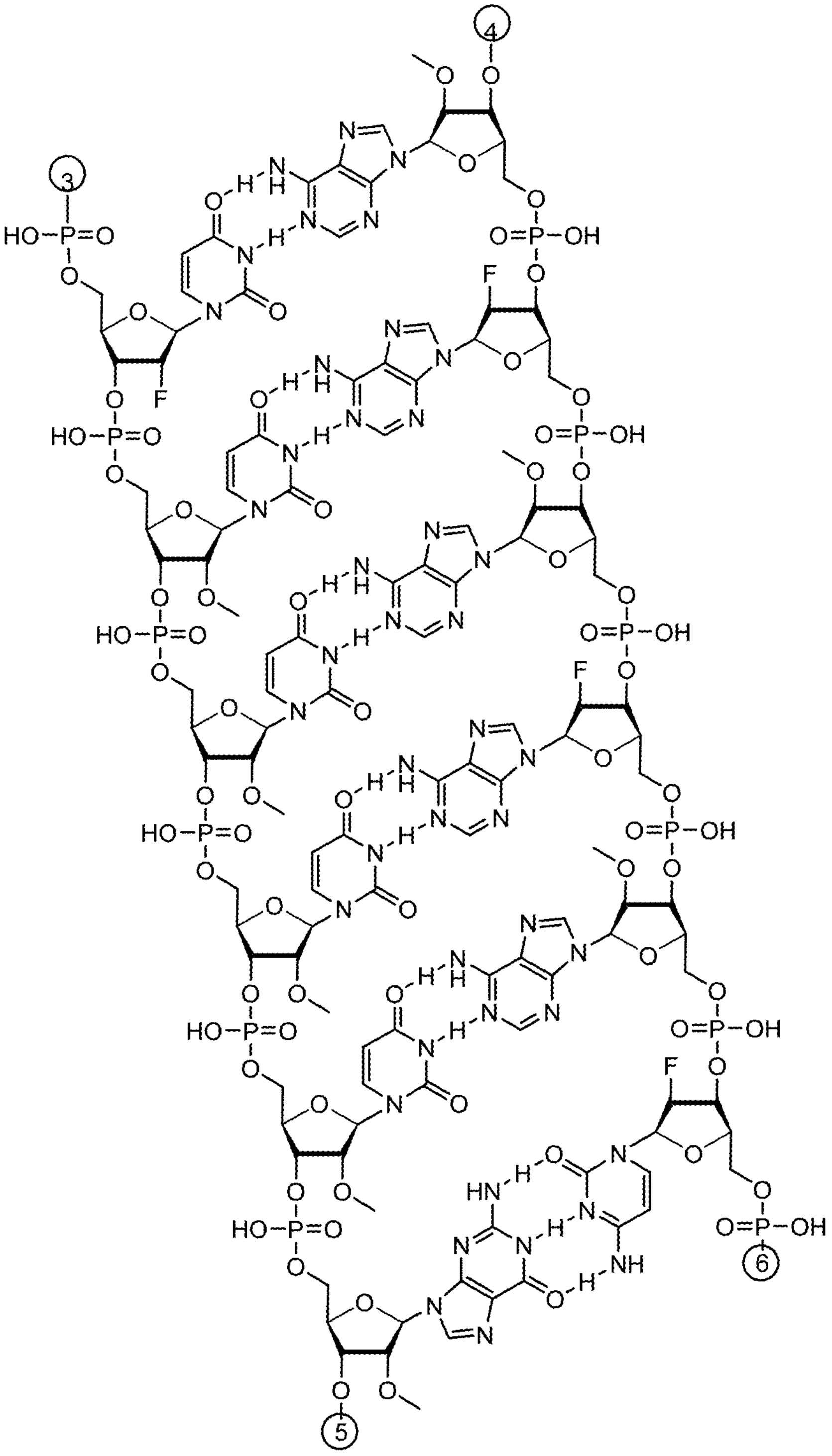
Figure 3D:
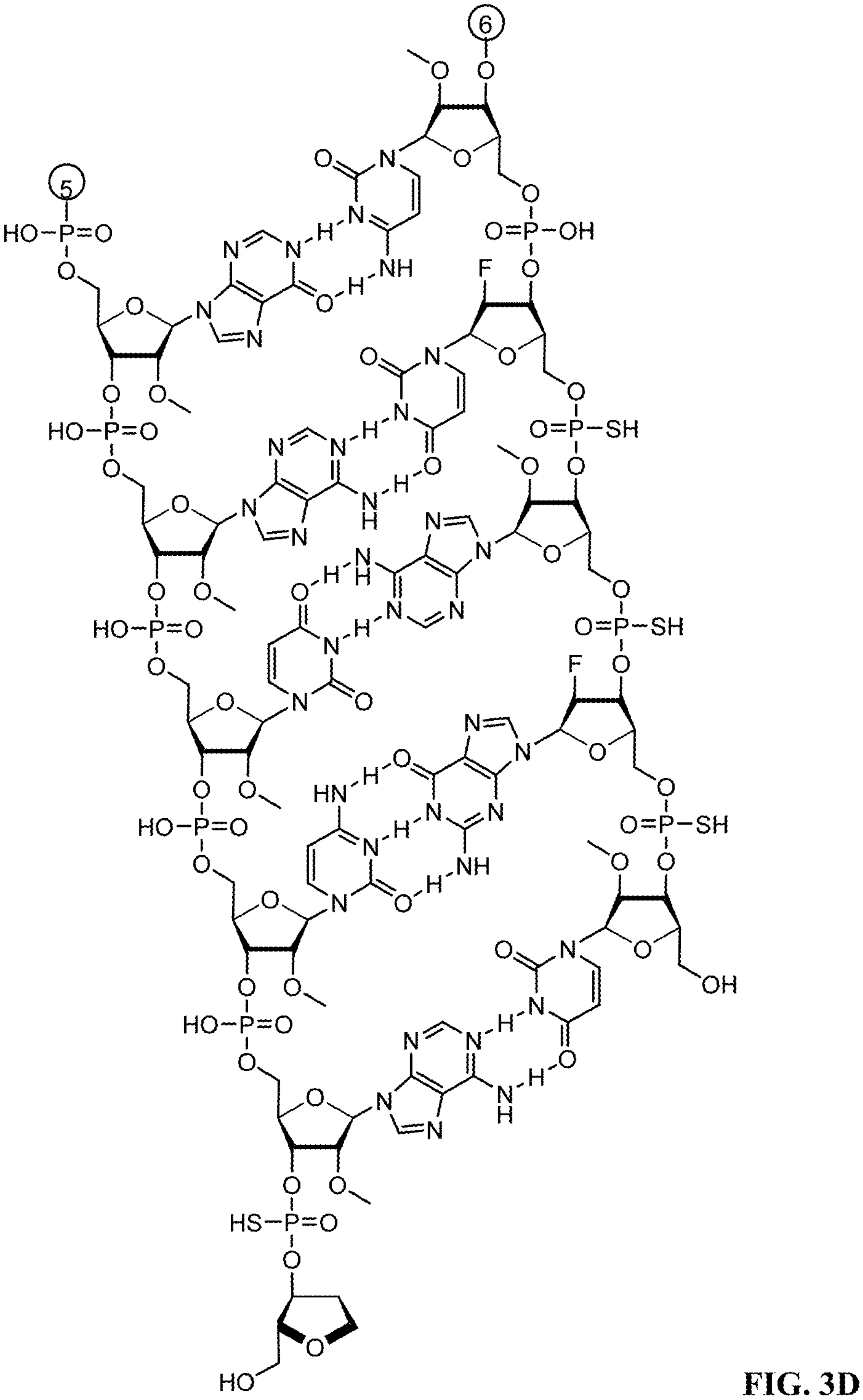
Figure 4A:
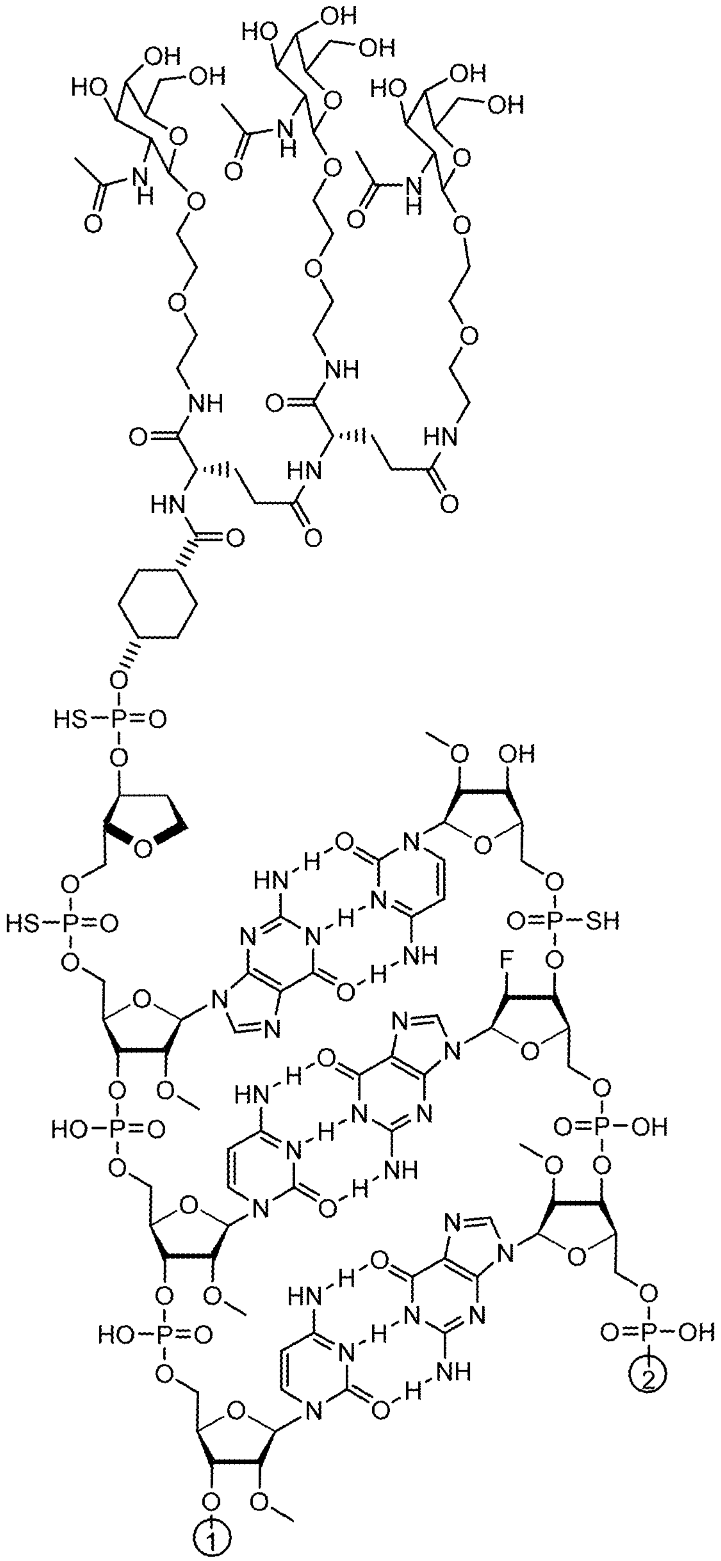
FIG. 4A to 4D. Chemical structure representation of HSD17B13 RNAi agent AD06276 conjugated to the tridentate N-acetyl-galactosamine targeting ligand of (NAG37)s at the 5' terminal end of the sense strand, shown in a free acid form.
Figure 4B:
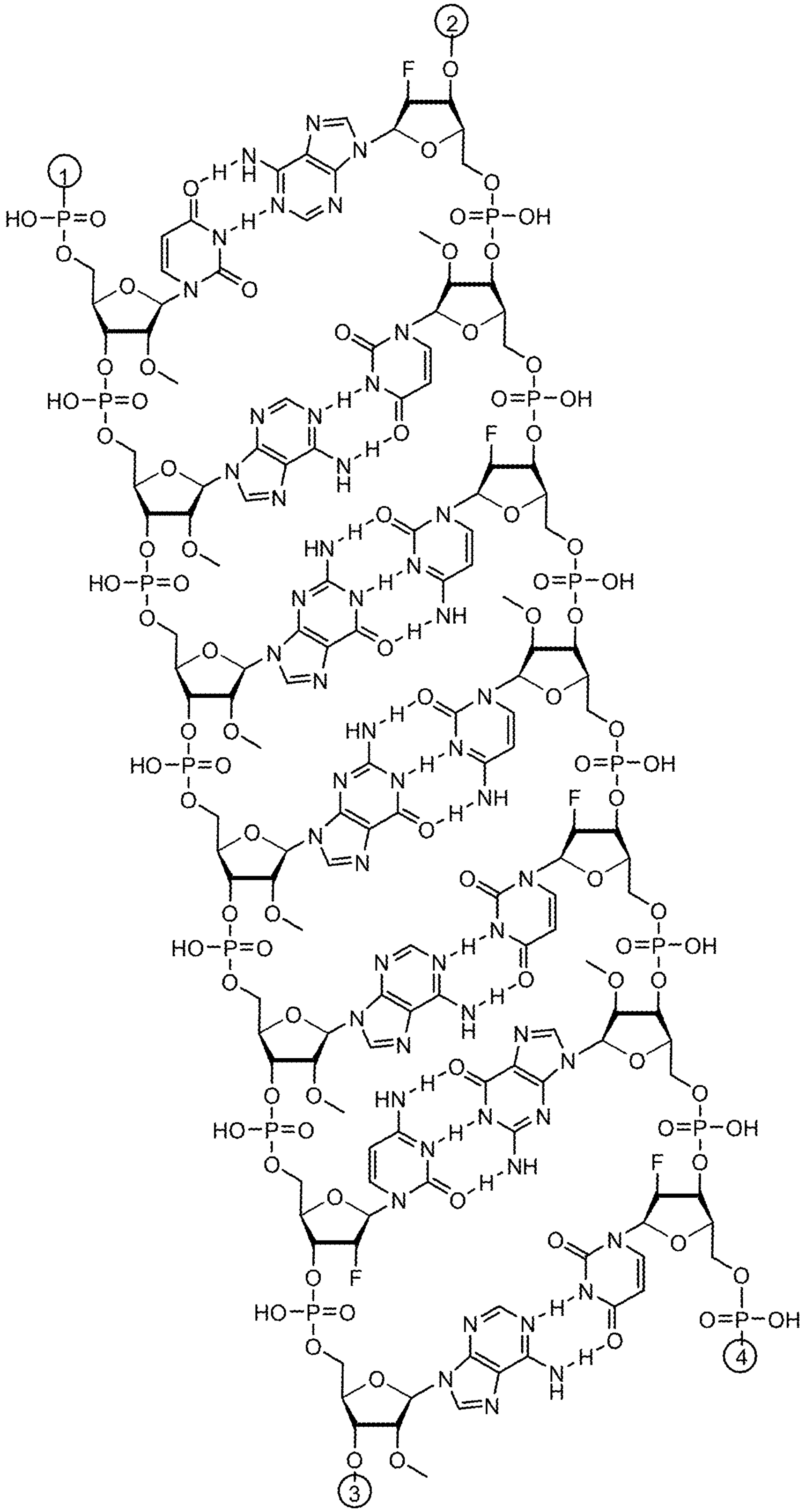
Figure 4C:
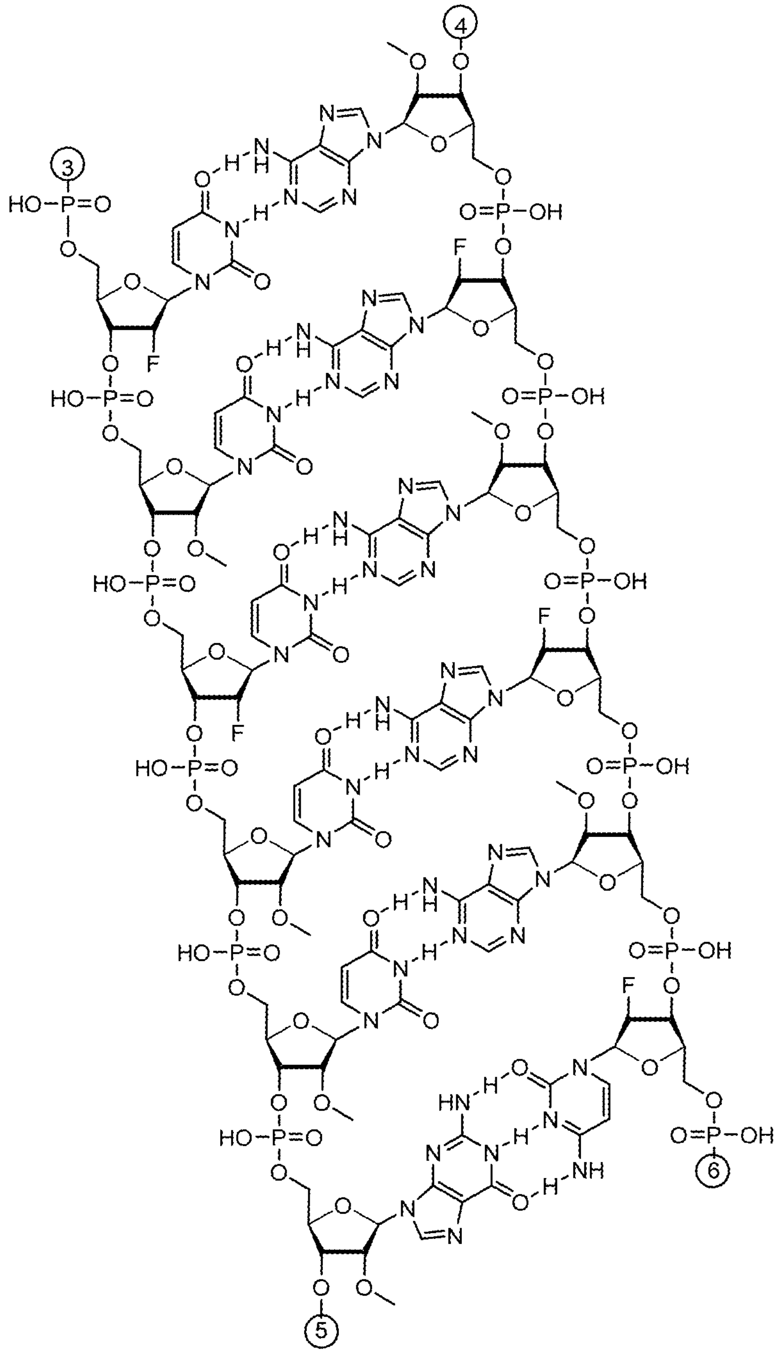
Figure 4D:
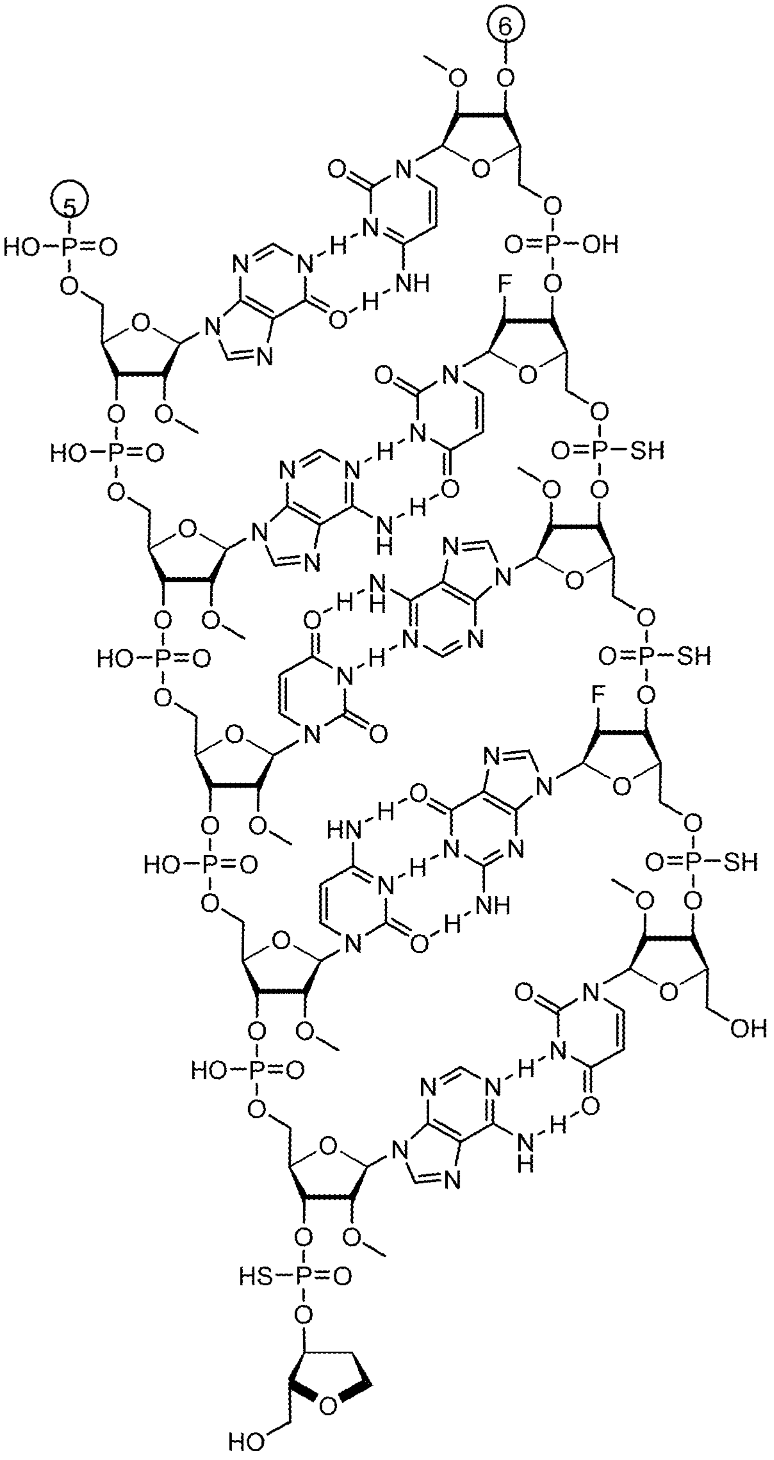
Figure 5A:
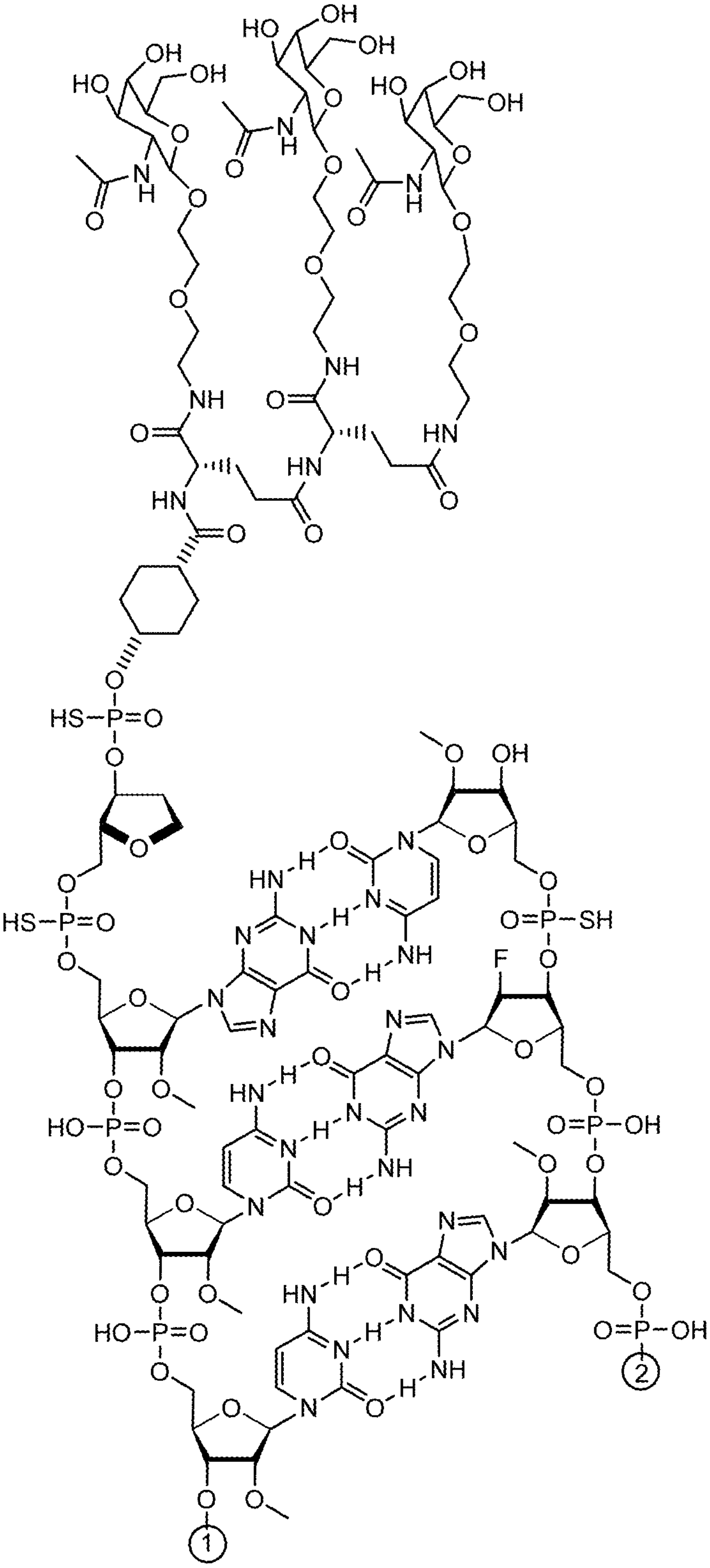
FIG. 5A to 5D. Chemical structure representation of HSD17B13 RNAi agent AD06277 conjugated to the tridentate N-acetyl-galactosamine targeting ligand of (NAG37)s at the 5' terminal end of the sense strand, shown in a free acid form.
Figure 5B:
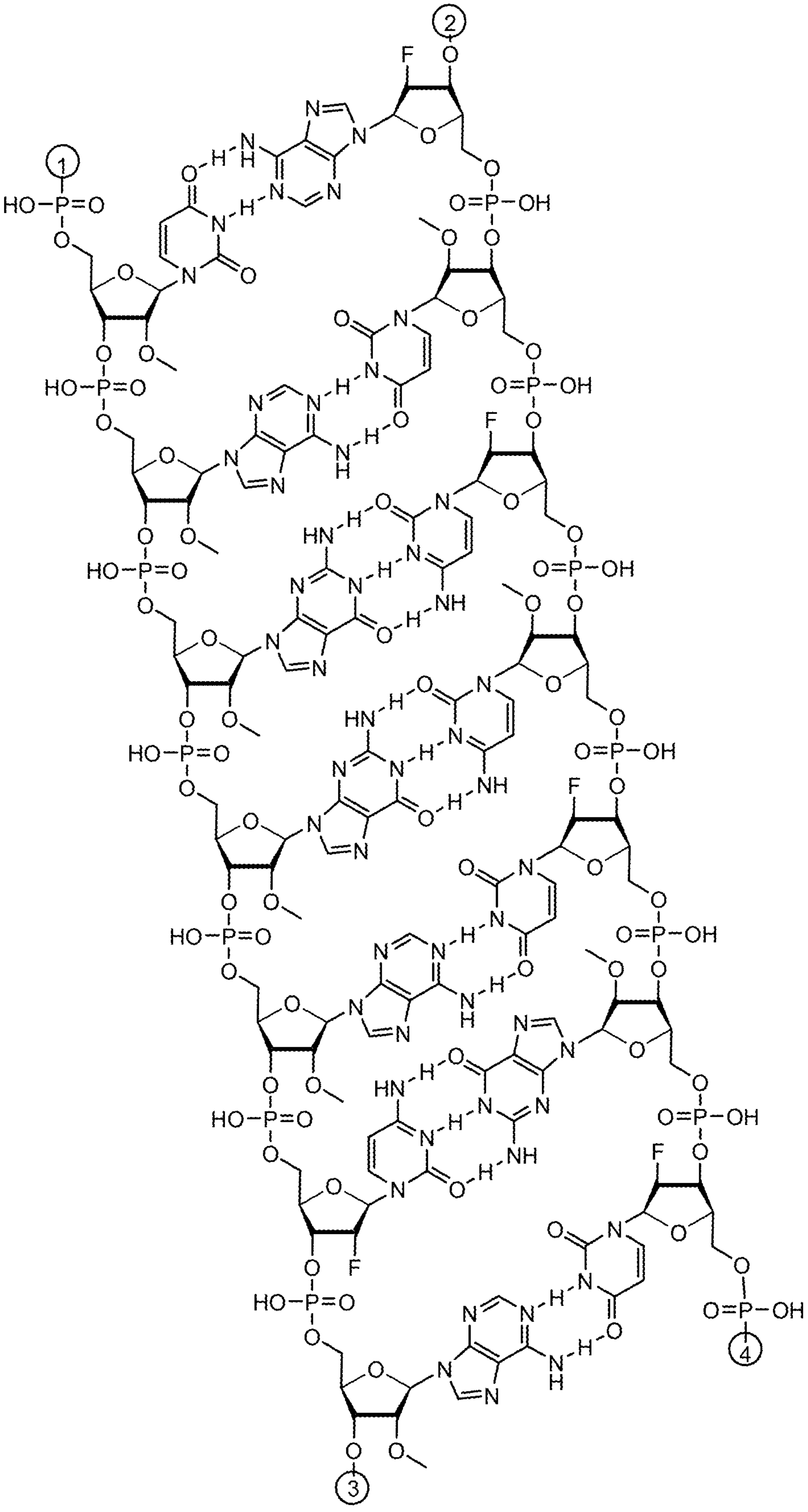
Figure 5C:
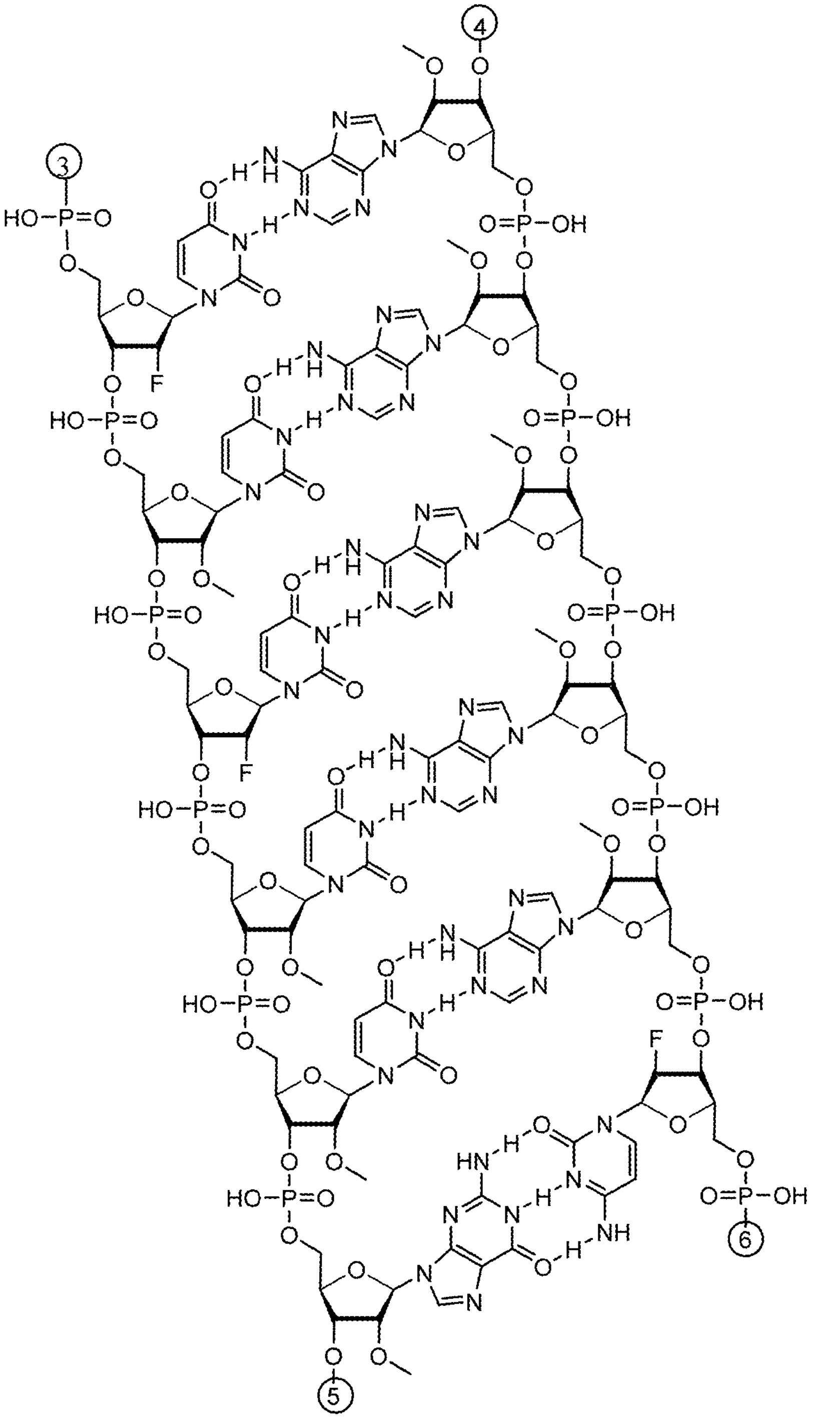
Figure 5D:
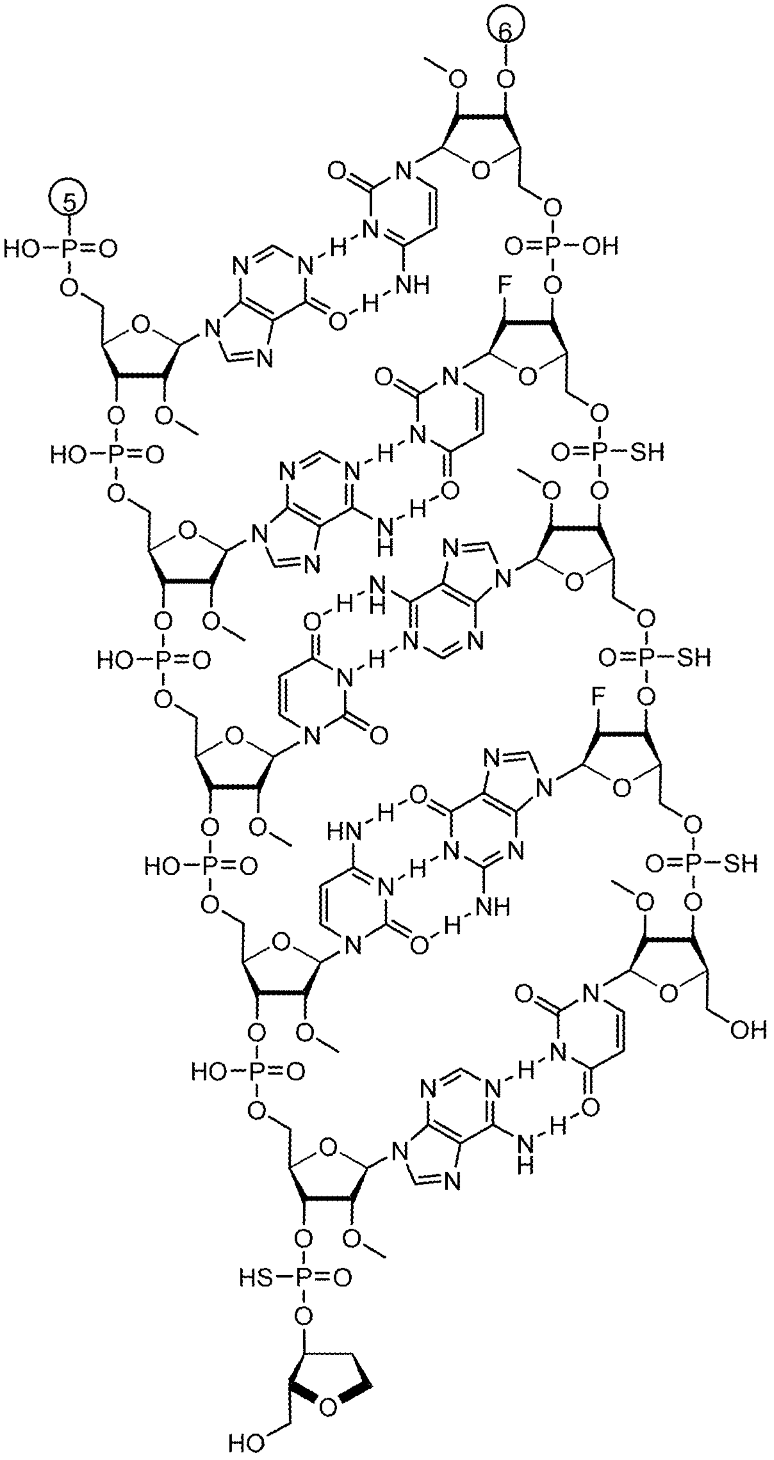
Figure 6A:
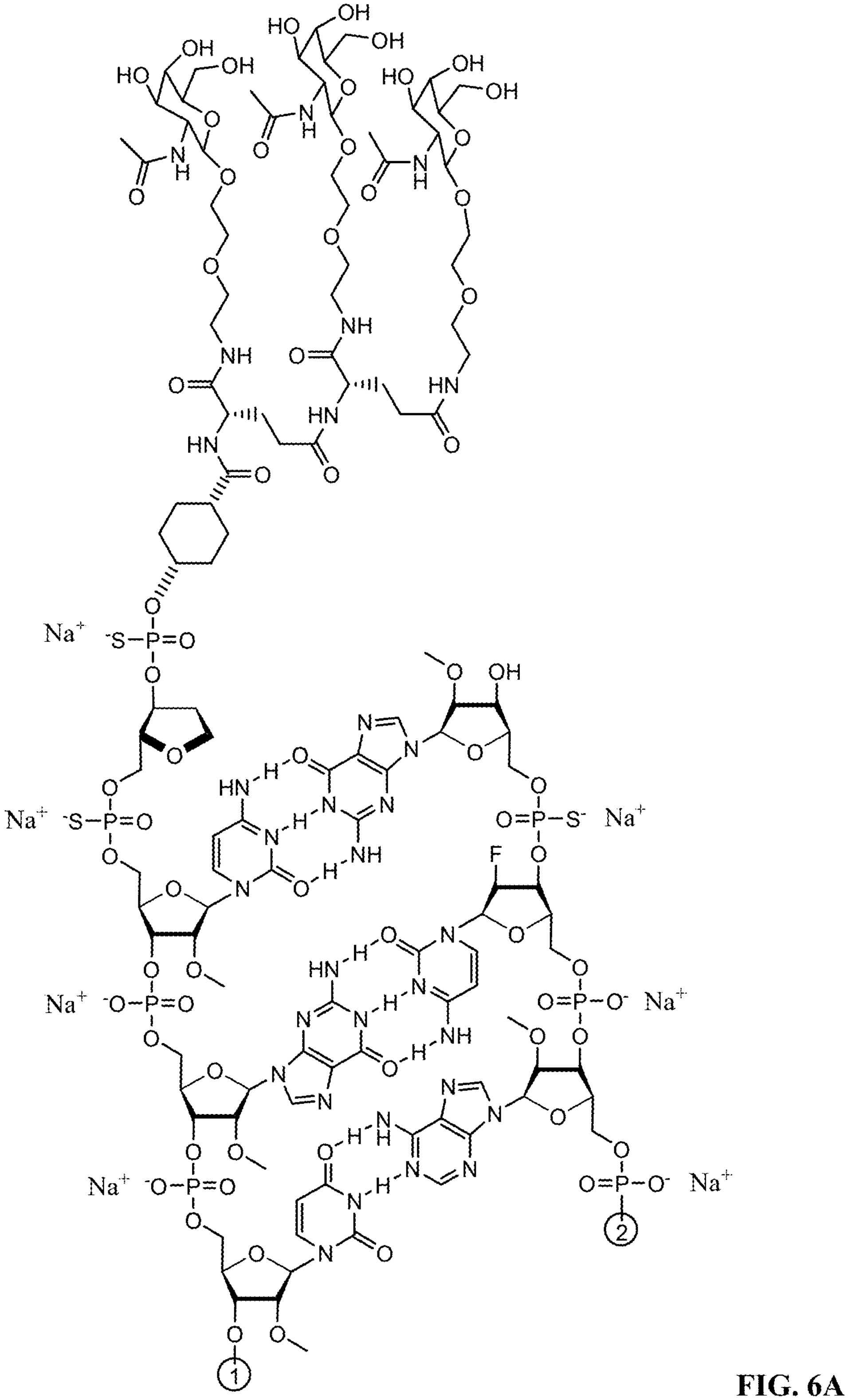
FIG. 6A to 6D. Chemical structure representation of HSD17B13 RNAi agent AD06214 conjugated to the tridentate N-acetyl-galactosamine targeting ligand of (NAG37)s at the 5' terminal end of the sense strand, shown in a sodium salt form.
Figure 6B:
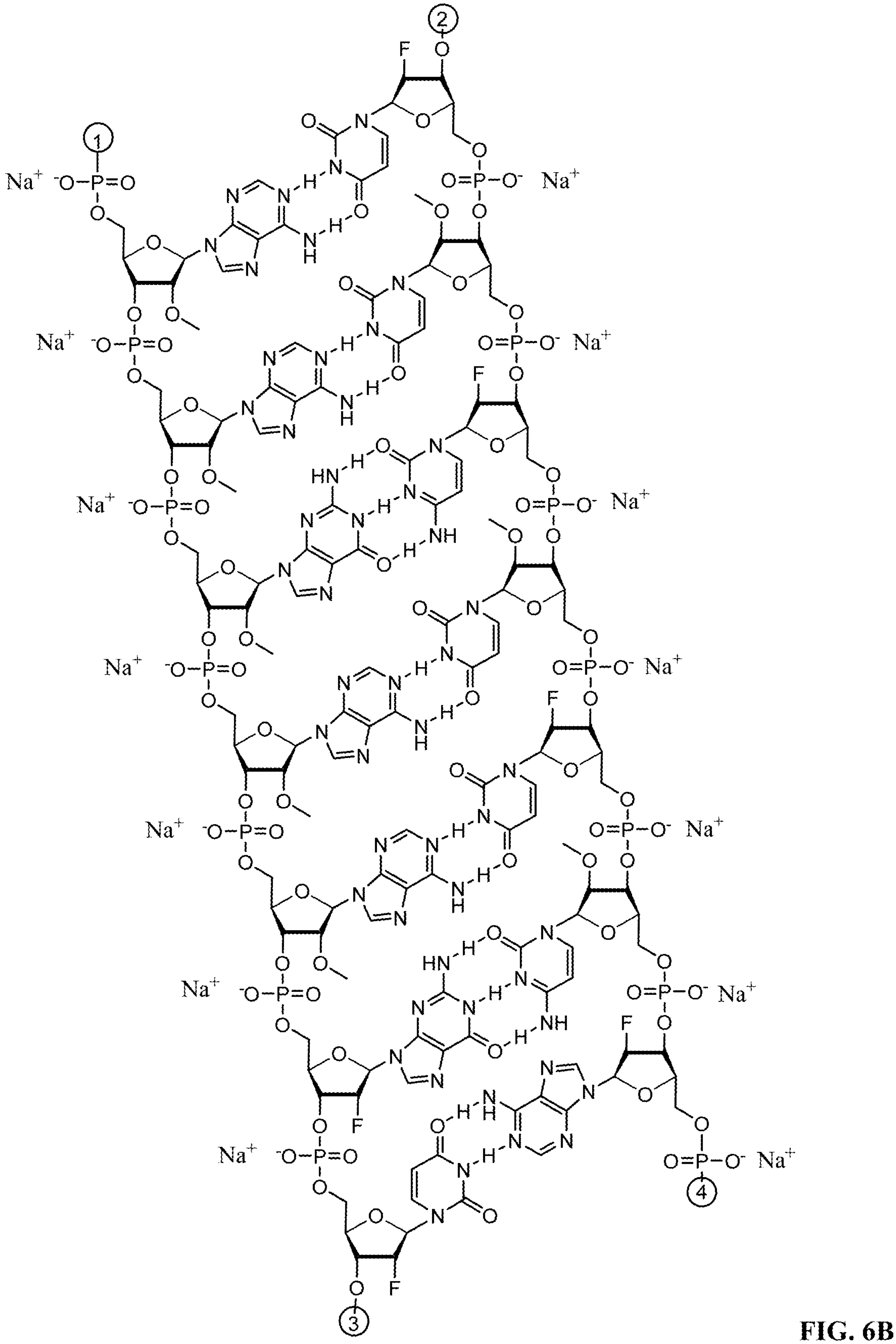
Figure 6C:
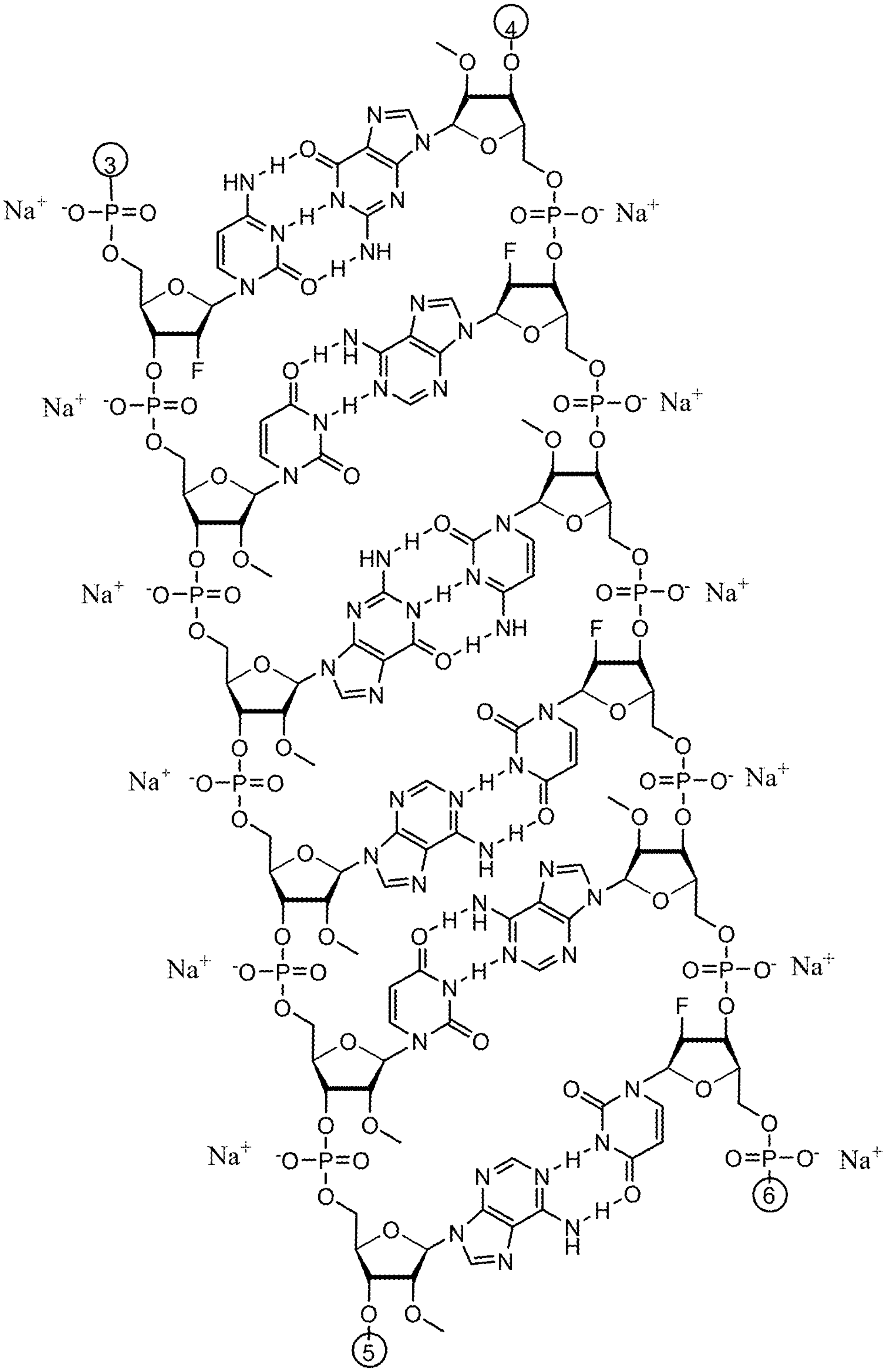
Figure 6D:
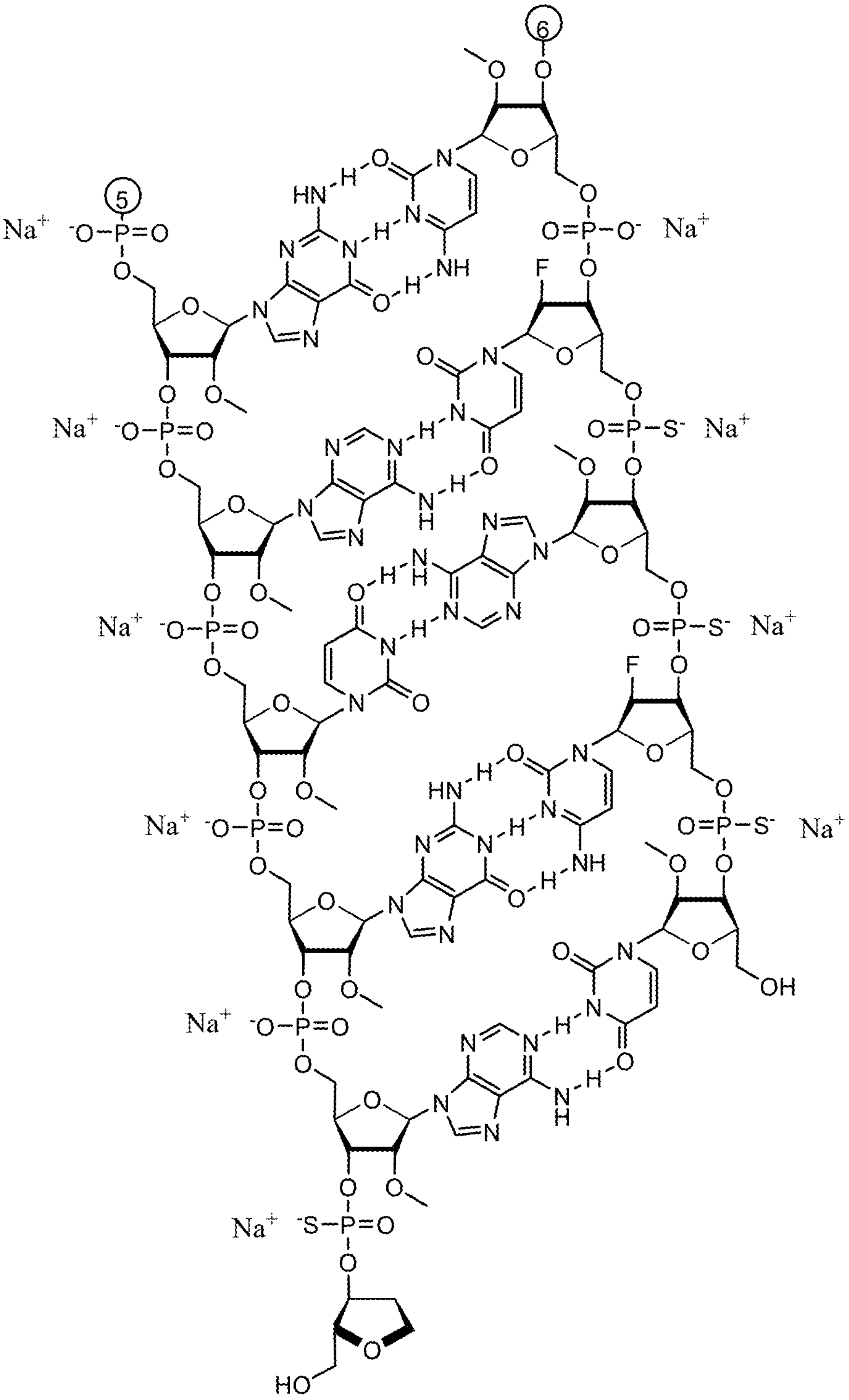
Figure 7A:
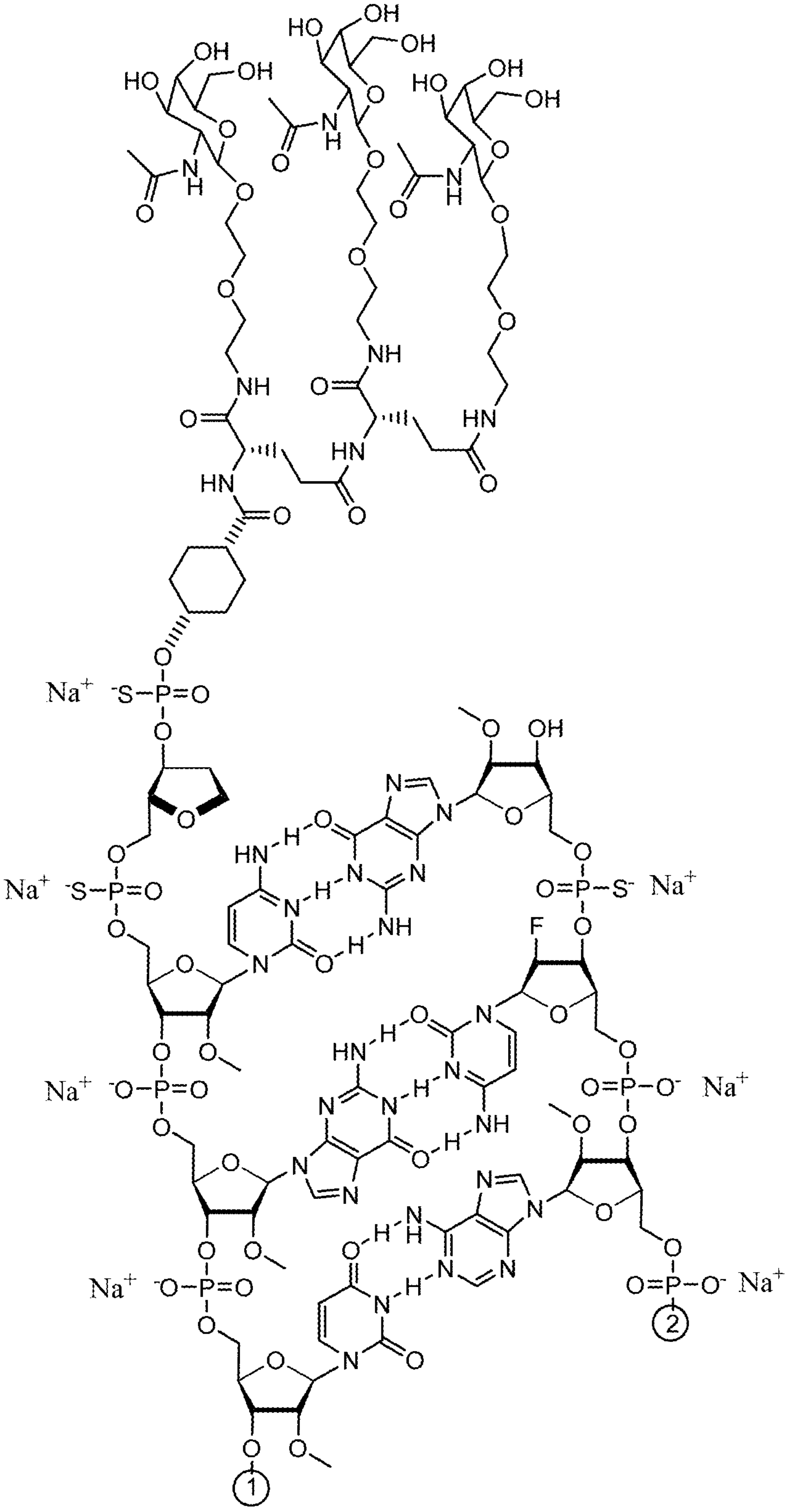
FIG. 7A to 7D. Chemical structure representation of HSD17B13 RNAi agent AD06280 conjugated to the tridentate N-acetyl-galactosamine targeting ligand of (NAG37)s at the 5' terminal end of the sense strand, shown in a sodium salt form.
Figure 7B:
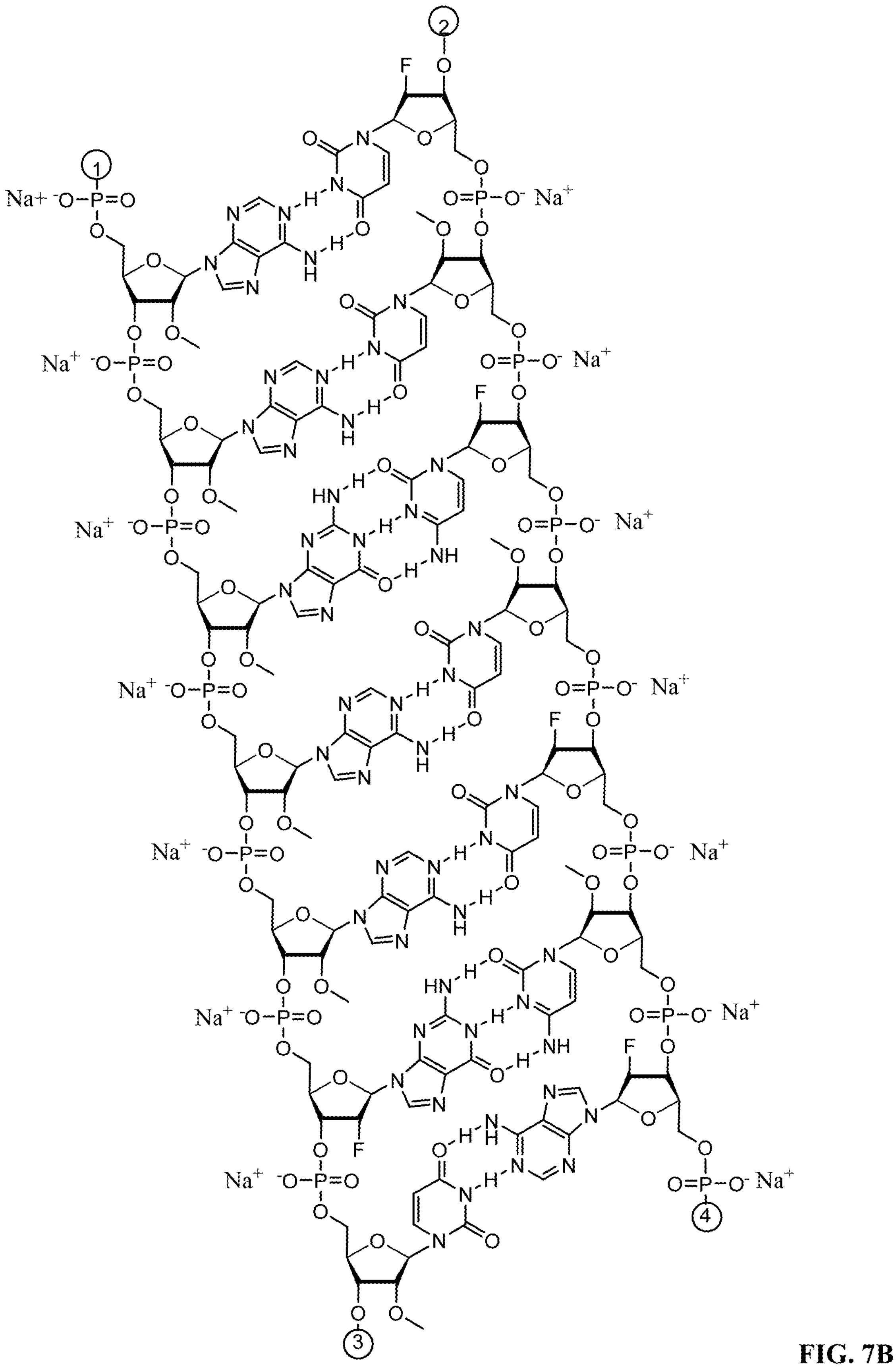
Figure 7C:
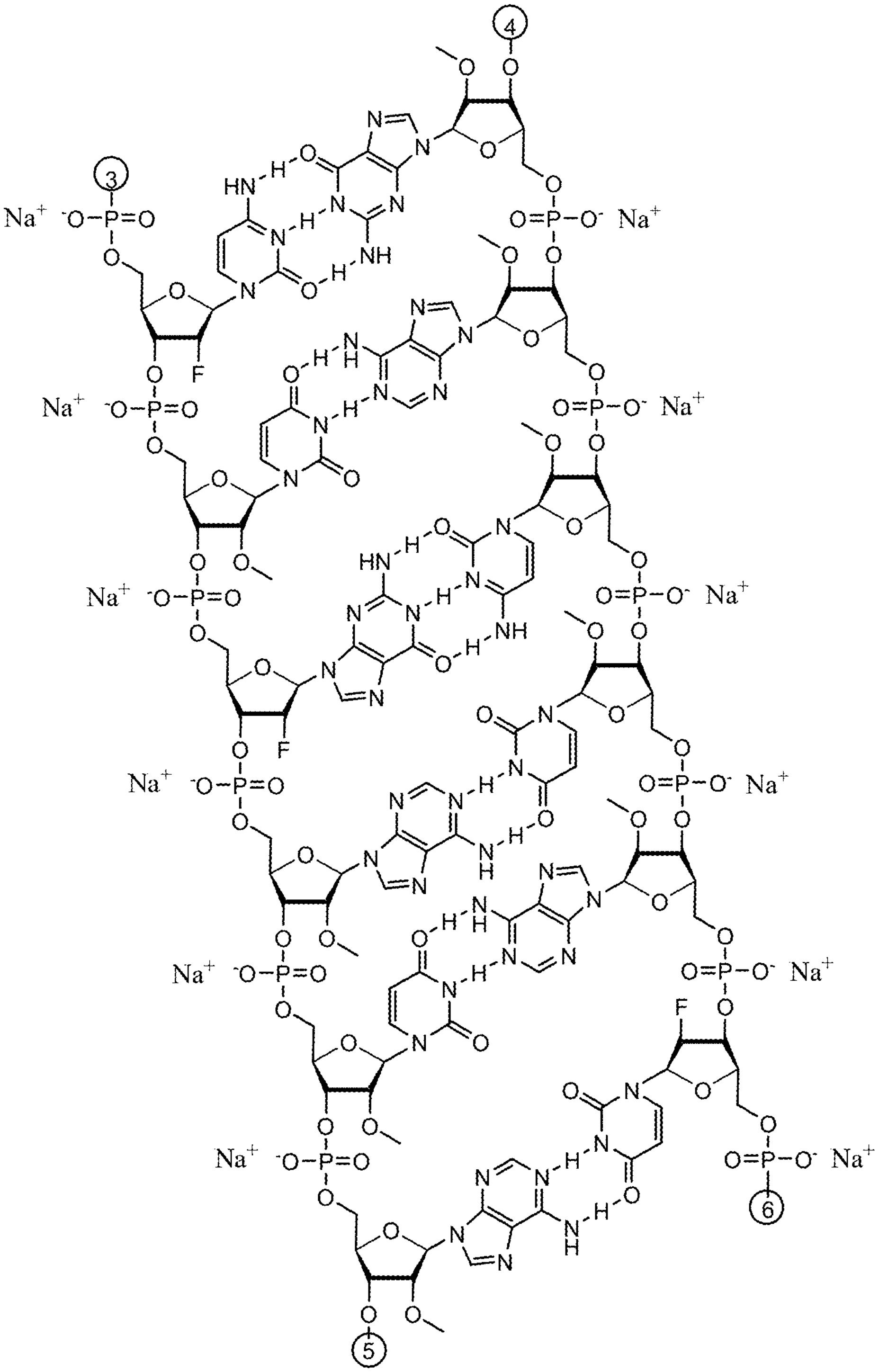
Figure 7D:
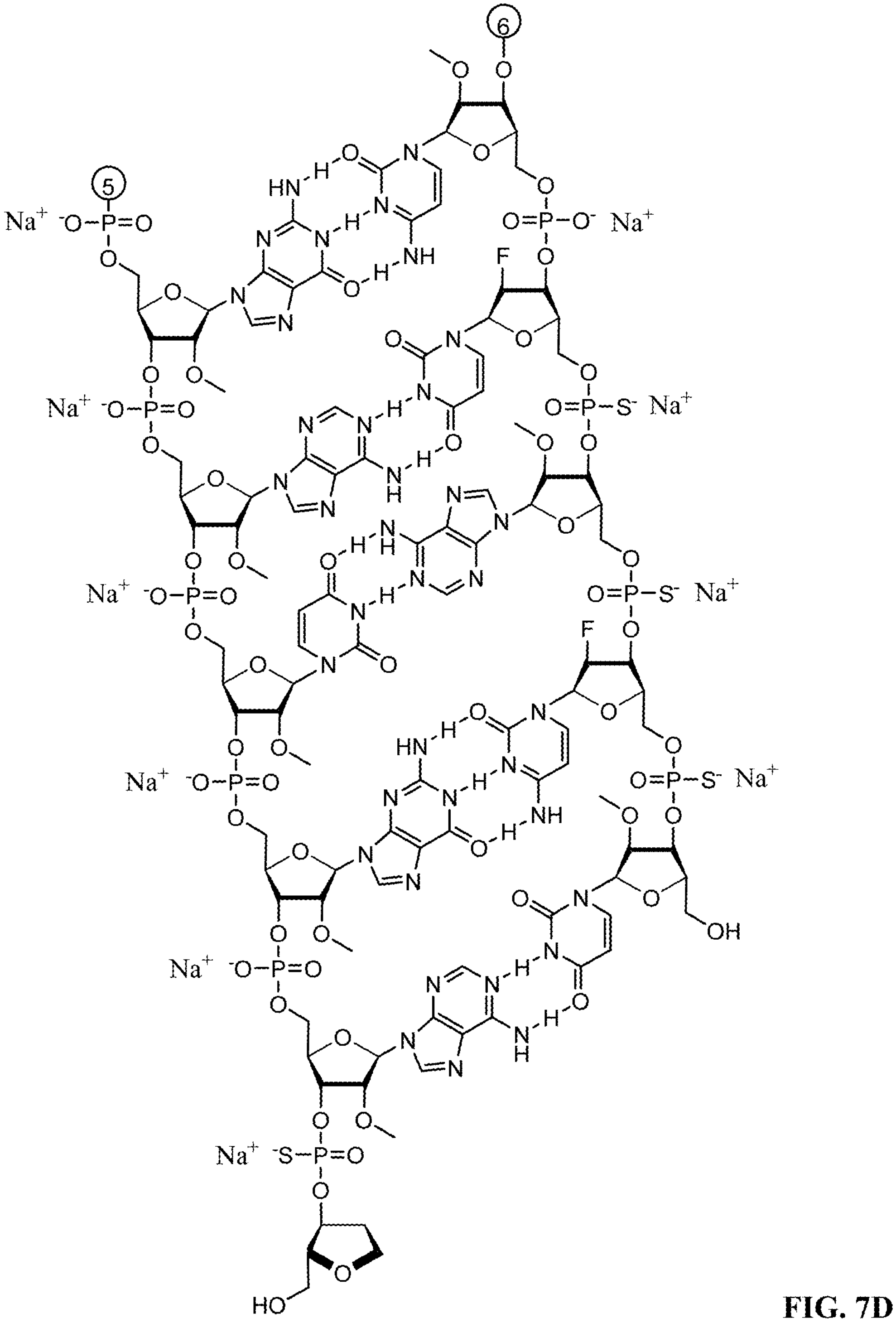
Figure 8A:
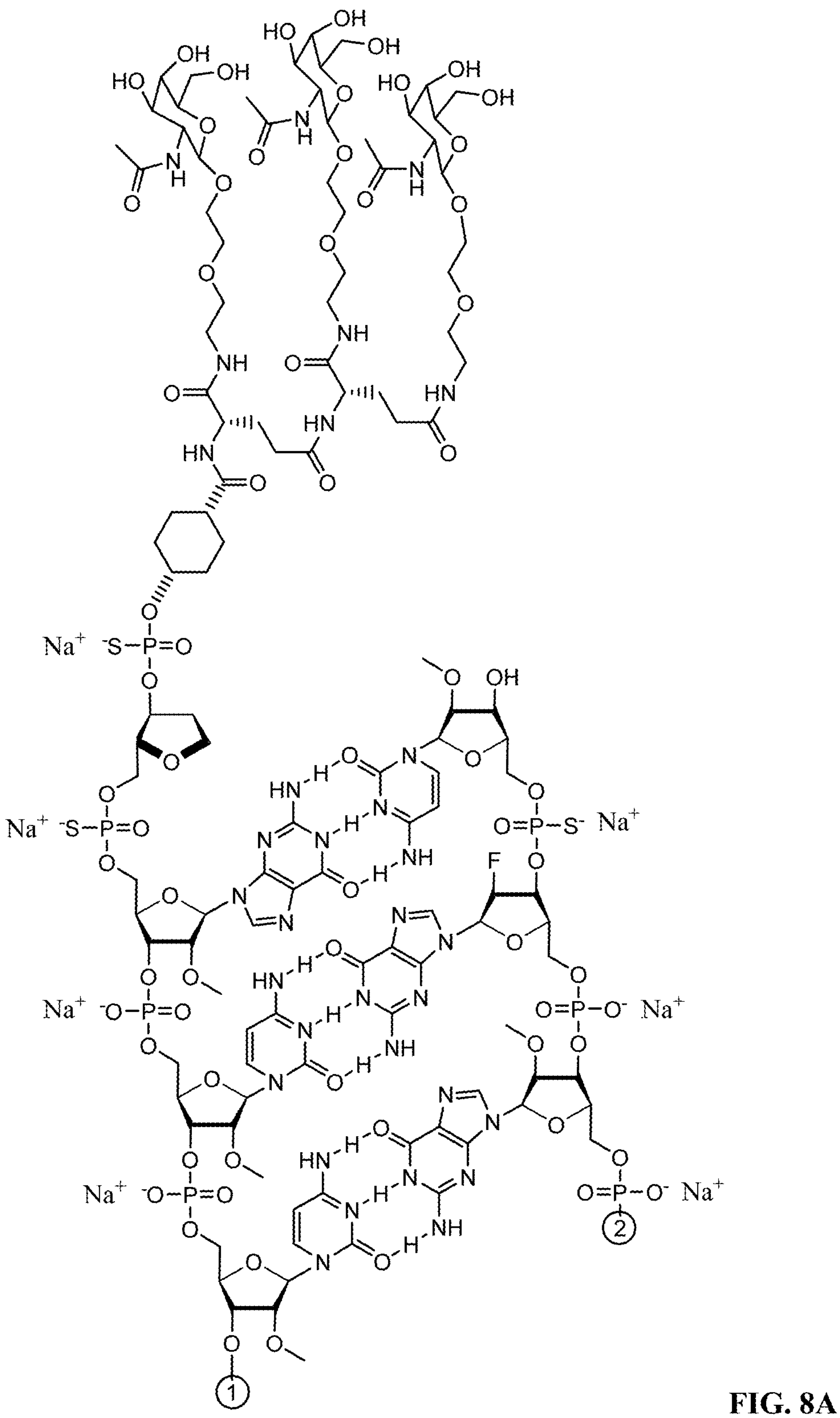
FIG. 8A to 8D. Chemical structure representation of HSD17B13 RNAi agent AD06187 conjugated to the tridentate N-acetyl-galactosamine targeting ligand of (NAG37)s at the 5' terminal end of the sense strand, shown in a sodium salt form.
Figure 8B:
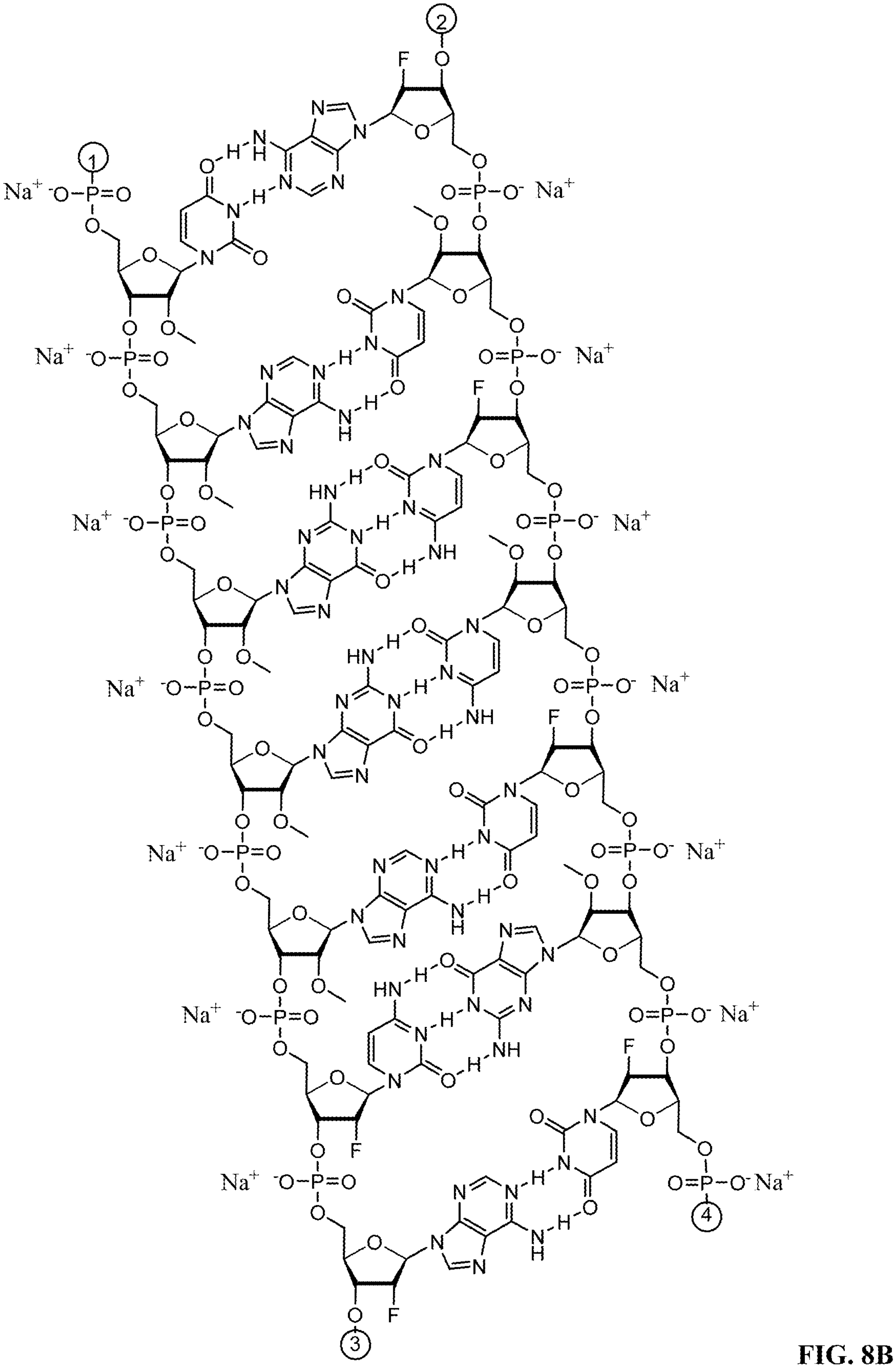
Figure 8C:
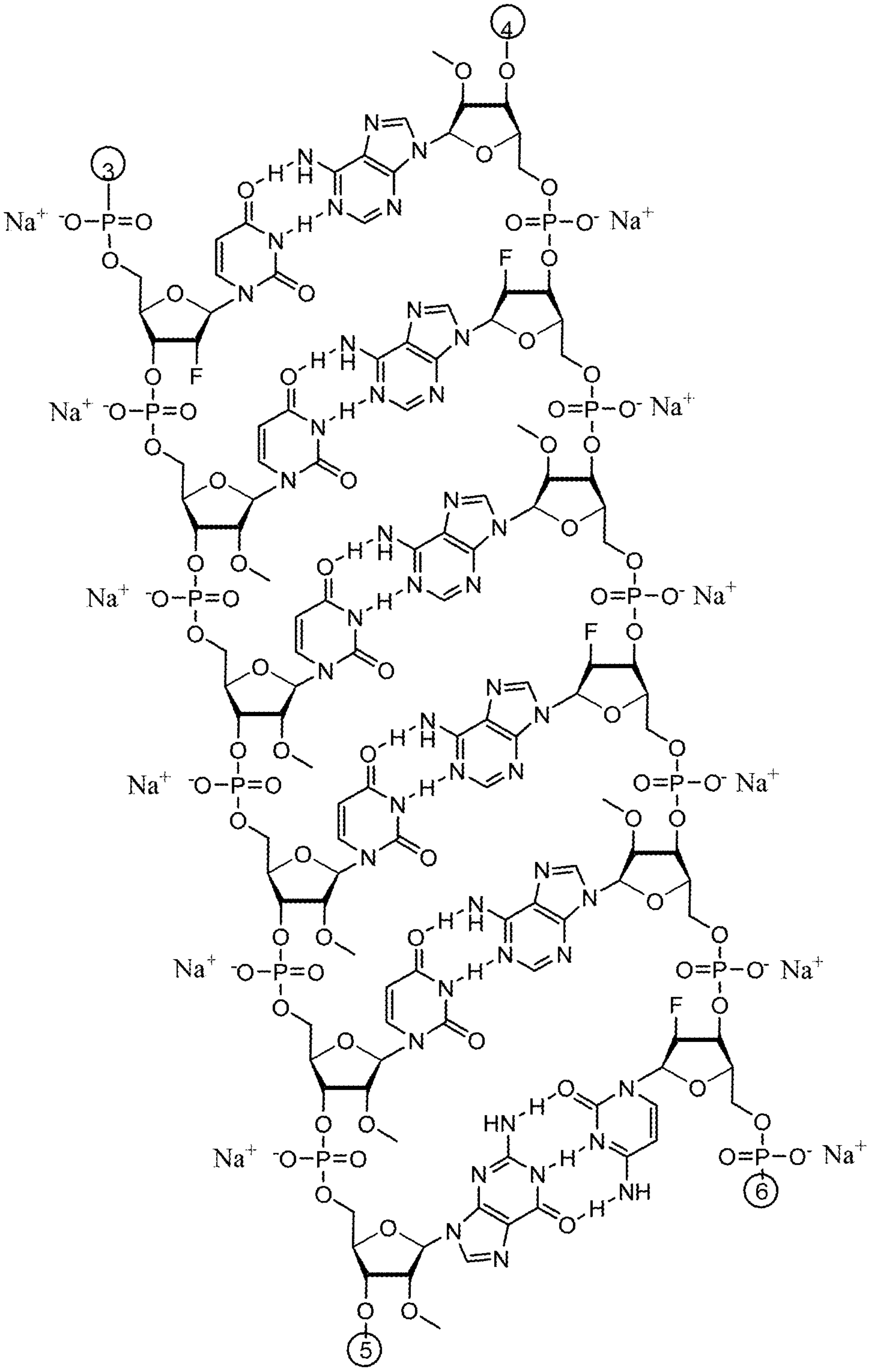
Figure 8D:
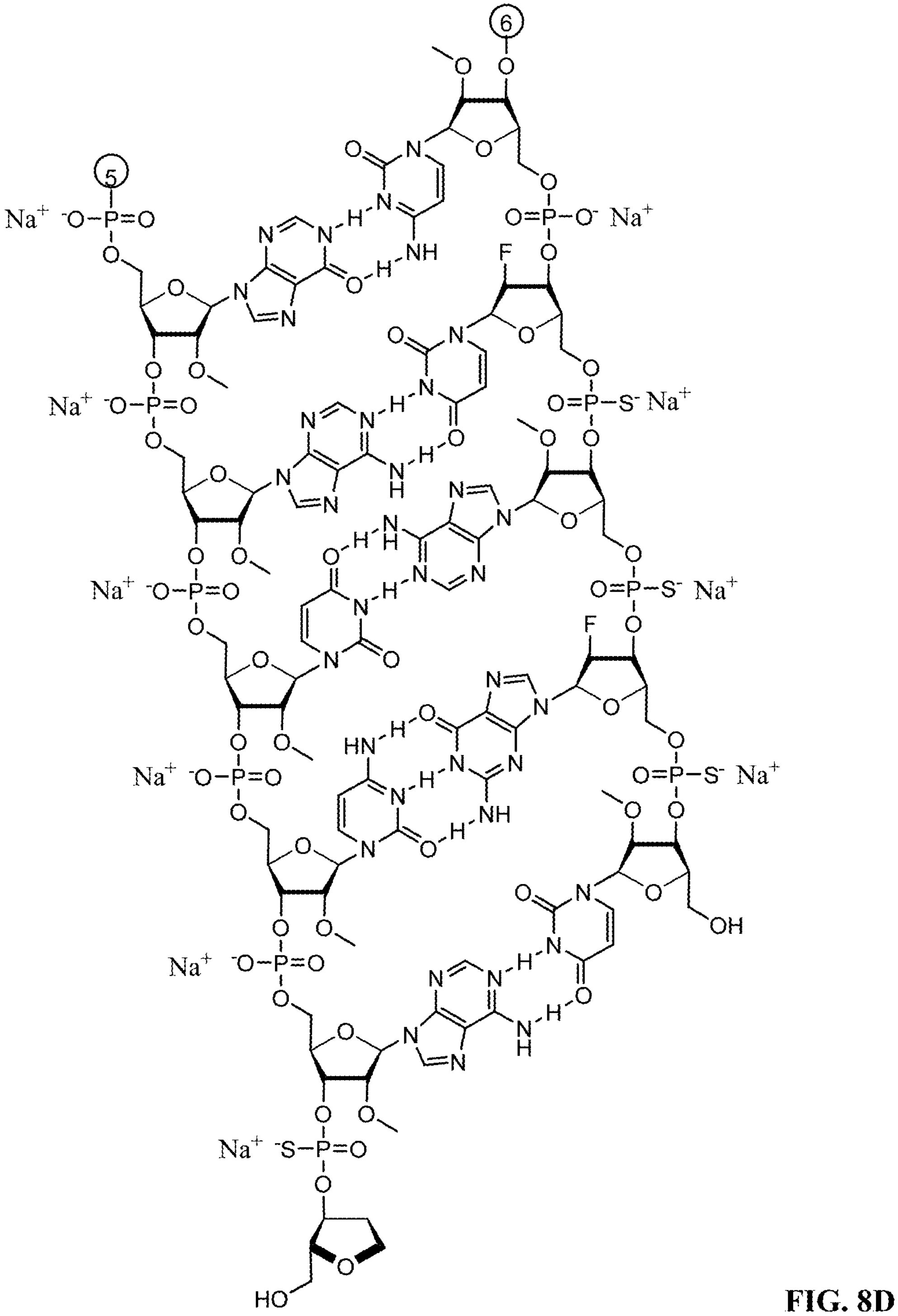
Figure 9A:
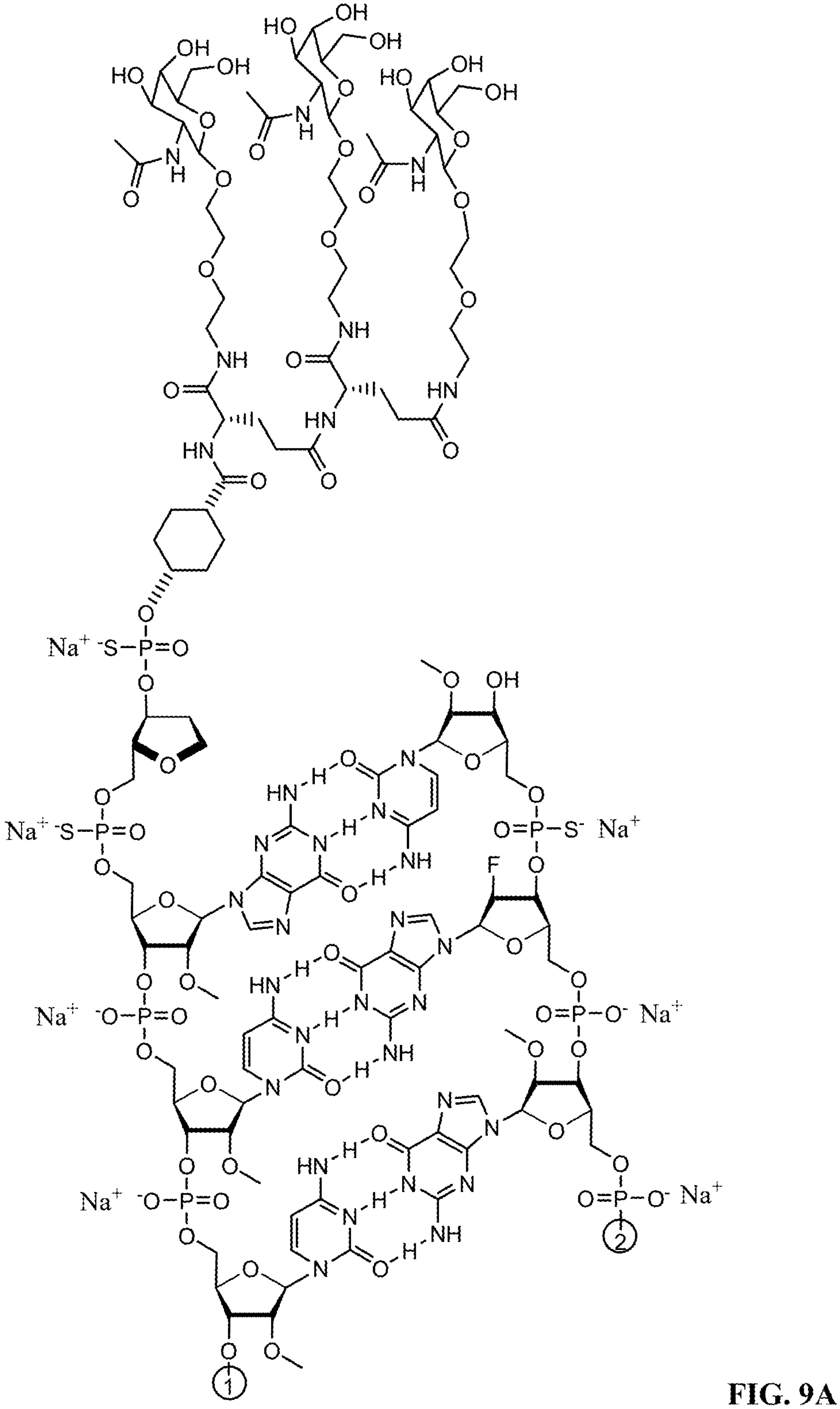
FIG. 9A to 9D. Chemical structure representation of HSD17B13 RNAi agent AD06276 conjugated to the tridentate N-acetyl-galactosamine targeting ligand of (NAG37)s at the 5' terminal end of the sense strand, shown in a sodium salt form.
Figure 9B:
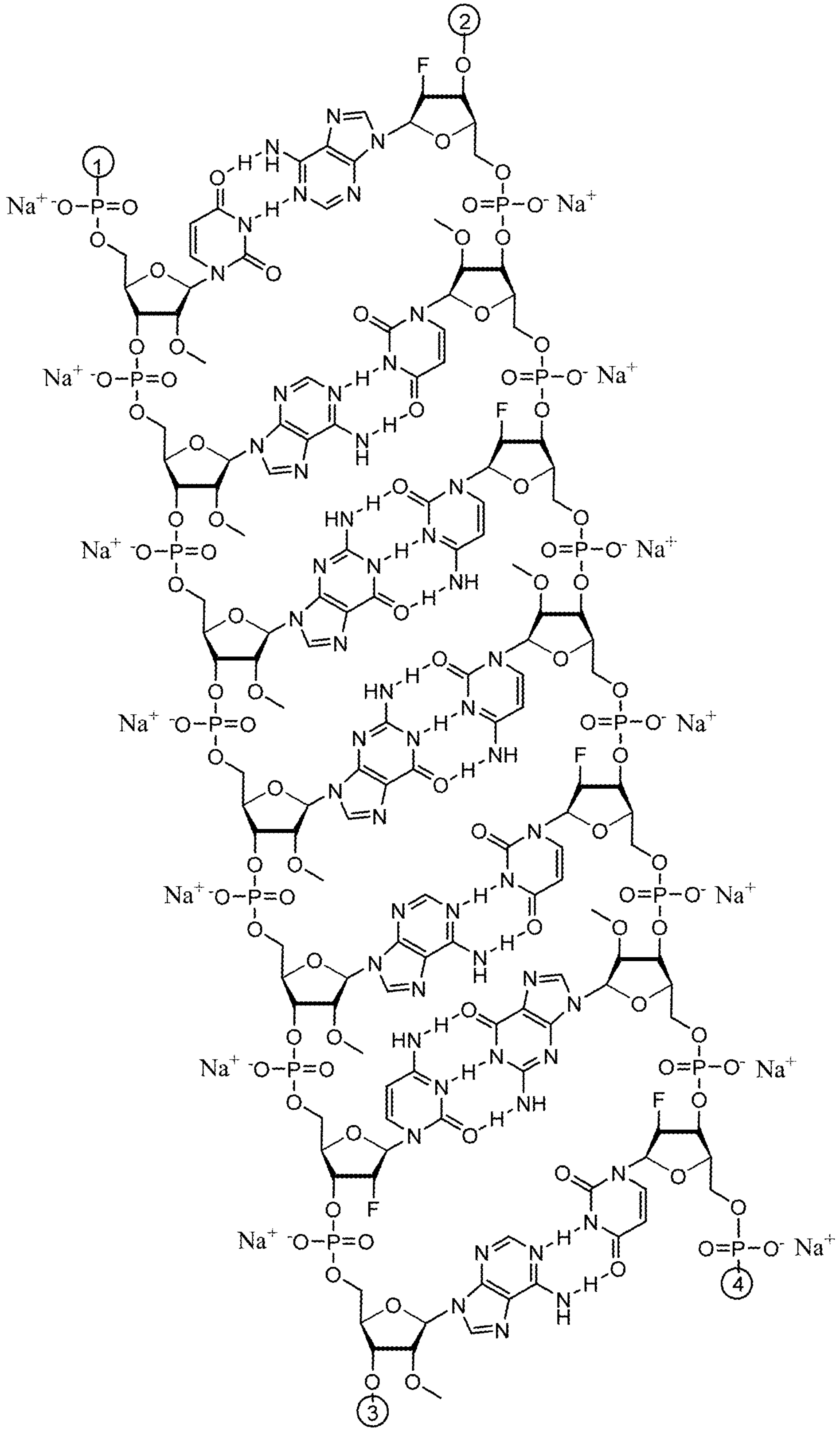
Figure 9C:
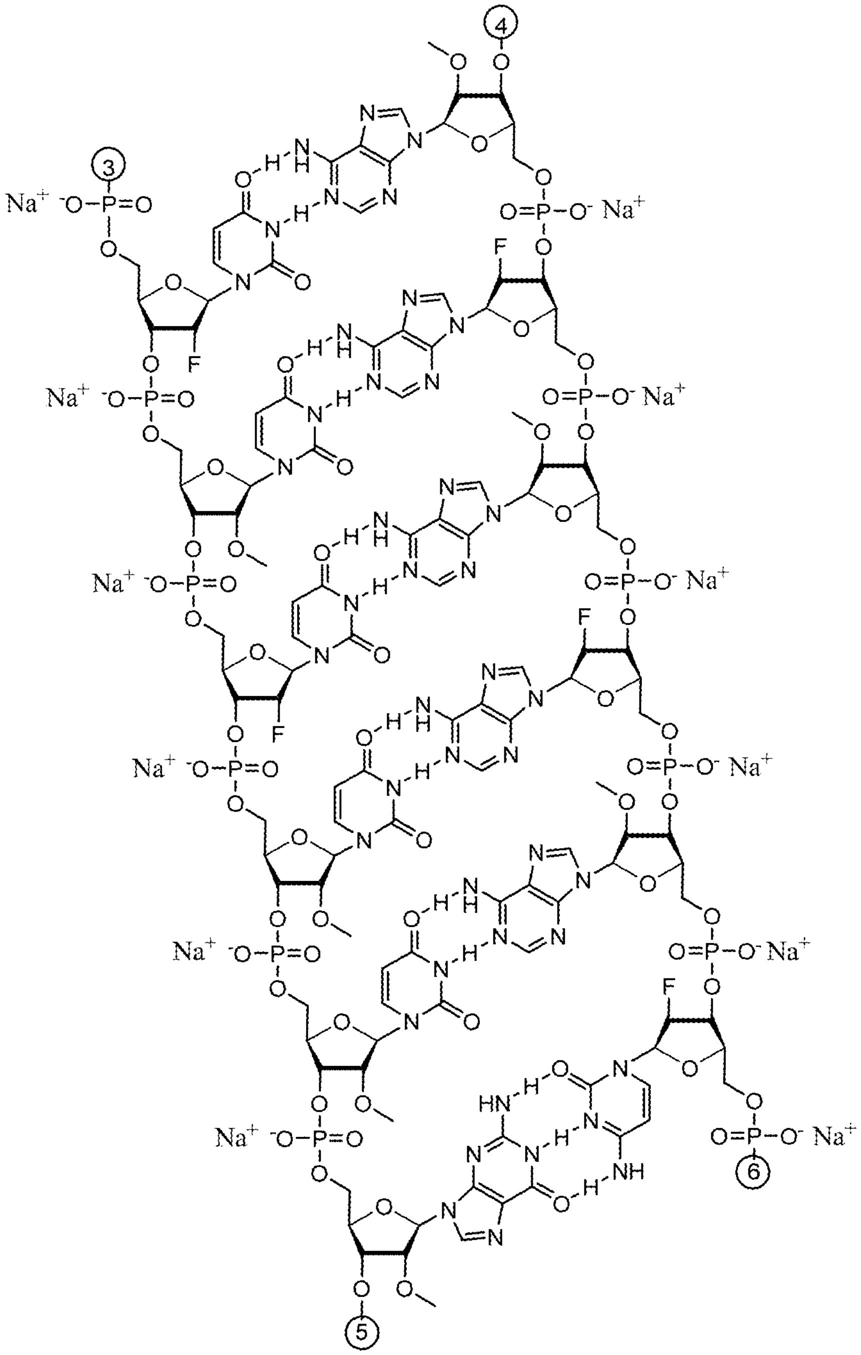
Figure 9D:
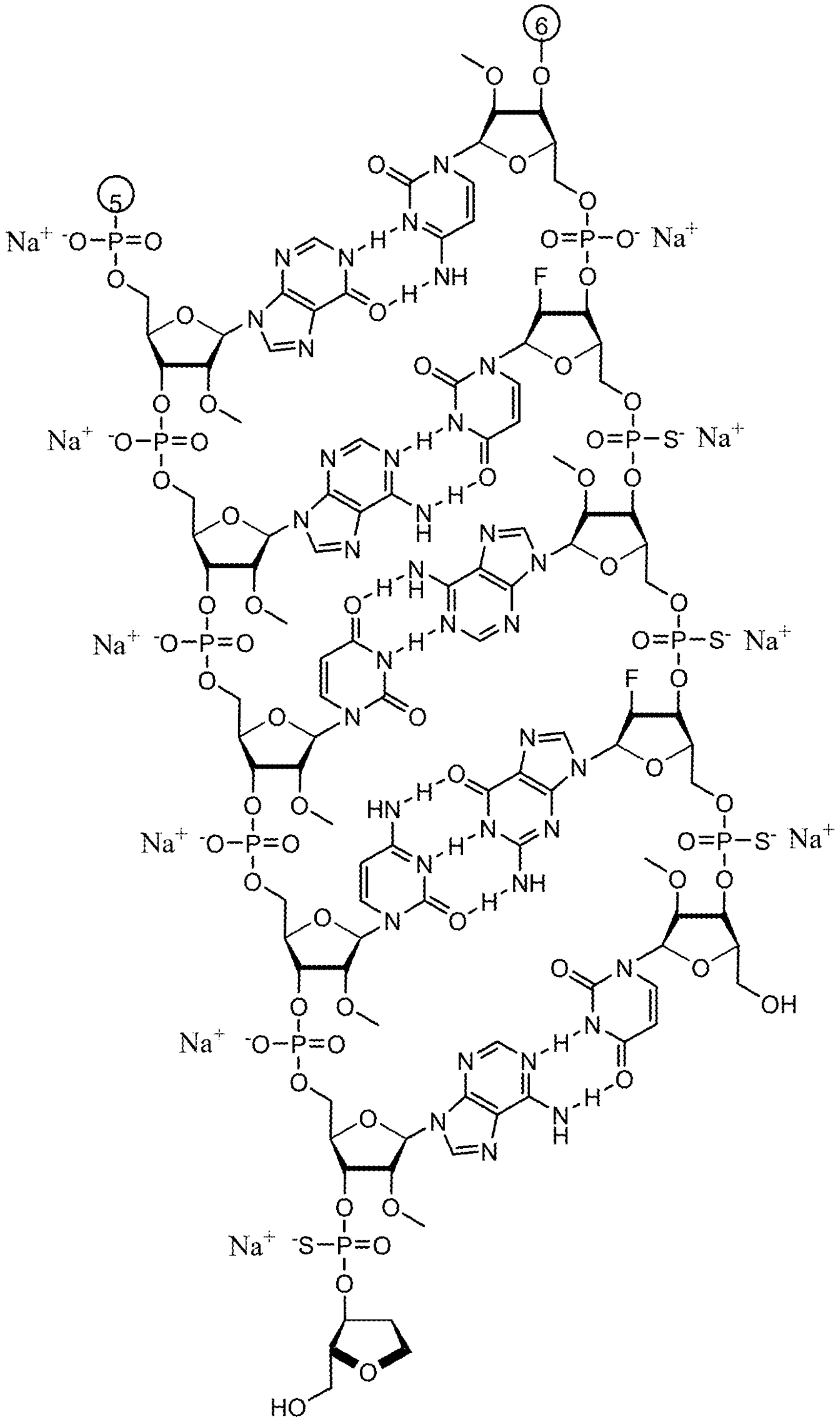
Figure 10A:
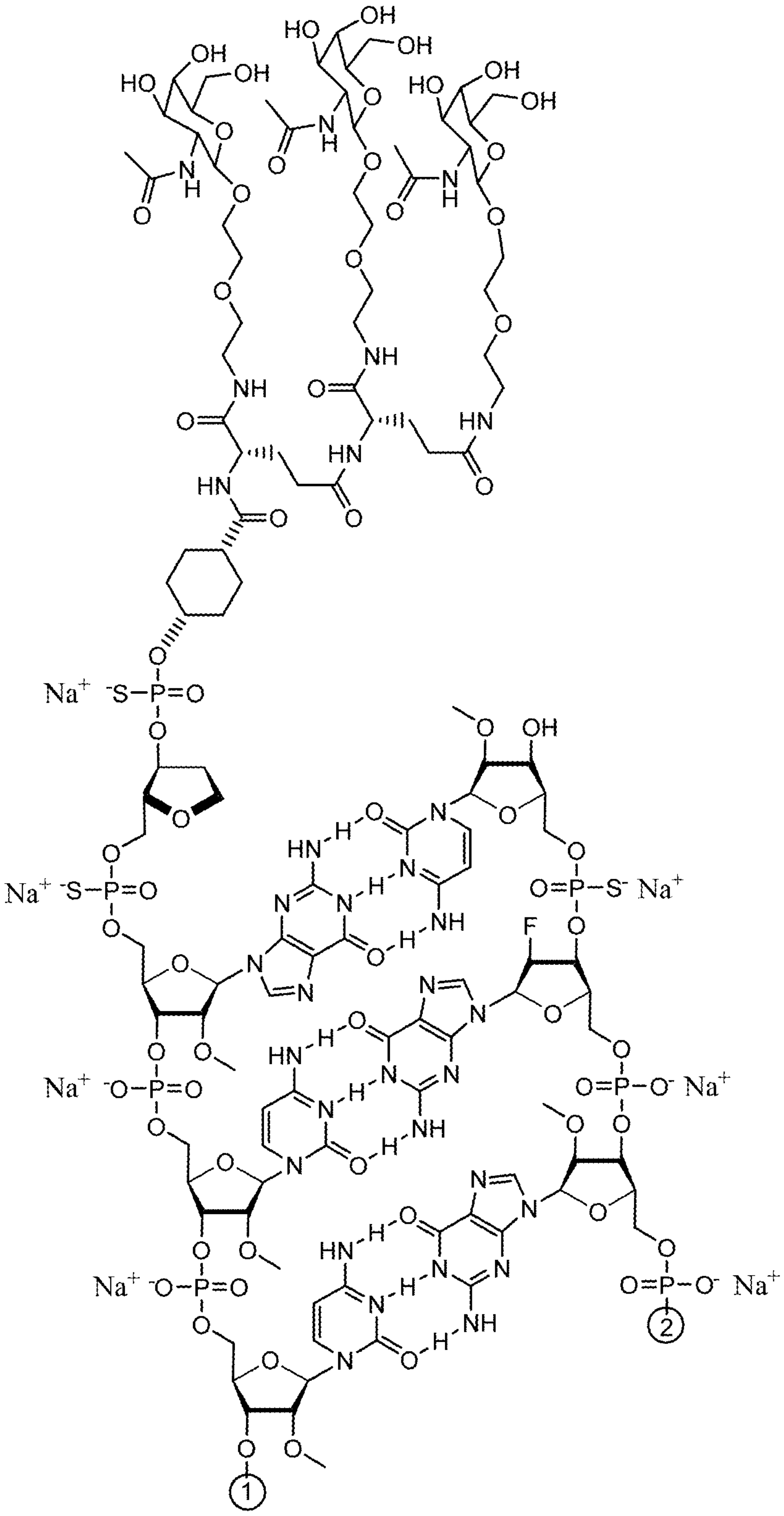
FIG. 10A to 10D. Chemical structure representation of HSD17B13 RNAi agent AD06277 conjugated to the tridentate N-acetyl-galactosamine targeting ligand of (NAG37)s at the 5' terminal end of the sense strand, shown in a sodium salt form.
Figure 10B:
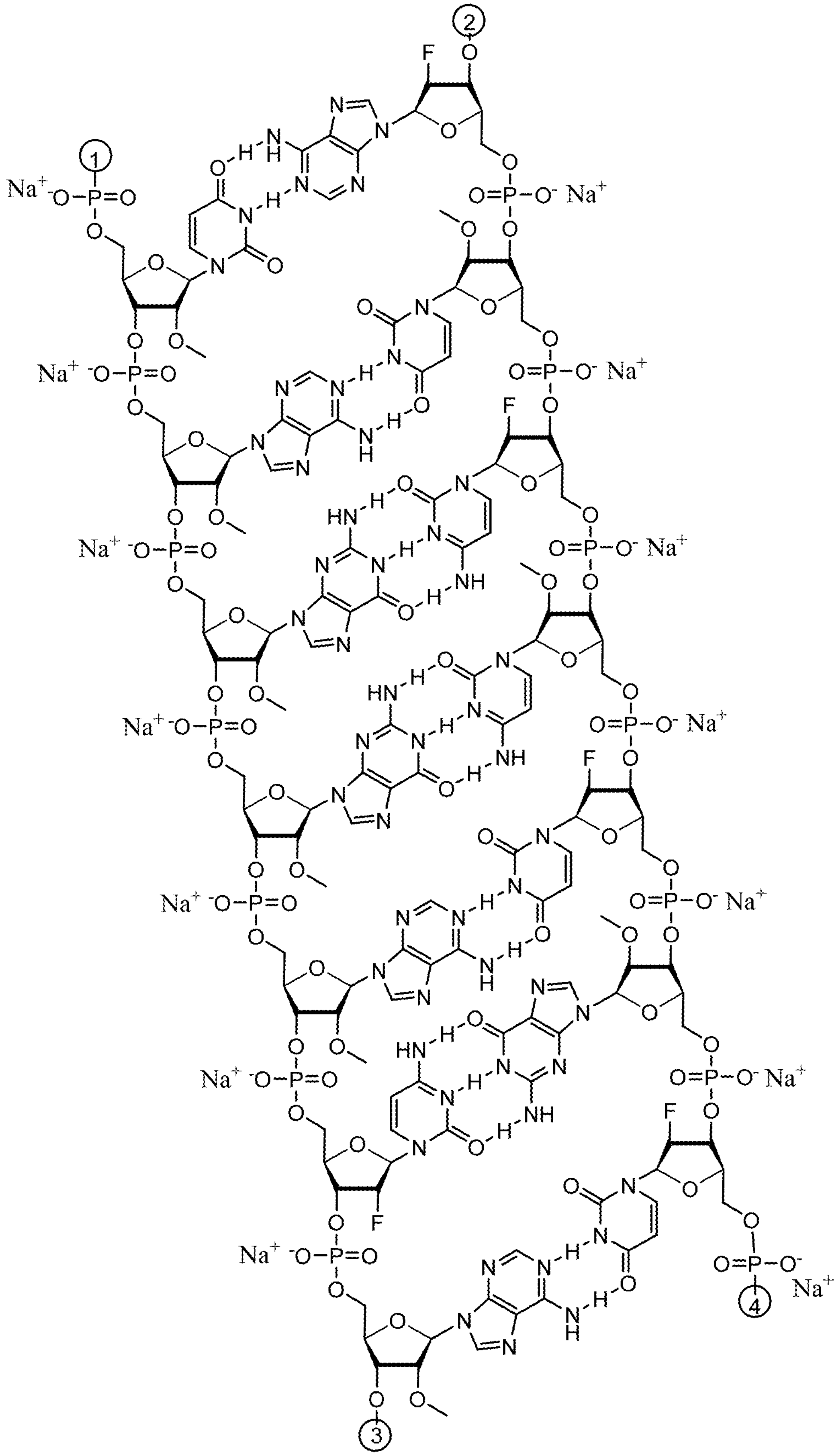
Figure 10C:
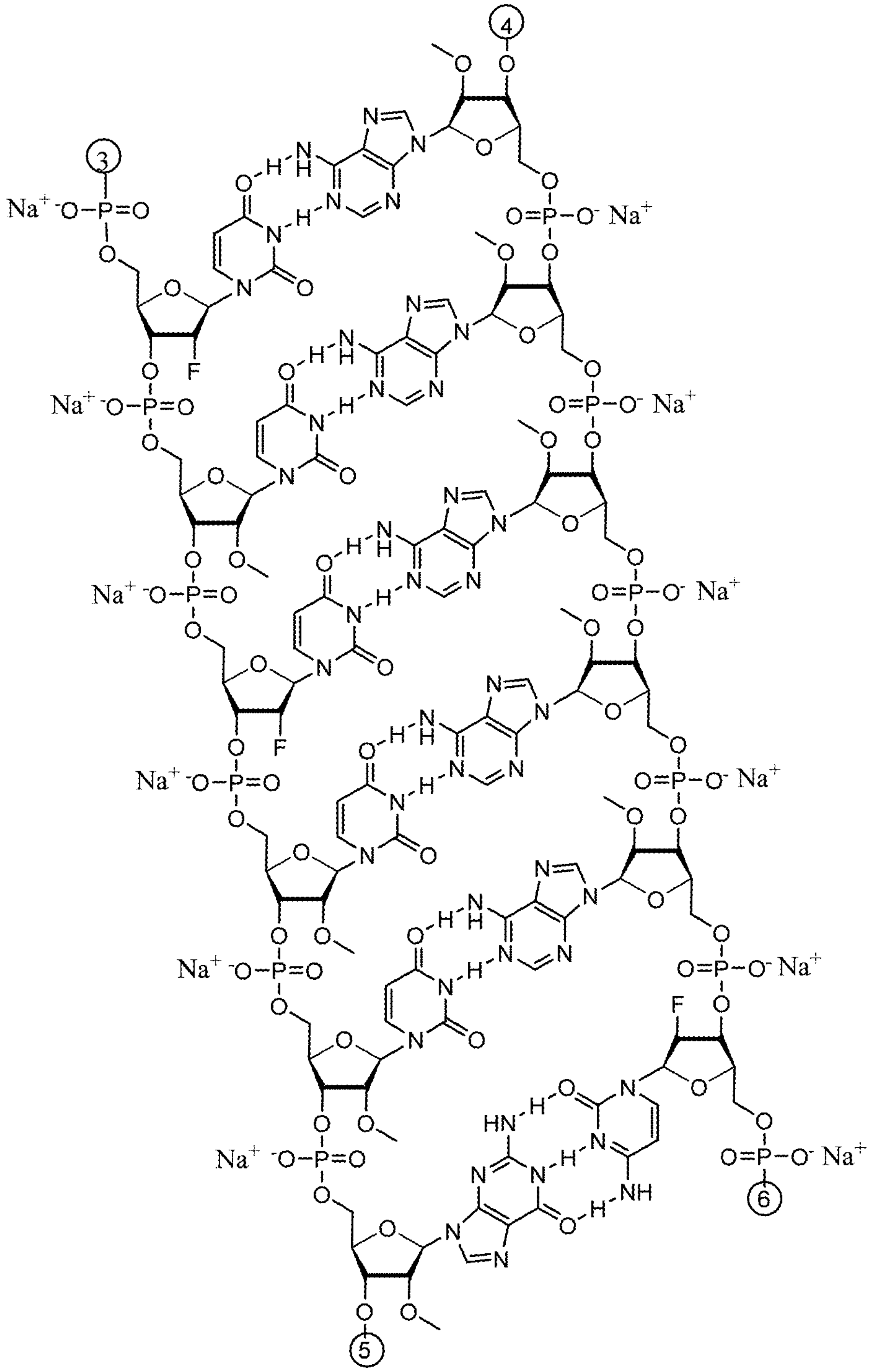
Figure 10D:
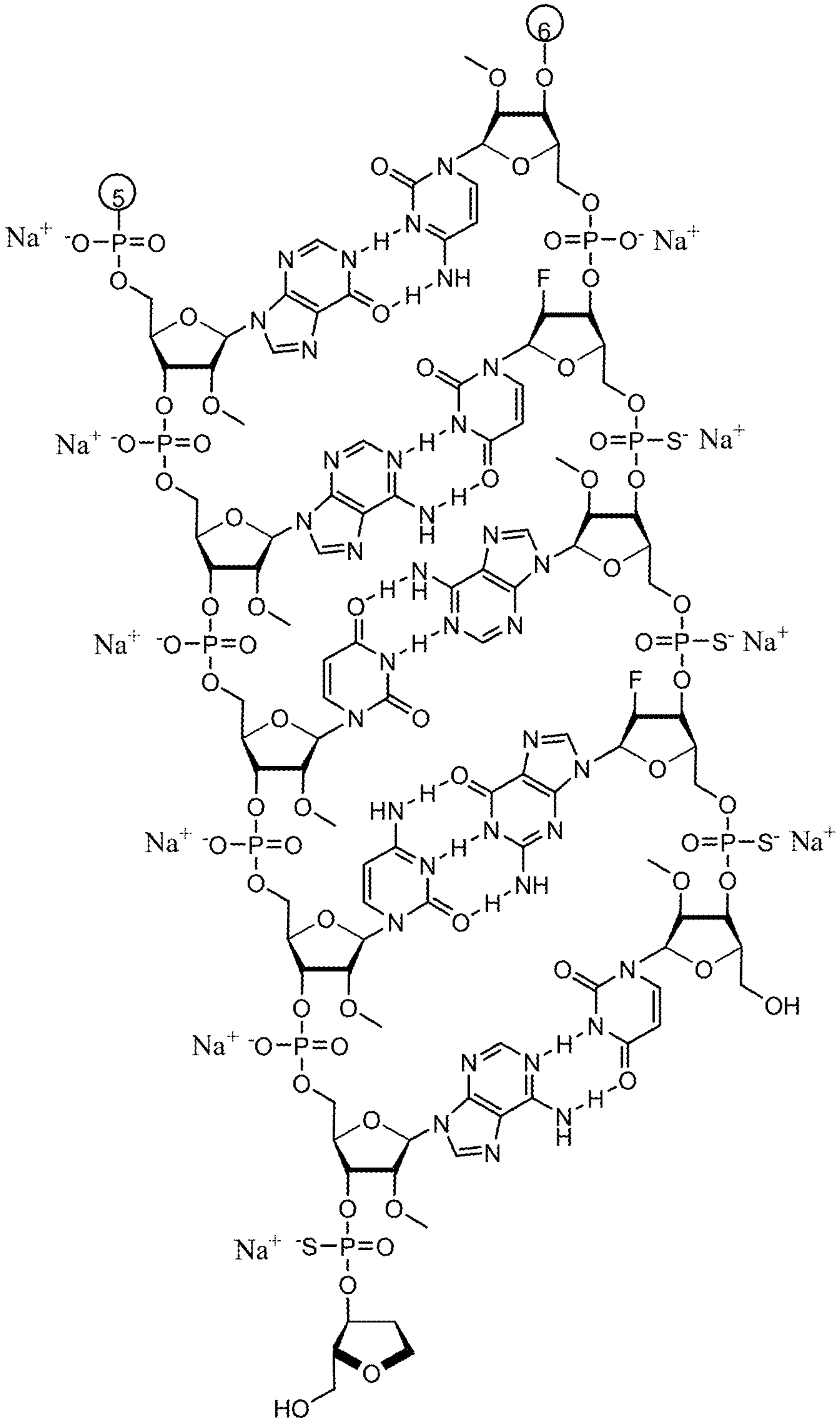
Figure 11A:
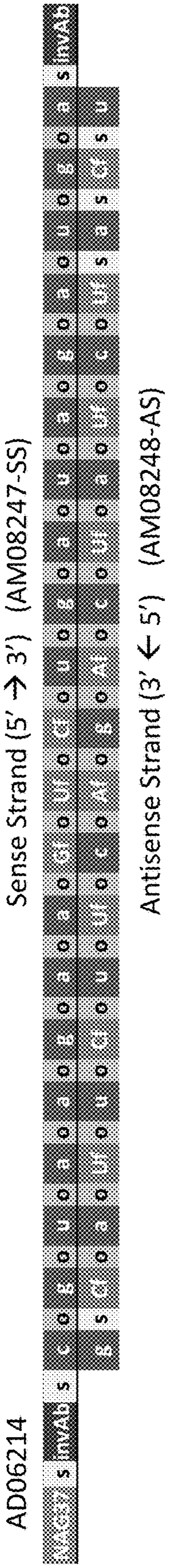
FIG. 11A. Schematic diagram of the modified sense and antisense strands of HSD17B13 RNAi agent AD06214 (see Tables 3-5), conjugated to an N-acetyl-galactosamine tridentate ligand having the structure of (NAG37)s (see Table 6.
Figure 11B:
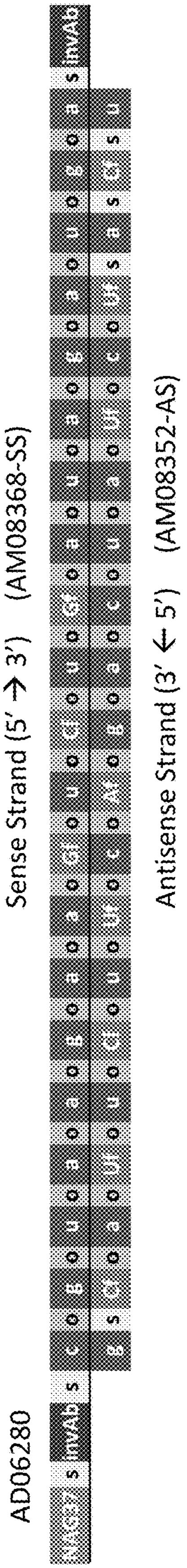
FIG. 11B. Schematic diagram of the modified sense and antisense strands of HSD17B13 RNAi agent AD06280 (see Tables 3-5), conjugated to an N-acetyl-galactosamine tridentate ligand having the structure of (NAG37)s (see Table 6).
Figure 11C:
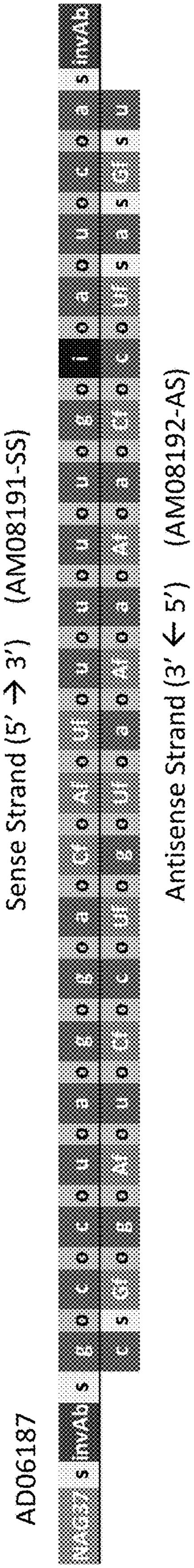
FIG. 11C. Schematic diagram of the modified sense and antisense strands of HSD17B13 RNAi agent AD06187 (see Tables 3-5), conjugated to an N-acetyl-galactosamine tridentate ligand having the structure of (NAG37)s (see Table 6).
Figure 11D:
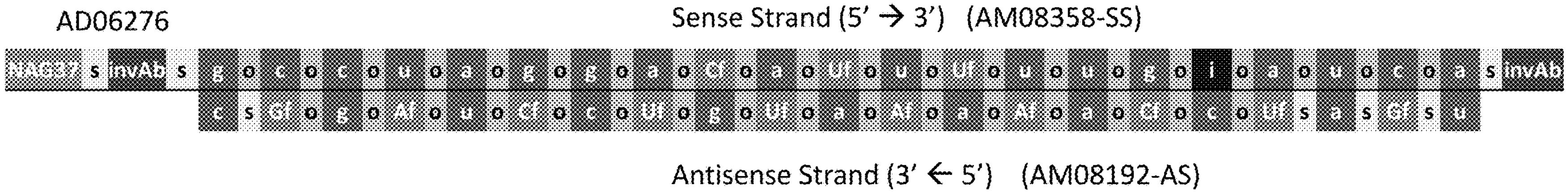
FIG. 11D. Schematic diagram of the modified sense and antisense strands of HSD17B13 RNAi agent AD06276 (see Tables 3-5), conjugated to an N-acetyl-galactosamine tridentate ligand having the structure of (NAG37)s (see Table 6).
Figure 11E:
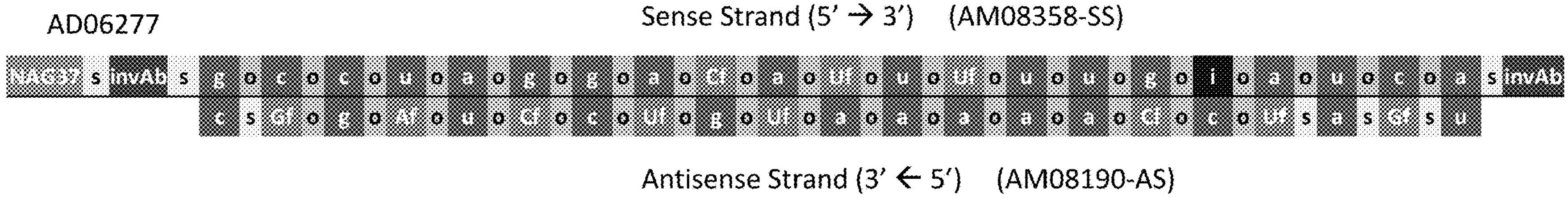
FIG. 11E. Schematic diagram of the modified sense and antisense strands of HSD17B13 RNAi agent AD06277 (see Tables 3-5), conjugated to an N-acetyl-galactosamine tridentate ligand having the structure of (NAG37)s (see Table 6).

Examples of nucleotide sequences used in forming HSD17B13 RNAi agents are provided in Tables 2, 3, and 4. Examples of RNAi agent duplexes, that include the sense strand and antisense strand sequences in Tables 2, 3, and 4, are shown in Table 5, and are also depicted in FIGS. 1A through 10D and FIGS. 11A through 11E.

In some embodiments, the region of perfect, substantial, or partial complementarity between the sense strand and the antisense strand is 16-26 (e.g., 16, 17, 18, 19, 20, 21, 22, 23, 24, 25, or 26) nucleotides in length and occurs at or near the 5' end of the antisense strand (e.g., this region may be separated from the 5' end of the antisense strand by 0, 1, 2, 3, or 4 nucleotides that are not perfectly, substantially, or partially complementary).

A sense strand of the HSD17B13 RNAi agents described herein includes at least 16 consecutive nucleotides that have at least 85% identity to a core stretch sequence (also referred to herein as a "core stretch" or "core sequence") of the same number of nucleotides in an HSD17B13 mRNA. In some embodiments, a sense strand core stretch sequence is 100% (perfectly) complementary or at least about 85% (substantially) complementary to a core stretch sequence in the antisense strand, and thus the sense strand core stretch sequence is typically perfectly identical or at least about 85% identical to a nucleotide sequence of the same length (sometimes referred to, e.g., as a target sequence) present in the HSD17B13 mRNA target. In some embodiments, this sense strand core stretch is 16, 17, 18, 19, 20, 21, 22, or 23 nucleotides in length. In some embodiments, this sense strand core stretch is 17 nucleotides in length. In some embodiments, this sense strand core stretch is 19 nucleotides in length.

An antisense strand of an HSD17B13 RNAi agent described herein includes at least 16 consecutive nucleotides that have at least 85% complementarity to a core stretch of the same number of nucleotides in an HSD17B13 mRNA and to a core stretch of the same number of nucleotides in the corresponding sense strand. In some embodiments, an antisense strand core stretch is 100% (perfectly) complementary or at least about 85% (substantially) complementary to a nucleotide sequence (e.g., target sequence) of the same length present in the HSD17B13 mRNA target. In some embodiments, this antisense strand core stretch is 16, 17, 18, 19, 20, 21, 22, or 23 nucleotides in length. In some embodiments, this antisense strand core stretch is 19 nucleotides in length. In some embodiments, this antisense strand core stretch is 17 nucleotides in length. A sense strand core stretch sequence can be the same length as a corresponding antisense core sequence or it can be a different length.

The HSD17B13 RNAi agent sense and antisense strands anneal to form a duplex. A sense strand and an antisense strand of an HSD17B13 RNAi agent can be partially, substantially, or fully complementary to each other. Within the complementary duplex region, the sense strand core stretch sequence is at least 85% complementary or 100% complementary to the antisense core stretch sequence. In some embodiments, the sense strand core stretch sequence contains a sequence of at least 16, at least 17, at least 18, at least 19, at least 20, at least 21, at least 22, or at least 23 nucleotides that is at least 85% or 100% complementary to a corresponding 16, 17, 18, 19, 20, 21, 22, or 23 nucleotide sequence of the antisense strand core stretch sequence (i.e., the sense and antisense core stretch sequences of an HSD17B13 RNAi agent have a region of at least 16, at least 17, at least 18, at least 19, at least 20, at least 21, at least 22, or at least 23 nucleotides that is at least 85% base paired or 100% base paired.)

In some embodiments, the antisense strand of an HSD17B13 RNAi agent disclosed herein differs by 0, 1, 2, or 3 nucleotides from any of the antisense strand sequences in Table 2 or Table 3. In some embodiments, the sense strand of an HSD17B13 RNAi agent disclosed herein differs by 0, 1, 2, or 3 nucleotides from any of the sense strand sequences in Table 2 or Table 4.

In some embodiments, the sense strand and/or the antisense strand can optionally and independently contain an additional 1, 2, 3, 4, 5, or 6 nucleotides (extension) at the 3' end, the 5' end, or both the 3' and 5' ends of the core stretch sequences. The antisense strand additional nucleotides, if present, may or may not be complementary to the corresponding sequence in the HSD17B13 mRNA. The sense strand additional nucleotides, if present, may or may not be identical to the corresponding sequence in the HSD17B13 mRNA. The antisense strand additional nucleotides, if present, may or may not be complementary to the corresponding sense strand's additional nucleotides, if present.

As used herein, an extension comprises 1, 2, 3, 4, 5, or 6 nucleotides at the 5' and/or 3' end of the sense strand core stretch sequence and/or antisense strand core stretch sequence. The extension nucleotides on a sense strand may or may not be complementary to nucleotides, either core stretch sequence nucleotides or extension nucleotides, in the corresponding antisense strand. Conversely, the extension nucleotides on an antisense strand may or may not be complementary to nucleotides, either core stretch nucleotides or extension nucleotides, in the corresponding sense strand. In some embodiments, both the sense strand and the antisense strand of an RNAi agent contain 3' and 5' extensions. In some embodiments, one or more of the 3' extension nucleotides of one strand base pairs with one or more 5' extension nucleotides of the other strand. In other embodiments, one or more of 3' extension nucleotides of one strand do not base pair with one or more 5' extension nucleotides of the other strand. In some embodiments, an HSD17B13 RNAi agent has an antisense strand having a 3' extension and a sense strand having a 5' extension. In some embodiments, the extension nucleotide(s) are unpaired and form an overhang. As used herein, an "overhang" refers to a stretch of one or more unpaired nucleotides located at a terminal end of either the sense strand or the antisense strand that does not form part of the hybridized or duplexed portion of an RNAi agent disclosed herein.

In some embodiments, an HSD17B13 RNAi agent comprises an antisense strand having a 3' extension of 1, 2, 3, 4, 5, or 6 nucleotides in length. In other embodiments, an HSD17B13 RNAi agent comprises an antisense strand having a 3' extension of 1, 2, or 3 nucleotides in length. In some embodiments, one or more of the antisense strand extension nucleotides comprise nucleotides that are complementary to the corresponding HSD17B13 mRNA sequence. In some embodiments, one or more of the antisense strand extension nucleotides comprise nucleotides that are not complementary to the corresponding HSD17B13 mRNA sequence.

In some embodiments, an HSD17B13 RNAi agent comprises a sense strand having a 3' extension of 1, 2, 3, 4, or 5 nucleotides in length. In some embodiments, one or more of the sense strand extension nucleotides comprises adenosine, uracil, or thymidine nucleotides, AT dinucleotide, or nucleotides that correspond to or are the identical to nucleotides in the HSD17B13 mRNA sequence. In some embodiments, the 3' sense strand extension includes or consists of one of the following sequences, but is not limited to: T, UT, TT, UU, UUT, TTT, or TTTT (each listed 5' to 3').

A sense strand can have a 3' extension and/or a 5' extension. In some embodiments, an HSD17B13 RNAi agent comprises a sense strand having a 5' extension of 1, 2, 3, 4, 5, or 6 nucleotides in length. In some embodiments, one or more of the sense strand extension nucleotides comprise nucleotides that correspond to or are identical to nucleotides in the HSD17B13 mRNA sequence. In some embodiments, the sense strand 5' extension is one of the following sequences, but is not limited to: CA, AUAGGC, AUAGG, AUAG, AUA, A, AA, AC, GCA, GGCA, GGC, UAUCA, UAUC, UCA, UAU, U, UU (each listed 5' to 3').

Examples of sequences used in forming HSD17B13 RNAi agents are provided in Tables 2, 3, and 4. In some embodiments, an HSD17B13 RNAi agent antisense strand includes a sequence of any of the sequences in Tables 2 or 3. In certain embodiments, an HSD17B13 RNAi agent antisense strand comprises or consists of any one of the modified sequences in Table 3. In some embodiments, an HSD17B13 RNAi agent antisense strand includes the sequence of nucleotides (from 5' end→3' end) 1-17, 2-15, 2-17, 1-18, 2-18, 1-19, 2-19, 1-20, 2-20, 1-21, or 2-21, of any of the sequences in Tables 2 or 3. In some embodiments, an HSD17B13 RNAi agent sense strand includes the sequence of any of the sequences in Tables 2 or 4. In some embodiments, an HSD17B13 RNAi agent sense strand includes the sequence of nucleotides (from 5' end→3' end) 1-18, 1-19, 1-20, 1-21, 2-19, 2-20, 2-21, 3-20, 3-21, or 4-21 of any of the sequences in Tables 2 or 4. In certain embodiments, an HSD17B13 RNAi agent sense strand comprises or consists of a modified sequence of any one of the modified sequences in Table 4.

In some embodiments, the sense and antisense strands of the RNAi agents described herein contain the same number of nucleotides. In some embodiments, the sense and antisense strands of the RNAi agents described herein contain different numbers of nucleotides. In some embodiments, the sense strand 5' end and the antisense strand 3' end of an RNAi agent form a blunt end. In some embodiments, the sense strand 3' end and the antisense strand 5' end of an RNAi agent form a blunt end. In some embodiments, both ends of an RNAi agent form blunt ends. In some embodiments, neither end of an RNAi agent is blunt-ended. As used herein a "blunt end" refers to an end of a double stranded RNAi agent in which the terminal nucleotides of the two annealed strands are complementary (form a complementary base-pair).

In some embodiments, the sense strand 5' end and the antisense strand 3' end of an RNAi agent form a frayed end. In some embodiments, the sense strand 3' end and the antisense strand 5' end of an RNAi agent form a frayed end. In some embodiments, both ends of an RNAi agent form a frayed end. In some embodiments, neither end of an RNAi agent is a frayed end. As used herein a frayed end refers to an end of a double stranded RNAi agent in which the terminal nucleotides of the two annealed strands from a pair (i.e., do not form an overhang) but are not complementary (i.e. form a non-complementary pair). In some embodiments, one or more unpaired nucleotides at the end of one strand of a double stranded RNAi agent form an overhang. The unpaired nucleotides may be on the sense strand or the antisense strand, creating either 3' or 5' overhangs. In some embodiments, the RNAi agent contains: a blunt end and a frayed end, a blunt end and 5' overhang end, a blunt end and a 3' overhang end, a frayed end and a 5' overhang end, a frayed end and a 3' overhang end, two 5' overhang ends, two 3' overhang ends, a 5' overhang end and a 3' overhang end, two frayed ends, or two blunt ends. Typically, when present, overhangs are located at the 3' terminal ends of the sense strand, the antisense strand, or both the sense strand and the antisense strand.

The HSD17B13 RNAi agents disclosed herein may also be comprised of one or more modified nucleotides. In some embodiments, substantially all of the nucleotides of the sense strand and substantially all of the nucleotides of the antisense strand of the HSD17B13 RNAi agent are modified nucleotides. The HSD17B13 RNAi agents disclosed herein may further be comprised of one or more modified internucleoside linkages, e.g., one or more phosphorothioate linkages. In some embodiments, an HSD17B13 RNAi agent contains one or more modified nucleotides and one or more modified internucleoside linkages. In some embodiments, a 2'-modified nucleotide is combined with modified internucleoside linkage.

In some embodiments, an HSD17B13 RNAi agent is prepared or provided as a salt, mixed salt, or a free-acid. In some embodiments, an HSD17B13 RNAi agent is prepared as a sodium salt. Such forms that are well known in the art are within the scope of the inventions disclosed herein.

Modified Nucleotides

Modified nucleotides, when used in various oligonucleotide constructs, can preserve activity of the compound in cells while at the same time increasing the serum stability of these compounds, and can also minimize the possibility of activating interferon activity in humans upon administering of the oligonucleotide construct.

In some embodiments, an HSD17B13 RNAi agent contains one or more modified nucleotides. As used herein, a "modified nucleotide" is a nucleotide other than a ribonucleotide (2'-hydroxyl nucleotide). In some embodiments, at least 50% (e.g., at least 60%, at least 70%, at least 80%, at least 90%, at least 95%, at least 97%, at least 98%, at least 99%, or 100%) of the nucleotides are modified nucleotides. As used herein, modified nucleotides can include, but are not limited to, deoxyribonucleotides, nucleotide mimics, abasic nucleotides, 2'-modified nucleotides, inverted nucleotides, modified nucleobase-comprising nucleotides, bridged nucleotides, peptide nucleic acids (PNAs), 2',3'-seco nucleotide mimics (unlocked nucleobase analogues), locked nucleotides, 3'-O-methoxy (2' internucleoside linked) nucleotides, 2'-F-Arabino nucleotides, 5'-Me, 2'-fluoro nucleotide, morpholino nucleotides, vinyl phosphonate deoxyribonucleotides, vinyl phosphonate containing nucleotides, and cyclopropyl phosphonate containing nucleotides. 2'-modified nucleotides (i.e., a nucleotide with a group other than a hydroxyl group at the 2' position of the five-membered sugar ring) include, but are not limited to, 2'-O-methyl nucleotides, 2'-fluoro nucleotides (also referred to herein as 2'-deoxy-2'-fluoro nucleotides), 2'-deoxy nucleotides, 2'-methoxyethyl (2'-O-2-methoxylethyl) nucleotides (also referred to as 2'-MOE), 2'-amino nucleotides, and 2'-alkyl nucleotides. It is not necessary for all positions in a given compound to be uniformly modified. Conversely, more than one modification can be incorporated in a single HSD17B13 RNAi agent or even in a single nucleotide thereof. The HSD17B13 RNAi agent sense strands and antisense strands can be synthesized and/or modified by methods known in the art. Modification at one nucleotide is independent of modification at another nucleotide.

Modified nucleobases include synthetic and natural nucleobases, such as 5-substituted pyrimidines, 6-azapyrimidines and N-2, N-6 and O-6 substituted purines, (e.g., 2-aminopropyladenine, 5-propynyluracil, or 5-propynylcytosine), 5-methylcytosine (5-me-C), 5-hydroxymethyl cytosine, inosine, xanthine, hypoxanthine, 2-aminoadenine, 6-alkyl (e.g., 6-methyl, 6-ethyl, 6-isopropyl, or 6-n-butyl) derivatives of adenine and guanine, 2-alkyl (e.g., 2-methyl, 2-ethyl, 2-isopropyl, or 2-n-butyl) and other alkyl derivatives of adenine and guanine, 2-thiouracil, 2-thiothymine, 2-thiocytosine, 5-halouracil, cytosine, 5-propynyl uracil, 5-propynyl cytosine, 6-azo uracil, 6-azo cytosine, 6-azo thymine, 5-uracil (pseudouracil), 4-thiouracil, 8-halo, 8-amino, 8-sulfhydryl, 8-thioalkyl, 8-hydroxyl and other 8-substituted adenines and guanines, 5-halo (e.g., 5-bromo), 5-trifluoromethyl, and other 5-substituted uracils and cytosines, 7-methylguanine and 7-methyladenine, 8-azaguanine and 8-azaadenine, 7-deazaguanine, 7-deazaadenine, 3-deazaguanine, and 3-deazaadenine.

In some embodiments, the 5' and/or 3' end of the antisense strand can include abasic residues (Ab), which can also be referred to as an "abasic site" or "abasic nucleotide." An abasic residue (Ab) is a nucleotide or nucleoside that lacks a nucleobase at the 1' position of the sugar moiety. (See, e.g., U.S. Pat. No. 5,998,203). In some embodiments, an abasic residue can be placed internally in a nucleotide sequence. In some embodiments, Ab or AbAb can be added to the 3' end of the antisense strand. In some embodiments, the 5' end of the sense strand can include one or more additional abasic residues (e.g., (Ab) or (AbAb)). In some embodiments, UUAb, UAb, or Ab are added to the 3' end of the sense strand. In some embodiments, an abasic (deoxyribose) residue can be replaced with a ribitol (abasic ribose) residue.

In some embodiments, all or substantially all of the nucleotides of an RNAi agent are modified nucleotides. As used herein, an RNAi agent wherein substantially all of the nucleotides present are modified nucleotides is an RNAi agent having four or fewer (i.e., 0, 1, 2, 3, or 4) nucleotides in both the sense strand and the antisense strand being ribonucleotides (i.e., unmodified). As used herein, a sense strand wherein substantially all of the nucleotides present are modified nucleotides is a sense strand having two or fewer (i.e., 0, 1, or 2) nucleotides in the sense strand being unmodified ribonucleotides. As used herein, an antisense sense strand wherein substantially all of the nucleotides present are modified nucleotides is an antisense strand having two or fewer (i.e., 0, 1, or 2) nucleotides in the sense strand being unmodified ribonucleotides. In some embodiments, one or more nucleotides of an RNAi agent is an unmodified ribonucleotide.

Modified Internucleoside Linkages

In some embodiments, one or more nucleotides of an HSD17B13 RNAi agent are linked by non-standard linkages or backbones (i.e., modified internucleoside linkages or modified backbones). Modified internucleoside linkages or backbones include, but are not limited to, phosphorothioate groups (represented herein as a lower case "s"), chiral phosphorothioates, thiophosphates, phosphorodithioates, phosphotriesters, aminoalkyl-phosphotriesters, alkyl phosphonates (e.g., methyl phosphonates or 3'-alkylene phosphonates), chiral phosphonates, phosphinates, phosphoramidates (e.g., 3'-amino phosphoramidate, aminoalkylphosphoramidates, or thionoalkyl-phosphonates, thionoalkylphosphotriesters, morpholino linkages, boranophosphates having normal 3'-5' linkages, 2'-5' linked analogs of boranophosphates, or boranophosphates having inverted polarity wherein the adjacent pairs of nucleoside units are linked 3'-5' to 5'-3' or 2'-5' to 5'-2'. In some embodiments, a modified internucleoside linkage or backbone lacks a phosphorus atom. Modified internucleoside linkages lacking a phosphorus atom include, but are not limited to, short chain alkyl or cycloalkyl inter-sugar linkages, mixed heteroatom and alkyl or cycloalkyl inter-sugar linkages, or one or more short chain heteroatomic or heterocyclic inter-sugar linkages. In some embodiments, modified internucleoside backbones include, but are not limited to, siloxane backbones, sulfide backbones, sulfoxide backbones, sulfone backbones, formacetyl and thioformacetyl backbones, methylene formacetyl and thioformacetyl backbones, alkene-containing backbones, sulfamate backbones, methyleneimino and methylenehydrazino backbones, sulfonate and sulfonamide backbones, amide backbones, and other backbones having mixed N, O, S, and $CH_2$ components.

In some embodiments, a sense strand of an HSD17B13 RNAi agent can contain 1, 2, 3, 4, 5, or 6 phosphorothioate linkages, an antisense strand of an HSD17B13 RNAi agent can contain 1, 2, 3, 4, 5, or 6 phosphorothioate linkages, or both the sense strand and the antisense strand independently can contain 1, 2, 3, 4, 5, or 6 phosphorothioate linkages. In some embodiments, a sense strand of an HSD17B13 RNAi agent can contain 1, 2, 3, or 4 phosphorothioate linkages, an antisense strand of an HSD17B13 RNAi agent can contain 1, 2, 3, or 4 phosphorothioate linkages, or both the sense strand and the antisense strand independently can contain 1, 2, 3, or 4 phosphorothioate linkages.

In some embodiments, an HSD17B13 RNAi agent sense strand contains at least two phosphorothioate internucleoside linkages. In some embodiments, the phosphorothioate internucleoside linkages are between the nucleotides at positions 1-3 from the 3' end of the sense strand. In some embodiments, one phosphorothioate internucleoside linkage is at the 5' end of the sense strand nucleotide sequence, and another phosphorothioate linkage is at the 3' end of the sense strand nucleotide sequence. In some embodiments, two phosphorothioate internucleoside linkage are located at the 5' end of the sense strand, and another phosphorothioate linkage is at the 3' end of the sense strand. In some embodiments, the sense strand does not include any phosphorothioate internucleoside linkages between the nucleotides, but contains one, two, or three phosphorothioate linkages between the terminal nucleotides on both the 5' and 3' ends and the optionally present inverted abasic residue terminal caps. In some embodiments, the targeting ligand is linked to the sense strand via a phosphorothioate linkage.

In some embodiments, an HSD17B13 RNAi agent antisense strand contains four phosphorothioate internucleoside linkages. In some embodiments, the four phosphorothioate internucleoside linkages are between the nucleotides at positions 1-3 from the 5' end of the antisense strand and between the nucleotides at positions 19-21, 20-22, 21-23, 22-24, 23-25, or 24-26 from the 5' end. In some embodiments, three phosphorothioate internucleoside linkages are located between positions 1~4 from the 5' end of the antisense strand, and a fourth phosphorothioate internucleoside linkage is located between positions 20-21 from the 5' end of the antisense strand. In some embodiments, an HSD17B13 RNAi agent contains at least three or four phosphorothioate internucleoside linkages in the antisense strand.

Capping Residues or Moieties

In some embodiments, the sense strand may include one or more capping residues or moieties, sometimes referred to in the art as a "cap," a "terminal cap," or a "capping residue." As used herein, a "capping residue" is a non-nucleotide compound or other moiety that can be incorporated at one or more termini of a nucleotide sequence of an RNAi agent disclosed herein. A capping residue can provide the RNAi agent, in some instances, with certain beneficial properties, such as, for example, protection against exonuclease degradation. In some embodiments, inverted abasic residues (invAb) (also referred to in the art as "inverted abasic sites") are added as capping residues (see Table A). (See, e.g., F. Czauderna, Nucleic Acids Res., 2003, 31 (11), 2705-16). Capping residues are generally known in the art, and include, for example, inverted abasic residues as well as carbon chains such as a terminal $C_3H_7$ (propyl), $C_6H_{13}$ (hexyl), or $C_{12}H_{25}$ (dodecyl) groups. In some embodiments, a capping residue is present at either the 5' terminal end, the 3' terminal end, or both the 5' and 3' terminal ends of the sense strand. In some embodiments, the 5' end and/or the 3' end of the sense strand may include more than one inverted abasic deoxyribose moiety as a capping residue.

In some embodiments, one or more inverted abasic residues (invAb) are added to the 3' end of the sense strand. In some embodiments, one or more inverted abasic residues (invAb) are added to the 5' end of the sense strand. In some embodiments, one or more inverted abasic residues or inverted abasic sites are inserted between the targeting ligand and the nucleotide sequence of the sense strand of the RNAi agent. In some embodiments, the inclusion of one or more inverted abasic residues or inverted abasic sites at or near the terminal end or terminal ends of the sense strand of an RNAi agent allows for enhanced activity or other desired properties of an RNAi agent.

In some embodiments, one or more inverted abasic residues (invAb) are added to the 5' end of the sense strand. In some embodiments, one or more inverted abasic residues can be inserted between the targeting ligand and the nucleotide sequence of the sense strand of the RNAi agent. The inverted abasic residues may be linked via phosphate, phosphorothioate (e.g., shown herein as (invAb)s)), or other internucleoside linkages. In some embodiments, the inclusion of one or more inverted abasic residues at or near the terminal end or terminal ends of the sense strand of an RNAi agent may allow for enhanced activity or other desired properties of an RNAi agent. In some embodiments, an inverted abasic (deoxyribose) residue can be replaced with an inverted ribitol (abasic ribose) residue. In some embodiments, the 3' end of the antisense strand core stretch sequence, or the 3' end of the antisense strand sequence, may include an inverted abasic residue. The chemical structures for inverted abasic deoxyribose residues are shown in Table 6 below, as well as in the chemical structures shown in FIGS. 1A through 10D.

HSD17B13 RNAi Agents

The HSD17B13 RNAi agents disclosed herein are designed to target specific positions on an HSD17B13 gene (SEQ ID NO:1). As defined herein, an antisense strand sequence is designed to target an HSD17B13 gene at a given position on the gene when the 5' terminal nucleobase of the antisense strand is aligned with a position that is 21 nucleotides downstream (towards the 3' end) from the position on the gene when base pairing to the gene. For example, as illustrated in Tables 1 and 2 herein, an antisense strand sequence designed to target an HSD17B13 gene at position 499 requires that when base pairing to the gene, the 5' terminal nucleobase of the antisense strand is aligned with position 519 of the HSD17B13 gene.

As provided herein, an HSD17B13 RNAi agent does not require that the nucleobase at position 1 (5'→3') of the antisense strand be complementary to the gene, provided that there is at least 85% complementarity (e.g., at least 85, 86, 87, 88, 89, 90, 91, 92, 93, 94, 95, 96, 97, 98, 99, or 100% complementarity) of the antisense strand and the gene across a core stretch sequence of at least 16 consecutive nucleotides. For example, for an HSD17B13 RNAi agent disclosed herein that is designed to target position 499 of an HSD17B13 gene, the 5' terminal nucleobase of the antisense strand of the of the HSD17B13 RNAi agent must be aligned with position 519 of the gene; however, the 5' terminal nucleobase of the antisense strand may be, but is not required to be, complementary to position 519 of an HSD17B13 gene, provided that there is at least 85% complementarity (e.g., at least 85, 86, 87, 88, 89, 90, 91, 92, 93, 94, 95, 96, 97, 98, 99, or 100% complementarity) of the antisense strand and the gene across a core stretch sequence of at least 16 consecutive nucleotides. As shown by, among other things, the various examples disclosed herein, the specific site of binding of the gene by the antisense strand of the HSD17B13 RNAi agent (e.g., whether the HSD17B13 RNAi agent is designed to target an HSD17B13 gene at position 499, at position 791, at position 513, or at some other position) is important to the level of inhibition achieved by the HSD17B13 RNAi agent.

In some embodiments, the HSD17B13 RNAi agents disclosed herein target an HSD17B13 gene at or near the positions of the HSD17B13 gene sequence shown in Table 1. In some embodiments, the antisense strand of an HSD17B13 RNAi agent disclosed herein includes a core stretch sequence that is fully, substantially, or at least partially complementary to a target HSD17B13 19-mer sequence disclosed in Table 1.

TABLE 1

HSD17B13 19-mer mRNA Target Sequences (taken from *homo sapiens* hydroxysteroid 17-beta dehydrogenase 13 (HSD17B13), transcript variant A, GenBank NM_178135.4 (SEQ ID NO: 1))

| SEQ ID No. | HSD17B13 19-mer Target Sequences (5' → 3') | Corresponding Positions of Sequence on SEQ ID NO: 1 | Targeted Gene Position (as referred to herein) |
|---|---|---|---|
| 18 | UAAGAAGUCUGAUAGAUGG | 793-811 | 791 |
| 19 | GAUCACAAAAGCACUUCUU | 515-533 | 513 |
| 20 | CUAGGACAUUUUUGGAUCA | 501-519 | 499 |
| 21 | AGGUCAACAUCCUAGGACA | 490-508 | 488 |
| 22 | CGGUGCAACUCUAUUCUGG | 1503-1521 | 1501 |
| 23 | CAACAUCCUAGGACAUUUU | 494-512 | 492 |
| 24 | AUUAUGGCCUGUAUUGGAG | 761-779 | 759 |

In some embodiments, an HSD17B13 RNAi agent includes an antisense strand wherein position 19 of the antisense strand (5'→3') is capable of forming a base pair with position 1 of a 19-mer target sequence disclosed in Table 1. In some embodiments, an HSD17B13 RNAi agent includes an antisense strand wherein position 1 of the antisense strand (5'→3') is capable of forming a base pair with position 19 of the 19-mer target sequence disclosed in Table 1.

In some embodiments, an HSD17B13 RNAi agent includes an antisense strand wherein position 2 of the antisense strand (5'→3') is capable of forming a base pair with position 18 of the 19-mer target sequence disclosed in Table 1. In some embodiments, an HSD17B13 RNAi agent includes an antisense strand wherein positions 2 through 18 of the antisense strand (5'→3') are capable of forming base pairs with each of the respective complementary bases located at positions 18 through 2 of the 19-mer target sequence disclosed in Table 1.

For the RNAi agents disclosed herein, the nucleotide at position 1 of the antisense strand (from 5' end→3' end) can be perfectly complementary to the HSD17B13 gene, or can be non-complementary to the HSD17B13 gene. In some embodiments, the nucleotide at position 1 of the antisense strand (from 5' end→3' end) is a U, A, or dT. In some embodiments, the nucleotide at position 1 of the antisense strand (from 5' end→3' end) forms an A:U or U:A base pair with the sense strand.

In some embodiments, an HSD17B13 RNAi agent antisense strand comprises the sequence of nucleotides (from 5' end→3' end) 2-18, 2-19, 2-20, or 2-21 of any of the antisense strand sequences in Table 2 or Table 3. In some embodiments, an HSD17B13 RNAi sense strand comprises the sequence of nucleotides (from 5' end→3' end) 3-21, 2-21, 1-21, 3-20, 2-20, 1-20, 3-19, 2-19, 2-19, 2-18, or 1-18, of any of the sense strand sequences in Table 2 or Table 4.

In some embodiments, an HSD17B13 RNAi agent is comprised of (i) an antisense strand comprising the sequence of nucleotides (from 5' end→3' end) 2-18 or 2-19 of any of the antisense strand sequences in Table 2 or Table 3, and (ii) a sense strand comprising the sequence of nucleotides (from 5' end→3' end) 3-21, 2-21, 1-21, 3-20, 2-20, 1-20, 3-19, 2-19, 2-19, 2-18, or 1-18 of any of the sense strand sequences in Table 2 or Table 4.

In some embodiments, the HSD17B13 RNAi agents include core 19-mer nucleotide sequences shown in the following Table 2.

TABLE 2

HSD17B13 RNAi Agent Antisense Strand and Sense Strand Core Stretch Base Sequences (N = any nucleobase; I = hypoxanthine (inosine nucleotide))

| SEQ ID No. | Antisense Strand Base Sequence (5' → 3') (Shown as an Unmodified Nucleotide Sequence) | SEQ ID No. | Sense Strand Base Sequence (5' → 3') (Shown as an Unmodified Nucleotide Sequence) | Corresponding Positions of Identified Sequence on SEQ ID NO: 1 | Targeted Gene Position |
|---|---|---|---|---|---|
| 25 | CCAUCUAUCAGACUUCUUA | 66 | UAAGAAGUCUGAUAGAUGG | 793-811 | 791 |
| 26 | UCAUCUAUCAGACUUCUUA | 67 | UAAGAAGUCUGAUAGAUGA | 793-811 | 791 |
| 27 | NCAUCUAUCAGACUUCUUA | 68 | UAAGAAGUCUGAUAGAUGN | 793-811 | 791 |
| 28 | NCAUCUAUCAGACUUCUUN | 69 | NAAGAAGUCUGAUAGAUGN | 793-811 | 791 |
| 25 | CCAUCUAUCAGACUUCUUA | 70 | UAAGAAGUCUGAUAGAUIG | 793-811 | 791 |
| 26 | UCAUCUAUCAGACUUCUUA | 71 | UAAGAAGUCUGAUAGAUIA | 793-811 | 791 |
| 27 | NCAUCUAUCAGACUUCUUA | 72 | UAAGAAGUCUGAUAGAUIN | 793-811 | 791 |

TABLE 2-continued

HSD17B13 RNAi Agent Antisense Strand and Sense Strand Core Stretch Base Sequences (N = any nucleobase; I = hypoxanthine (inosine nucleotide))

| SEQ ID No. | Antisense Strand Base Sequence (5' → 3') (Shown as an Unmodified Nucleotide Sequence) | SEQ ID No. | Sense Strand Base Sequence (5' → 3') (Shown as an Unmodified Nucleotide Sequence) | Corresponding Positions of Identified Sequence on SEQ ID NO: 1 | Targeted Gene Position |
|---|---|---|---|---|---|
| 28 | NCAUCUAUCAGACUUCUUN | 73 | NAAGAAGUCUGAUAGAUIN | 793-811 | 791 |
| 25 | CCAUCUAUCAGACUUCUUA | 74 | UAAGAAGUCUGAUAIAUGG | 793-811 | 791 |
| 26 | UCAUCUAUCAGACUUCUUA | 75 | UAAGAAGUCUGAUAIAUGA | 793-811 | 791 |
| 27 | NCAUCUAUCAGACUUCUUA | 76 | UAAGAAGUCUGAUAIAUGN | 793-811 | 791 |
| 28 | NCAUCUAUCAGACUUCUUN | 77 | NAAGAAGUCUGAUAIAUGN | 793-811 | 791 |
| 37 | AAGAAGUGCUUUUGUGAUC | 78 | GAUCACAAAAGCACUUCUU | 515-533 | 513 |
| 38 | UAGAAGUGCUUUUGUGAUC | 79 | GAUCACAAAAGCACUUCUA | 515-533 | 513 |
| 39 | NAGAAGUGCUUUUGUGAUC | 80 | GAUCACAAAAGCACUUCUN | 515-533 | 513 |
| 40 | NAGAAGUGCUUUUGUGAUN | 81 | NAUCACAAAAGCACUUCUN | 515-533 | 513 |
| 41 | UGAUCCAAAAAUGUCCUAG | 82 | CUAGGACAUUUUUGGAUCA | 501-519 | 499 |
| 42 | AGAUCCAAAAAUGUCCUAG | 83 | CUAGGACAUUUUUGGAUCU | 501-519 | 499 |
| 43 | NGAUCCAAAAAUGUCCUAG | 84 | CUAGGACAUUUUUGGAUCN | 501-519 | 499 |
| 44 | NGAUCCAAAAAUGUCCUAN | 85 | NUAGGACAUUUUUGGAUCN | 501-519 | 499 |
| 41 | UGAUCCAAAAAUGUCCUAG | 86 | CUAGGACAUUUUUGIAUCA | 501-519 | 499 |
| 42 | AGAUCCAAAAAUGUCCUAG | 87 | CUAGGACAUUUUUGIAUCU | 501-519 | 499 |
| 43 | NGAUCCAAAAAUGUCCUAG | 88 | CUAGGACAUUUUUGIAUCN | 501-519 | 499 |
| 44 | NGAUCCAAAAAUGUCCUAN | 89 | NUAGGACAUUUUUGIAUCN | 501-519 | 499 |
| 49 | UGUCCUAGGAUGUUGACCU | 90 | AGGUCAACAUCCUAGGACA | 490-508 | 488 |
| 50 | AGUCCUAGGAUGUUGACCU | 91 | AGGUCAACAUCCUAGGACU | 490-508 | 488 |
| 51 | NGUCCUAGGAUGUUGACCU | 92 | AGGUCAACAUCCUAGGACN | 490-508 | 488 |
| 52 | NGUCCUAGGAUGUUGACCN | 93 | NGGUCAACAUCCUAGGACN | 490-508 | 488 |
| 53 | CCAGAAUAGAGUUGCACCG | 94 | CGGUGCAACUCUAUUCUGG | 1503-1521 | 1501 |
| 54 | UCAGAAUAGAGUUGCACCG | 95 | CGGUGCAACUCUAUUCUGA | 1503-1521 | 1501 |
| 55 | ACAGAAUAGAGUUGCACCG | 96 | CGGUGCAACUCUAUUCUGU | 1503-1521 | 1501 |
| 56 | NCAGAAUAGAGUUGCACCG | 97 | CGGUGCAACUCUAUUCUGN | 1503-1521 | 1501 |
| 57 | NCAGAAUAGAGUUGCACCN | 98 | NGGUGCAACUCUAUUCUGN | 1503-1521 | 1501 |
| 58 | AAAAUGUCCUAGGAUGUUG | 99 | CAACAUCCUAGGACAUUUU | 494-512 | 492 |
| 59 | UAAAUGUCCUAGGAUGUUG | 100 | CAACAUCCUAGGACAUUUA | 494-512 | 492 |
| 60 | NAAAUGUCCUAGGAUGUUG | 101 | CAACAUCCUAGGACAUUUN | 494-512 | 492 |
| 61 | NAAAUGUCCUAGGAUGUUN | 102 | NAACAUCCUAGGACAUUUN | 494-512 | 492 |
| 62 | CUCCAAUACAGGCCAUAAU | 103 | AUUAUGGCCUGUAUUGGAG | 761-779 | 759 |
| 63 | UUCCAAUACAGGCCAUAAU | 104 | AUUAUGGCCUGUAUUGGAA | 761-779 | 759 |
| 64 | NUCCAAUACAGGCCAUAAU | 105 | AUUAUGGCCUGUAUUGGAN | 761-779 | 759 |
| 65 | NUCCAAUACAGGCCAUAAN | 106 | NUUAUGGCCUGUAUUGGAN | 761-779 | 759 |

The HSD17B13 RNAi agent sense strands and antisense strands that comprise or consist of the sequences in Table 2 can be modified nucleotides or unmodified nucleotides. In some embodiments, the HSD17B13 RNAi agents having the sense and antisense strand sequences that comprise or consist of the sequences in Table 2 are all or substantially all modified nucleotides.

In some embodiments, the antisense strand of an HSD17B13 RNAi agent disclosed herein differs by 0, 1, 2, or 3 nucleotides from any of the antisense strand sequences in Table 2. In some embodiments, the sense strand of an HSD17B13 RNAi agent disclosed herein differs by 0, 1, 2, or 3 nucleotides from any of the sense strand sequences in Table 2.

As used herein, each N listed in a sequence disclosed in Table 2 may be independently selected from any and all nucleobases (including those found on both modified and unmodified nucleotides). In some embodiments, an N nucleotide listed in a sequence disclosed in Table 2 has a nucleobase that is complementary to the N nucleotide at the corresponding position on the other strand. In some embodiments, an N nucleotide listed in a sequence disclosed in Table 2 has a nucleobase that is not complementary to the N nucleotide at the corresponding position on the other strand. In some embodiments, an N nucleotide listed in a sequence disclosed in Table 2 has a nucleobase that is the same as the N nucleotide at the corresponding position on the other strand. In some embodiments, an N nucleotide listed in a sequence disclosed in Table 2 has a nucleobase that is different from the N nucleotide at the corresponding position on the other strand.

Certain modified HSD17B13 RNAi agent antisense strands, as well as their underlying unmodified nucleobase sequences, are provided in Table 3. Certain modified HSD17B13 RNAi agent sense strands, as well as their underlying unmodified nucleobase sequences, are provided in Table 4. In forming HSD17B13 RNAi agents, each of the nucleotides in each of the underlying base sequences listed in Tables 3 and 4, as well as in Table 2, above, can be a modified nucleotide.

The HSD17B13 RNAi agents described herein are formed by annealing an antisense strand with a sense strand. A sense strand containing a sequence listed in Table 2 or Table 4, can be hybridized to any antisense strand containing a sequence listed in Table 2 or Table 3, provided the two sequences have a region of at least 85% complementarity over a contiguous 16, 17, 18, 19, 20, or 21 nucleotide sequence.

In some embodiments, an HSD17B13 RNAi agent antisense strand comprises a nucleotide sequence of any of the sequences in Table 2 or Table 3.

In some embodiments, an HSD17B13 RNAi agent comprises or consists of a duplex having the nucleobase sequences of the sense strand and the antisense strand of any of the sequences in Table 2, Table 3 or Table 4.

Examples of antisense strands containing modified nucleotides are provided in Table 3. Examples of sense strands containing modified nucleotides are provided in Table 4.

As used in Tables 3 and 4, the following notations are used to indicate modified nucleotides and linking groups:

A=adenosine-3'-phosphate;
C=cytidine-3'-phosphate;
G=guanosine-3'-phosphate;
U=uridine-3'-phosphate
I=inosine-3'-phosphate
a=2'-O-methyladenosine-3'-phosphate
as=2'-O-methyladenosine-3'-phosphorothioate
c=2'-O-methylcytidine-3'-phosphate
cs=2'-O-methylcytidine-3'-phosphorothioate
g=2'-O-methylguanosine-3'-phosphate
gs=2'-O-methylguanosine-3'-phosphorothioate
t=2'-O-methyl-5-methyluridine-3'-phosphate
ts=2'-O-methyl-5-methyluridine-3'-phosphorothioate
u=2'-O-methyluridine-3'-phosphate
us=2'-O-methyluridine-3'-phosphorothioate
i=2'-O-methylinosine-3'-phosphate
is=2'-O-methylinosine-3'-phosphorothioate
Af=2'-fluoroadenosine-3'-phosphate
Afs=2'-fluoroadenosine-3'-phosporothioate
Cf=2'-fluorocytidine-3'-phosphate
Cfs=2'-fluorocytidine-3'-phosphorothioate
Gf=2'-fluoroguanosine-3'-phosphate
Gfs=2'-fluoroguanosine-3'-phosphorothioate
Tf=2'-fluoro-5'-methyluridine-3'-phosphate
Tfs=2'-fluoro-5'-methyluridine-3'-phosphorothioate
Uf=2'-fluorouridine-3'-phosphate
Ufs=2'-fluorouridine-3'-phosphorothioate
$A_{UNA}$=2',3'-seco-adenosine-3'-phosphate
$A_{UNA}$s=2',3'-seco-adenosine-3'-phosphorothioate
$C_{UNA}$=2',3'-seco-cytidine-3'-phosphate
$C_{UNA}$s=2',3'-seco-cytidine-3'-phosphorothioate
$G_{UNA}$=2',3'-seco-guanosine-3'-phosphate
$G_{UNA}$s=2',3'-seco-guanosine-3'-phosphorothioate
$U_{UNA}$=2',3'-seco-uridine-3'-phosphate
$U_{UNA}$s=2',3'-seco-uridine-3'-phosphorothioate
a_2N=see Table 6
a_2Ns=see Table 6
(invAb)=inverted abasic deoxyribonucleotide, see Table 6
(invAb)s=inverted abasic deoxyribonucleotide-5'-phosphorothioate, see Table 6

As the person of ordinary skill in the art would readily understand, unless otherwise indicated by the sequence (such as, for example, by a phosphorothioate linkage "s"), when present in an oligonucleotide, the nucleotide monomers are mutually linked by 5'-3'-phosphodiester bonds. As the person of ordinary skill in the art would clearly understand, the inclusion of a phosphorothioate linkage as shown in the modified nucleotide sequences disclosed herein replaces the phosphodiester linkage typically present in oligonucleotides (see, e.g., FIGS. 1A to 10D showing chemical structures and FIGS. 11A through 11E showing a schematic of all internucleoside linkages in certain HSD17B13 RNAi agents). Further, the person of ordinary skill in the art would readily understand that the terminal nucleotide at the 3' end of a given oligonucleotide sequence would typically have a hydroxyl (—OH) group at the respective 3' position of the given monomer instead of a phosphate moiety ex vivo. Additionally, for the embodiments disclosed herein, when viewing the respective strand 5'→3', the inverted abasic residues are inserted such that the 3' position of the deoxyribose is linked at the 3' end of the preceding monomer on the respective strand (see, e.g., FIGS. 1A through 10D and Table 6). Moreover, as the person of ordinary skill would readily understand and appreciate, while the phosphorothioate chemical structures depicted herein typically show the anion on the sulfur atom, the inventions disclosed herein encompass all phosphorothioate tautomers (e.g., where the sulfur atom has a double-bond and the anion is on an oxygen atom). Unless expressly indicated otherwise herein, such understandings of the person of ordinary skill in the art are used when describing the HSD17B13 RNAi agents and compositions of HSD17B13 RNAi agents disclosed herein.

Certain examples of targeting ligands, targeting groups, and linking groups used with the HSD17B13 RNAi agents disclosed herein are provided below in Table 6. More specifically, targeting groups and linking groups (which together can form a targeting ligand) include the following, for which their chemical structures are provided below in Table 6: (NAG13), (NAG13)s, (NAG18), (NAG18)s, (NAG24), (NAG24)s, (NAG25), (NAG25)s, (NAG26), (NAG26)s, (NAG27), (NAG27)s, (NAG28), (NAG28)s, (NAG29), (NAG29)s, (NAG30), (NAG30)s, (NAG31), (NAG31)s, (NAG32), (NAG32)s, (NAG33), (NAG33)s, (NAG34), (NAG34)s, (NAG35), (NAG35)s, (NAG36), (NAG36)s, (NAG37), (NAG37)s, (NAG38), (NAG38)s, (NAG39), (NAG39) s. Each sense strand and/or antisense strand can have any targeting ligands, targeting groups, or linking groups listed herein, as well as other groups, conjugated to the 5' and/or 3' end of the sequence.

TABLE 3

HSD17B13 RNAi Agent Antisense Strand Sequences

| Antisense Strand ID: | Modified Antisense Strand (5' → 3') | SEQ ID NO. | Underlying Base Sequence (5' → 3') (Shown as an Unmodified Nucleotide Sequence) | SEQ ID NO. |
|---|---|---|---|---|
| AM08050-AS | usCfsasGfaAfuagagUfuGfcAfcCfgUfsc | 107 | UCAGAAUAGAGUUGCACCGUC | 221 |
| AM08052-AS | usGfsusCfcUfaggauGfuUfgAfcCfuCfsa | 108 | UGUCCUAGGAUGUUGACCUCA | 222 |
| AM08054-AS | usGfsusCfcUfA$_{UNA}$ggauGfuUfgAfcCfuCfsa | 109 | UGUCCUAGGAUGUUGACCUCA | 222 |
| AM08056-AS | asAfsasAfuGfuccuaGfgAfuGfuUfgAfsc | 110 | AAAAUGUCCUAGGAUGUUGAC | 223 |
| AM08059-AS | usGfsasUfcCfaaaaaUfgUfcCfuAfgGfsa | 111 | UGAUCCAAAAAUGUCCUAGGA | 224 |
| AM08178-AS | usGfsusCfcUfaggauGfuUfgAfcCfuCfsc | 112 | UGUCCUAGGAUGUUGACCUCC | 225 |
| AM08180-AS | usGfsusCfcUfA$_{UNA}$ggauGfuUfgAfcCfuCfsu | 113 | UGUCCUAGGAUGUUGACCUCU | 226 |
| AM08181-AS | usGfsusCfcUfA$_{UNA}$ggauGfuUfgAfcCfuCfsc | 114 | UGUCCUAGGAUGUUGACCUCC | 225 |
| AM08182-AS | usGfsusCfcUfA$_{UNA}$GfgAfuGfuUfgAfcCfuCfsc | 115 | UGUCCUAGGAUGUUGACCUCC | 225 |
| AM08184-AS | usGfsusCfcUfaG$_{UNA}$gauGfuUfgAfcCfuCfsc | 116 | UGUCCUAGGAUGUUGACCUCC | 225 |
| AM08185-AS | usGfsusC$_{UNA}$CUfaggauGfuUfgAfcCfuCfsc | 117 | UGUCCUAGGAUGUUGACCUCC | 225 |
| AM08186-AS | usGfsusCfC$_{UNA}$UfaggauGfuUfgAfcCfuCfsc | 118 | UGUCCUAGGAUGUUGACCUCC | 225 |
| AM08188-AS | usGfsasUfcCfaaaaaUfgUfcCfuAfgGfsu | 119 | UGAUCCAAAAAUGUCCUAGGU | 227 |
| AM08190-AS | usGfsasUfcCfaaaaaUfgUfcCfuAfgGfsc | 7 | UGAUCCAAAAAUGUCCUAGGC | 6 |
| AM08192-AS | usGfsasUfcCfaAfaAfaUfgUfcCfuAfgGfsc | 5 | UGAUCCAAAAAUGUCCUAGGC | 6 |
| AM08193-AS | usGfsasUfcC$_{UNA}$aaaaaUfgUfcCfuAfgGfsc | 122 | UGAUCCAAAAAUGUCCUAGGC | 6 |
| AM08194-AS | usGfsasUfcCfA$_{UNA}$aaaaUfgUfcCfuAfgGfsc | 123 | UGAUCCAAAAAUGUCCUAGGC | 6 |
| AM08195-AS | usGfsasUfC$_{UNA}$CfaaaaaUfgUfcCfuAfgGfsc | 124 | UGAUCCAAAAAUGUCCUAGGC | 6 |
| AM08196-AS | asAfsasAfuGfuCfcUfaG$_{UNA}$gAfuGfuUfgAfsc | 125 | AAAAUGUCCUAGGAUGUUGAC | 223 |
| AM08236-AS | usAfsgsAfuGfaUfgGfuGfaUfcAfgAfaGfsc | 126 | UAGAUGAUGGUGAUCAGAAGC | 229 |
| AM08238-AS | usAfscsUfgUfcCfcAfgCfaUfuAfuUfcAfsc | 127 | UACUGUCCCAGCAUUAUUCAC | 230 |
| AM08240-AS | asAfsgsAfaGfuGfcUfuUfuGfuGfaUfcCfsa | 128 | AAGAAGUGCUUUUGUGAUCCA | 231 |
| AM08242-AS | usGfsusCfaGfaccucUfgUfgAfaAfgCfsc | 129 | UGUCAGACCUCUGUGAAAGCC | 232 |
| AM08244-AS | usUfsgsAfuGfucagaCfcUfcUfgUfgAfsc | 130 | UUGAUGUCAGACCUCUGUGAC | 233 |
| AM08246-AS | usUfscsCfaAfuAfcAfgGfcCfaUfaAfuCfsc | 131 | UUCCAAUACAGGCCAUAAUCC | 234 |
| AM08248-AS | usCfsasUfcUfaUfcAfgAfcUfuCfuUfaCfsg | 2 | UCAUCUAUCAGACUUCUUACG | 3 |
| AM08250-AS | usCfsasGfgUfuGfaGfaUfaAfaGfcUfgCfsc | 133 | UCAGGUUGAGAUAAAGCUGCC | 236 |
| AM08252-AS | usCfscsAfgAfaUfaGfaGfuUfgCfaCfcGfsu | 134 | UCCAGAAUAGAGUUGCACCGU | 237 |
| AM08254-AS | asAfsgsUfcCfaGfaAfuAfgAfgUfuGfcAfsc | 135 | AAGUCCAGAAUAGAGUUGCAC | 238 |
| AM08256-AS | usCfsusUfgAfuguagUfgGfgAfgUfcGfsg | 136 | UCUUGAUGUAGUGGGAGUCGG | 239 |
| AM08258-AS | asCfsasAfgAfuUfaGfuCfuUfgAfuGfuAfsg | 137 | ACAAGAUUAGUCUUGAUGUAG | 240 |

TABLE 3-continued

HSD17B13 RNAi Agent Antisense Strand Sequences

| Antisense Strand ID: | Modified Antisense Strand (5' → 3') | SEQ ID NO. | Underlying Base Sequence (5' → 3') (Shown as an Unmodified Nucleotide Sequence) | SEQ ID NO. |
|---|---|---|---|---|
| AM08260-AS | usCfsasGfaAfuagagUfuGfcAfcCfgUfsu | 138 | UCAGAAUAGAGUUGCACCGUU | 241 |
| AM08262-AS | usCfsasGfaAfuagagUfuGfcAfcCfgCfsu | 139 | UCAGAAUAGAGUUGCACCGCU | 242 |
| AM08264-AS | usCfsasGfaAfuagagUfuGfcAfcCfgUfsg | 140 | UCAGAAUAGAGUUGCACCGUG | 243 |
| AM08266-AS | usCfsasGfaAfuagagUfuGfcAfcCfgGfsu | 141 | UCAGAAUAGAGUUGCACCGGU | 244 |
| AM08270-AS | usCfsasGfaAf$U_{UNA}$agagUfuGfcAfcCfgUfsc | 142 | UCAGAAUAGAGUUGCACCGUC | 22 |
| AM08272-AS | usCfsasGfaAfuagagUfuGfcAfcCfgCfsc | 143 | UCAGAAUAGAGUUGCACCGCC | 245 |
| AM08274-AS | usCfsasGfaAfuagagUfuGfcAfcCfgGfsc | 144 | UCAGAAUAGAGUUGCACCGGC | 246 |
| AM08275-AS | usCfsasGfaAfuAfgagUfuGfcAfcCfgUfsc | 145 | UCAGAAUAGAGUUGCACCGUC | 221 |
| AM08303-AS | asGfsusGfaCfuccagGfuAfgGfaGfuAfsg | 146 | AGUGACUCCAGGUAGGAGUAG | 247 |
| AM08305-AS | asAfsgsAfaCfuUfuAfcCfaGfuGfaCfuCfsc | 147 | AAGAACUUUACCAGUGACUCC | 248 |
| AM08307-AS | asAfsgsAfaCfuUfuAfcCfaGfuGfaCfuCfsg | 148 | AAGAACUUUACCAGUGACUCG | 249 |
| AM08309-AS | usUfsgsCfaGfuccacCfaCfaAfaCfaCfsg | 149 | UUGCAGUCCACCACAAACACG | 250 |
| AM08311-AS | usCfsasGfcAfucgauGfgAfaGfgAfgUfsg | 150 | UCAGCAUCGAUGGAAGGAGUG | 251 |
| AM08313-AS | asGfsasGfuUfuCfuUfcUfcAfgCfaUfcGfsa | 151 | AGAGUUUCUUCUCAGCAUCGA | 252 |
| AM08315-AS | usCfsasGfuAfuUfcAfcGfaAfcAfcAfgGfsg | 152 | UCAGUAUUCACGAACACAGGG | 253 |
| AM08317-AS | usCfsasGfuAfuUfcAfcGfaAfcAfcAfgGfsc | 153 | UCAGUAUUCACGAACACAGGC | 254 |
| AM08319-AS | usGfsasAfgAfuCfaUfuUfuCfuUfgUfuGfsg | 154 | UGAAGAUCAUUUUCUUGUUGG | 255 |
| AM08341-AS | asAfsgsAfaGfuGfcUfuUfuGfuGfaUfcCfsg | 155 | AAGAAGUGCUUUUGUGAUCCG | 256 |
| AM08343-AS | asAfsgsAfaGfuGfcUfuUfuGfuGfaUfcCfsc | 156 | AAGAAGUGCUUUUGUGAUCCC | 257 |
| AM08345-AS | usAfsgsAfaGfuGfcUfuUfuGfuGfaUfcCfsc | 157 | UAGAAGUGCUUUUGUGAUCCC | 258 |
| AM08347-AS | asAfsgsAfaGf$U_{UNA}$GfcUfuUfuGfuGfaUfcCfsc | 158 | AAGAAGUGCUUUUGUGAUCCC | 257 |
| AM08348-AS | asAfsgsAfaGfu$G_{UNA}$CUfuUfuGfuGfaUfcCfsc | 159 | AAGAAGUGCUUUUGUGAUCCC | 257 |
| AM08350-AS | usAfsgsAfaGfugcuuUfuGfuGfaUfcCfsc | 160 | UAGAAGUGCUUUUGUGAUCCC | 258 |
| AM08352-AS | usCfsasUfcUfaucagAfcUfuCfuUfaCfsg | 4 | UCAUCUAUCAGACUUCUUACG | 3 |
| AM08354-AS | usCfsasUfcUfaUfcAfgAfcUfuCfuUfaCfsc | 162 | UCAUCUAUCAGACUUCUUACC | 259 |
| AM08356-AS | usCfsasUfcUfaucagAfcUfuCfuUfaCfsc | 163 | UCAUCUAUCAGACUUCUUACC | 259 |
| AM08366-AS | asAfsgsAfaGfugcuuUfuGfuGfaUfcCfsg | 164 | AAGAAGUGCUUUUGUGAUCCG | 256 |
| AM08367-AS | asAfsgsAfaGfugcuuUfuGfuGfaUfcCfsc | 165 | AAGAAGUGCUUUUGUGAUCCC | 257 |

TABLE 4

HSD17B13 RNAi Agent Sense Strand Sequences

| Sense Strand ID: | Modified Sense Strand (5' → 3') | SEQ ID NO. | Underlying Base Sequence (5' → 3') (Shown as an Unmodified Nucleotide Sequence) | SEQ ID NO. |
|---|---|---|---|---|
| AM08049-SS | (NAG37)s(invAb)sgacggugcAfAfCfucuauucugas(invAb) | 166 | GACGGUGCAACUCUAUUCUGA | 260 |
| AM08051-SS | (NAG37)s(invAb)sugaggucaAfCfAfuccuaggacas(invAb) | 167 | UGAGGUCAACAUCCUAGGACA | 261 |

TABLE 4-continued

| HSD17B13 RNAi Agent Sense Strand Sequences | | | | |
|---|---|---|---|---|
| Sense Strand ID: | Modified Sense Strand (5' → 3') | SEQ ID NO. | Underlying Base Sequence (5' → 3') (Shown as an Unmodified Nucleotide Sequence) | SEQ ID NO. |
| AM08053-SS | (NAG37)s(invAb)sugaggucaAfCfAfuccuagiacas(invAb) | 168 | UGAGGUCAACAUCCUAGIACA | 262 |
| AM08055-SS | (NAG37)s(invAb)sgucaacauCfCfUfaggacauuuus(invAb) | 169 | GUCAACAUCCUAGGACAUUUU | 263 |
| AM08057-SS | (NAG37)s(invAb)sgucaacauCfCfUfaggaca_2Nuuuus(invAb) | 170 | GUCAACAUCCUAGGAC(A$^{2N}$)UUUU | 264 |
| AM08058-SS | (NAG37)s(invAb)succuaggaCfAfUfuuuuggaucas(invAb) | 171 | UCCUAGGACAUUUUUGGAUCA | 265 |
| AM08060-SS | (NAG37)s(invAb)succuaggaCfAfUfuuuugiaucas(invAb) | 172 | UCCUAGGACAUUUUUGIAUCA | 266 |
| AM08177-SS | (NAG37)s(invAb)sggaggucaAfCfAfuccuaggacas(invAb) | 173 | GGAGGUCAACAUCCUAGGACA | 267 |
| AM08179-SS | (NAG37)s(invAb)sagaggucaAfCfAfuccuaggacas(invAb) | 174 | AGAGGUCAACAUCCUAGGACA | 268 |
| AM08183-SS | (NAG37)s(invAb)sggaggucaAfCfAfuccuagiacas(invAb) | 175 | GGAGGUCAACAUCCUAGIACA | 269 |
| AM08187-SS | (NAG37)s(invAb)saccuaggaCfAfUfuuuugiaucas(invAb) | 176 | ACCUAGGACAUUUUUGIAUCA | 270 |
| AM08189-SS | (NAG37)s(invAb)sgccuaggaCfAfUfuuuuggaucas(invAb) | 177 | GCCUAGGACAUUUUUGGAUCA | 271 |
| AM08191-SS | (NAG37)s(invAb)sgccuaggaCfAfUfuuuugiaucas(invAb) | 16 | GCCUAGGACAUUUUUGIAUCA | 11 |
| AM08235-SS | (NAG37)s(invAb)sgcuucugaUfCfAfccaucaucuas(invAb) | 179 | GCUUCUGAUCACCAUCAUCUA | 273 |
| AM08237-SS | (NAG37)s(invAb)sgugaauaaUfGfCfugggacaguas(invAb) | 180 | GUGAAUAAUGCUGGGACAGUA | 274 |
| AM08239-SS | (NAG37)s(invAb)suggaucacAfAfAfagcacuucuus(invAb) | 181 | UGGAUCACAAAAGCACUUCUU | 275 |
| AM08241-SS | (NAG37)s(invAb)sggcuuucaCfAfGfaggucugacas(invAb) | 182 | GGCUUUCACAGAGGUCUGACA | 276 |
| AM08243-SS | (NAG37)s(invAb)sgucacagaGfGfUfcugacaucaas(invAb) | 183 | GUCACAGAGGUCUGACAUCAA | 277 |
| AM08245-SS | (NAG37)s(invAb)sggauuaugGfCfCfuguauuggaas(invAb) | 184 | GGAUUAUGGCCUGUAUUGGAA | 278 |
| AM08247-SS | (NAG37)s(invAb)scguaagaaGfUfCfugauagaugas(invAb) | 14 | CGUAAGAAGUCUGAUAGAUGA | 8 |
| AM08249-SS | (NAG37)s(invAb)sggcagcuuUfAfUfcucaaccugas(invAb) | 186 | GGCAGCUUUAUCUCAACCUGA | 280 |
| AM08251-SS | (NAG37)s(invAb)sacggugcaAfCfUfcuauucuggas(invAb) | 187 | ACGGUGCAACUCUAUUCUGGA | 281 |
| AM08253-SS | (NAG37)s(invAb)sgugcaacuCfUfAfuucuggacuus(invAb) | 188 | GUGCAACUCUAUUCUGGACUU | 282 |
| AM08255-SS | (NAG37)s(invAb)sccgacuccCfAfCfuacaucaagas(invAb) | 189 | CCGACUCCCACUACAUCAAGA | 283 |
| AM08257-SS | (NAG37)s(invAb)scuacaucaAfGfAfcuaaucuugus(invAb) | 190 | CUACAUCAAGACUAAUCUUGU | 284 |
| AM08259-SS | (NAG37)s(invAb)scggugcAfAfCfucuauucugauus(invAb) | 191 | CGGUGCAACUCUAUUCUGAUU | 285 |
| AM08261-SS | (NAG37)s(invAb)sagcggugcAfAfCfucuauucugas(invAb) | 192 | AGCGGUGCAACUCUAUUCUGA | 286 |
| AM08263-SS | (NAG37)s(invAb)scacggugcAfAfCfucuauucugas(invAb) | 193 | CACGGUGCAACUCUAUUCUGA | 287 |
| AM08265-SS | (NAG37)s(invAb)saccggugcAfAfCfucuauucugas(invAb) | 194 | ACCGGUGCAACUCUAUUCUGA | 288 |
| AM08267-SS | (NAG37)s(invAb)sgacgguicAfAfCfucuauucugas(invAb) | 195 | GACGGUICAACUCUAUUCUGA | 289 |
| AM08268-SS | (NAG37)s(invAb)sgacgiugcAfAfCfucuauucugas(invAb) | 196 | GACGIUGCAACUCUAUUCUGA | 290 |
| AM08269-SS | (NAG37)s(invAb)sgacggugcAfAfCfucuauucuias(invAb) | 197 | GACGGUGCAACUCUAUUCUIA | 291 |
| AM08271-SS | (NAG37)s(invAb)sggcggugcAfAfCfucuauucugas(invAb) | 198 | GGCGGUGCAACUCUAUUCUGA | 292 |
| AM08273-SS | (NAG37)s(invAb)sgccggugcAfAfCfucuauucugas(invAb) | 199 | GCCGGUGCAACUCUAUUCUGA | 293 |
| AM08302-SS | (NAG37)s(invAb)scuacuccuAfCfCfuggagucacus(invAb) | 200 | CUACUCCUACCUGGAGUCACU | 294 |
| AM08304-SS | (NAG37)s(invAb)sggagucacUfGfGfuaaaguucuus(invAb) | 201 | GGAGUCACUGGUAAAGUUCUU | 295 |
| AM08306-SS | (NAG37)s(invAb)scgagucacUfGfGfuaaaguucuus(invAb) | 202 | CGAGUCACUGGUAAAGUUCUU | 296 |
| AM08308-SS | (NAG37)s(invAb)scguguuugUfGfGfuggacugcaas(invAb) | 203 | CGUGUUUGUGGUGGACUGCAA | 297 |
| AM08310-SS | (NAG37)s(invAb)scacuccuuCfCfAfucgaugcugas(invAb) | 204 | CACUCCUUCCAUCGAUGCUGA | 298 |

TABLE 4-continued

| HSD17B13 RNAi Agent Sense Strand Sequences | | | | |
|---|---|---|---|---|
| Sense Strand ID: | Modified Sense Strand (5' → 3') | SEQ ID NO. | Underlying Base Sequence (5' → 3') (Shown as an Unmodified Nucleotide Sequence) | SEQ ID NO. |
| AM08312-SS | (NAG37)s(invAb)sucgaugcuGfAfGfaagaaacucus(invAb) | 205 | UCGAUGCUGAGAAGAAACUCU | 299 |
| AM08314-SS | (NAG37)s(invAb)scccuguguUfCfGfugaauacugas(invAb) | 206 | CCCUGUGUUCGUGAAUACUGA | 300 |
| AM08316-SS | (NAG37)s(invAb)sgccuguguUfCfGfugaauacugas(invAb) | 207 | GCCUGUGUUCGUGAAUACUGA | 301 |
| AM08318-SS | (NAG37)s(invAb)sccaacaagAfAfAfaugaucuucas(invAb) | 208 | CCAACAAGAAAAUGAUCUUCA | 302 |
| AM08340-SS | (NAG37)s(invAb)scggaucacAfAfAfagcacuucuus(invAb) | 209 | CGGAUCACAAAAGCACUUCUU | 303 |
| AM08342-SS | (NAG37)s(invAb)sgggaucacAfAfAfagcacuucuus(invAb) | 210 | GGGAUCACAAAAGCACUUCUU | 304 |
| AM08344-SS | (NAG37)s(invAb)sgggaucacAfAfAfagcacuucuas(invAb) | 211 | GGGAUCACAAAAGCACUUCUA | 305 |
| AM08346-SS | (NAG37)s(invAb)sgggaucacAfaAfaGfcacuucuus(invAb) | 212 | GGGAUCACAAAAGCACUUCUU | 304 |
| AM08349-SS | (NAG37)s(invAb)sgggaucacAfaAfaGfcacuucuas(invAb) | 213 | GGGAUCACAAAAGCACUUCUA | 305 |
| AM08351-SS | (NAG37)s(invAb)scguaagaaGfuCfuGfauagauias(invAb) | 214 | CGUAAGAAGUCUGAUAGAUIA | 306 |
| AM08353-SS | (NAG37)s(invAb)sgguaagaaGfuCfuGfauagaugas(invAb) | 215 | GGUAAGAAGUCUGAUAGAUGA | 307 |
| AM08355-SS | (NAG37)s(invAb)sgguaagaaGfuCfuGfauagauias(invAb) | 216 | GGUAAGAAGUCUGAUAGAUIA | 308 |
| AM08357-SS | (NAG37)s(invAb)sgguaagaaGfuCfuGfauaiaugas(invAb) | 217 | GGUAAGAAGUCUGAUAIAUGA | 309 |
| AM08358-SS | (NAG37)s(invAb)sgccuaggaCfaUfuUfuugiaucas(invAb) | 17 | GCCUAGGACAUUUUUGIAUCA | 11 |
| AM08365-SS | (NAG37)s(invAb)scggaucacAfaAfaGfcacuucuus(invAb) | 219 | CGGAUCACAAAAGCACUUCUU | 303 |
| AM08368-SS | (NAG37)s(invAb)scguaagaaGfuCfuGfauagaugas(invAb) | 15 | CGUAAGAAGUCUGAUAGAUGA | 8 |

($A^{2N}$) = 2-aminoadenine nucleotide

The HSD17B13 RNAi agents described herein are formed by annealing an antisense strand with a sense strand. A sense strand containing a sequence listed in Table 2 or Table 4 can be hybridized to any antisense strand containing a sequence listed in Table 2 or Table 3, provided the two sequences have a region of at least 85% complementarity over a contiguous 16, 17, 18, 19, 20, or 21 nucleotide sequence.

In some embodiments, the antisense strand of an HSD17B13 RNAi agent disclosed herein differs by 0, 1, 2, or 3 nucleotides from any of the antisense strand sequences in Table 3. In some embodiments, the sense strand of an HSD17B13 RNAi agent disclosed herein differs by 0, 1, 2, or 3 nucleotides from any of the sense strand sequences in Table 4.

In some embodiments, an HSD17B13 RNAi agent antisense strand comprises a nucleotide sequence of any of the sequences in Table 2 or Table 3. In some embodiments, an HSD17B13 RNAi agent antisense strand comprises the sequence of nucleotides (from 5' end→3' end) 1-17, 2-17, 1-18, 2-18, 1-19, 2-19, 1-20, 2-20, 1-21, or 2-21, of any of the sequences in Table 2 or Table 3. In certain embodiments, an HSD17B13 RNAi agent antisense strand comprises or consists of a modified sequence of any one of the modified sequences in Table 3.

In some embodiments, an HSD17B13 RNAi agent sense strand comprises the nucleotide sequence of any of the sequences in Table 2 or Table 4. In some embodiments, an HSD17B13 RNAi agent sense strand comprises the sequence of nucleotides (from 5' end→3' end) 1-17, 2-17, 3-17, 4-17, 1-18, 2-18, 3-18, 4-18, 1-19, 2-19, 3-19, 4-19, 1-20, 2-20, 3-20, 4-20, 1-21, 2-21, 3-21, or 4-21, of any of the sequences in Table 2 or Table 4. In certain embodiments, an HSD17B13 RNAi agent sense strand comprises or consists of a modified sequence of any one of the modified sequences in Table 4.

For the HSD17B13 RNAi agents disclosed herein, the nucleotide at position 1 of the antisense strand (from 5' end→3' end) can be perfectly complementary to an HSD17B13 gene, or can be non-complementary to an HSD17B13 gene. In some embodiments, the nucleotide at position 1 of the antisense strand (from 5' end→3' end) is a U, A, or dT (or a modified version thereof). In some embodiments, the nucleotide at position 1 of the antisense strand (from 5' end→3' end) forms an A:U or U:A base pair with the sense strand.

A sense strand containing a sequence listed in Table 2 or Table 4 can be hybridized to any antisense strand containing a sequence listed in Table 2 or Table 3, provided the two sequences have a region of at least 85% complementarity over a contiguous 16, 17, 18, 19, 20, or 21 nucleotide sequence. In some embodiments, the HSD17B13 RNAi agent has a sense strand consisting of the modified sequence of any of the modified sequences in Table 4, and an antisense strand consisting of the modified sequence of any of the modified sequences in Table 3. Certain representative sequence pairings are exemplified by the Duplex ID Nos. shown in Table 5.

In some embodiments, an HSD17B13 RNAi agent comprises, consists of, or consists essentially of a duplex represented by any one of the Duplex ID Nos. presented herein.

In some embodiments, an HSD17B13 RNAi agent comprises the sense strand and antisense strand nucleotide sequences of any of the duplexes represented by any of the Duplex ID Nos. presented herein. In some embodiments, an HSD17B13 RNAi agent comprises the sense strand and antisense strand nucleotide sequences of any of the duplexes represented by any of the Duplex ID Nos. presented herein and a targeting group and/or linking group wherein the targeting group and/or linking group is covalently linked (i.e., conjugated) to the sense strand or the antisense strand. In some embodiments, an HSD17B13 RNAi agent includes the sense strand and antisense strand modified nucleotide sequences of any of the Duplex ID Nos. presented herein. In some embodiments, an HSD17B13 RNAi agent comprises the sense strand and antisense strand modified nucleotide sequences of any of the Duplex ID Nos. presented herein and a targeting group and/or linking group, wherein the targeting group and/or linking group is covalently linked to the sense strand or the antisense strand.

In some embodiments, an HSD17B13 RNAi agent comprises an antisense strand and a sense strand having the nucleotide sequences of any of the antisense strand/sense strand duplexes of Table 2 or Table 5, and further comprises a targeting group or targeting ligand. In some embodiments, an HSD17B13 RNAi agent comprises an antisense strand and a sense strand having the nucleotide sequences of any of the antisense strand/sense strand duplexes of Table 2 or Table 5, and further comprises an asialoglycoprotein receptor ligand targeting group.

A targeting group, with or without a linker, can be linked to the 5' or 3' end of any of the sense and/or antisense strands disclosed in Tables 2, 3, and 4. A linker, with or without a targeting group, can be attached to the 5' or 3' end of any of the sense and/or antisense strands disclosed in Tables 2, 3, and 4.

In some embodiments, an HSD17B13 RNAi agent comprises an antisense strand and a sense strand having the nucleotide sequences of any of the antisense strand/sense strand duplexes of Table 2 or Table 5, and further comprises a targeting ligand selected from the group consisting of: (NAG13), (NAG13)s, (NAG18), (NAG18)s, (NAG24), (NAG24)s, (NAG25), (NAG25)s, (NAG26), (NAG26)s, (NAG27), (NAG27)s, (NAG28), (NAG28)s, (NAG29), (NAG29)s, (NAG30), (NAG30)s, (NAG31), (NAG31)s, (NAG32), (NAG32)s, (NAG33), (NAG33)s, (NAG34), (NAG34)s, (NAG35), (NAG35)s, (NAG36), (NAG36)s, (NAG37), (NAG37)s, each as defined in Table 6. In some embodiments, the targeting ligand is (NAG25) or (NAG25)s as defined in Table 6. In other embodiments, the targeting ligand is (NAG37) or (NAG37)s as defined in Table 6.

In some embodiments, an HSD17B13 RNAi agent comprises an antisense strand and a sense strand having the modified nucleotide sequence of any of the antisense strand and/or sense strand nucleotide sequences in Table 3 or Table 4.

In some embodiments, an HSD17B13 RNAi agent comprises an antisense strand and a sense strand having a modified nucleotide sequence of any of the antisense strand and/or sense strand nucleotide sequences of any of the duplexes Table 5, and further comprises an asialoglycoprotein receptor ligand targeting group.

In some embodiments, an HSD17B13 RNAi agent comprises, consists of, or consists essentially of any of the duplexes of Table 5.

TABLE 5

HSD17B13 RNAi Agents Duplexes with Corresponding Sense and Antisense Strand ID Numbers

| Duplex ID | Antisense Strand ID | Sense Strand ID |
|---|---|---|
| AD06078 | AM08050-AS | AM08049-SS |
| AD06079 | AM08052-AS | AM08051-SS |
| AD06080 | AM08052-AS | AM08053-SS |
| AD06081 | AM08054-AS | AM08051-SS |
| AD06082 | AM08056-AS | AM08055-SS |
| AD06083 | AM08056-AS | AM08057-SS |
| AD06084 | AM08059-AS | AM08058-SS |
| AD06085 | AM08059-AS | AM08060-SS |
| AD06176 | AM08178-AS | AM08177-SS |
| AD06177 | AM08180-AS | AM08179-SS |
| AD06178 | AM08181-AS | AM08177-SS |
| AD06179 | AM08182-AS | AM08177-SS |
| AD06180 | AM08181-AS | AM08183-SS |
| AD06181 | AM08184-AS | AM08177-SS |
| AD06182 | AM08185-AS | AM08177-SS |
| AD06183 | AM08186-AS | AM08177-SS |
| AD06184 | AM08188-AS | AM08187-SS |
| AD06185 | AM08190-AS | AM08189-SS |
| AD06186 | AM08190-AS | AM08191-SS |
| AD06187 | AM08192-AS | AM08191-SS |
| AD06188 | AM08193-AS | AM08191-SS |
| AD06189 | AM08194-AS | AM08191-SS |
| AD06190 | AM08195-AS | AM08189-SS |
| AD06191 | AM08196-AS | AM08055-SS |
| AD06208 | AM08236-AS | AM08235-SS |
| AD06209 | AM08238-AS | AM08237-SS |
| AD06210 | AM08240-AS | AM08239-SS |
| AD06211 | AM08242-AS | AM08241-SS |
| AD06212 | AM08244-AS | AM08243-SS |
| AD06213 | AM08246-AS | AM08245-SS |
| AD06214 | AM08248-AS | AM08247-SS |
| AD06215 | AM08250-AS | AM08249-SS |
| AD06216 | AM08252-AS | AM08251-SS |
| AD06217 | AM08254-AS | AM08253-SS |
| AD06218 | AM08256-AS | AM08255-SS |
| AD06219 | AM08258-AS | AM08257-SS |
| AD06220 | AM08260-AS | AM08259-SS |
| AD06221 | AM08262-AS | AM08261-SS |
| AD06222 | AM08264-AS | AM08263-SS |
| AD06223 | AM08266-AS | AM08265-SS |
| AD06224 | AM08050-AS | AM08267-SS |
| AD06225 | AM08050-AS | AM08268-SS |
| AD06226 | AM08050-AS | AM08269-SS |
| AD06227 | AM08270-AS | AM08049-SS |
| AD06228 | AM08272-AS | AM08271-SS |
| AD06229 | AM08274-AS | AM08273-SS |
| AD06230 | AM08275-AS | AM08049-SS |
| AD06244 | AM08303-AS | AM08302-SS |
| AD06245 | AM08305-AS | AM08304-SS |
| AD06246 | AM08307-AS | AM08306-SS |
| AD06247 | AM08309-AS | AM08308-SS |
| AD06248 | AM08311-AS | AM08310-SS |
| AD06249 | AM08313-AS | AM08312-SS |
| AD06250 | AM08315-AS | AM08314-SS |
| AD06251 | AM08317-AS | AM08316-SS |
| AD06252 | AM08319-AS | AM08318-SS |
| AD06265 | AM08341-AS | AM08340-SS |
| AD06266 | AM08343-AS | AM08342-SS |
| AD06267 | AM08345-AS | AM08344-SS |
| AD06268 | AM08347-AS | AM08346-SS |
| AD06269 | AM08348-AS | AM08346-SS |
| AD06270 | AM08343-AS | AM08346-SS |
| AD06271 | AM08350-AS | AM08349-SS |
| AD06272 | AM08352-AS | AM08351-SS |
| AD06273 | AM08354-AS | AM08353-SS |
| AD06274 | AM08356-AS | AM08355-SS |
| AD06275 | AM08356-AS | AM08357-SS |
| AD06276 | AM08192-AS | AM08358-SS |
| AD06277 | AM08190-AS | AM08358-SS |
| AD06278 | AM08366-AS | AM08365-SS |
| AD06279 | AM08367-AS | AM08346-SS |
| AD06280 | AM08352-AS | AM08368-SS |
| AD06281 | AM08356-AS | AM08353-SS |

In some embodiments, an HSD17B13 RNAi agent is prepared or provided as a salt, mixed salt, or a free-acid. The RNAi agents described herein, upon delivery to a cell expressing an HSD17B13 gene, inhibit or knockdown expression of one or more HSD17B13 genes in vivo and/or in vitro.

Targeting Ligands or Groups, Linking Groups, and Delivery Vehicles

In some embodiments, an HSD17B13 RNAi agent is conjugated to one or more non-nucleotide groups including, but not limited to, a targeting group, a linking group, a targeting ligand, a delivery polymer, or a delivery vehicle. The non-nucleotide group can enhance targeting, delivery or attachment of the RNAi agent. Examples of targeting groups and linking groups are provided in Table 6. The non-nucleotide group can be covalently linked to the 3' and/or 5' end of either the sense strand and/or the antisense strand. In some embodiments, an HSD17B13 RNAi agent contains a non-nucleotide group linked to the 3' and/or 5' end of the sense strand. In some embodiments, a non-nucleotide group is linked to the 5' end of an HSD17B13 RNAi agent sense strand. A non-nucleotide group may be linked directly or indirectly to the RNAi agent via a linker/linking group. In some embodiments, a non-nucleotide group is linked to the RNAi agent via a labile, cleavable, or reversible bond or linker.

In some embodiments, a non-nucleotide group enhances the pharmacokinetic or biodistribution properties of an RNAi agent or conjugate to which it is attached to improve cell- or tissue-specific distribution and cell-specific uptake of the RNAi agent or conjugate. In some embodiments, a non-nucleotide group enhances endocytosis of the RNAi agent.

Targeting groups or targeting moieties enhance the pharmacokinetic or biodistribution properties of a conjugate or RNAi agent to which they are attached to improve cell-specific (including, in some cases, organ specific) distribution and cell-specific (or organ specific) uptake of the conjugate or RNAi agent. A targeting group can be monovalent, divalent, trivalent, tetravalent, or have higher valency for the target to which it is directed. Representative targeting groups include, without limitation, compounds with affinity to cell surface molecules, cell receptor ligands, haptens, antibodies, monoclonal antibodies, antibody fragments, and antibody mimics with affinity to cell surface molecules.

In some embodiments, a targeting group is linked to an RNAi agent using a linker, such as a PEG linker or one, two, or three abasic and/or ribitol (abasic ribose) residues, which can in some instances serve as linkers. In some embodiments, a targeting ligand comprises a galactose-derivative cluster.

The HSD17B13 RNAi agents described herein can be synthesized having a reactive group, such as an amino group (also referred to herein as an amine), at the 5'-terminus and/or the 3'-terminus. The reactive group can be used subsequently to attach a targeting moiety using methods typical in the art.

In some embodiments, a targeting group comprises an asialoglycoprotein receptor ligand. As used herein, an asialoglycoprotein receptor ligand is a ligand that contains a compound having affinity for the asialoglycoprotein receptor. As noted herein, the asialoglycoprotein receptor is highly expressed on hepatocytes. In some embodiments, an asialoglycoprotein receptor ligand includes or consists of one or more galactose derivatives. As used herein, the term galactose derivative includes both galactose and derivatives of galactose having affinity for the asialoglycoprotein receptor that is equal to or greater than that of galactose. Galactose derivatives include, but are not limited to: galactose, galactosamine, N-formylgalactosamine, N-acetyl-galactosamine, N-propionyl-galactosamine, N-n-butanoyl-galactosamine, and N-iso-butanoylgalactos-amine (see for example: S. T. Iobst and K. Drickamer, J.B.C., 1996, 271, 6686). Galactose derivatives, and clusters of galactose derivatives, that are useful for in vivo targeting of oligonucleotides and other molecules to the liver are known in the art (see, for example, Baenziger and Fiete, 1980, Cell, 22, 611-620; Connolly et al., 1982, J. Biol. Chem., 257, 939-945).

Galactose derivatives have been used to target molecules to hepatocytes in vivo through their binding to the asialoglycoprotein receptor expressed on the surface of hepatocytes. Binding of asialoglycoprotein receptor ligands to the asialoglycoprotein receptor(s) facilitates cell-specific targeting to hepatocytes and endocytosis of the molecule into hepatocytes. Asialoglycoprotein receptor ligands can be monomeric (e.g., having a single galactose derivative, also referred to as monovalent or monodentate) or multimeric (e.g., having multiple galactose derivatives). The galactose derivative or galactose derivative cluster can be attached to the 3' or 5' end of the sense or antisense strand of the RNAi agent using methods known in the art. The preparation of targeting ligands, such as galactose derivative clusters, is described in, for example, International Patent Application Publication No. WO 2018/044350 to Arrowhead Pharmaceuticals, Inc., and International Patent Application Publication No. WO 2017/156012 to Arrowhead Pharmaceuticals, Inc., the contents of both of which are incorporated by reference herein in their entirety.

As used herein, a galactose derivative cluster comprises a molecule having two to four terminal galactose derivatives. A terminal galactose derivative is attached to a molecule through its C-1 carbon. In some embodiments, the galactose derivative cluster is a galactose derivative trimer (also referred to as tri-antennary galactose derivative or trivalent galactose derivative). In some embodiments, the galactose derivative cluster comprises N-acetyl-galactosamines. In some embodiments, the galactose derivative cluster comprises three N-acetyl-galactosamines. In some embodiments, the galactose derivative cluster is a galactose derivative tetramer (also referred to as tetra-antennary galactose derivative or tetra-valent galactose derivative). In some embodiments, the galactose derivative cluster comprises four N-acetyl-galactosamines.

As used herein, a galactose derivative trimer contains three galactose derivatives, each linked to a central branch point. As used herein, a galactose derivative tetramer contains four galactose derivatives, each linked to a central branch point. The galactose derivatives can be attached to the central branch point through the C-1 carbons of the saccharides. In some embodiments, the galactose derivatives are linked to the branch point via linkers or spacers. In some embodiments, the linker or spacer is a flexible hydrophilic spacer, such as a PEG group (see, e.g., U.S. Pat. No. 5,885,968; Biessen et al. J. Med. Chem. 1995 Vol. 39 p. 1538-1546). In some embodiments, the PEG spacer is a PEG3 spacer. The branch point can be any small molecule which permits attachment of three galactose derivatives and further permits attachment of the branch point to the RNAi agent. An example of branch point group is a di-lysine or di-glutamate. Attachment of the branch point to the RNAi agent can occur through a linker or spacer. In some embodiments, the linker or spacer comprises a flexible hydrophilic spacer, such as, but not limited to, a PEG spacer. In some embodiments, the linker comprises a rigid linker, such as a cyclic group. In some embodiments, a galactose derivative comprises or consists of N-acetyl-galactosamine. In some embodiments, the galactose derivative cluster is comprised of a galactose derivative tetramer, which can be, for example, an N-acetyl-galactosamine tetramer.

Embodiments of the present disclosure include pharmaceutical compositions for delivering an HSD17B13 RNAi agent to a liver cell in vivo. Such pharmaceutical compositions can include, for example, an HSD17B13 RNAi agent conjugated to a galactose derivative cluster. In some embodiments, the galactose derivative cluster is comprised of a galactose derivative trimer, which can be, for example, an N-acetyl-galactosamine trimer, or galactose derivative tetramer, which can be, for example, an N-acetyl-galactosamine tetramer.

A targeting ligand or targeting group can be linked to the 3' or 5' end of a sense strand or an antisense strand of an HSD17B13 RNAi agent disclosed herein.

Targeting ligands include, but are not limited to, (NAG13), (NAG13)s, (NAG18), (NAG18)s, (NAG24), (NAG24)s, (NAG25), (NAG25)s, (NAG26), (NAG26)s, (NAG27), (NAG27)s, (NAG28), (NAG28)s, (NAG29), (NAG29)s, (NAG30), (NAG30)s, (NAG31), (NAG31)s, (NAG32), (NAG32)s, (NAG33), (NAG33)s, (NAG34), (NAG34)s, (NAG35), (NAG35)s, (NAG36), (NAG36)s, (NAG37), (NAG37)s, (NAG38), (NAG38)s, (NAG39), and (NAG39)s as defined in Table 6. Other targeting groups and targeting ligands, including galactose cluster targeting ligands, are known in the art.

In some embodiments, a linking group is conjugated to the RNAi agent. The linking group facilitates covalent linkage of the agent to a targeting group, delivery polymer, or delivery vehicle. The linking group can be linked to the 3' and/or the 5' end of the RNAi agent sense strand or antisense strand. In some embodiments, the linking group is linked to the RNAi agent sense strand. In some embodiments, the linking group is conjugated to the 5' or 3' end of an RNAi agent sense strand. In some embodiments, a linking group is conjugated to the 5' end of an RNAi agent sense strand. Examples of linking groups, can include, but are not limited to: reactive groups such a primary amines and alkynes, alkyl groups, abasic nucleotides, ribitol (abasic ribose), and/or PEG groups.

In some embodiments, a targeting group is linked internally to a nucleotide on the sense strand and/or the antisense strand of the RNAi agent. In some embodiments, a targeting group is linked to the RNAi agent via a linker.

A linker or linking group is a connection between two atoms that links one chemical group (such as an RNAi agent) or segment of interest to another chemical group (such as a targeting group or delivery polymer) or segment of interest via one or more covalent bonds. A labile linkage contains a labile bond. A linkage can optionally include a spacer that increases the distance between the two joined atoms. A spacer can further add flexibility and/or length to the linkage. Spacers include, but are not be limited to, alkyl groups, alkenyl groups, alkynyl groups, aryl groups, aralkyl groups, aralkenyl groups, and aralkynyl groups; each of which can contain one or more heteroatoms, heterocycles, amino acids, nucleotides, and saccharides. Spacer groups are well known in the art and the preceding list is not meant to limit the scope of the description.

In some embodiments, when two or more RNAi agents are included in a single composition, each of the RNAi agents may be linked to the same targeting group or two a different targeting groups (i.e., targeting groups having different chemical structure). In some embodiments, targeting groups are linked to the HSD17B13 RNAi agents disclosed herein without the use of an additional linker. In some embodiments, the targeting group itself is designed having a linker or other site to facilitate conjugation readily present. In some embodiments, when two or more HSD17B13 RNAi agents are included in a single, each of the RNAi agents may utilize the same linker or different linkers (i.e., linkers having different chemical structures).

Any of the HSD17B13 RNAi agent nucleotide sequences listed in Tables 2, 3, or 4, whether modified or unmodified, can contain 3' and/or 5' targeting group(s) or linking group(s). Any of the HSD17B13 RNAi agent sequences listed in Table 3 or 4, or are otherwise described herein, which contain a 3' or 5' targeting group or linking group, can alternatively contain no 3' or 5' targeting group or linking group, or can contain a different 3' or 5' targeting group or linking group including, but not limited to, those depicted in Table 6. Any of the HSD17B13 RNAi agent duplexes listed in Table 5, whether modified or unmodified, can further comprise a targeting group or linking group, including, but not limited to, those depicted in Table 6, and the targeting group or linking group can be attached to the 3' or 5' terminus of either the sense strand or the antisense strand of the HSD17B13 RNAi agent duplex.

Examples of targeting groups and linking groups (which when combined can form targeting ligands) are provided in Table 6. Table 4 provides several embodiments of HSD17B13 RNAi agent sense strands having a targeting group or linking group linked to the 5' or 3' end.

TABLE 6
| Structures Representing Various Modified Nucleotides, Targeting Ligands or Targeting Groups, Capping Residues, and Linking Groups |
|---|
| 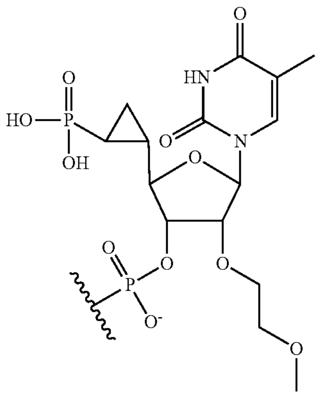 [SMILES: *P(=O)([O-])OC1C(C2CC2P(=O)(O)O)OC(n2cc(C)c(=O)[nH]c2=O)C1OCCOC] |
| cPrpTM |
| 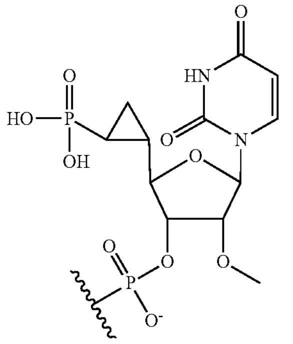 [SMILES: *P(=O)([S-])OC1C(C2CC2P(=O)(O)O)OC(n2ccc(=O)[nH]c2=O)C1OC] |
| cPrpu |
| 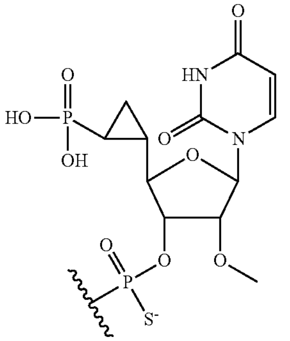 |
| cPrpus |
| 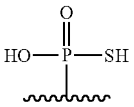 |
| sp |

TABLE 6-continued
| Structures Representing Various Modified Nucleotides, Targeting Ligands or Targeting Groups, Capping Residues, and Linking Groups |
|---|
| 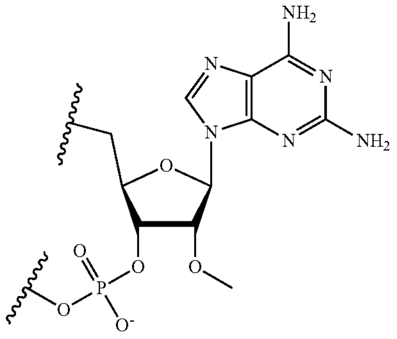 |
| a_2N |
| 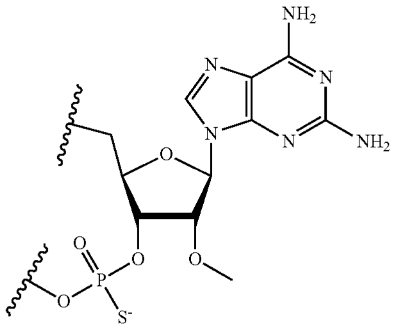 |
| a_2Ns |
| 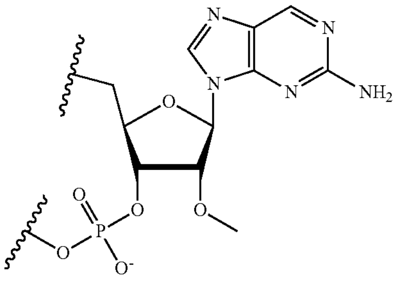 |
| pu_2N |
| 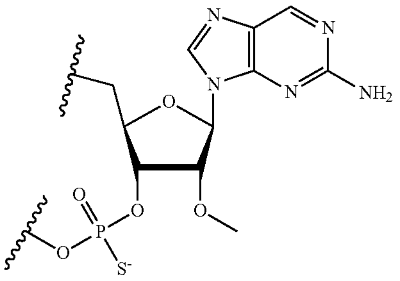 |

TABLE 6-continued
Structures Representing Various Modified Nucleotides, Targeting Ligands or Targeting Groups, Capping Residues, and Linking Groups
pu_2Ns
When positioned internally in oligonucleotide:
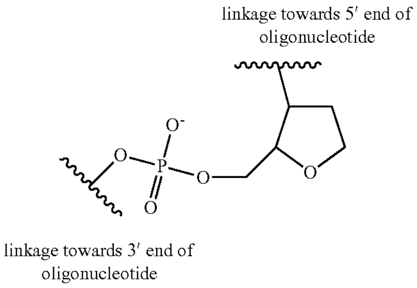 [SMILES: *OP(=O)([O-])OCC1OCCC1*]
(invAb)
When positioned internally in oligonucleotide:
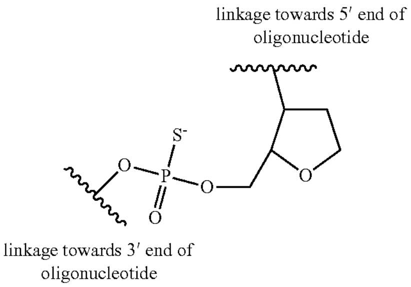 [SMILES: *OP(=O)([S-])OCC1OCCC1*]
(invAb)s
When positioned at the 3' terminal end of oligonucleotide:
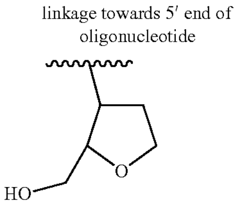 [SMILES: *C1CCOC1CO]
(invAb)
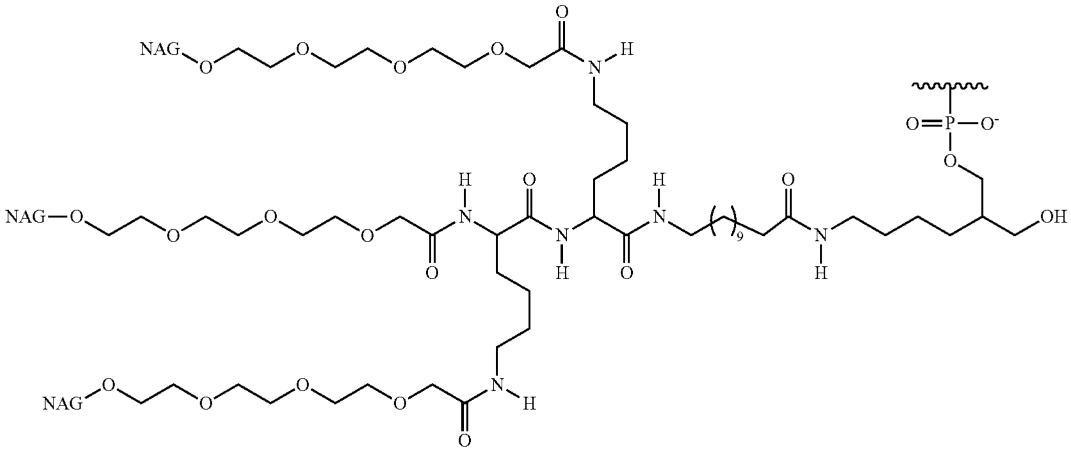

TABLE 6-continued
Structures Representing Various Modified Nucleotides, Targeting Ligands or Targeting Groups, Capping Residues, and Linking Groups
(NAG13)
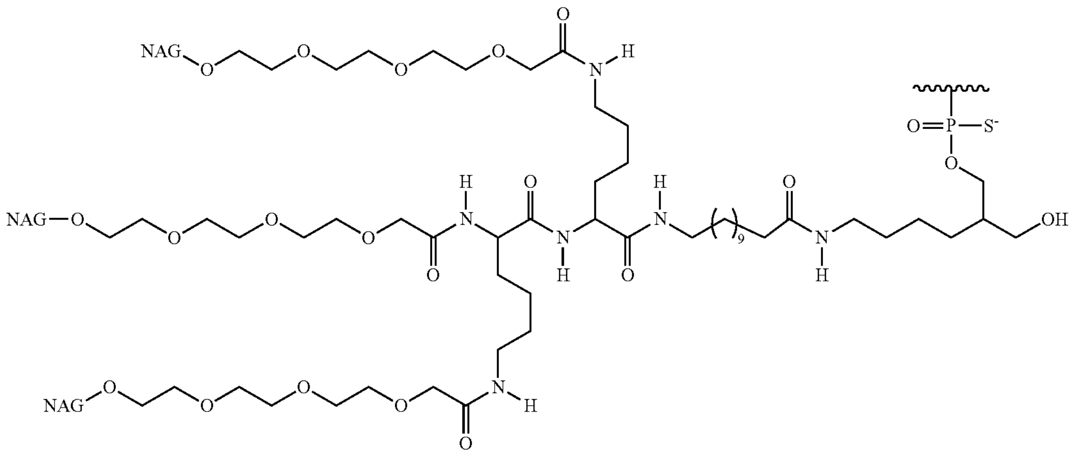
(NAG13)s
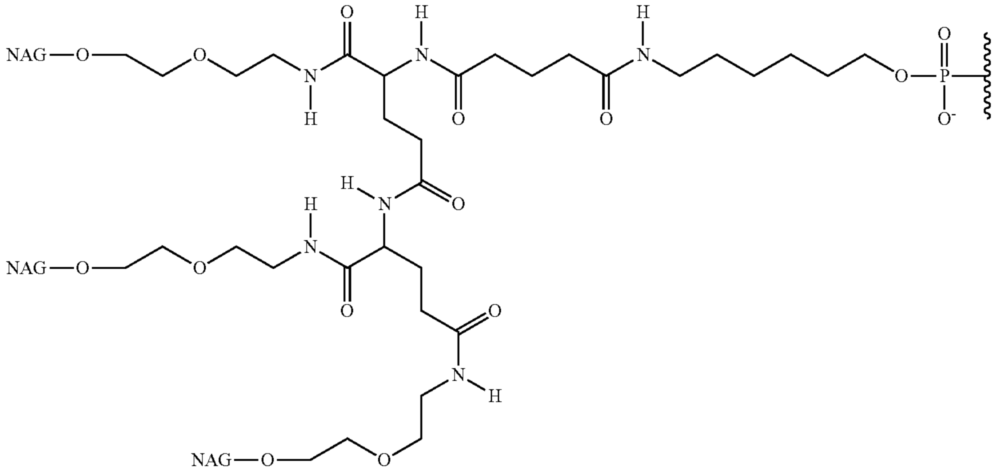
(NAG18)
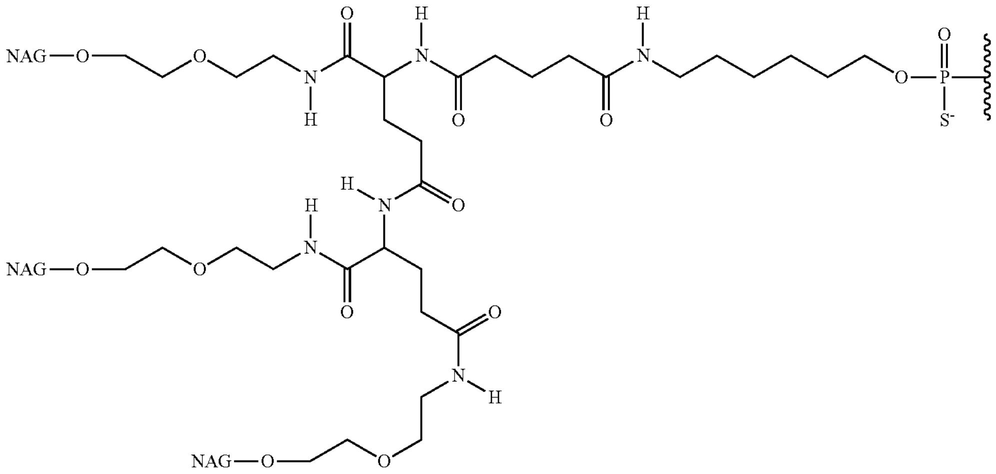

TABLE 6-continued
Structures Representing Various Modified Nucleotides, Targeting Ligands or Targeting Groups, Capping Residues, and Linking Groups
(NAG18)s
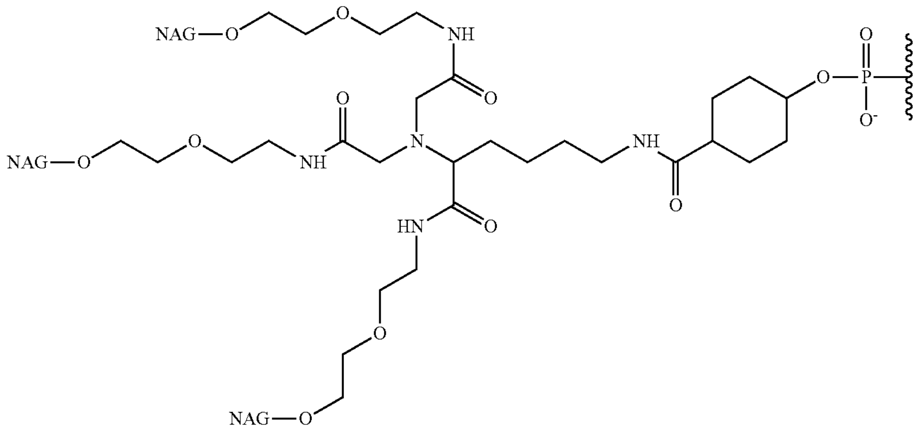
(NAG24)
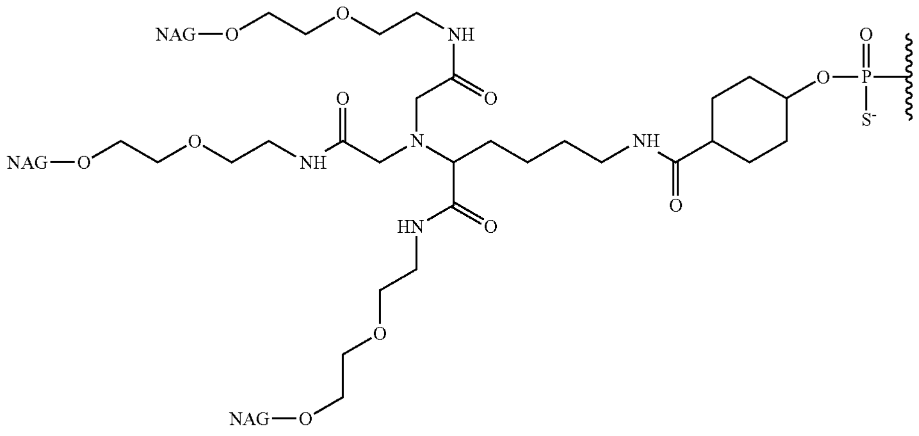
(NAG24)s
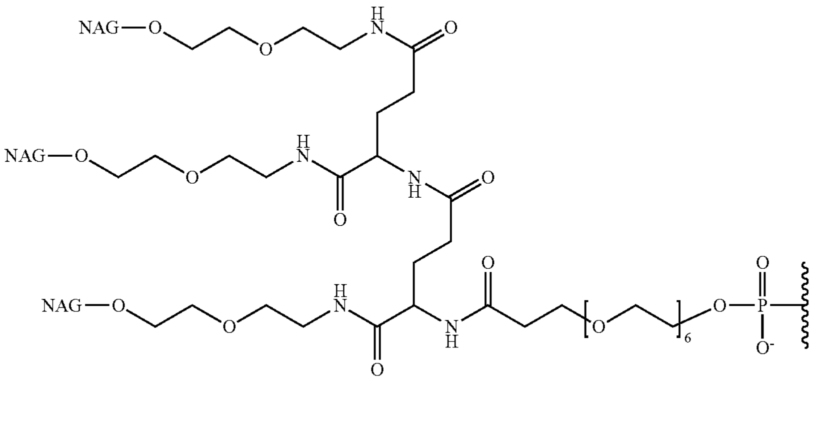

TABLE 6-continued
Structures Representing Various Modified Nucleotides, Targeting Ligands or Targeting Groups, Capping Residues, and Linking Groups
(NAG25)
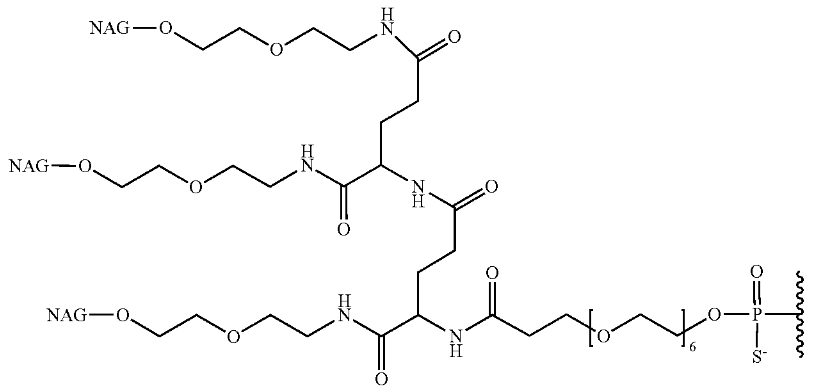
(NAG25)s
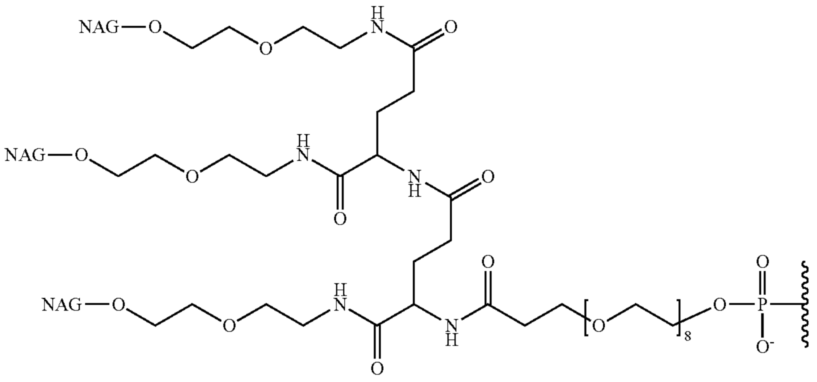
(NAG26)
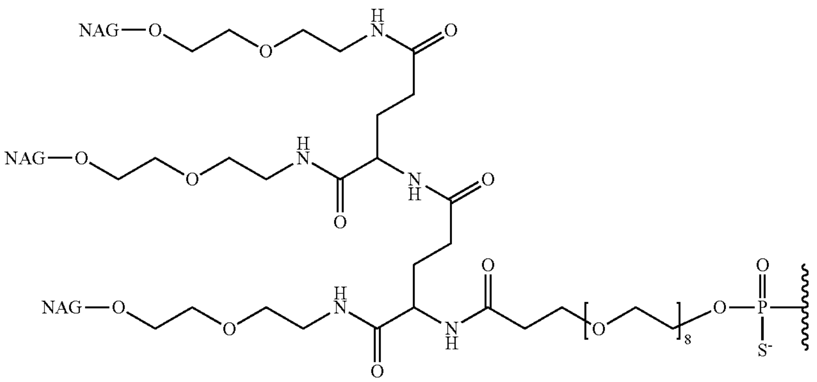

TABLE 6-continued
| Structures Representing Various Modified Nucleotides, Targeting Ligands or Targeting Groups, Capping Residues, and Linking Groups |
| --- |
(NAG26)s
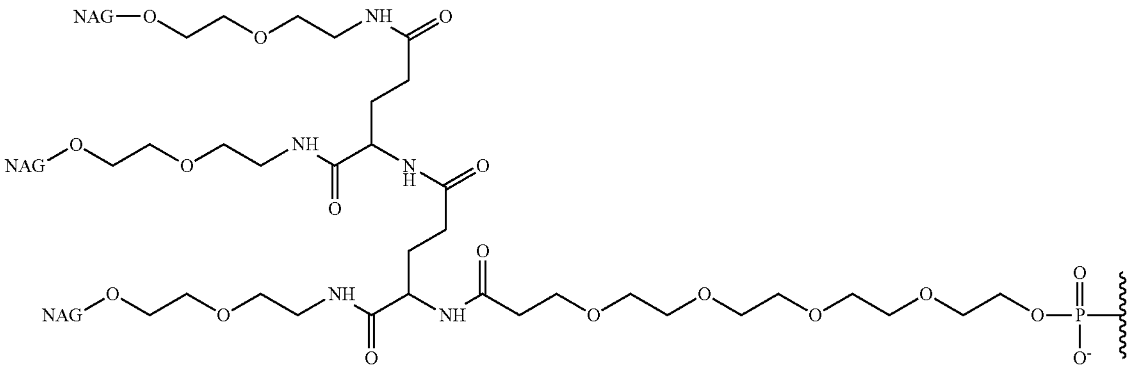
(NAG27)
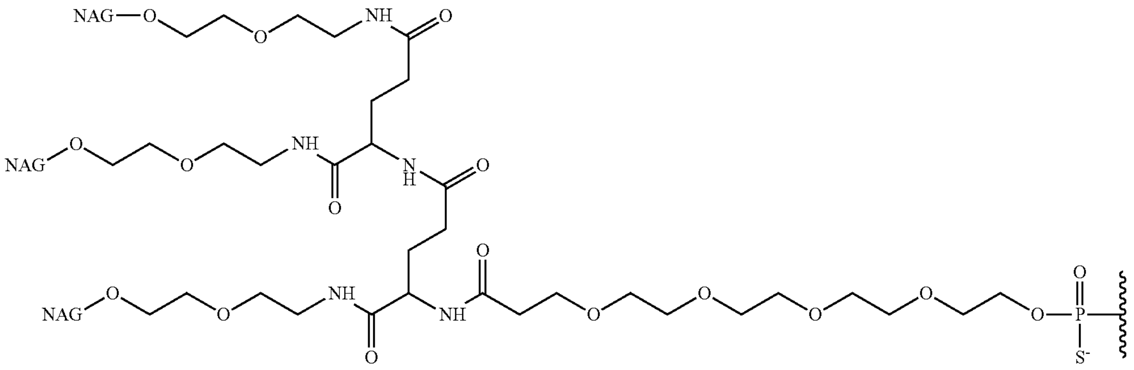
(NAG27)s
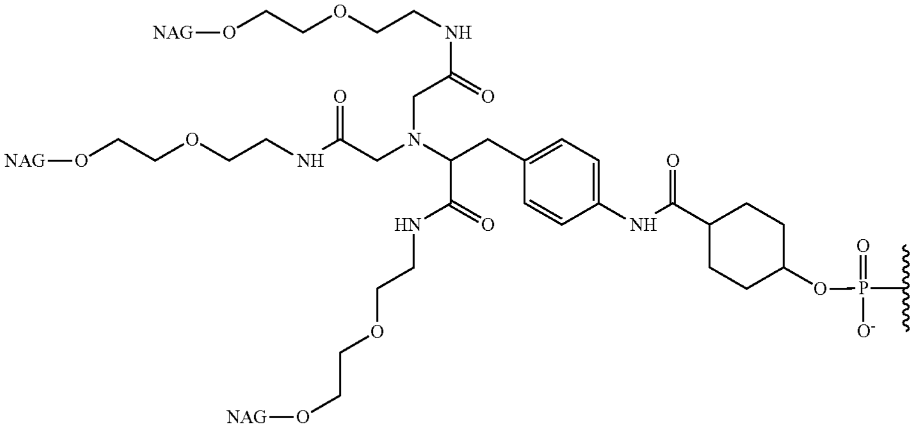

TABLE 6-continued
Structures Representing Various Modified Nucleotides, Targeting Ligands or Targeting Groups, Capping Residues, and Linking Groups
(NAG28)
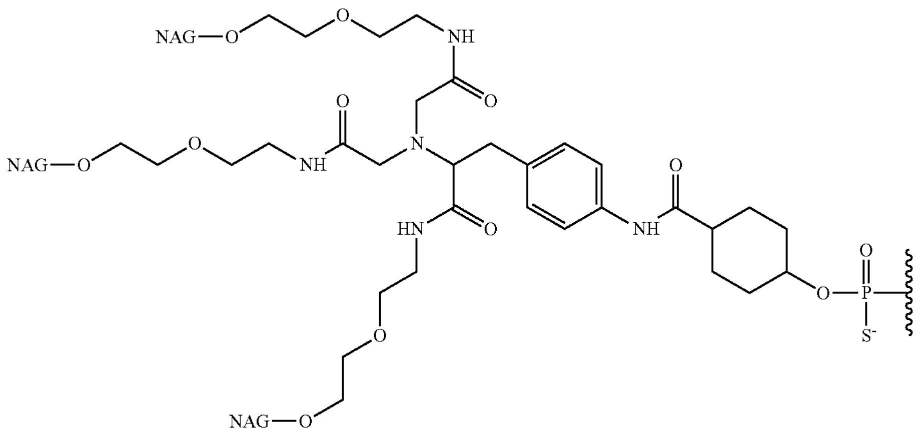
(NAG28)s
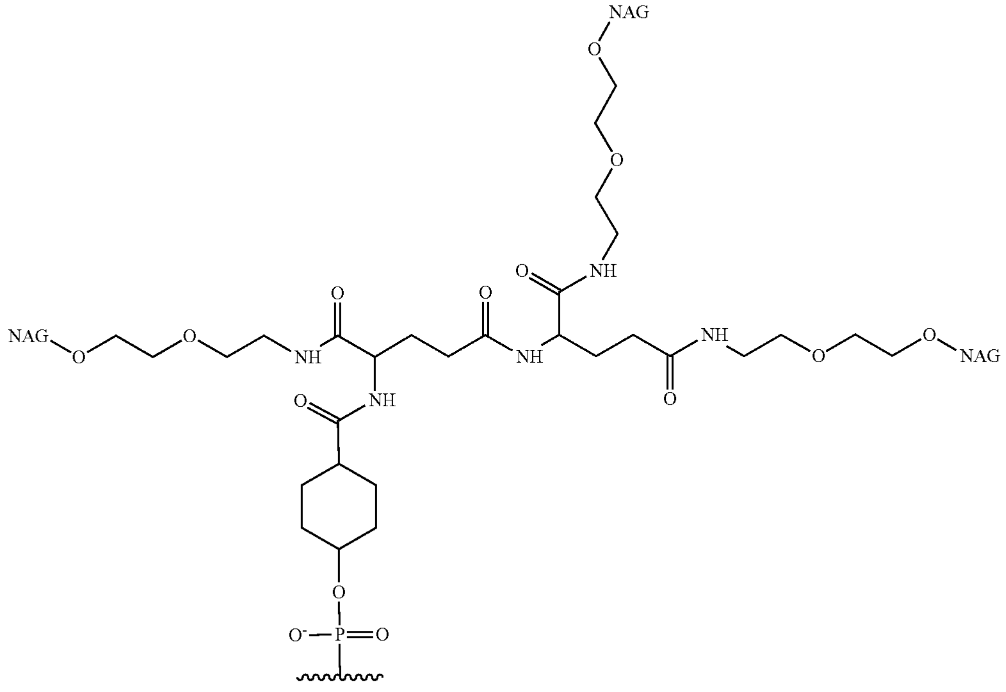

TABLE 6-continued
Structures Representing Various Modified Nucleotides, Targeting Ligands or Targeting Groups, Capping Residues, and Linking Groups
(NAG29)
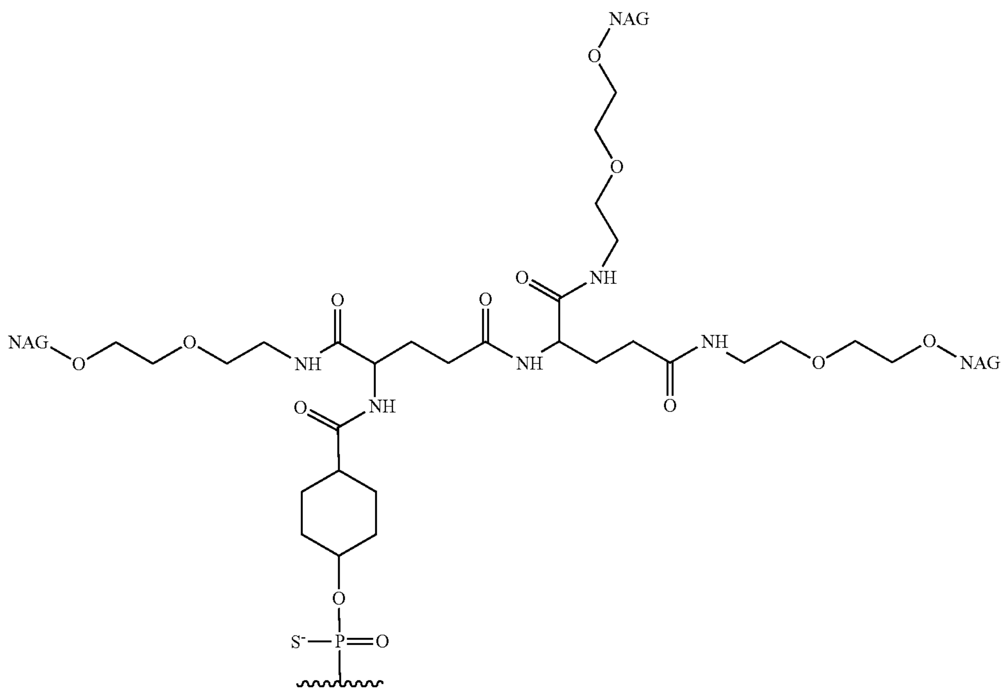
(NAG29)s
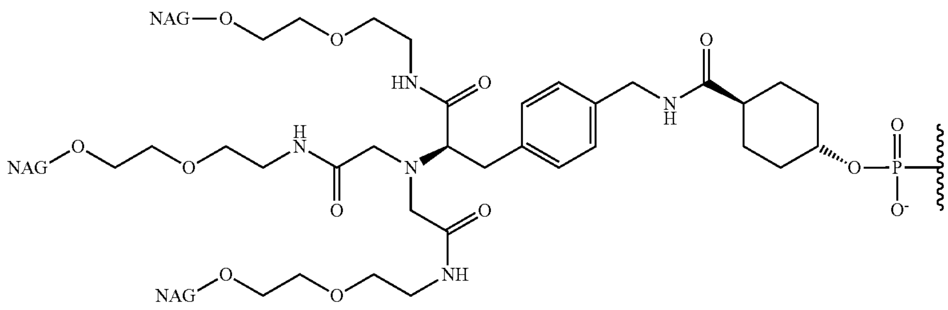
(NAG30)
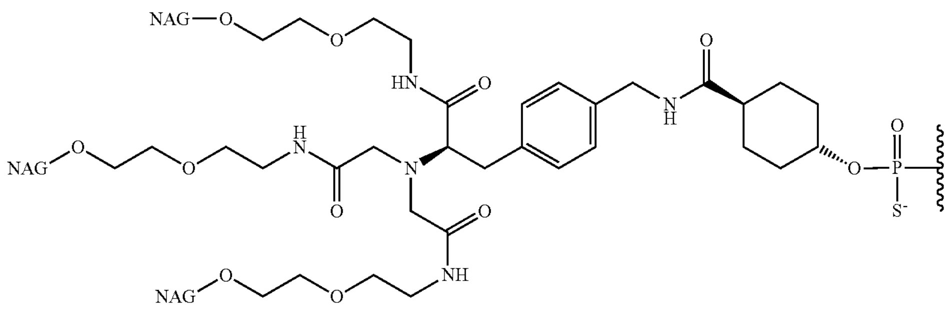

TABLE 6-continued
Structures Representing Various Modified Nucleotides, Targeting Ligands or Targeting Groups, Capping Residues, and Linking Groups
(NAG30)s
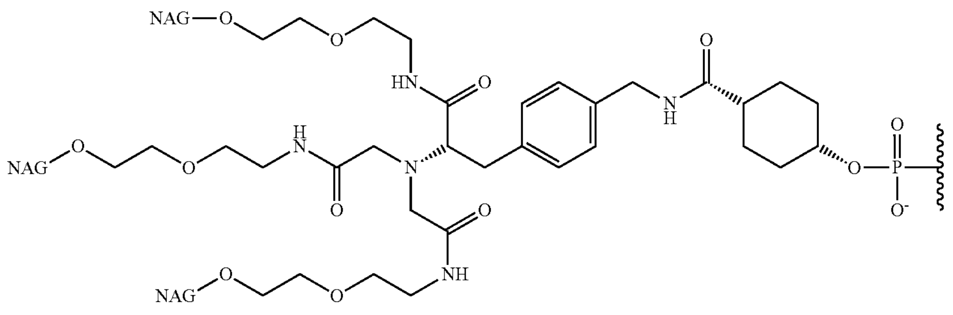
(NAG31)
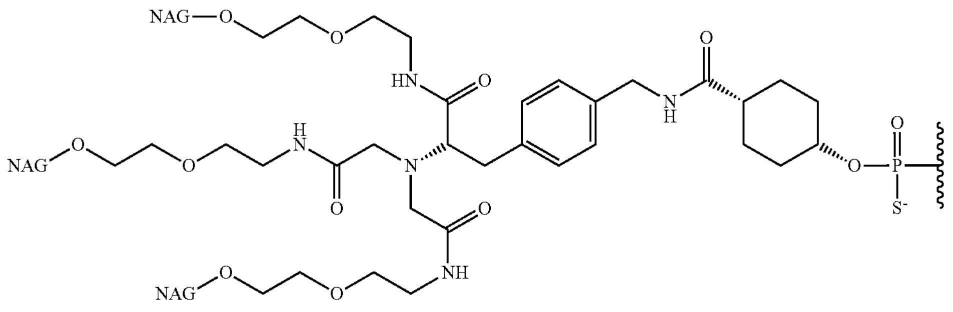
(NAG31)s
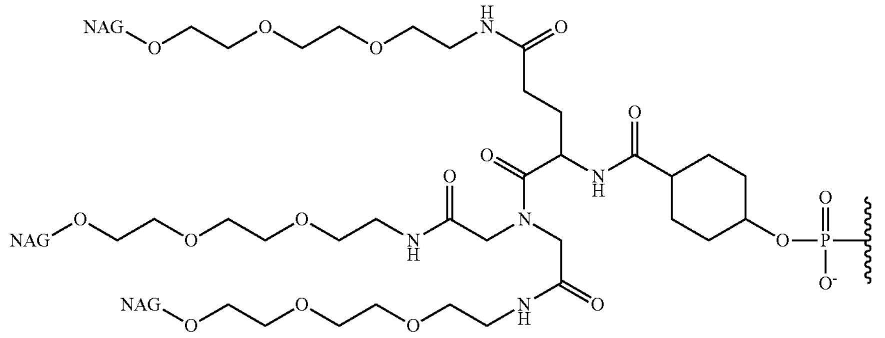
(NAG32)
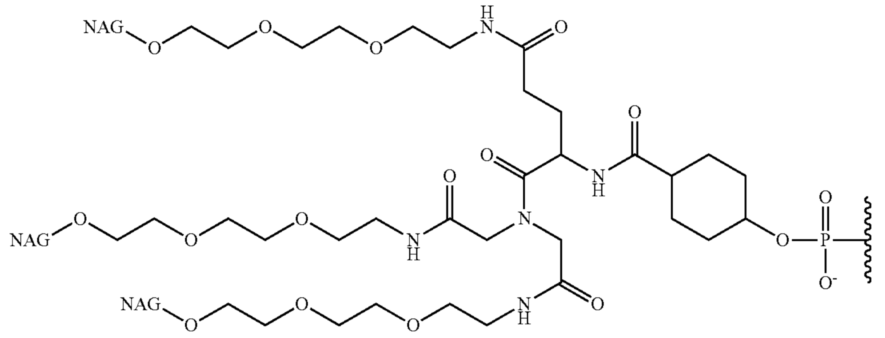

TABLE 6-continued
Structures Representing Various Modified Nucleotides, Targeting Ligands or Targeting Groups, Capping Residues, and Linking Groups
(NAG32)s
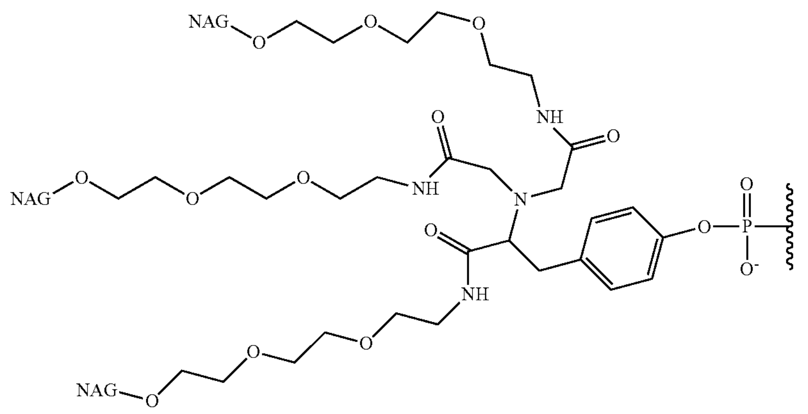
(NAG33)
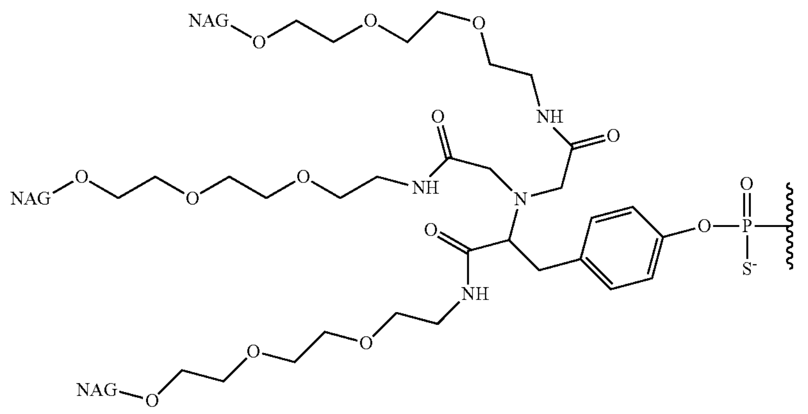
(NAG33)s
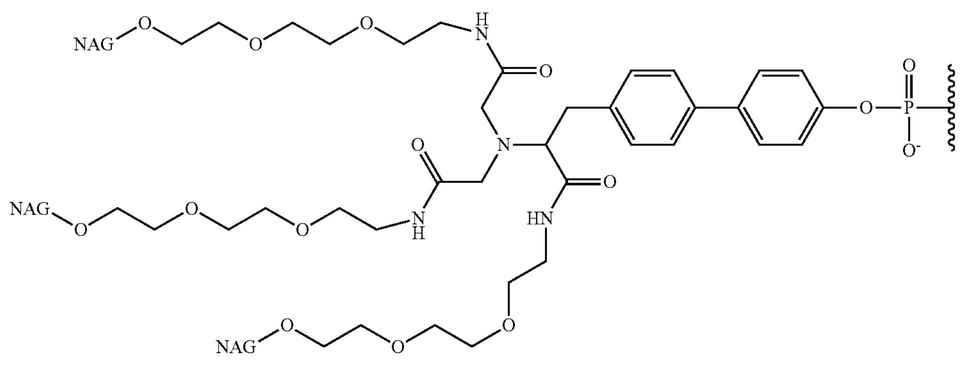

TABLE 6-continued
| Structures Representing Various Modified Nucleotides, Targeting Ligands or Targeting Groups, Capping Residues, and Linking Groups |
| --- |
| (NAG34) |
| 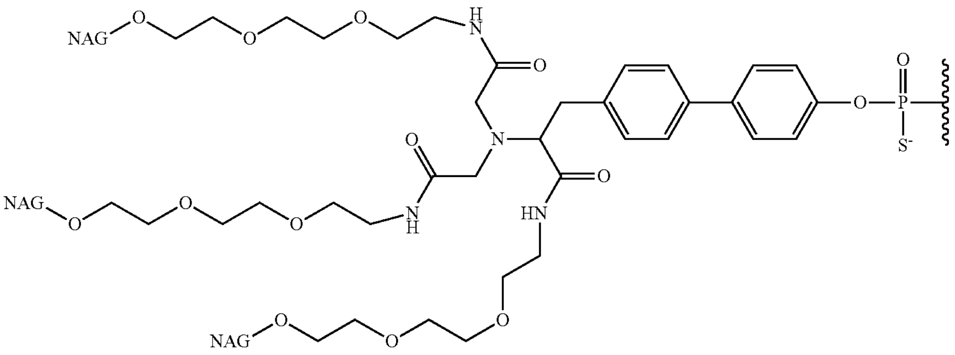 |
| (NAG34)s |
| 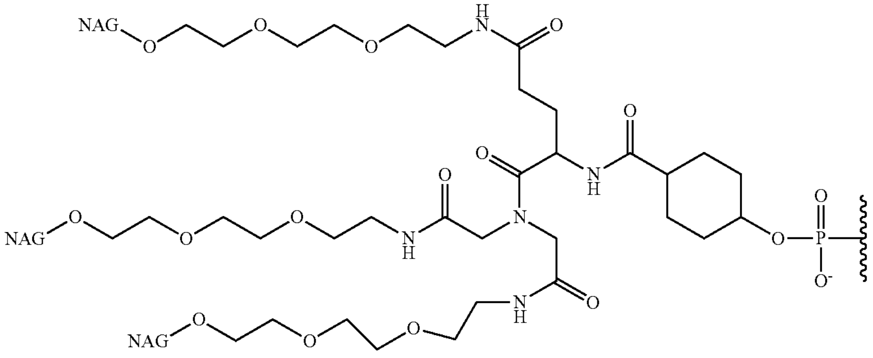 |
| (NAG35) |
| 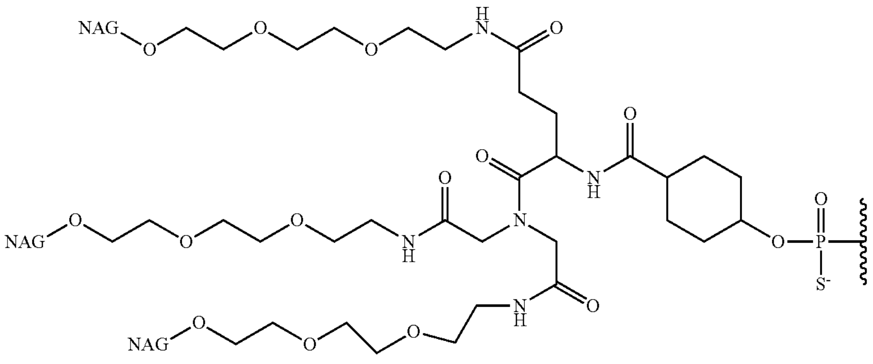 |

TABLE 6-continued
Structures Representing Various Modified Nucleotides, Targeting Ligands or Targeting Groups, Capping Residues, and Linking Groups
(NAG35)s
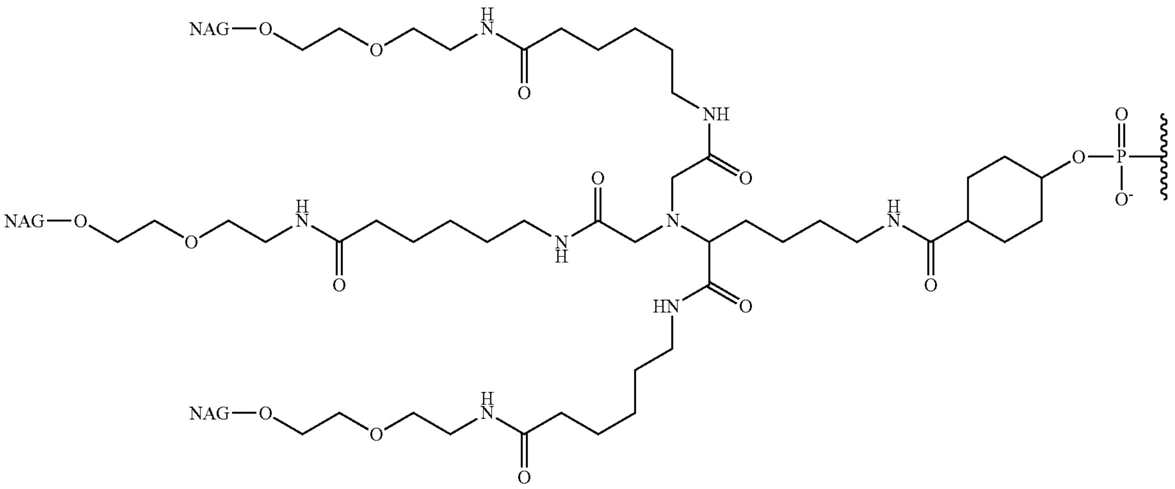
(NAG36)
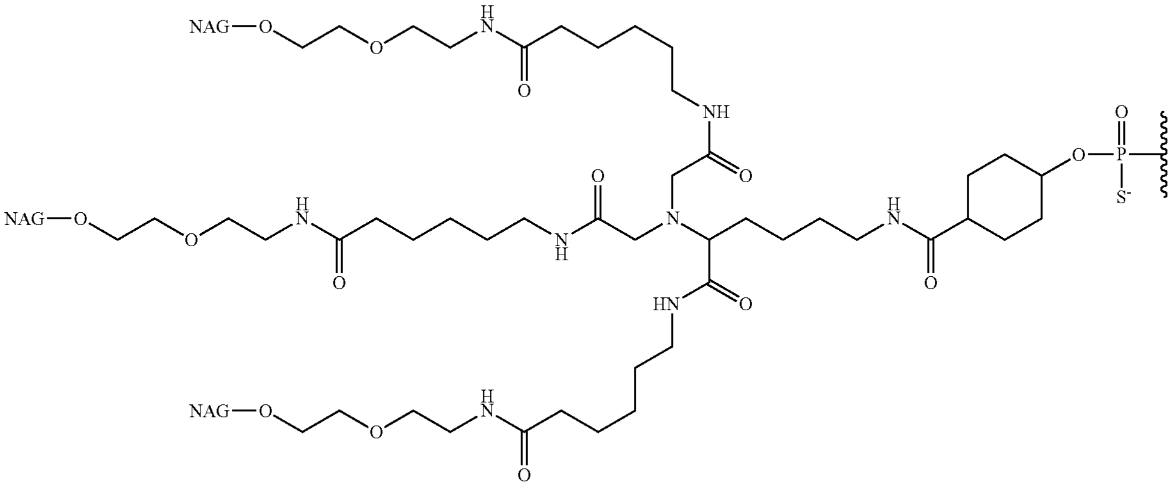
(NAG36)s
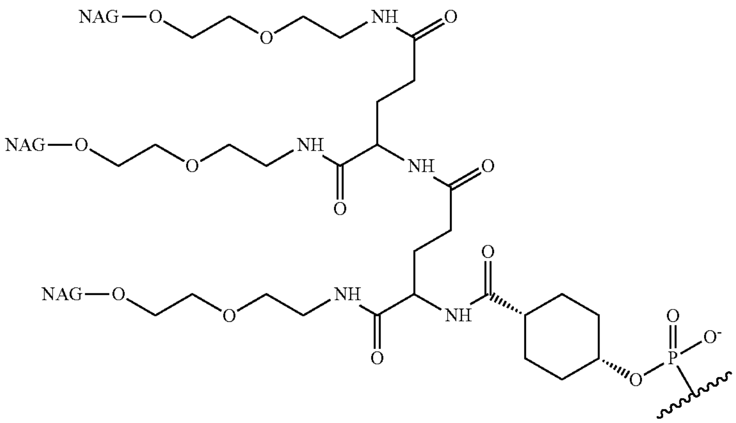

TABLE 6-continued
Structures Representing Various Modified Nucleotides, Targeting Ligands or Targeting Groups, Capping Residues, and Linking Groups
(NAG37)
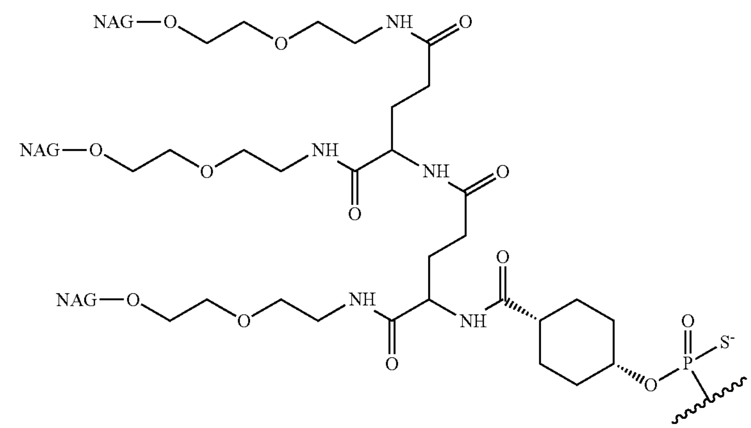
(NAG37)s
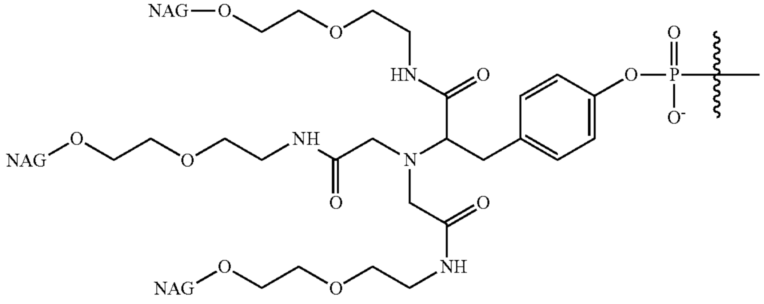
(NAG 38)
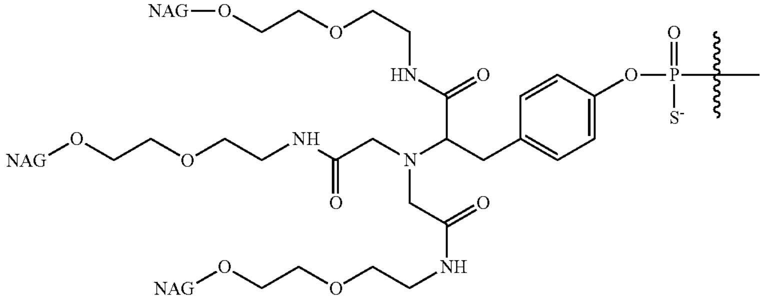

TABLE 6-continued

Structures Representing Various Modified Nucleotides, Targeting Ligands or Targeting Groups, Capping Residues, and Linking Groups (NAG 38)s

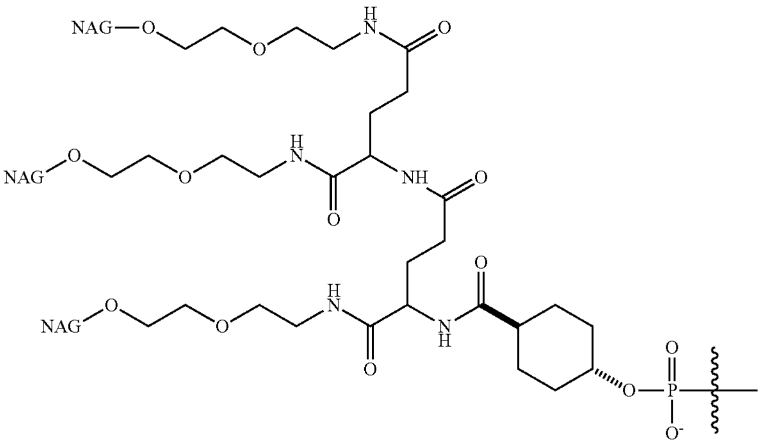

(NAG39)

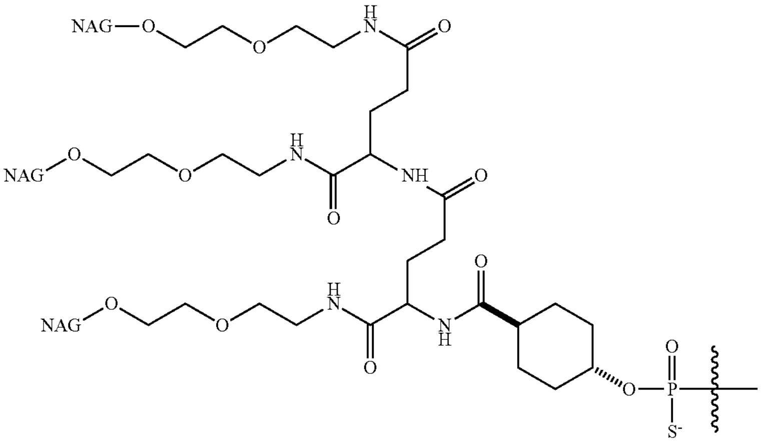

(NAG39)s

In each of the above structures in Table 6, NAG comprises an N-acetyl-galactosamine or another galactose derivative, as would be understood by a person of ordinary skill in the art to be attached in view of the structures above and description provided herein. For example, in some embodiments, NAG in the structures provided is N-acetyl-galactosamine.

Each (NAGx) may be attached to an HSD17B13 RNAi agent via a phosphate group (as in (NAG25), (NAG30), and (NAG31)), or a phosphorothioate group, (as is (NAG25)s, (NAG29)s, (NAG30)s, (NAG31)s, or (NAG37)s), or another linking group.

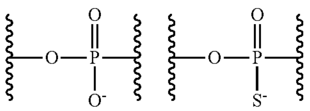 [SMILES: *OP(*)(=O)[O-] ; *OP(*)(=O)[S-]]

Other linking groups known in the art may be used.

In some embodiments, a delivery vehicle can be used to deliver an RNAi agent to a cell or tissue. A delivery vehicle is a compound that improves delivery of the RNAi agent to a cell or tissue. A delivery vehicle can include, or consist of, but is not limited to: a polymer, such as an amphipathic polymer, a membrane active polymer, a peptide, a melittin peptide, a melittin-like peptide (MLP), a lipid, a reversibly modified polymer or peptide, or a reversibly modified membrane active polyamine. In some embodiments, the RNAi agents can be combined with lipids, nanoparticles, polymers, liposomes, micelles, DPCs or other delivery systems available in the art. The RNAi agents can also be chemically conjugated to targeting groups, lipids (including, but not limited to cholesterol and cholesteryl derivatives), nanoparticles, polymers, liposomes, micelles, DPCs (see, for example WO 2000/053722, WO 2008/0022309, WO 2011/104169, and WO 2012/083185, WO 2013/032829, WO 2013/158141, each of which is incorporated herein by reference), hydrogels, cyclodextrins, biodegradable nanocapsules, and bioadhesive microspheres, proteinaceous vectors, or other delivery systems suitable for nucleic acid or oligonucleotide delivery as known and available in the art.

Pharmaceutical Compositions and Formulations

The HSD17B13 RNAi agents disclosed herein can be prepared as pharmaceutical compositions or formulations (also referred to herein as "medicaments"). In some embodiments, pharmaceutical compositions include at least one HSD17B13 RNAi agent. These pharmaceutical compositions are particularly useful in the inhibition of the expression of the target mRNA in a target cell, a group of cells, a tissue, or an organism.

The pharmaceutical compositions can be used to treat a subject having a disease, disorder, or condition that would benefit from reduction in the level of the target HSD17B13 mRNA, or inhibition in expression of the target gene. The pharmaceutical compositions can be used to treat a subject at risk of developing a disease, disorder, or condition that would benefit from reduction of the level of the target mRNA or an inhibition in expression the target gene. In one embodiment, the method includes administering an HSD17B13 RNAi agent linked to a targeting ligand as described herein, to a subject to be treated. In some embodiments, one or more pharmaceutically acceptable excipients (including vehicles, carriers, diluents, and/or delivery polymers) are added to the pharmaceutical compositions that include an HSD17B13 RNAi agent, thereby forming a pharmaceutical formulation or medicament suitable for in vivo delivery to a subject, including a human.

The pharmaceutical compositions that include an HSD17B13 RNAi agent and methods disclosed herein decrease the level of the target mRNA in a cell, group of cells, group of cells, tissue, organ, or subject, including by administering to the subject a therapeutically effective amount of a herein described HSD17B13 RNAi agent, thereby inhibiting the expression of HSD17B13 mRNA in the subject. In some embodiments, the subject has been previously identified or diagnosed as having a pathogenic upregulation of the target gene in the targeted cell or tissue. In some embodiments, the subject has been previously identified or diagnosed as having NAFLD, NASH, hepatic fibrosis, and/or alcoholic or non-alcoholic liver disease, such as cirrhosis. In some embodiments, the subject has been suffering from symptoms associated with NAFLD, NASH, hepatic fibrosis, and/or alcoholic or non-alcoholic liver disease, such as cirrhosis.

In some embodiments, the described pharmaceutical compositions including an HSD17B13 RNAi agent are used for treating or managing clinical presentations associated with NAFLD, NASH, hepatic fibrosis, alcoholic or non-alcoholic liver diseases, including cirrhosis, and/or over-expression of HSD17B13 in a subject. In some embodiments, a therapeutically (including prophylactically) effective amount of one or more of pharmaceutical compositions is administered to a subject in need of such treatment. In some embodiments, administration of any of the disclosed HSD17B13 RNAi agents can be used to decrease the number, severity, and/or frequency of symptoms of a disease in a subject.

The described pharmaceutical compositions that include an HSD17B13 RNAi agent can be used to treat at least one symptom in a subject having a disease or disorder that would benefit from reduction or inhibition in expression of HSD17B13 mRNA. In some embodiments, the subject is administered a therapeutically effective amount of one or more pharmaceutical compositions that include an HSD17B13 RNAi agent thereby treating the symptom. In other embodiments, the subject is administered a prophylactically effective amount of one or more HSD17B13 RNAi agents, thereby preventing or inhibiting the at least one symptom.

The route of administration is the path by which an HSD17B13 RNAi agent is brought into contact with the body. In general, methods of administering drugs and oligonucleotides and nucleic acids for treatment of a mammal are well known in the art and can be applied to administration of the compositions described herein. The HSD17B13 RNAi agents disclosed herein can be administered via any suitable route in a preparation appropriately tailored to the particular route. Thus, herein described pharmaceutical compositions can be administered by injection, for example, intravenously, intramuscularly, intracutaneously, subcutaneously, intraarticularly, or intraperitoneally. In some embodiments, the herein described pharmaceutical compositions are administered via subcutaneous injection.

The pharmaceutical compositions including an HSD17B13 RNAi agent described herein can be delivered to a cell, group of cells, tissue, or subject using oligonucleotide delivery technologies known in the art. In general, any suitable method recognized in the art for delivering a nucleic acid molecule (in vitro or in vivo) can be adapted for use with the compositions described herein. For example, delivery can be by local administration, (e.g., direct injection, implantation, or topical administering), systemic administration, or subcutaneous, intravenous, intraperitoneal, or parenteral routes, including intracranial (e.g., intraventricular, intraparenchymal and intrathecal), intramuscular, transdermal, airway (aerosol), nasal, oral, rectal, or topical (including buccal and sublingual) administration. In certain embodiments, the compositions are administered by subcutaneous or intravenous infusion or injection.

In some embodiments, the pharmaceutical compositions described herein comprise one or more pharmaceutically acceptable excipients. The pharmaceutical compositions described herein are formulated for administration to a subject.

As used herein, a pharmaceutical composition or medicament includes a pharmacologically effective amount of at least one of the described therapeutic compounds and one or more pharmaceutically acceptable excipients. Pharmaceutically acceptable excipients (excipients) are substances other than the Active Pharmaceutical Ingredient (API, therapeutic product, e.g., HSD17B13 RNAi agent) that are intentionally included in the drug delivery system. Excipients do not exert or are not intended to exert a therapeutic effect at the intended dosage. Excipients can act to a) aid in processing of the drug delivery system during manufacture, b) protect, support or enhance stability, bioavailability or patient acceptability of the API, c) assist in product identification, and/or d) enhance any other attribute of the overall safety, effectiveness, of delivery of the API during storage or use. A pharmaceutically acceptable excipient may or may not be an inert substance.

Excipients include, but are not limited to: absorption enhancers, anti-adherents, anti-foaming agents, anti-oxidants, binders, buffering agents, carriers, coating agents, colors, delivery enhancers, delivery polymers, detergents, dextran, dextrose, diluents, disintegrants, emulsifiers, extenders, fillers, flavors, glidants, humectants, lubricants, oils, polymers, preservatives, saline, salts, solvents, sugars, surfactants, suspending agents, sustained release matrices, sweeteners, thickening agents, tonicity agents, vehicles, water-repelling agents, and wetting agents.

Pharmaceutical compositions suitable for injectable use include sterile aqueous solutions (where water-soluble) or dispersions and sterile powders for the extemporaneous preparation of sterile injectable solutions or dispersion. For intravenous administration, suitable carriers include physiological saline, bacteriostatic water, Cremophor® EL™ (BASF, Parsippany, NJ) or phosphate buffered saline (PBS). Suitable carriers should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle, which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient from a previously sterile-filtered solution thereof.

In some embodiments, pharmaceutical formulations that include the HSD17B13 RNAi agents disclosed herein suitable for subcutaneous administration can be prepared in an aqueous sodium phosphate buffer (e.g., the HSD17B13 RNAi agent formulated in 0.5 mM sodium phosphate monobasic, 0.5 mM sodium phosphate dibasic, in water)

Formulations suitable for intra-articular administration can be in the form of a sterile aqueous preparation of the drug that can be in microcrystalline form, for example, in the form of an aqueous microcrystalline suspension. Liposomal formulations or biodegradable polymer systems can also be used to present the drug for both intra-articular and ophthalmic administration.

Formulations suitable for oral administration of the HSD17B13 RNAi agents disclosed herein can also be prepared. In some embodiments, the HSD17B13 RNAi agents disclosed herein are administered orally. In some embodiments, the HSD17B13 RNAi agents disclosed herein are formulated in a capsule for oral administration.

The active compounds can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions can also be used as pharmaceutically acceptable carriers. These can be prepared according to methods known to those skilled in the art, for example, as described in U.S. Pat. No. 4,522,811.

The HSD17B13 RNAi agents can be formulated in compositions in dosage unit form for ease of administration and uniformity of dosage. Dosage unit form refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the therapeutic effect to be achieved, and the limitations inherent in the art of compounding such an active compound for the treatment of individuals.

A pharmaceutical composition can contain other additional components commonly found in pharmaceutical compositions. Such additional components include, but are not limited to: anti-pruritics, astringents, local anesthetics, analgesics, antihistamines, or anti-inflammatory agents (e.g., acetaminophen, NSAIDs, diphenhydramine, etc.). It is also envisioned that cells, tissues, or isolated organs that express or comprise the herein defined RNAi agents may be used as "pharmaceutical compositions." As used herein, "pharmacologically effective amount," "therapeutically effective amount," or simply "effective amount" refers to that amount of an RNAi agent to produce a pharmacological, therapeutic, or preventive result.

In some embodiments, the methods disclosed herein further comprise the step of administering a second therapeutic or treatment in addition to administering an RNAi agent disclosed herein. In some embodiments, the second therapeutic is another HSD17B13 RNAi agent (e.g., an HSD17B13 RNAi agent that targets a different sequence within the HSD17B13 target). In other embodiments, the second therapeutic can be a small molecule drug, an antibody, an antibody fragment, or an aptamer.

In some embodiments, the described HSD17B13 RNAi agent(s) are optionally combined with one or more additional therapeutics. The HSD17B13 RNAi agent and additional therapeutic(s) can be administered in a single composition or they can be administered separately. In some embodiments, the one or more additional therapeutics is administered separately in separate dosage forms from the RNAi agent (e.g., the HSD17B13 RNAi agent is administered by subcutaneous injection, while the additional therapeutic involved in the method of treatment dosing regimen is administered orally). In some embodiments, the described HSD17B13 RNAi agent(s) are administered to a subject in need thereof via subcutaneous injection, and the one or more optional additional therapeutics are administered orally, which together provide for a treatment regimen for diseases and conditions associated with NAFLD, NASH, hepatic fibrosis, and/or alcoholic or non-alcoholic liver diseases, including cirrhosis. In some embodiments, the described HSD17B13 RNAi agent(s) are administered to a subject in need thereof via subcutaneous injection, and the one or more optional additional therapeutics are administered via a separate subcutaneous injection. In some embodiments, the HSD17B13 RNAi agent and one or more additional therapeutics are combined into a single dosage form (e.g., a "cocktail" formulated into a single composition for subcutaneous injection). The HSD17B13 RNAi agents, with or without the one or more additional therapeutics, can be combined with one or more excipients to form pharmaceutical compositions.

Generally, an effective amount of an HSD17B13 RNAi agent will be in the range of from about 0.1 to about 100 mg/kg of body weight/dose, e.g., from about 1.0 to about 50 mg/kg of body weight/dose. In some embodiments, an effective amount of an active compound will be in the range of from about 0.25 to about 5 mg/kg of body weight per dose. In some embodiments, an effective amount of an active ingredient will be in the range of from about 0.5 to about 4 mg/kg of body weight per dose. Dosing may be weekly, bi-weekly, monthly, or at any other interval depending on the dose of HSD17B13 RNAi agent administered, the activity level of the particular HSD17B13 RNAi agent, and the desired level of inhibition for the particular subject. The Examples herein show suitable levels for inhibition in certain animal species. The amount administered will depend on such variables as the overall health status of the patient, the relative biological efficacy of the compound delivered, the formulation of the drug, the presence and types of excipients in the formulation, and the route of administration. Also, it is to be understood that the initial dosage administered can be increased beyond the above upper level to rapidly achieve the desired blood-level or tissue level, or the initial dosage can be smaller than the optimum.

For treatment of disease or for formation of a medicament or composition for treatment of a disease, the pharmaceutical compositions described herein including an HSD17B13 RNAi agent can be combined with an excipient or with a second therapeutic agent or treatment including, but not limited to: a second or other RNAi agent, a small molecule drug, an antibody, an antibody fragment, peptide and/or an aptamer.

The described HSD17B13 RNAi agents, when added to pharmaceutically acceptable excipients or adjuvants, can be packaged into kits, containers, packs, or dispensers. The pharmaceutical compositions described herein may be packaged in pre-filled syringes or vials.

Methods of Treatment and Inhibition of Expression

The HSD17B13 RNAi agents disclosed herein can be used to treat a subject (e.g., a human or other mammal) having a disease or disorder that would benefit from administration of the RNAi agent. In some embodiments, the RNAi agents disclosed herein can be used to treat a subject (e.g., a human) that would benefit from reduction and/or inhibition in expression of HSD17B13 mRNA and/or HSD17B13 (alternatively referred to herein as 17β-HSD13) protein levels, for example, a subject that has been diagnosed with or is suffering from symptoms related to NAFLD, NASH, hepatic fibrosis, or alcoholic or non-alcoholic liver diseases, including cirrhosis.

In some embodiments, the subject is administered a therapeutically effective amount of any one or more HSD17B13 RNAi agents. Treatment of a subject can include therapeutic and/or prophylactic treatment. The subject is administered a therapeutically effective amount of any one or more HSD17B13 RNAi agents described herein. The subject can be a human, patient, or human patient. The subject may be an adult, adolescent, child, or infant. Administration of a pharmaceutical composition described herein can be to a human being or animal.

The HSD17B13 RNAi agents described herein can be used to treat at least one symptom in a subject having an HSD17B13-related disease or disorder, or having a disease or disorder that is mediated at least in part by HSD17B13 gene expression. In some embodiments, the HSD17B13 RNAi agents are used to treat or manage a clinical presentation of a subject with a disease or disorder that would benefit from or be mediated at least in party by a reduction in HSD17B13 mRNA. The subject is administered a therapeutically effective amount of one or more of the HSD17B13 RNAi agents or HSD17B13 RNAi agent-containing compositions described herein. In some embodiments, the methods disclosed herein comprise administering a composition comprising an HSD17B13 RNAi agent described herein to a subject to be treated. In some embodiments, the subject is administered a prophylactically effective amount of any one or more of the described HSD17B13 RNAi agents, thereby treating the subject by preventing or inhibiting the at least one symptom.

In certain embodiments, the present disclosure provides methods for treatment of diseases, disorders, conditions, or pathological states mediated at least in part by HSD17B13 gene expression, in a patient in need thereof, wherein the methods include administering to the patient any of the HSD17B13 RNAi agents described herein.

In some embodiments, the gene expression level and/or mRNA level of an HSD17B13 gene in a subject to whom a described HSD17B13 RNAi agent is administered is reduced by at least about 30%, 35%, 40%, 45%, 50%, 55%, 60%, 65%, 70%, 75%, 80%, 85%, 95%, 96%, 97%, 98%, 99%, or greater than 99% relative to the subject prior to being administered the HSD17B13 RNAi agent or to a subject not receiving the HSD17B13 RNAi agent. The gene expression level and/or mRNA level in the subject may be reduced in a cell, group of cells, and/or tissue of the subject.

In some embodiments, the HSD17B13 protein level in a subject to whom a described HSD17B13 RNAi agent has been administered is reduced by at least about 30%, 35%, 40%, 45%, 50%, 55%, 60%, 65%, 70%, 75%, 80%, 85%, 90%, 95%, 96%, 97%, 98%, 99%, or greater than 99% relative to the subject prior to being administered the HSD17B13 RNAi agent or to a subject not receiving the HSD17B13 RNAi agent. The protein level in the subject may be reduced in a cell, group of cells, tissue, blood, and/or other fluid of the subject.

A reduction in HSD17B13 mRNA levels and HSD17B13 protein levels can be assessed by any methods known in the art. As used herein, a reduction or decrease in HSD17B13 mRNA level and/or protein level are collectively referred to herein as a reduction or decrease in HSD17B13 or inhibiting or reducing the expression of HSD17B13. The Examples set forth herein illustrate known methods for assessing inhibition of HSD17B13 gene expression. The person of ordinary skill in the art would further know suitable methods for assessing inhibition of HSD17B13 gene expression in vivo and/or in vitro.

In some embodiments, disclosed herein are methods of treatment (including prophylactic or preventative treatment) of diseases, disorders, or symptoms caused by caused by NAFLD, NASH, hepatic fibrosis, and/or alcoholic or non-alcoholic liver diseases, including cirrhosis, wherein the methods include administering to a subject in need thereof a therapeutically effective amount of an HSD17B13 RNAi agent that includes an antisense strand that is at least partially complementary to the portion of the HSD17B13 mRNA having the sequence in Table 1. In some embodiments, disclosed herein are methods of treatment (including prophylactic or preventative treatment) of diseases or symptoms caused by caused by NAFLD, NASH, hepatic fibrosis, and/or alcoholic or non-alcoholic liver diseases, including cirrhosis, wherein the methods include administering to a subject in need thereof a therapeutically effective amount of an HSD17B13 RNAi agent that includes an antisense strand comprising the sequence of any of the sequences in Tables 2 or 3, and a sense strand that comprises any of the sequences in Tables 2 or 4 that is at least partially complementary to the antisense strand. In some embodiments, disclosed herein are methods of treatment (including prophylactic or preventative treatment) of diseases or symptoms caused by caused by NAFLD, NASH, hepatic fibrosis, and/or alcoholic or non-alcoholic liver diseases, including cirrhosis, wherein the methods include administering to a subject in need thereof a therapeutically effective amount of an HSD17B13 RNAi agent that includes a sense strand that comprises any of the sequences in Tables 2 or 4, and an antisense strand comprising the sequence of any of the sequences in Tables 2 or 3 that is at least partially complementary to the sense strand.

In some embodiments, disclosed herein are methods for inhibiting expression of an HSD17B13 gene in a cell, wherein the methods include administering to the cell an HSD17B13 RNAi agent that includes an antisense strand that is at least partially complementary to the portion of the HSD17B13 mRNA having the sequence in Table 1. In some embodiments, disclosed herein are methods of inhibiting expression of an HSD17B13 gene in a cell, wherein the methods include administering to a cell an HSD17B13 RNAi agent that includes an antisense strand comprising the sequence of any of the sequences in Tables 2 or 3, and a sense strand that comprises any of the sequences in Tables 2 or 4 that is at least partially complementary to the antisense strand. In some embodiments, disclosed herein are methods of inhibiting expression of an HSD17B13 gene in a cell, wherein the methods include administering an HSD17B13 RNAi agent that includes a sense strand that comprises any of the sequences in Tables 2 or 4, and an antisense strand that includes the sequence of any of the sequences in Tables 2 or 3 that is at least partially complementary to the sense strand.

The use of HSD17B13 RNAi agents provides methods for therapeutic (including prophylactic) treatment of diseases/disorders associated with NAFLD, NASH, hepatic fibrosis, alcoholic or non-alcoholic liver diseases, including cirrhosis, and/or enhanced or elevated HSD17B13 expression. The described HSD17B13 RNAi agents mediate RNA interference to inhibit the expression of one or more genes necessary for production of HSD17B13 protein. HSD17B13 RNAi agents can also be used to treat or prevent various diseases, disorders, or conditions, including NAFLD, NASH, hepatic fibrosis, and/or alcoholic or non-alcoholic liver diseases, including cirrhosis. Furthermore, compositions for delivery of HSD17B13 RNAi agents to liver cells in vivo are described.

Cells, Tissues, Organs, and Non-Human Organisms

Cells, tissues, organs, and non-human organisms that include at least one of the HSD17B13 RNAi agents described herein are contemplated. The cell, tissue, organ, or non-human organism is made by delivering the RNAi agent to the cell, tissue, organ or non-human organism.

The above provided embodiments and items are now illustrated with the following, non-limiting examples.

EXAMPLES

Example 1. Synthesis of HSD17B13 RNAi Agents

HSD17B13 RNAi agent duplexes shown in Table 5, above, were synthesized in accordance with the following general procedures:

A. Synthesis.

The sense and antisense strands of the RNAi agents were synthesized according to phosphoramidite technology on solid phase used in oligonucleotide synthesis. Such standard synthesis is generally known in the art. Depending on the scale, either a MerMade96E® (Bioautomation), a MerMade12® (Bioautomation), or an OP Pilot 100 (GE Healthcare) was used. Syntheses were performed on a solid support made of controlled pore glass (CPG, 500 Å or 600 Å, obtained from Prime Synthesis, Aston, PA, USA). The monomer positioned at the 3' end of the respective strand was attached to the solid support as a starting point for synthesis. All RNA and 2'-modified RNA phosphoramidites were purchased from Thermo Fisher Scientific (Milwaukee, WI, USA) or Hongene Biotech (Shanghai, PRC). The 2'-O-methyl phosphoramidites included the following: (5'-O-dimethoxytrityl-$N^6$-(benzoyl)-2'-O-methyl-adenosine-3'-O-(2-cyanoethyl-N,N-diisopropylamino) phosphoramidite, 5'-O-dimethoxy-trityl-$N^4$-(acetyl)-2'-O-methyl-cytidine-3'-O-(2-cyanoethyl-N,N-diisopropyl-amino) phosphoramidite, (5'-O-dimethoxytrityl-$N^2$-(isobutyryl)-2'-O-methyl-guanosine-3'-O-(2-cyanoethyl-N,N-diisopropylamino) phosphoramidite, and 5'-O-dimethoxytrityl-2'-O-methyl-uridine-3'-O-(2-cyanoethyl-N,N-diisopropylamino) phosphoramidite. The 2'-deoxy-2'-fluoro-phosphoramidites carried the same protecting groups as the 2'-O-methyl amidites. 5'-(4,4'-Dimethoxytrityl)-2',3'-seco-uridine, 2'-benzoyl-3'-[(2-cyanoethyl)-(N,N-diisopropyl)]-phosphoramidite was also purchased from Thermo Fisher Scientific or Hongene Biotech. 5'-dimethoxytrityl-2'-O-methyl-inosine-3'-O-(2-cyanoethyl-N,N-diisopropylamino) phosphoramidites were purchased from Glen Research (Virginia) or Hongene Biotech. The inverted abasic (3'-O-dimethoxytrityl-2'-deoxyribose-5'-O-(2-cyanoethyl-N,N-diisopropylamino) phosphoramidites were purchased from ChemGenes (Wilmington, MA, USA) or SAFC (St Louis, MO, USA). 5'-O-dimethoxytrityl-$N^2$,$N^6$-(phenoxyacetate)-2'-O-methyl-diaminopurine-3'-O-(2-cyanoethyl-N,N-diisopropylamino) phosphoramidites were obtained from ChemGenes or Hongene Biotech.

Targeting ligand-containing phosphoramidites were dissolved in anhydrous dichloromethane or anhydrous acetonitrile (50 mM), while all other amidites were dissolved in anhydrous acetonitrile (50 mM), or anhydrous dimethylformamide and molecular sieves (3 Å) were added. 5-Benzylthio-1H-tetrazole (BTT, 250 mM in acetonitrile) or 5-Ethylthio-1H-tetrazole (ETT, 250 mM in acetonitrile) was used as activator solution. Coupling times were 12 min (RNA), 15 min (targeting ligand), 90 sec (2'OMe), and 60 sec (2'F). In order to introduce phosphorothioate linkages, a 100 mM solution of 3-phenyl 1,2,4-dithiazoline-5-one (POS, obtained from PolyOrg, Inc., Leominster, MA, USA) in anhydrous Acetonitrile was employed. Unless specifically identified as a "naked" RNAi agent having no targeting ligand present, each of the HSD17B13 RNAi agent duplexes synthesized and tested in the following Examples utilized N-acetyl-galactosamine as "NAG" in the targeting ligand chemical structures represented in Table 6. The chemical structures of certain duplexes used in the Examples reported herein may be found in FIGS. 1A through 10D.

B. Cleavage and Deprotection of Support Bound Oligomer.

After finalization of the solid phase synthesis, the dried solid support was treated with a 1:1 volume solution of 40 wt. % methylamine in water and 28% ammonium hydroxide solution (Aldrich) for 1.5 hours at 30° C. The solution was evaporated and the solid residue was reconstituted in water (see below).

C. Purification.

Crude oligomers were purified by anionic exchange HPLC using a TSKgel SuperQ-5 PW 13 μm column and Shimadzu LC-8 system. Buffer A was 20 mM Tris, 5 mM EDTA, pH 9.0 and contained 20% Acetonitrile and buffer B was the same as buffer A with the addition of 1.5 M sodium chloride. UV traces at 260 nm were recorded. Appropriate fractions were pooled then run on size exclusion HPLC using a GE Healthcare XK 26/40 column packed with Sephadex G-25 fine with a running buffer of filtered DI water or 100 mM ammonium bicarbonate, pH 6.7 and 20% Acetonitrile.

D. Annealing.

Complementary strands were mixed by combining equimolar RNA solutions (sense and antisense) in 1× Phosphate-Buffered Saline (Corning, Cellgro) to form the RNAi agents. Some RNAi agents were lyophilized and stored at −15 to −25° C. Duplex concentration was determined by measuring the solution absorbance on a UV-Vis spectrometer in 1× Phosphate-Buffered Saline. The solution absorbance at 260 nm was then multiplied by a conversion factor and the dilution factor to determine the duplex concentration. The conversion factor used was either 0.050 mg/(mL·cm) or was calculated from an experimentally determined extinction coefficient.

Example 2. In Vivo Testing of HSD17B13 RNAi Agents in Rats

To assess the in vivo activity of HSD17B13 RNAi agents that are designed to target different positions on the HSD17B13 gene, Sprague Dawley rats were used. At day 1, each rat was administered a single subcutaneous injection of 500 µl/200 g animal weight, containing 3.0 mg/kg (mpk) of an HSD17B13 RNAi agent formulated in a pharmaceutically acceptable saline buffer, or vehicle control (saline buffer with no RNAi agent), according to the dosing groups recited in Table 7.

TABLE 7

Dosing Groups of Example 2

| Group | RNAi Agent and Dose | Dosing Regimen |
|---|---|---|
| 1 | Saline (no RNAi agent) | Single injection on day 1 |
| 2 | 3.0 mg/kg AD06079 | Single injection on day 1 |
| 3 | 3.0 mg/kg AD06080 | Single injection on day 1 |
| 4 | 3.0 mg/kg AD06081 | Single injection on day 1 |
| 5 | 3.0 mg/kg AD06082 | Single injection on day 1 |
| 6 | 3.0 mg/kg AD06083 | Single injection on day 1 |
| 7 | 3.0 mg/kg AD06084 | Single injection on day 1 |
| 8 | 3.0 mg/kg AD06085 | Single injection on day 1 |

Each of the RNAi agents included a modified sequence and a tridentate N-acetyl-galactosamine-containing targeting ligand conjugated to the 5' terminal end of the sense strand. (See Tables 3-6 for modified sequences and targeting ligand structures). The HSD17B13 RNAi agents AD06079, AD06080, and AD06081 (Groups 2, 3, and 4) each included nucleotide sequences that were designed to inhibit expression of an HSD17B13 gene at position 488 of the gene; the HSD17B13 RNAi agents AD06082 and AD06083 (Groups 5 and 6) each included nucleotide sequences that were designed to inhibit expression of an HSD17B13 gene at position 492 of the gene; and the HSD17B13 RNAi agents AD06084 and AD06085 (Groups 7 and 8) each included nucleotide sequences that were designed to inhibit expression of an HSD17B13 gene at position 499 of the gene. (See, e.g., SEQ ID NO:1 and Table 2 for the HSD17B13 gene referenced).

The injections were performed between the skin and muscle (i.e. subcutaneous injections) into the loose skin over the neck and shoulder area. Three (3) rats in each group were tested (n=3). All of the rats were sacrificed on day 15. Livers were harvested, and approximately 100 mg liver samples were collected and snap-frozen in liquid nitrogen for RNA isolation. Relative expression of each of the HSD17B13 RNAi agents was determined by qRT-PCR by normalizing the HSD17B13 mRNA expression levels of the animals from each respective treatment Group to the animals in Group 1 (vehicle control, no RNAi agent) ($\Delta\Delta C_T$ analysis), the results of which are set forth in the following Table 8:

TABLE 8

Relative HSD17B13 mRNA Level at Day 15, Normalized to Control from Example 2

| Group ID | Day 15 Relative HSD17B13 mRNA | Low Variance (Error) | High Variance (Error) |
|---|---|---|---|
| Group 1 (Saline vehicle) | 1.000 | 0.057 | 0.060 |
| Group 2 (3.0 mg/kg AD06079) | 0.247 | 0.064 | 0.086 |
| Group 3 (3.0 mg/kg AD06080) | 0.214 | 0.006 | 0.006 |
| Group 4 (3.0 mg/kg AD06081) | 0.155 | 0.016 | 0.017 |
| Group 5 (3.0 mg/kg AD06082) | 0.543 | 0.090 | 0.108 |
| Group 6 (3.0 mg/kg AD06083) | 0.484 | 0.037 | 0.040 |
| Group 7 (3.0 mg/kg AD06084) | 0.179 | 0.054 | 0.077 |
| Group 8 (3.0 mg/kg AD06085) | 0.131 | 0.034 | 0.045 |

As shown in Table 8, above, at day 15, each of the RNAi agents in Groups 2 through 8 showed a reduction in HSD17B13 mRNA levels compared to vehicle control. For example, a single subcutaneous administration of 3.0 mg/kg of HSD17B13 RNAi agent AD06085 showed a reduction of approximately 87% (0.131) of HSD17B13 mRNA on day 15.

Example 3. In Vivo Testing of HSD17B13 RNAi Agents in Rats

To assess the in vivo activity of additional HSD17B13 RNAi agents, Sprague Dawley rats were used. At day 1, each rat was administered a single subcutaneous injection of 500 µl/200 g animal weight, containing 3.0 mg/kg (mpk) of an HSD17B13 RNAi agent formulated in a pharmaceutically acceptable saline buffer, or vehicle control (saline buffer with no RNAi agent), according to the dosing groups recited in Table 9.

TABLE 9

Dosing Groups of Example 3

| Group | RNAi Agent and Dose | Dosing Regimen |
|---|---|---|
| 1 | Saline (no RNAi agent) | Single injection on day 1 |
| 2 | 3.0 mg/kg AD06081 | Single injection on day 1 |
| 3 | 3.0 mg/kg AD06079 | Single injection on day 1 |
| 4 | 3.0 mg/kg AD06177 | Single injection on day 1 |
| 5 | 3.0 mg/kg AD06178 | Single injection on day 1 |
| 6 | 3.0 mg/kg AD06179 | Single injection on day 1 |
| 7 | 3.0 mg/kg AD06180 | Single injection on day 1 |
| 8 | 3.0 mg/kg AD06181 | Single injection on day 1 |
| 9 | 3.0 mg/kg AD06182 | Single injection on day 1 |
| 10 | 3.0 mg/kg AD06183 | Single injection on day 1 |

Each of the RNAi agents included a modified sequence and a tridentate N-acetyl-galactosamine-containing targeting ligand conjugated to the 5' terminal end of the sense strand. (See Tables 3-6 for modified sequences and targeting ligand structures). All of the HSD17B13 RNAi agents tested (Groups 2 through 10) included nucleotide sequences that were designed to inhibit expression of an HSD17B13 gene at position 488 of the gene. (See, e.g., SEQ ID NO: 1 and Table 2 for the HSD17B13 gene referenced).

The injections were performed between the skin and muscle (i.e. subcutaneous injections) into the loose skin over the neck and shoulder area. Four (4) rats in each group were tested (n=4). All of the rats were sacrificed on day 15. Livers were harvested, and approximately 100 mg liver samples were collected and snap-frozen in liquid nitrogen for RNA isolation. Relative expression of each of the HSD17B13 RNAi agents was determined by qRT-PCR by normalizing the HSD17B13 mRNA expression levels of the animals from each respective treatment Group to the animals in Group 1 (vehicle control, no RNAi agent) ($\Delta\Delta C_T$ analysis), the results of which are set forth in the following Table 10:

TABLE 10

Relative HSD17B13 mRNA Level at Day 15, Normalized to Control from Example 3

| Group ID | Day 15 Relative HSD17B13 mRNA | Low Variance (Error) | High Variance (Error) |
|---|---|---|---|
| Group 1 (Saline vehicle) | 1.000 | 0.113 | 0.128 |
| Group 2 (3.0 mg/kg AD06081) | 0.248 | 0.039 | 0.046 |
| Group 3 (3.0 mg/kg AD06079) | 0.196 | 0.062 | 0.091 |
| Group 4 (3.0 mg/kg AD06177) | 0.317 | 0.057 | 0.070 |
| Group 5 (3.0 mg/kg AD06178) | 0.316 | 0.085 | 0.116 |
| Group 6 (3.0 mg/kg AD06179) | 0.308 | 0.106 | 0.161 |
| Group 7 (3.0 mg/kg AD06180) | 0.326 | 0.100 | 0.145 |
| Group 8 (3.0 mg/kg AD06181) | 0.295 | 0.038 | 0.043 |
| Group 9 (3.0 mg/kg AD06182) | 0.800 | 0.070 | 0.077 |
| Group 10 (3.0 mg/kg AD06183) | 0.348 | 0.018 | 0.019 |

As shown in Table 10, above, each of the RNAi agents in Groups 2 through 10 showed a reduction in HSD17B13 mRNA levels compared to vehicle control at day 15. Group 9 (AD06182), showed only approximately 20% (0.800) reduction in HSD17B13 mRNA on day 15. However, each of the remaining HSD17B13 RNAi agents tested (i.e., Groups 2-8 and 10) showed a reduction of between approximately 65% (Group 10, 0.348) to approximately 81% (Group 3, 0.196) of HSD17B13 mRNA on day 15 after a single subcutaneous administration.

Example 4. In Vivo Testing of HSD17B13 RNAi Agents in Rats

To assess the in vivo activity of certain additional HSD17B13 RNAi agents, Sprague Dawley rats were used. At day 1, each rat was administered a single subcutaneous injection of 500 μl/200 g animal weight, containing 3.0 mg/kg (mpk) of an HSD17B13 RNAi agent formulated in a pharmaceutically acceptable saline buffer, or vehicle control (saline buffer with no RNAi agent), according to the dosing groups recited in Table 11.

TABLE 11

Dosing Groups of Example 4

| Group | RNAi Agent and Dose | Dosing Regimen |
|---|---|---|
| 1 | Saline (no RNAi agent) | Single injection on day 1 |
| 2 | 3.0 mg/kg AD06085 | Single injection on day 1 |
| 3 | 3.0 mg/kg AD06184 | Single injection on day 1 |
| 4 | 3.0 mg/kg AD06185 | Single injection on day 1 |
| 5 | 3.0 mg/kg AD06186 | Single injection on day 1 |
| 6 | 3.0 mg/kg AD06187 | Single injection on day 1 |
| 7 | 3.0 mg/kg AD06188 | Single injection on day 1 |
| 8 | 3.0 mg/kg AD06189 | Single injection on day 1 |
| 9 | 3.0 mg/kg AD06190 | Single injection on day 1 |
| 10 | 3.0 mg/kg AD06082 | Single injection on day 1 |
| 11 | 3.0 mg/kg AD06191 | Single injection on day 1 |

Each of the RNAi agents included a modified sequence and a tridentate N-acetyl-galactosamine-containing targeting ligand conjugated to the 5' terminal end of the sense strand. (See Tables 3-6 for modified sequences and targeting ligand structures). The HSD17B13 RNAi agents AD06085, AD06184, AD06185, AD06186, AD06187, AD06188, AD06189, and AD06190 (Groups 2 through 9) each included nucleotide sequences that were designed to inhibit expression of an HSD17B13 gene at position 499 of the gene; and the HSD17B13 RNAi agents AD06082 and AD06191 included nucleotide sequences that were designed to inhibit expression of an HSD17B13 gene at position 492 of the gene. (See, e.g., SEQ ID NO: 1 and Table 2 for the HSD17B13 gene referenced).

The injections were performed between the skin and muscle (i.e. subcutaneous injections) into the loose skin over the neck and shoulder area. Four (4) rats in each group were tested (n=4). All of the rats were sacrificed on day 15. Livers were harvested, and approximately 100 mg liver samples were collected and snap-frozen in liquid nitrogen for RNA isolation. Relative expression of each of the HSD17B13 RNAi agents was determined by qRT-PCR by normalizing the HSD17B13 mRNA expression levels of the animals from each respective treatment Group to the animals in Group 1 (vehicle control, no RNAi agent) ($\Delta\Delta C_T$ analysis), the results of which are set forth in the following Table 12:

TABLE 12

Relative HSD17B13 mRNA Level at Day 15, Normalized to Control from Example 4

| Group ID | Day 15 Relative HSD17B13 mRNA | Low Variance (Error) | High Variance (Error) |
|---|---|---|---|
| Group 1 (Saline vehicle) | 1.000 | 0.151 | 0.178 |
| Group 2 (3.0 mg/kg AD06085) | 0.211 | 0.080 | 0.128 |
| Group 3 (3.0 mg/kg AD06184) | 0.153 | 0.029 | 0.035 |
| Group 4 (3.0 mg/kg AD06185) | 0.113 | 0.025 | 0.032 |
| Group 5 (3.0 mg/kg AD06186) | 0.133 | 0.041 | 0.059 |
| Group 6 (3.0 mg/kg AD06187) | 0.099 | 0.014 | 0.016 |
| Group 7 (3.0 mg/kg AD06188) | 0.682 | 0.090 | 0.104 |
| Group 8 (3.0 mg/kg AD06189) | 0.142 | 0.027 | 0.033 |
| Group 9 (3.0 mg/kg AD06190) | 0.477 | 0.060 | 0.068 |
| Group 10 (3.0 mg/kg AD06082) | 0.526 | 0.053 | 0.059 |
| Group 11 (3.0 mg/kg AD06191) | 0.774 | 0.089 | 0.101 |

As shown in Table 12, above, each of the RNAi agents in Groups 2 through 11 showed a reduction in HSD17B13 mRNA levels compared to control at day 15. More specifically, at day 15, HSD17B13 RNAi agent AD06187 showed an approximately 90% (0.099) reduction in HSD17B13 mRNA after a single subcutaneous administration, and HSD17B13 RNAi agent AD06085 showed an approximately 79% (0.211) reduction in HSD17B13 mRNA.

Example 5. In Vivo Testing of HSD17B13 RNAi Agents in Cynomolgus Monkeys

HSD17B13 RNAi agent AD06078 was evaluated in cynomolgus monkeys. On day 1 and day 22, two cynomolgus macaque (*Macaca fascicularis*) primates (also referred to herein as "cynos") were administered a subcutaneous injection of 0.4 mL/kg (approximately 3 mL volume, depending on animal mass) containing 4.0 mg/kg of HSD17B13 RNAi agent AD06078, formulated in saline. HSD17B13 RNAi agent AD06078 included modified nucleotides and a tridentate N-acetyl-galactosamine-containing targeting ligand ((NAG37)s) conjugated to the 5'-terminal end of the sense strand, as shown in Tables 3-6. HSD17B13 RNAi agent AD06078 included nucleotide sequences that were designed to inhibit expression of an HSD17B13 gene at position 1501 of the gene. (See, e.g., SEQ ID NO: 1 and Table 2 for the HSD17B13 gene referenced).

On days −8 (pre-dose), 15, 29, and 43, liver biopsies were taken. On the date of each biopsy collection, cynos were anesthetized and ultrasound-guided liver biopsies were performed to extract two or three liver tissue samples approximately 1 mm×2 mm in size. The biopsy samples were then homogenized, and levels of HSD17B13 mRNA in the cyno livers were measured by RT-qPCR. Resulting values were then normalized to the pre-dose (in this case, at day −8) HSD17B13 mRNA measurements. The resulting mRNA data are reflected in the following Tables 13 and 14:

TABLE 13

HSD17B13 mRNA Levels Normalized to Pre-Dose from Example 5 of Cyno #1 (cy0595)

| Day 15 | | | Day 43 | | |
|---|---|---|---|---|---|
| Relative HSD17B13 mRNA Expression | Low Error | High Error | Relative HSD17B13 mRNA Expression | Low Error | High Error |
| 0.570 | 0.035 | 0.037 | 0.576 | 0.050 | 0.055 |

** The day 29 biopsy samples for cyno #1 were smaller than normal and, based on an overly pale appearance, were suspected to be fat tissue and not liver tissue. The analysis at day 29 was therefore discarded.

TABLE 14

HSD17B13 mRNA Levels Normalized to Pre-Dose from Example 5 of Cyno #2 (cy0471)

| Day 15 | | | Day 29 | | |
|---|---|---|---|---|---|
| Relative HSD17B13 mRNA Expression | Low Error | High Error | Relative HSD17B13 mRNA Expression | Low Error | High Error |
| 0.416 | 0.010 | 0.010 | 0.383 | 0.015 | 0.015 |

| Day 43 | | |
|---|---|---|
| Relative HSD17B13 mRNA Expression | Low Error | High Error |
| 0.335 | 0.019 | 0.020 |

Both of the cynos dosed with AD06078 showed a reduction in liver-specific HSD17B13 mRNA compared to pre-treatment measurements through day 43. On day 43, for example, the second cyno had a reduction of HSD17B13 mRNA of approximately 67% (0.335) compared to pre-dose levels.

Example 6. HSD17B13-SEAP Mouse Model

To evaluate certain additional HSD17B13 RNAi agents, a HSD17B13-SEAP mouse model was used. Six- to eight-week-old female C57BL/6 albino mice were transiently transfected in vivo with plasmid by hydrodynamic tail vein injection, administered at least 29 days prior to administration of an HSD17B13 RNAi agent or control. The plasmid contains the HSD17B13 cDNA sequence (GenBank NM_178135.4 (SEQ ID NO:1)) inserted into the 3' UTR of the SEAP (secreted human placental alkaline phosphatase) reporter gene. 50 μg of the plasmid containing the HSD17B13 cDNA sequence in Ringer's Solution in a total volume of 10% of the animal's body weight was injected into mice via the tail vein to create HSD17B13-SEAP model mice. The solution was injected through a 27-gauge needle in 5-7 seconds as previously described (Zhang G et al., "High levels of foreign gene expression in hepatocytes after tail vein injection of naked plasmid DNA." Human Gene Therapy 1999 Vol. 10, p 1735-1737). Inhibition of expression of HSD17B13 by an HSD17B13 RNAi agent results in concomitant inhibition of SEAP expression, which is measured. Prior to administration of a treatment (between day −7 and day 1 pre-dose), SEAP expression levels in serum were measured by the Phospha-Light™ SEAP Reporter Gene Assay System (Invitrogen), and the mice were grouped according to average SEAP levels.

Mice were anesthetized with 2-3% isoflurane and blood samples were collected from the submandibular area into serum separation tubes (Sarstedt AG & Co., Nümbrecht, Germany). Blood was allowed to coagulate at ambient temperature for 20 min. The tubes were centrifuged at 8,000×g for 3 min to separate the serum and stored at 4° C. Serum was collected and measured by the Phospha-Light™ SEAP Reporter Gene Assay System (Invitrogen) according to the manufacturer's instructions. Serum SEAP levels for each animal can be normalized to the control group of mice injected with vehicle control in order to account for the non-treatment related decline in HSD17B13 expression with this model. To do so, first, the SEAP level for each animal at a time point was divided by the pre-treatment level of expression in that animal (Day −1) in order to determine the ratio of expression "normalized to pre-treatment". Expression at a specific time point was then normalized to the control group by dividing the "normalized to pre-treatment" ratio for an individual animal by the average "normalized to pre-treatment" ratio of all mice in the normal vehicle control group. Alternatively, the serum SEAP levels for each animal was assessed by normalizing to pre-treatment levels only.

Example 7. In Vivo Testing of HSD17B13 RNAi Agents in HSD17B13-SEAP Mice

The HSD17B13-SEAP mouse model described in Example 6, above, was used. At day 1, each mouse was given a single subcutaneous administration of 200 μl/20 g animal weight containing either 3.0 mg/kg (mpk) of an HSD17B13 RNAi agent formulated in a pharmaceutically acceptable saline buffer, or vehicle control (saline buffer with no RNAi agent), according to the following Table 15.

TABLE 15

Dosing Groups of Example 7

| Group | RNAi Agent and Dose | Dosing Regimen |
|---|---|---|
| 1 | Saline (no RNAi agent) | Single injection on day 1 |
| 2 | 3.0 mg/kg AD06078 | Single injection on day 1 |
| 3 | 3.0 mg/kg AD06081 | Single injection on day 1 |
| 4 | 3.0 mg/kg AD06084 | Single injection on day 1 |
| 5 | 3.0 mg/kg AD06085 | Single injection on day 1 |

Each of the HSD17B13 RNAi agents included modified nucleotides that were conjugated at the 5' terminal end of the sense strand to a targeting ligand that included three N-acetyl-galactosamine groups (tridentate ligand) having the modified sequences as set forth in the duplex structures herein. (See Tables 3-6 for specific modifications and structure information related to the HSD17B13 RNAi agents). The HSD17B13 RNAi agent AD06078 (Group 2) included nucleotide sequences that were designed to inhibit expression of an HSD17B13 gene at position 1501 of the gene; the HSD17B13 RNAi agent AD06081 (Group 3) included nucleotide sequences that were designed to inhibit expression of an HSD17B13 gene at position 488 of the gene; and the HSD17B13 RNAi agents AD06084 and AD06085 included nucleotide sequences that were designed to inhibit expression of an HSD17B13 gene at position 499 of the gene. (See SEQ ID NO:1 and Table 2 for the HSD17B13 gene referenced).

The injections were performed between the skin and muscle (i.e. subcutaneous injections) into the loose skin over the neck and shoulder area. Four (4) mice in each group were tested (n=4). Serum was collected on day −2 (pre-treatment), day 8, day 15, day 22, and day 29, and SEAP expression levels were determined pursuant to the procedure set forth in Example 6, above. Data from the experiment are shown in the following Tables 16 and 17:

TABLE 16

Average SEAP Normalized to Pre-Treatment (Day −2) in HSD17B13-SEAP Mice from Example 7

| | Day 8 | | Day 15 | | Day 22 | | Day 29 | |
|---|---|---|---|---|---|---|---|---|
| Group ID | Avg SEAP | Std Dev (+/−) | Avg SEAP | Std Dev (+/−) | Avg SEAP | Std Dev (+/−) | Avg SEAP | Std Dev (+/−) |
| Group 1 (Saline vehicle) | 0.852 | 0.189 | 0.524 | 0.220 | 0.481 | 0.168 | 0.440 | 0.118 |
| Group 2 (3.0 mg/kg AD06078) | 0.516 | 0.133 | 0.264 | 0.119 | 0.316 | 0.198 | 0.223 | 0.097 |
| Group 3 (3.0 mg/kg AD06081) | 0.629 | 0.098 | 0.389 | 0.110 | 0.487 | 0.163 | 0.381 | 0.075 |
| Group 4 (3.0 mg/kg AD06084) | 0.213 | 0.139 | 0.082 | 0.017 | 0.122 | 0.030 | 0.129 | 0.031 |
| Group 5 (3.0 mg/kg AD06085) | 0.168 | 0.022 | 0.053 | 0.013 | 0.083 | 0.022 | 0.083 | 0.016 |

* As noted in Example 6, above, the gradual reduction in SEAP in the vehicle control group (Group 1) over time is due to the loss of the SEAP reporter gene in the cells of the mice due to natural cell replication in the animals, and is not the result of any inhibitory compound.

TABLE 17

Average SEAP Normalized to Pre-Treatment (Day −2) and Vehicle Control in HSD17B13-SEAP Mice from Example 7

| | Day 8 | | Day 15 | | Day 22 | | Day 29 | |
|---|---|---|---|---|---|---|---|---|
| Group ID | Avg SEAP | Std Dev (+/−) | Avg SEAP | Std Dev (+/−) | Avg SEAP | Std Dev (+/−) | Avg SEAP | Std Dev (+/−) |
| Group 1 (Saline vehicle) | 1.000 | 0.221 | 1.000 | 0.419 | 1.000 | 0.349 | 1.000 | 0.267 |
| Group 2 (3.0 mg/kg AD06078) | 0.606 | 0.156 | 0.504 | 0.228 | 0.657 | 0.412 | 0.507 | 0.221 |
| Group 3 (3.0 mg/kg AD06081) | 0.738 | 0.115 | 0.741 | 0.210 | 1.012 | 0.340 | 0.865 | 0.169 |
| Group 4 (3.0 mg/kg AD06084) | 0.250 | 0.163 | 0.156 | 0.033 | 0.254 | 0.063 | 0.293 | 0.070 |
| Group 5 (3.0 mg/kg AD06085) | 0.197 | 0.025 | 0.101 | 0.025 | 0.173 | 0.047 | 0.189 | 0.037 |

Each of the HSD17B13 RNAi agents in each of the dosing groups (i.e., Groups 2 through 5) showed reduction in SEAP as compared to the vehicle control (Group 1) at days 8 and 15. Further, the HSD17B13 RNAi agents AD06084 and AD06085, which both included nucleotide sequences designed to inhibit expression at position 499 of the HSD17B13 gene, showed particularly high levels of knock-down through day 22 measurements. (Compare Groups 4 and 5 with Group 1).

Example 8. In Vivo Testing of HSD17B13 RNAi Agents in Cynomolgus Monkeys

HSD17B13 RNAi agents AD06078, AD06187, AD06278, and AD06280 were evaluated in cynomolgus monkeys. On day 1 and day 30, three cynos for each group (n=3) were administered a subcutaneous injection of 0.3 mL/kg (approximately 3 mL volume, depending on animal mass) containing 3.0 mg/kg of the respective HSD17B13 RNAi agent, formulated in saline. The HSD17B13 RNAi agents included modified nucleotides and a tridentate N-acetyl-galactosamine-containing targeting ligand ((NAG37)s) conjugated to the 5'-terminal end of the sense strand, as shown in Tables 3-6. HSD17B13 RNAi agent AD06078 (Group 1) included nucleotide sequences that were designed to inhibit expression of an HSD17B13 gene at position 1501 of the gene; HSD17B13 RNAi agent AD06187 (Group 2) included nucleotide sequences that were designed to inhibit expression of an HSD17B13 gene at position 499 of the gene; HSD17B13 RNAi agent AD06278 (Group 3) included nucleotide sequences that were designed to inhibit expression of an HSD17B13 gene at position 513 of the gene; and HSD17B13 RNAi agent AD06280 (Group 4) included nucleotide sequences that were designed to inhibit expression of an HSD17B13 gene at position 791 of the gene. (See, e.g., SEQ ID NO:1 and Table 2 for the HSD17B13 gene referenced).

On days −7 (pre-dose), 15, 29, and 43 liver biopsies were taken. On the date of each biopsy collection, cynos were anesthetized and laparoscopy was used to extract two liver tissue samples approximately 80 mg to 120 mg each. The biopsy samples were then homogenized, and levels of HSD17B13 mRNA in the cyno livers were measured by RT-qPCR. Resulting values were then normalized to the pre-dose (in this case, at day −7) HSD17B13 mRNA measurements. The resulting mRNA data are reflected in the following Table 18:

TABLE 18

HSD17B13 mRNA Levels Normalized to Pre-Dose (Day −7) from Example 8 for Each Group (n = 3)

| | Day 15 | | | Day 29 | | |
|---|---|---|---|---|---|---|
| | Relative HSD17B13 mRNA Expression | Low Error | High Error | Relative HSD17B13 mRNA Expression | Low Error | High Error |
| Group 1: AD06078 | 1.339 | 0.368 | 0.507 | 1.355 | 0.364 | 0.498 |
| Group 2: AD06187 | 0.806 | 0.233 | 0.328 | 0.540 | 0.217 | 0.362 |
| Group 3: AD06278 | 1.137 | 0.193 | 0.233 | 0.802 | 0.120 | 0.141 |
| Group 4: AD06280 | 0.343 | 0.098 | 0.137 | 0.235 | 0.077 | 0.115 |

TABLE 18-continued

| HSD17B13 mRNA Levels Normalized to Pre-Dose (Day −7) from Example 8 for Each Group (n = 3) | | | |
|---|---|---|---|
| | Day 43 | | |
| | Relative HSD17B13 mRNA Expression | Low Error | High Error |
| Group 1: AD06078 | 0.506 | 0.078 | 0.092 |
| Group 2: AD06187 | 0.396 | 0.069 | 0.083 |
| Group 3: AD06278 | 1.091 | 0.074 | 0.079 |
| Group 4: AD06280 | 0.265 | 0.111 | 0.191 |

Example 9. In Vivo Testing of HSD17B13 RNAi Agents in HSD17B13-SEAP Mice

The HSD17B13-SEAP mouse model described in Example 6, above, was used. At day 1, each mouse was given a single subcutaneous administration of 200 μl/20 g animal weight containing either 3.0 mg/kg (mpk) of an HSD17B13 RNAi agent formulated in a pharmaceutically acceptable saline buffer, or vehicle control (saline buffer with no RNAi agent), according to the following Table 19:

TABLE 19

Dosing Groups of Example 9

| Group | RNAi Agent and Dose | Dosing Regimen |
|---|---|---|
| 1 | Saline (no RNAi agent) | Single injection on day 1 |
| 2 | 3.0 mg/kg AD06210 | Single injection on day 1 |
| 3 | 3.0 mg/kg AD06211 | Single injection on day 1 |
| 4 | 3.0 mg/kg AD06212 | Single injection on day 1 |
| 5 | 3.0 mg/kg AD06213 | Single injection on day 1 |
| 6 | 3.0 mg/kg AD06214 | Single injection on day 1 |
| 7 | 3.0 mg/kg AD06217 | Single injection on day 1 |
| 8 | 3.0 mg/kg AD06218 | Single injection on day 1 |

Each of the HSD17B13 RNAi agents included modified nucleotides that were conjugated at the 5' terminal end of the sense strand to a targeting ligand that included three N-acetyl-galactosamine groups (tridentate ligand) having the modified sequences as set forth in the duplex structures herein. (See Tables 3-6 for specific modifications and structure information related to the HSD17B13 RNAi agents). The HSD17B13 RNAi agent AD06210 (Group 2) included nucleotide sequences that were designed to inhibit expression of an HSD17B13 gene at position 513 of the gene; the HSD17B13 RNAi agent AD06211 (Group 3) included nucleotide sequences that were designed to inhibit expression of an HSD17B13 gene at position 645 of the gene; the HSD17B13 RNAi agent AD06212 (Group 4) included nucleotide sequences that were designed to inhibit expression of an HSD17B13 gene at position 649 of the gene; the HSD17B13 RNAi agent AD06213 (Group 5) included nucleotide sequences that were designed to inhibit expression of an HSD17B13 gene at position 759 of the gene; the HSD17B13 RNAi agent AD06214 (Group 6) included nucleotide sequences that were designed to inhibit expression of an HSD17B13 gene at position 791 of the gene; the HSD17B13 RNAi agent AD06217 (Group 7) included nucleotide sequences that were designed to inhibit expression of an HSD17B13 gene at position 1505 of the gene; and the HSD17B13 RNAi agent AD06218 (Group 8) included nucleotide sequences that were designed to inhibit expression of an HSD17B13 gene at position 2185 of the gene. (See SEQ ID NO:1 and Table 2 for the HSD17B13 gene referenced).

The injections were performed between the skin and muscle (i.e. subcutaneous injections) into the loose skin over the neck and shoulder area. Four (4) mice in each group were tested (n=4). Serum was collected on day −1 (pre-treatment), day 8, day 15, and day 22, and SEAP expression levels were determined pursuant to the procedure set forth in Example 6, above. Data from the experiment are shown in the following Table 20:

TABLE 20

| Average SEAP Normalized to Pre-Treatment (Day −1) in HSD17B13-SEAP Mice from Example 9 | | | | | | |
|---|---|---|---|---|---|---|
| | Day 8 | | Day 15 | | Day 22 | |
| Group ID | Avg SEAP | Std Dev (+/−) | Avg SEAP | Std Dev (+/−) | Avg SEAP | Std Dev (+/−) |
| Group 1 (Saline vehicle) | 0.965 | 0.263 | 0.586 | 0.283 | 0.506 | 0.249 |
| Group 2 (3.0 mg/kg AD06210) | 0.409 | 0.132 | 0.157 | 0.068 | 0.210 | 0.086 |
| Group 3 (3.0 mg/kg AD06211) | 0.983 | 0.638 | 0.340 | 0.223 | 0.397 | 0.266 |
| Group 4 (3.0 mg/kg AD06212) | 0.505 | 0.228 | 0.241 | 0.105 | 0.264 | 0.100 |
| Group 5 (3.0 mg/kg AD06213) | 0.533 | 0.125 | 0.167 | 0.070 | 0.230 | 0.145 |
| Group 6 (3.0 mg/kg AD06214) | 0.468 | 0.063 | 0.151 | 0.028 | 0.171 | 0.022 |
| Group 7 (3.0 mg/kg AD06217) | 0.678 | 0.221 | 0.325 | 0.150 | 0.345 | 0.186 |
| Group 8 (3.0 mg/kg AD06218) | 0.903 | 0.230 | 0.451 | 0.143 | 0.440 | 0.206 |

* As noted in Example 6, above, the gradual reduction in SEAP in the vehicle control group (Group 1) over time is due to the loss of the SEAP reporter gene in the cells of the mice due to natural cell replication in the animals, and is not the result of any inhibitory compound.

Each of the HSD17B13 RNAi agents in each of the dosing groups (i.e., Groups 2 through 8) showed reduction in SEAP as compared to the vehicle control (Group 1) at days 15, and 22. Further, the HSD17B13 RNAi agent AD06210 (Group 2), which included nucleotide sequences designed to inhibit expression at position 513 of the HSD17B13 gene, and AD06214 (Group 6), which included nucleotide sequences designed to inhibit expression at position 791 of the HSD17B13 gene, showed particularly high levels of knockdown compared to the other RNAi agents tested. For example, at day 15, AD06210 (Group 2) showed a reduction of approximately 84% (0.157), while AD06214 (Group 6) showed a reduction of approximately 85% (0.151). (Compare to, e.g., AD06218 (Group 8), which showed knockdown levels that were only slightly greater than the control group (Group 1)). HSD17B13 RNAi agent AD06214 (Group 6) also showed approximately 83% knockdown (0.171) at day 22.

Example 10. In Vivo Testing of HSD17B13 RNAi Agents in HSD17B13-SEAP Mice

The HSD17B13-SEAP mouse model described in Example 6, above, was used. At day 1, each mouse was given a single subcutaneous administration of 200 μl/20 g animal weight containing either 3.0 mg/kg (mpk) of an HSD17B13 RNAi agent formulated in a pharmaceutically acceptable saline buffer, or vehicle control (saline buffer with no RNAi agent), according to the following Table 21.

TABLE 21

Dosing Groups of Example 10

| Group | RNAi Agent and Dose | Dosing Regimen |
|---|---|---|
| 1 | Saline (no RNAi agent) | Single injection on day 1 |
| 2 | 3.0 mg/kg AD06185 | Single injection on day 1 |
| 3 | 3.0 mg/kg AD06187 | Single injection on day 1 |
| 4 | 3.0 mg/kg AD06210 | Single injection on day 1 |
| 5 | 3.0 mg/kg AD06213 | Single injection on day 1 |
| 6 | 3.0 mg/kg AD06214 | Single injection on day 1 |

Each of the HSD17B13 RNAi agents included modified nucleotides that were conjugated at the 5' terminal end of the sense strand to a targeting ligand that included three N-acetyl-galactosamine groups (tridentate ligand) having the modified sequences as set forth in the duplex structures herein. (See Tables 3-6 for specific modifications and structure information related to the HSD17B13 RNAi agents).

The HSD17B13 RNAi agents AD06185 (Group 2) and AD06187 (Group 3) included nucleotide sequences that were designed to inhibit expression of an HSD17B13 gene at position 499 of the gene; the HSD17B13 RNAi agent AD06210 (Group 4) included nucleotide sequences that were designed to inhibit expression of an HSD17B13 gene at position 513 of the gene; the HSD17B13 RNAi agent AD06213 (Group 5) included nucleotide sequences that were designed to inhibit expression of an HSD17B13 gene at position 759 of the gene; the HSD17B13 RNAi agent AD06214 (Group 6) included nucleotide sequences that were designed to inhibit expression of an HSD17B13 gene at position 791 of the gene. (See SEQ ID NO: 1 and Table 2 for the HSD17B13 gene referenced).

The injections were performed between the skin and muscle (i.e. subcutaneous injections) into the loose skin over the neck and shoulder area. Four (4) mice in each group were tested (n=4). Serum was collected on day −1 (pre-treatment), day 8, day 15, and day 22, and SEAP expression levels were determined pursuant to the procedure set forth in Example 6, above. Data from the experiment are shown in the following Table 22:

TABLE 22

Average SEAP Normalized to Pre-Treatment (Day −1) in HSD17B13-SEAP Mice from Example 10

| | Day 8 | | Day 15 | | Day 22 | |
|---|---|---|---|---|---|---|
| Group ID | Avg SEAP | Std Dev (+/−) | Avg SEAP | Std Dev (+/−) | Avg SEAP | Std Dev (+/−) |
| Group 1 (Saline vehicle) | 0.735 | 0.042 | 0.751 | 0.063 | 0.651 | 0.200 |
| Group 2 (3.0 mg/kg AD06185) | 0.233 | 0.045 | 0.136 | 0.061 | 0.111 | 0.054 |
| Group 3 (3.0 mg/kg AD06187) | 0.191 | 0.028 | 0.097 | 0.067 | 0.080 | 0.039 |
| Group 4 (3.0 mg/kg AD06210) | 0.256 | 0.038 | 0.201 | 0.062 | 0.195 | 0.079 |
| Group 5 (3.0 mg/kg AD06213) | 0.315 | 0.054 | 0.235 | 0.045 | 0.163 | 0.015 |
| Group 6 (3.0 mg/kg AD06214) | 0.417 | 0.099 | 0.344 | 0.050 | 0.304 | 0.100 |

* As noted in Example 6, above, the gradual reduction in SEAP in the vehicle control group (Group 1) over time is due to the loss of the SEAP reporter gene in the cells of the mice due to natural cell replication in the animals, and is not the result of any inhibitory compound.

Each of the HSD17B13 RNAi agents in each of the dosing groups (i.e., Groups 2 through 6) showed reduction in SEAP as compared to the vehicle control (Group 1) at all measured timepoints.

Example 11. In Vivo Testing of HSD17B13 RNAi Agents in HSD17B13-SEAP Mice

The HSD17B13-SEAP mouse model described in Example 6, above, was used. At day 1, each mouse was given a single subcutaneous administration of 200 μl/20 g animal weight containing a mg/kg (mpk) dose of an HSD17B13 RNAi agent formulated in a pharmaceutically acceptable saline buffer, or vehicle control (saline buffer with no RNAi agent), according to the following Table 23.

TABLE 23

Dosing Groups of Example 11

| Group | RNAi Agent and Dose | Dosing Regimen |
|---|---|---|
| 1 | Saline (no RNAi agent) | Single injection on day 1 |
| 2 | 0.625 mg/kg AD06280 | Single injection on day 1 |
| 3 | 1.25 mg/kg AD06280 | Single injection on day 1 |
| 4 | 2.5 mg/kg AD06280 | Single injection on day 1 |

TABLE 23-continued

| Dosing Groups of Example 11 | | |
|---|---|---|
| Group | RNAi Agent and Dose | Dosing Regimen |
| 5 | 5.0 mg/kg AD06280 | Single injection on day 1 |
| 6 | 0.625 mg/kg AD06187 | Single injection on day 1 |
| 7 | 1.25 mg/kg AD06187 | Single injection on day 1 |
| 8 | 2.5 mg/kg AD06187 | Single injection on day 1 |
| 9 | 5.0 mg/kg AD06187 | Single injection on day 1 |

Both of the HSD17B13 RNAi agents included modified nucleotides that were conjugated at the 5' terminal end of the sense strand to a targeting ligand that included three N-acetyl-galactosamine groups (tridentate ligand) having the modified sequences as set forth in the duplex structures herein. (See Tables 3-6 for specific modifications and structure information related to the HSD17B13 RNAi agents).

The injections were performed between the skin and muscle (i.e. subcutaneous injections) into the loose skin over the neck and shoulder area. Four (4) mice in each group were tested (n=4), except for the vehicle control group which had only two (2) mice. Serum was collected on day −1 (pre-treatment), day 8, day 15, day 22, and day 29, and SEAP expression levels were determined pursuant to the procedure set forth in Example 6, above. Data from the experiment are shown in the following Table 24:

TABLE 24

Average SEAP Normalized to Pre-Treatment (Day −1) and Control in HSD17B13-SEAP Mice from Example 11

| Group ID | Day 8 Avg SEAP | Day 8 Std Dev (+/−) | Day 15 Avg SEAP | Day 15 Std Dev (+/−) | Day 22 Avg SEAP | Day 22 Std Dev (+/−) | Day 29 Avg SEAP | Day 29 Std Dev (+/−) |
|---|---|---|---|---|---|---|---|---|
| Group 1 (Saline vehicle) | 1.000 | 0.079 | 1.000 | 0.231 | 1.000 | 0.284 | 1.000 | 0.105 |
| Group 2 (0.625 mg/kg AD06280) | 1.000 | 0.186 | 0.827 | 0.177 | 0.767 | 0.338 | 0.741 | 0.271 |
| Group 3 (1.25 mg/kg AD06280) | 0.889 | 0.161 | 0.585 | 0.102 | 0.477 | 0.128 | 0.406 | 0.099 |
| Group 4 (2.5 mg/kg AD06280) | 0.813 | 0.103 | 0.579 | 0.151 | 0.558 | 0.283 | 0.517 | 0.277 |
| Group 5 (5.0 mg/kg AD06280) | 0.214 | 0.098 | 0.109 | 0.047 | 0.080 | 0.024 | 0.081 | 0.028 |
| Group 6 (0.625 mg/kg AD06187) | 0.605 | 0.132 | 0.525 | 0.187 | 0.520 | 0.209 | 0.522 | 0.182 |
| Group 7 (1.25 mg/kg AD06187) | 0.656 | 0.152 | 0.514 | 0.176 | 0.569 | 0.130 | 0.600 | 0.109 |
| Group 8 (2.5 mg/kg AD06187) | 0.480 | 0.124 | 0.223 | 0.114 | 0.203 | 0.123 | 0.177 | 0.107 |
| Group 9 (5.0 mg/kg AD06187) | 0.203 | 0.056 | 0.050 | 0.015 | 0.045 | 0.008 | 0.054 | 0.014 |

Both of the HSD17B13 RNAi agents tested (i.e., AD06280 and AD06187) showed reduction in SEAP as compared to the vehicle control (Group 1).

Example 12. In Vivo Testing of HSD17B13 RNAi Agents in HSD17B13-SEAP Mice

The HSD17B13-SEAP mouse model described in Example 6, above, was used. At day 1, each mouse was given a single subcutaneous administration of 200 μl/20 g animal weight containing a 3 mg/kg (mpk) dose of an HSD17B13 RNAi agent formulated in a pharmaceutically acceptable saline buffer, or vehicle control (saline buffer with no RNAi agent), according to the following Table 25.

TABLE 25

| Dosing Groups of Example 12 | | |
|---|---|---|
| Group | RNAi Agent and Dose | Dosing Regimen |
| 1 | Saline (no RNAi agent) | Single injection on day 1 |
| 2 | 3 mg/kg AD06187 | Single injection on day 1 |

TABLE 25-continued

| Dosing Groups of Example 12 | | |
|---|---|---|
| Group | RNAi Agent and Dose | Dosing Regimen |
| 3 | 3 mg/kg AD06208 | Single injection on day 1 |
| 4 | 3 mg/kg AD06209 | Single injection on day 1 |
| 5 | 3 mg/kg AD06215 | Single injection on day 1 |
| 6 | 3 mg/kg AD06216 | Single injection on day 1 |
| 7 | 3 mg/kg AD06219 | Single injection on day 1 |

All of the HSD17B13 RNAi agents included modified nucleotides that were conjugated at the 5' terminal end of the sense strand to a targeting ligand that included three N-acetyl-galactosamine groups (tridentate ligand) having the modified sequences as set forth in the duplex structures herein. (See Tables 3-6 for specific modifications and structure information related to the HSD17B13 RNAi agents). The HSD17B13 RNAi agents AD06187 (Group 2) included nucleotide sequences that were designed to inhibit expression of an HSD17B13 gene at position 499 of the gene; the HSD17B13 RNAi agent AD06208 (Group 3) included nucleotide sequences that were designed to inhibit expression of an HSD17B13 gene at position 92 of the gene; the HSD17B13 RNAi agent AD06209 (Group 4) included nucleotide sequences that were designed to inhibit expression of an HSD17B13 gene at position 417 of the gene; the HSD17B13 RNAi agent AD06215 (Group 5) included nucleotide sequences that were designed to inhibit expression of an HSD17B13 gene at position 1418 of the gene; the HSD17B13 RNAi agent AD06216 (Group 6) included nucleotide sequences that were designed to inhibit expression of an HSD17B13 gene at position 1502 of the gene; the HSD17B13 RNAi agent AD06219 (Group 7) included nucleotide sequences that were designed to inhibit expression of an HSD17B13 gene at position 2195 of the gene. (See SEQ ID NO:1 and Table 2 for the HSD17B13 gene referenced).

The injections were performed between the skin and muscle (i.e. subcutaneous injections) into the loose skin over the neck and shoulder area. Four (4) mice in each group were tested (n=4). Serum was collected on day −1 (pre-treatment), day 8, day 15, and day 22 and SEAP expression levels were determined pursuant to the procedure set forth in Example 6, above. Data from the experiment are shown in the following Table 26:

TABLE 26

Average SEAP Normalized to Pre-Treatment (Day −1) and Control in HSD17B13-SEAP Mice from Example 12

| | Day 8 | | Day 15 | | Day 22 | |
|---|---|---|---|---|---|---|
| Group ID | Avg SEAP | Std Dev (+/−) | Avg SEAP | Std Dev (+/−) | Avg SEAP | Std Dev (+/−) |
| Group 1 (Saline vehicle) | 1.000 | 0.29 | 1.000 | 0.112 | 1.000 | 0.207 |
| Group 2 (3 mg/kg AD06187) | 0.288 | 0.156 | 0.205 | 0.131 | 0.186 | 0.151 |
| Group 3 (3 mg/kg AD06208) | 0.393 | 0.048 | 0.323 | 0.088 | 0.268 | 0.054 |
| Group 4 (3 mg/kg AD06209) | 0.614 | 0.106 | 0.481 | 0.146 | 0.315 | 0.06 |
| Group 5 (3 mg/kg AD06215) | 0.790 | 0.355 | 0.662 | 0.281 | 0.578 | 0.202 |
| Group 6 (3 mg/kg AD06216) | 0.962 | 0.556 | 0.867 | 0.681 | 0.612 | 0.404 |
| Group 7 (3 mg/kg AD06219) | 0.878 | 0.425 | 0.848 | 0.479 | 0.688 | 0.352 |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. An RNAi agent for inhibiting expression of an HSD17B13 gene, comprising:

an antisense strand, wherein the nucleotide sequence of the antisense strand comprises one of the following nucleotide sequences (5'→3');

usCfsasUfcUfaUfcAfgAfcUfuCfuUfaCfsg (SEQ ID NO:2); or usCfsasUfcUfaucagAfcUfuCfuUfaCfsg (SEQ ID NO:4), and a sense strand, wherein the nucleobase sequence of the sense strand differs by 0 or 1 nucleobase from the nucleobase sequence (5'→3') CGUAAGAAGUCUGAUAGAUGA (SEQ ID NO: 8), wherein a, c, g, and u represent 2'-O-methyl adenosine, 2'-O-methyl cytidine, 2'-O-methyl guanosine, and 2'-O-methyl uridine, respectively; Af, Cf, Gf, and Uf represent 2'-fluoro adenosine, 2'-fluoro cytidine, 2'-fluoro guanosine, and 2'-fluoro uridine, respectively; and s represents a phosphorothioate linkage.

2. The RNAi agent of claim 1, wherein at least one nucleotide of the sense strand is a modified nucleotide or includes a modified internucleoside linkage.

3. The RNAi agent of claim 2, wherein the modified nucleotide of the sense strand is selected from the group consisting of: 2'-O-methyl nucleotide, 2'-fluoro nucleotide, 2'-deoxy nucleotide, 2',3'-seco nucleotide mimic, locked nucleotide, 2'-F-arabino nucleotide, 2'-methoxyethyl nucleotide, abasic nucleotide, ribitol, inverted nucleotide, inverted 2'-O-methyl nucleotide, inverted 2'-deoxy nucleotide, 2'-amino-modified nucleotide, 2'-alkyl-modified nucleotide, morpholino nucleotide, vinyl phosphonate deoxyribonucleotide, cyclopropyl phosphonate deoxyribonucleotide, and 3'-O-methyl nucleotide.

4. The RNAi agent of claim 3, wherein the modified nucleotide of the sense strand is a 2'-O-methyl nucleotide or 2'-fluoro nucleotide.

5. The RNAi agent of claim 1, wherein all of the nucleotides of the sense strand of the RNAi agent are modified nucleotides.

6. The RNAi agent of claim 1, wherein the RNAi agent is linked to a targeting ligand.

7. The RNAi agent of claim 6, wherein the targeting ligand comprises N-acetyl-galactosamine.

8. The RNAi agent of claim 7, wherein the targeting ligand comprises a structure selected from the group consisting of: (NAG13), (NAG13)s, (NAG18), (NAG18)s, (NAG24), (NAG24)s, (NAG25), (NAG25)s, (NAG26), (NAG26)s, (NAG27), (NAG27)s, (NAG28), (NAG28)s, (NAG29), (NAG29)s, (NAG30), (NAG30)s, (NAG31), (NAG31)s, (NAG32), (NAG32)s, (NAG33), (NAG33)s, (NAG34), (NAG34)s, (NAG35), (NAG35)s, (NAG36), (NAG36)s, (NAG37), (NAG37)s, (NAG38), (NAG38)s, (NAG39), (NAG39) s.

9. The RNAi agent of claim 8, wherein the targeting ligand comprises the structure of (NAG37) or (NAG37)s.

10. The RNAi agent of claim 9, wherein the targeting ligand is linked to the sense strand.

11. The RNAi agent of claim 10, wherein the targeting ligand is linked to the 5' terminal end of the sense strand.

12. The RNAi agent of claim 1, wherein the sense strand and the antisense strand are each 21 nucleotides in length.

13. The RNAi agent of claim 1, wherein the RNAi agent has two blunt ends.

14. The RNAi agent of claim 1, wherein the sense strand comprises one or two terminal caps.

15. The RNAi agent of claim 1, wherein the sense strand comprises one or two inverted abasic residues.

16. The RNAi agent of claim 1, wherein the nucleobase sequence of the sense strand (5'→3') is CGUAAGAAGUCUGAUAGAUGA (SEQ ID NO:8).

17. The RNAi agent of claim 1, wherein all of the nucleotides are modified nucleotides.

18. The RNAi agent of claim 1, wherein the sense strand further includes inverted abasic residues at the 3' terminal end of the nucleotide sequence, or at the 5' end of the nucleotide sequence.

19. The RNAi agent of claim 1, wherein the antisense strand has the nucleotide sequence (5'→3') usCfsasUfcUfaucagAfcUfuCfuUfaCfsg (SEQ ID NO:4)

wherein a, c, g, and u represent 2'-O-methyl adenosine, 2'-O-methyl cytidine, 2'-O-methyl guanosine, and 2'-O-methyl uridine, respectively; Af, Cf, Gf, and Uf represent 2'-fluoro adenosine, 2'-fluoro cytidine, 2'-fluoro guanosine, and 2'-fluoro uridine, respectively; s represents a phosphorothioate linkage; and wherein all of the nucleotides on the sense strand are modified nucleotides.

20. The RNAi agent of claim 1, wherein the sense strand differs by 0 or 1 nucleotide from one of the following nucleotide sequences (5'→3'):

cguaagaaGfUfCfugauagauga (SEQ ID NO:9); or cguaagaaGfuCfuGfauagauga (SEQ ID NO: 10);

wherein a, c, g, and u represent 2'-O-methyl adenosine, 2'-O-methyl cytidine, 2'-O-methyl guanosine, and 2'-O-methyl uridine, respectively; Af, Cf, Gf, and Uf represent 2'-fluoro adenosine, 2'-fluoro cytidine, 2'-fluoro guanosine, and 2'-fluoro uridine, respectively; s represents a phosphorothioate linkage.

21. The RNAi agent of claim 1, wherein the sense strand further includes inverted abasic residues at the 3' terminal end of the nucleotide sequence, and at the 5' end of the nucleotide sequence.

22. The RNAi agent of claim 1, wherein the sense strand of the RNAi agent is linked to a targeting ligand.

23. The RNAi agent of claim 22, wherein the targeting ligand has affinity for the asialoglycoprotein receptor.

24. The RNAi agent of claim 23, wherein the targeting ligand comprises N-acetyl-galactosamine.

25. The RNAi agent of claim 22, wherein the RNAi agent has the duplex structure that is AD06214 (SEQ ID NOs: 2 and 14) or AD06280 (SEQ ID NOs: 4 and 15).

26. The RNAi agent of claim 22, wherein the targeting ligand comprises:

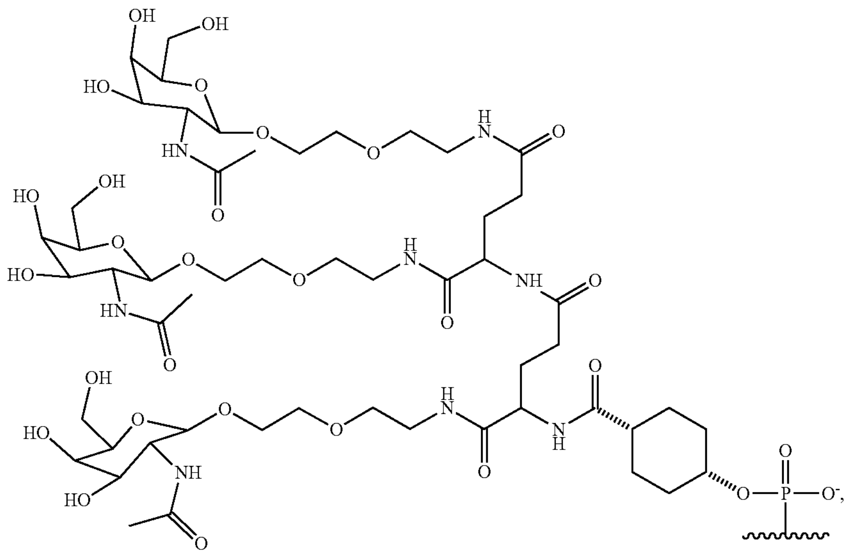

or

-continued

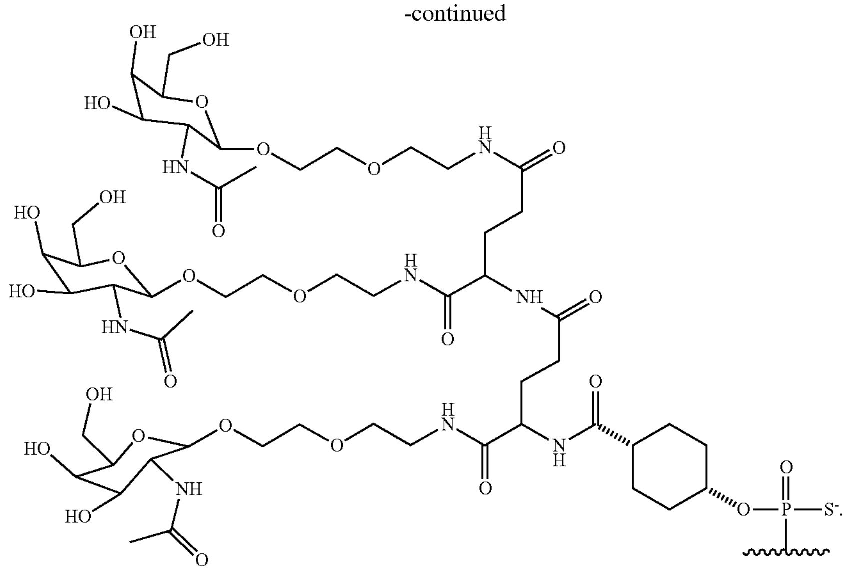

27. The RNAi agent of claim 1, wherein the antisense strand consists of the modified nucleotide sequence of (5'→3') usCfsasUfcUfaUfcAfgAfcUfuCfuUfaCfsg (SEQ ID NO:2), and the sense strand consists of the modified nucleotide sequence of (5'→3') (NAG37)s(invAb) scguaagaaGfUfCfugauagaugas(invAb) (SEQ ID NO:14);

wherein a, c, g, and u are 2'-O-methyl adenosine, 2'-O-methyl cytidine, 2'-O-methyl guanosine, and 2'-O-methyl uridine, respectively; Af, Cf, Gf, and Uf are 2'-fluoro adenosine, 2'-fluoro cytidine, 2'-fluoro guanosine, and 2'-fluoro uridine, respectively; s is a phosphorothioate linkage; (invAb) is an inverted abasic deoxyribose residue; and (NAG37)s comprises the following chemical structure:

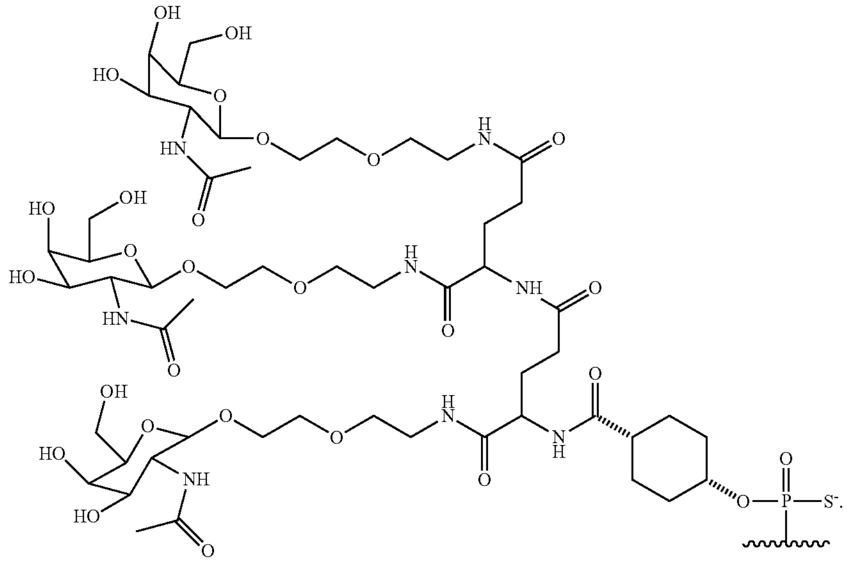

28. The RNAi agent of claim 1, wherein the antisense strand consists of the modified nucleotide sequence of (5'→3') usCfsasUfcUfaucagAfcUfuCfuUfaCfsg (SEQ ID NO:4), and wherein the sense strand consists of the modified nucleotide sequence of (5'→3') (NAG37)s (invAb) scguaagaaGfuCfuGfauagaugas (invAb) (SEQ ID NO:15);

wherein a, c, g, and u are 2'-O-methyl adenosine, 2'-O-methyl cytidine, 2'-O-methyl guanosine, and 2'-O-methyl uridine, respectively; Af, Cf, Gf, and Uf are 2'-fluoro adenosine, 2'-fluoro cytidine, 2'-fluoro guanosine, and 2'-fluoro uridine, respectively; s is a phosphorothioate linkage; (invAb) is an inverted abasic deoxyribose residue; and (NAG37)s comprises the following chemical structure:

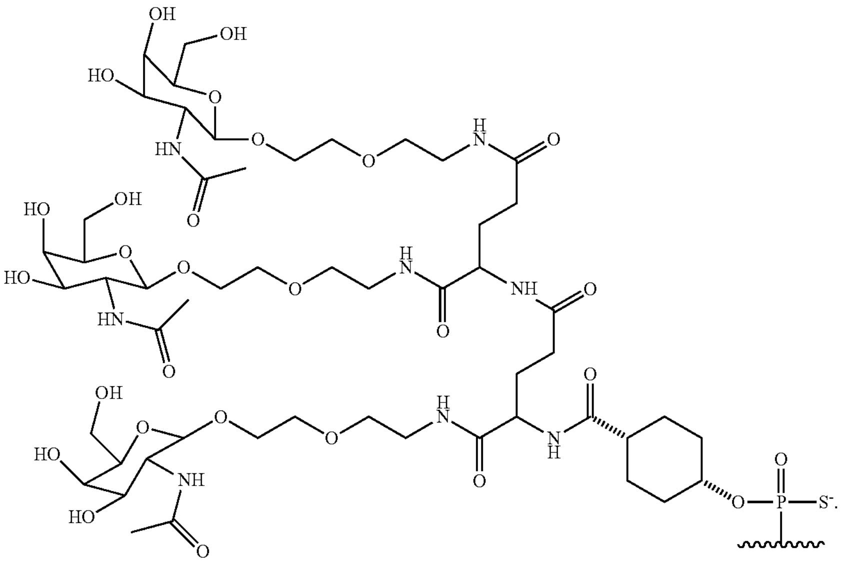

29. A composition comprising the RNAi agent of claim 28, wherein the composition further comprises a pharmaceutically acceptable excipient.

30. A composition comprising the RNAi agent of claim 1, wherein the composition further comprises a pharmaceutically acceptable excipient.

31. The composition of claim 30, further comprising a second RNAi agent for inhibiting the expression of HSD17B13.

32. The composition of claim 30, further comprising one or more additional therapeutics.

33. The composition of claim 32, wherein the additional therapeutics comprises an anti-inflammatory agent.

34. The RNAi agent of claim 1, wherein the nucleobase sequence of the sense strand (5'→3') is CGUAAGAAGUCUGAUAGAUGA (SEQ ID NO:8) and at least one of the nucleotides of the sense strand is a modified nucleotide or includes a modified internucleotide linkage.

35. The RNAi agent of claim 1, wherein the antisense strand comprises the nucleotide sequence (5'→3'):

usCfsasUfcUfaucagAfcUfuCfuUfaCfsg (SEQ ID NO:4); wherein a, c, g, and u represent 2'-O-methyl adenosine, 2'-O-methyl cytidine, 2'-O-methyl guanosine, and 2'-O-methyl uridine, respectively; Af, Cf, Gf, and Uf represent 2'-fluoro adenosine, 2'-fluoro cytidine, 2'-fluoro guanosine, and 2'-fluoro uridine, respectively; s represents a phosphorothioate linkage; and wherein all of the nucleotides on the sense strand are modified nucleotides.

36. The RNAi agent of claim 1, wherein the sense strand differs by 0 or 1 nucleotide from the nucleotide sequences (5'→3'):

cguaagaaGfuCfuGfauagauga (SEQ ID NO:10);

wherein a, c, g, and u represent 2'-O-methyl adenosine, 2'-O-methyl cytidine, 2'-O-methyl guanosine, and 2'-O-methyl uridine, respectively; Af, Cf, Gf, and Uf represent 2'-fluoro adenosine, 2'-fluoro cytidine, 2'-fluoro guanosine, and 2'-fluoro uridine, respectively; s represents a phosphorothioate linkage; and wherein all of the nucleotides on the antisense strand are modified nucleotides.

37. The RNAi agent of claim 1, wherein the antisense strand has the nucleotide sequence (5'→3'):

usCfsasUfcUfaucagAfcUfuCfuUfaCfsg (SEQ ID NO:4), wherein the sense strand differs by 0 or 1 nucleotide from the nucleotide sequences (5'→3'):

cguaagaaGfuCfuGfauagauga (SEQ ID NO:10), and wherein a, c, g, and u represent 2'-O-methyl adenosine, 2'-O-methyl cytidine, 2'-O-methyl guanosine, and 2'-O-methyl uridine, respectively; Af, Cf, Gf, and Uf represent 2'-fluoro adenosine, 2'-fluoro cytidine, 2'-fluoro guanosine, and 2'-fluoro uridine, respectively; s represents a phosphorothioate linkage; and wherein all of the nucleotides on the sense strand and the antisense strand are modified nucleotides.

38. The RNAi agent of claim 1, wherein the RNAi agent is in a free acid form.

39. The RNAi agent of claim 1, wherein the RNAi agent is in a sodium salt form.

40. An RNAi agent comprising a chemical structure as follows with the antisense strand (5'→3') SEQ ID NO:4 and the sense strand (5'→3') SEQ ID NO:15:

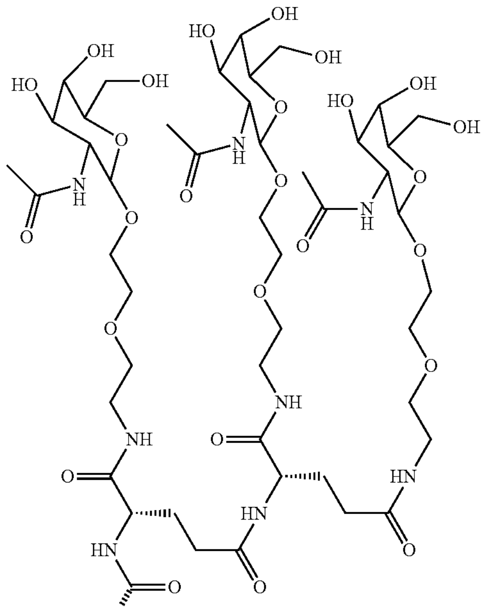
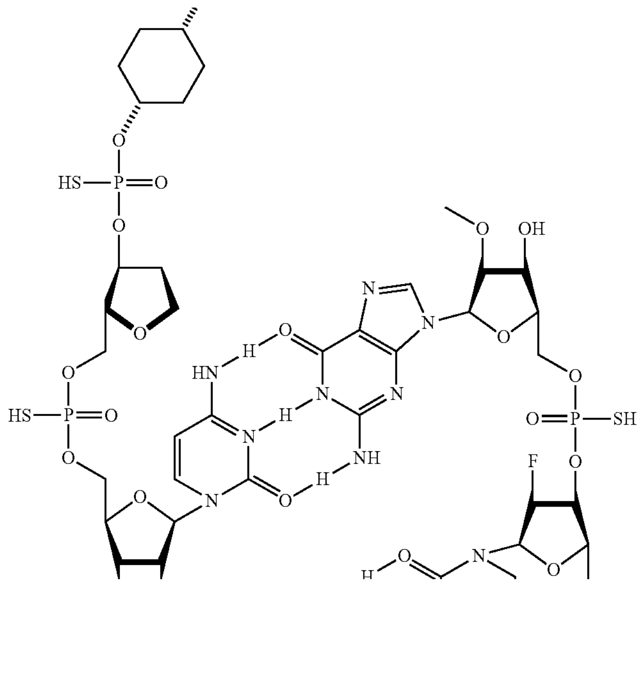

-continued
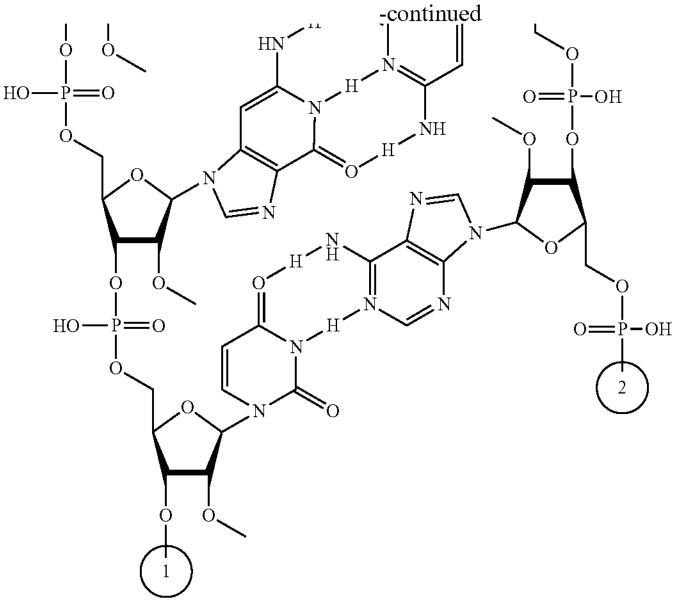
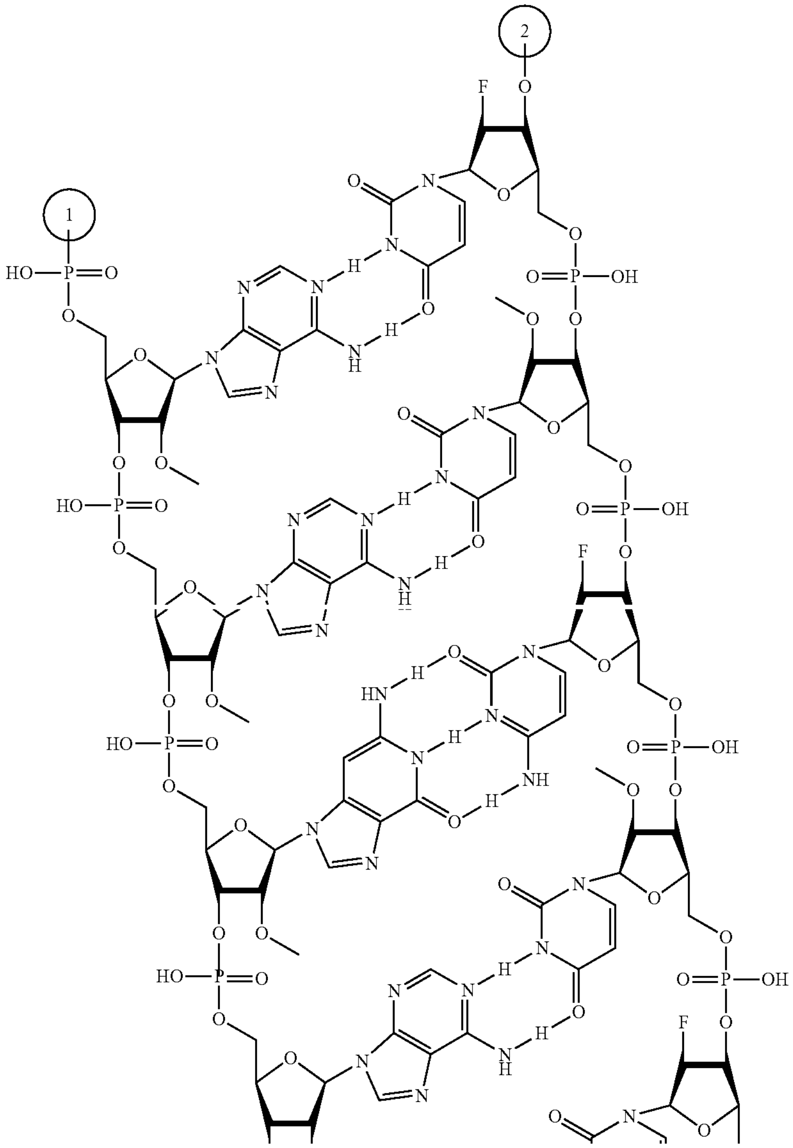

-continued
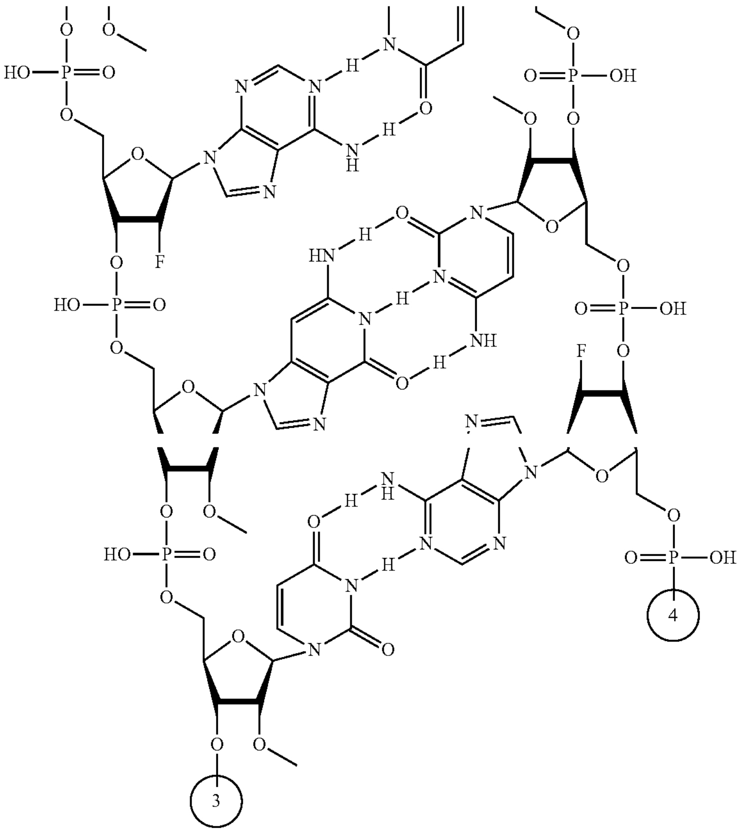
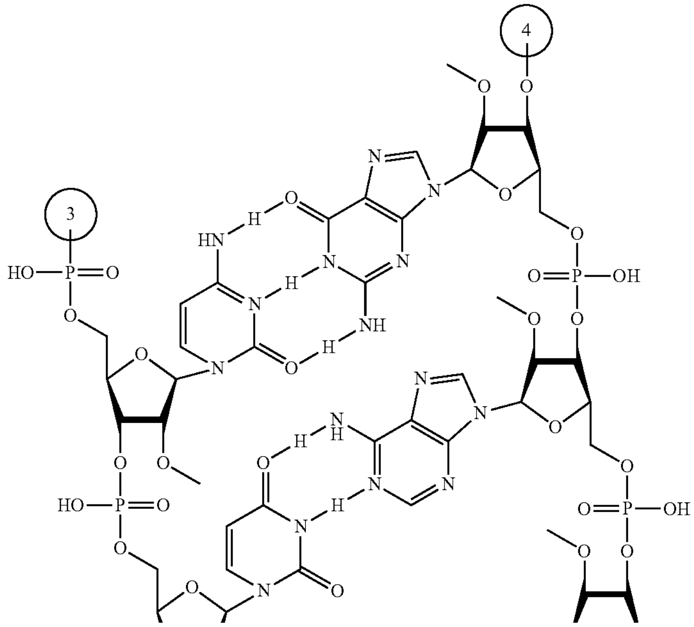

-continued
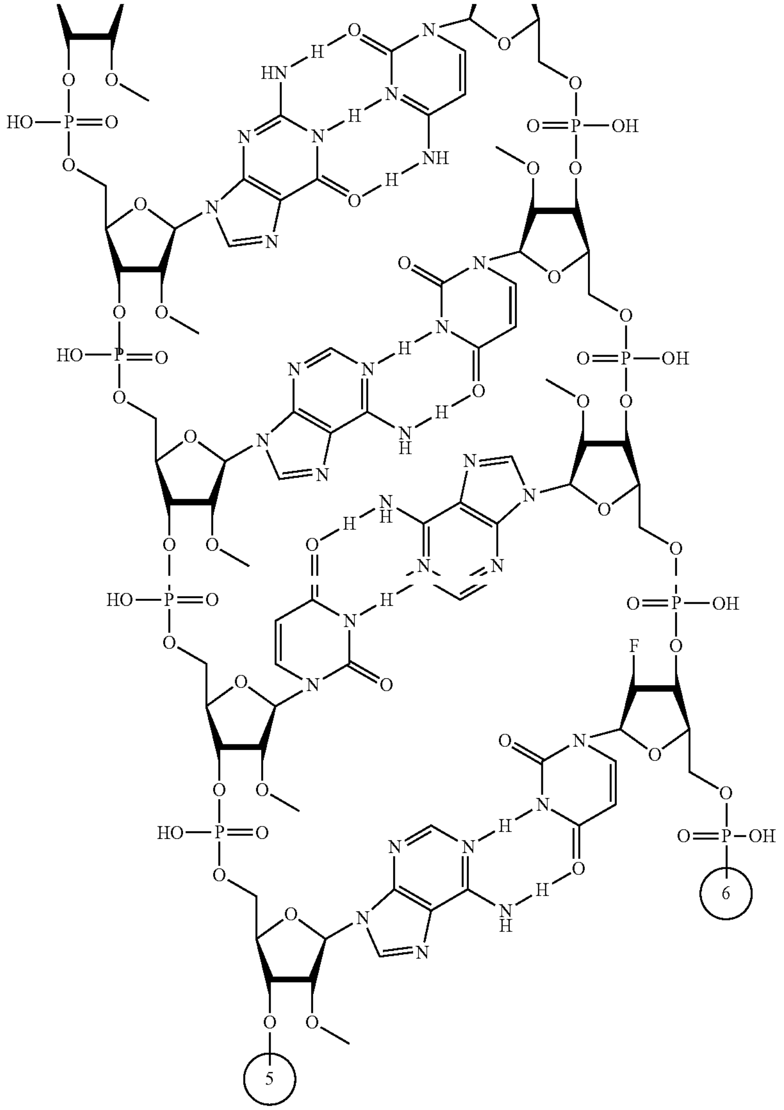
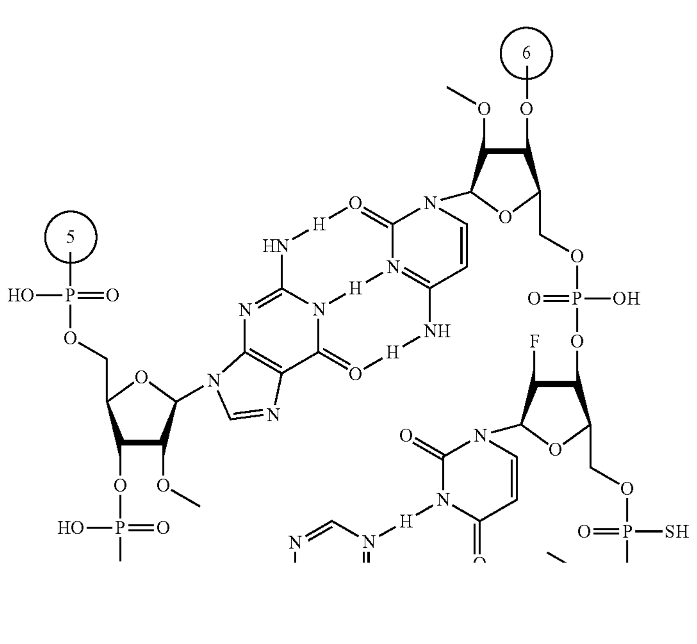

-continued
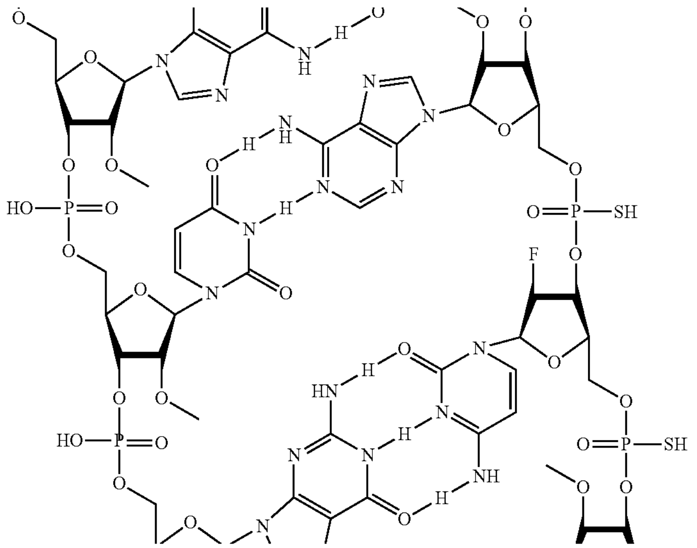
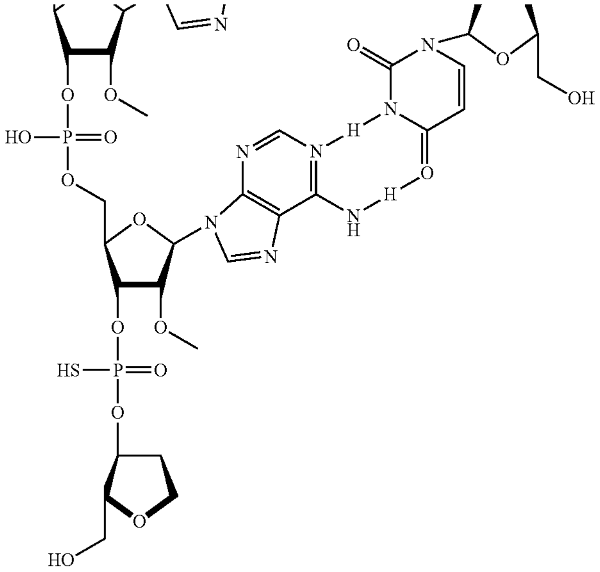

41. A composition comprising the RNAi agent of claim 40, wherein the composition further comprises a pharmaceutically acceptable excipient.
42. An RNAi agent comprising a chemical structure as follows with the antisense strand (5'→3') SEQ ID NO:4 and the sense strand (5'→3') SEQ ID NO: 15:
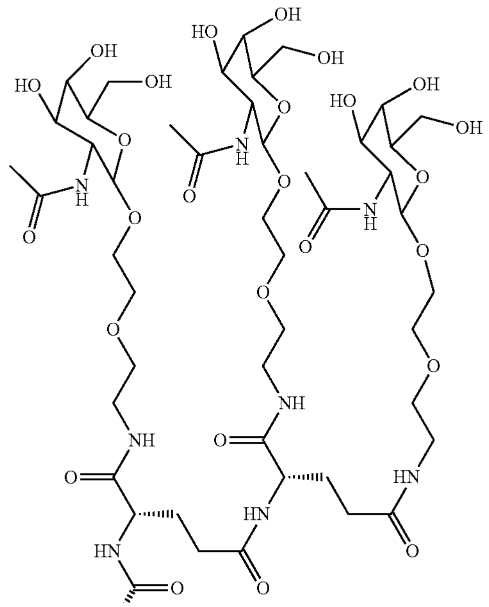
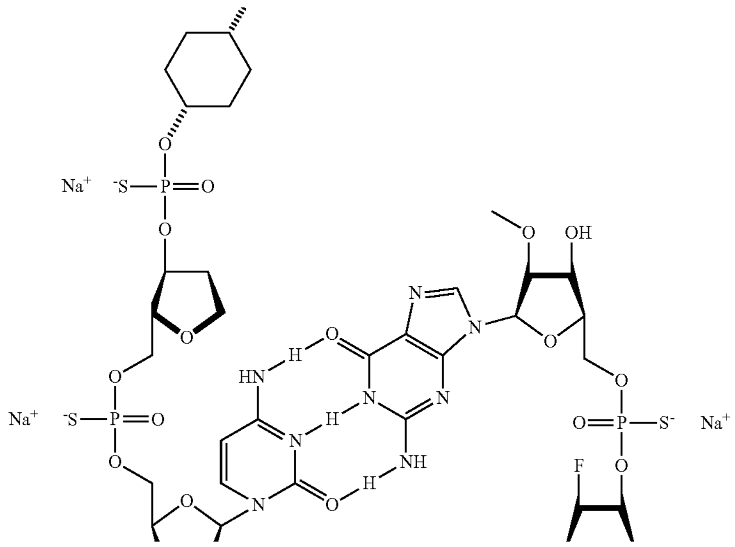

-continued
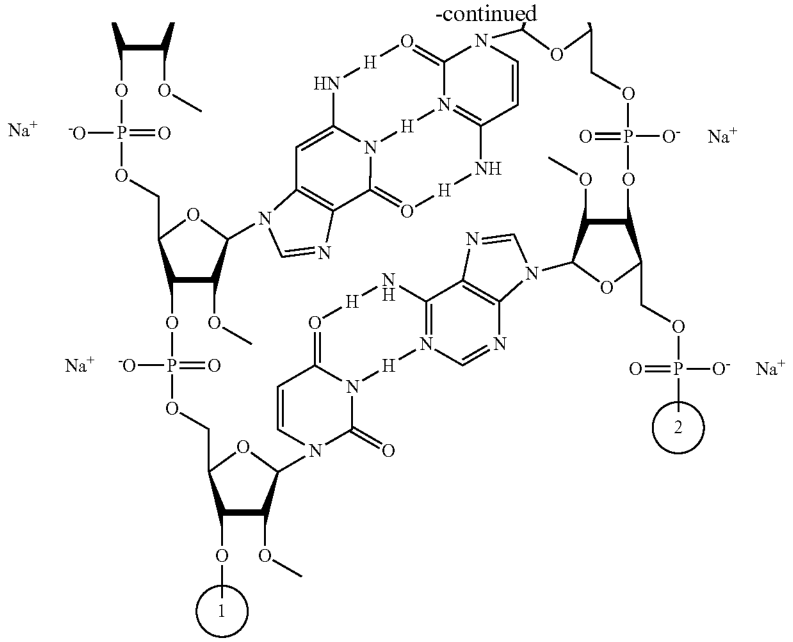
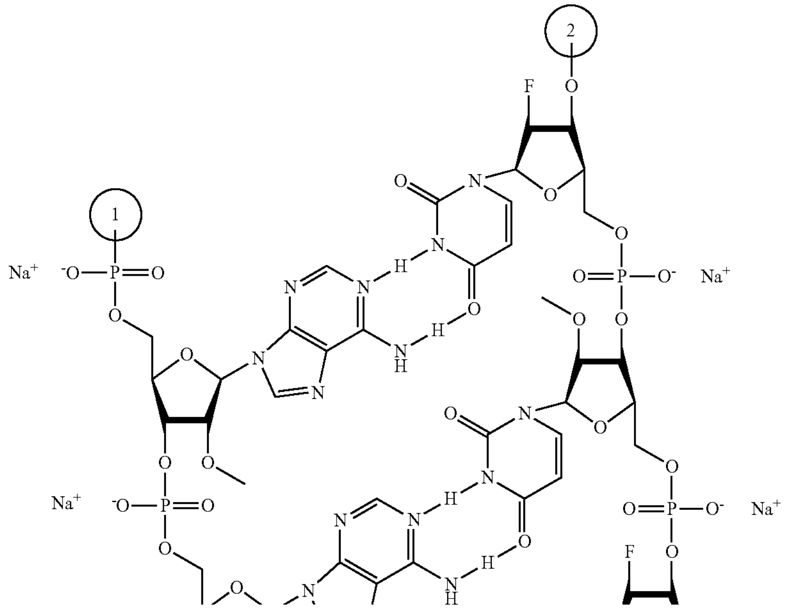

-continued
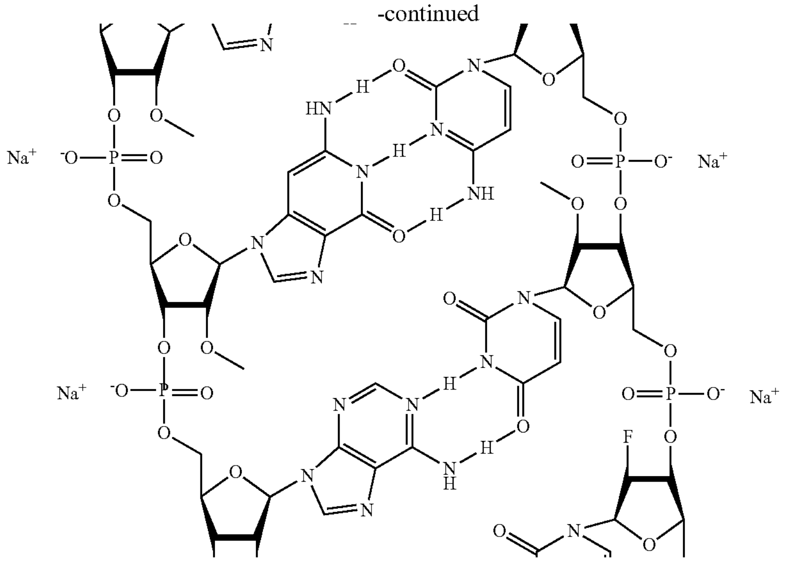
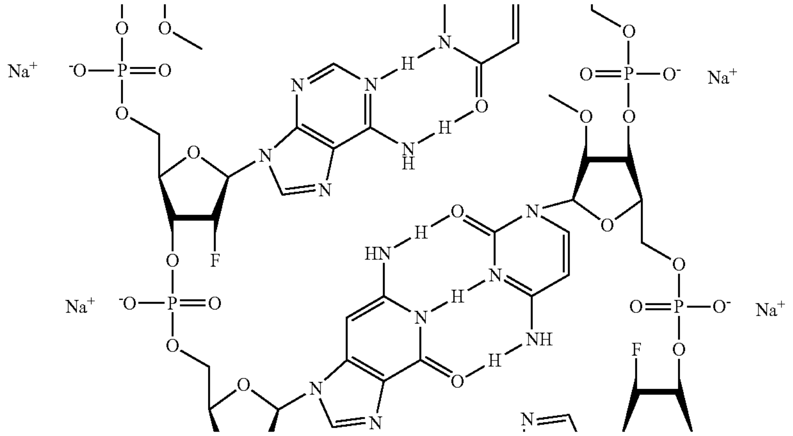
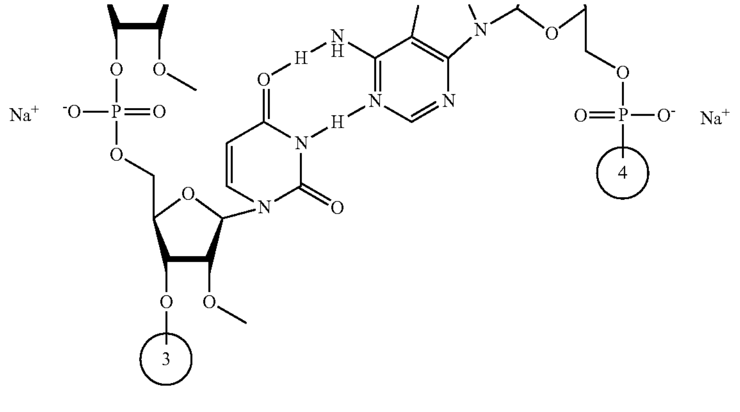

-continued
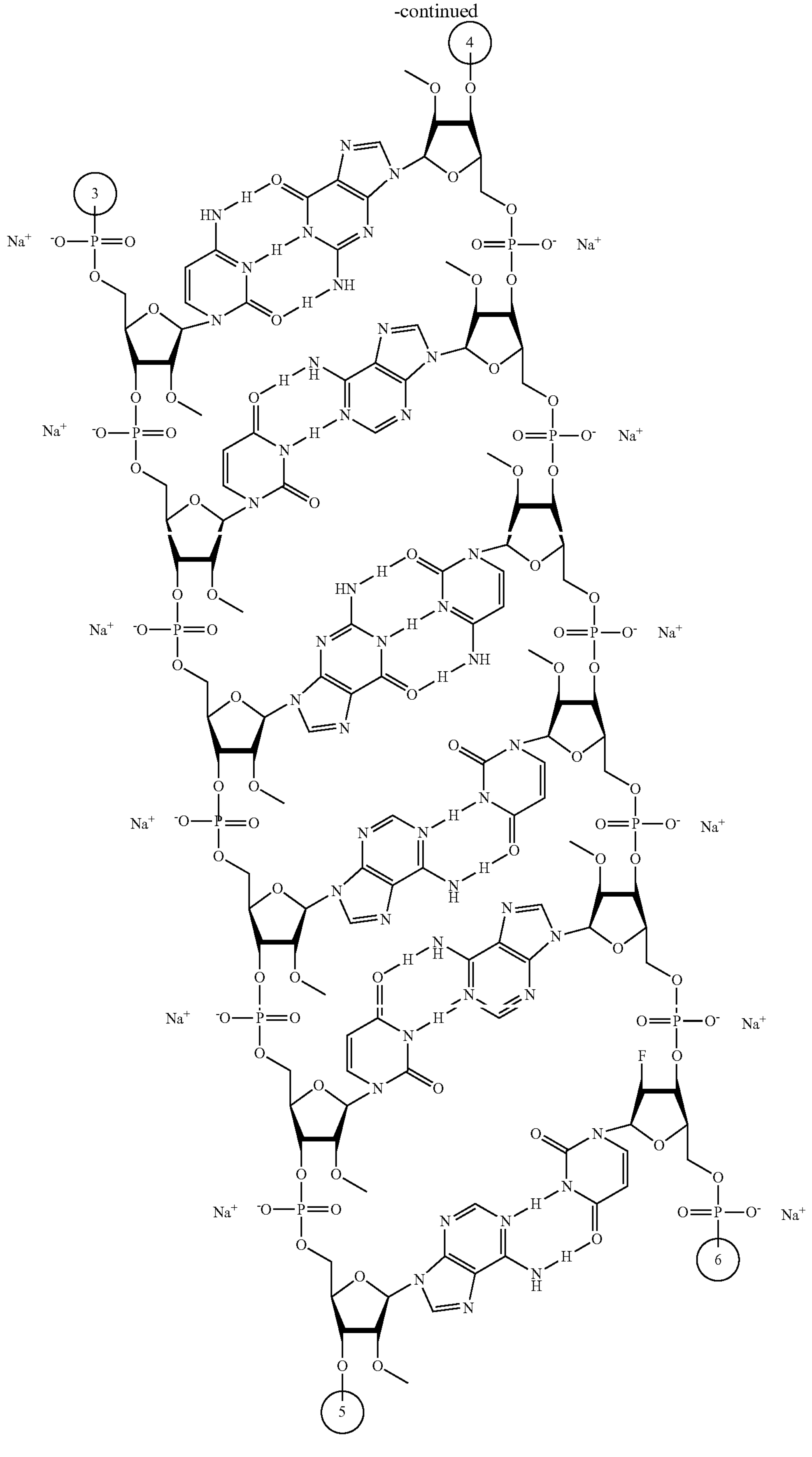

-continued
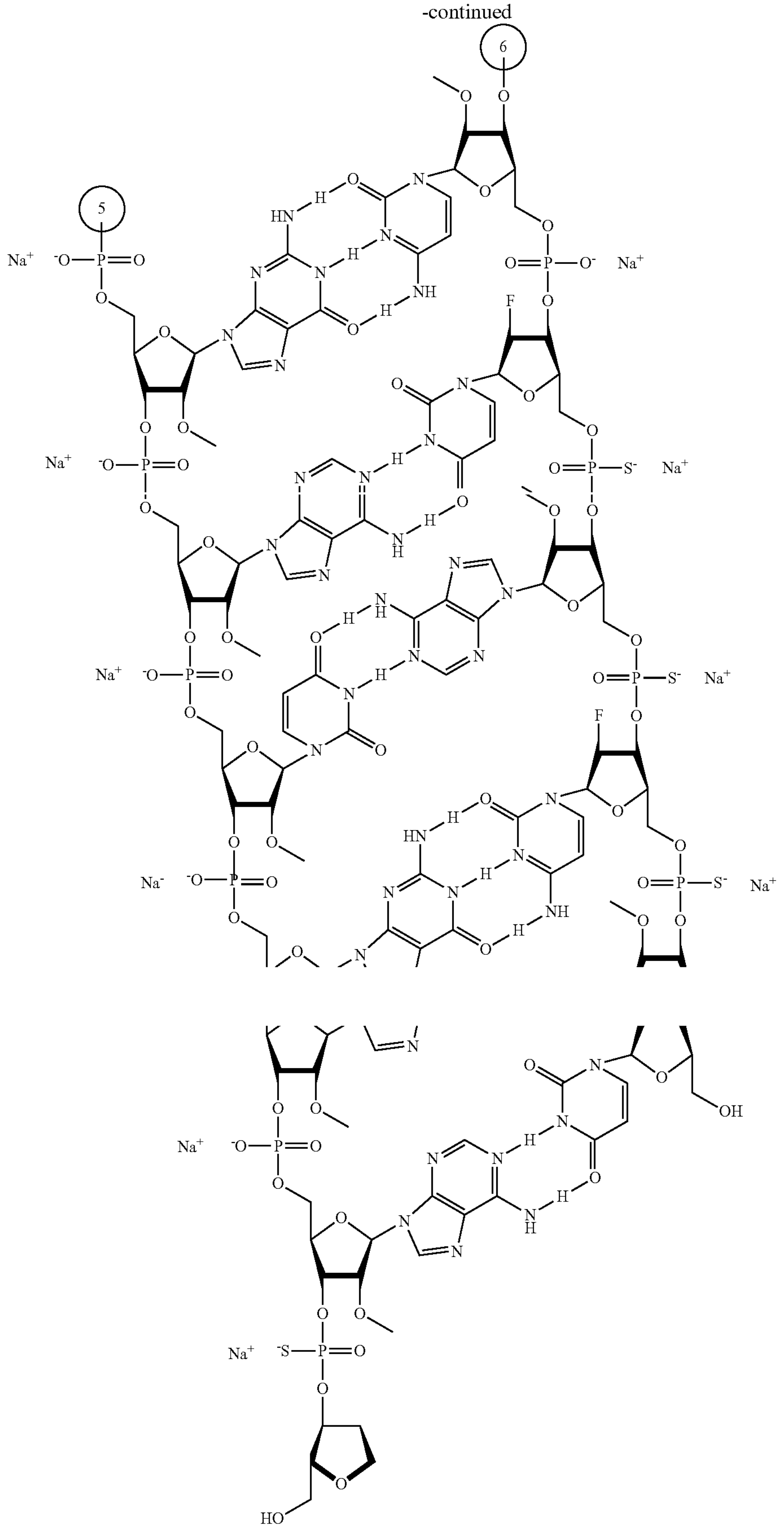

43. A composition comprising the RNAi agent of claim 42, wherein the composition further comprises a pharmaceutically acceptable excipient.

44. An RNAi agent comprising 1) an antisense strand that comprises the structure of (5'→3') usCfsasUfcUfaucagAfcUfuCfuUfaCfsg (SEQ ID NO:4), and 2) a sense strand that comprises the structure of (5'→3') (NAG37)s(invAb) scguaagaaGfuCfuGfauagaugas(invAb) (SEQ ID NO:15), wherein: a, c, g, and u are 2'-O-methyl adenosine, 2'-O-methyl cytidine, 2'-O-methyl guanosine, and 2'-O-methyl uridine, respectively; Af, Cf, Gf, and Uf are 2'-fluoro adenosine, 2'-fluoro cytidine, 2'-fluoro guanosine, and 2'-fluoro uridine, respectively; s is a phosphorothioate linkage; (invAb) is an inverted abasic deoxyribose residue; and (NAG37)s comprises the following chemical structure:

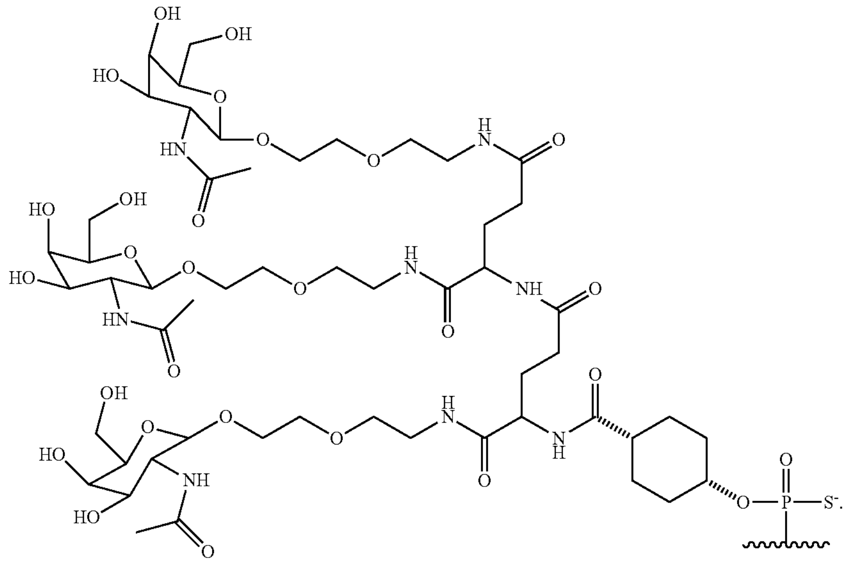
.

45. A composition comprising the RNAi agent of claim 44, wherein the composition further comprises a pharmaceutically acceptable excipient.

* * * * *